United States Patent
Piasecki et al.

(10) Patent No.: US 11,401,339 B2
(45) Date of Patent: Aug. 2, 2022

(54) ANTI-TIGIT ANTIBODIES

(71) Applicant: Seagen, Inc., Bothell, WA (US)

(72) Inventors: Julia C. Piasecki, Bothell, WA (US);
Courtney Beers, Bothell, WA (US);
Scott Peterson, Bothell, WA (US);
Bianka Prinz, Lebanon, NH (US);
Shyra Gardai, Bothell, WA (US)

(73) Assignee: Seagen Inc., Bothell, WA (US)

( * ) Notice: Subject to any disclaimer, the term of this patent is extended or adjusted under 35 U.S.C. 154(b) by 187 days.

(21) Appl. No.: 16/547,824

(22) Filed: Aug. 22, 2019

(65) Prior Publication Data

US 2020/0062859 A1 Feb. 27, 2020

Related U.S. Application Data

(60) Provisional application No. 62/722,063, filed on Aug. 23, 2018, provisional application No. 62/734,130, filed on Sep. 20, 2018, provisional application No. 62/822,674, filed on Mar. 22, 2019.

(51) Int. Cl.
*C07K 16/30* (2006.01)
*A61K 47/68* (2017.01)
*A61P 35/00* (2006.01)

(52) U.S. Cl.
CPC .......... *C07K 16/30* (2013.01); *A61K 47/6803* (2017.08); *A61K 47/6849* (2017.08); *A61P 35/00* (2018.01); *C07K 2317/31* (2013.01); *C07K 2317/32* (2013.01); *C07K 2317/41* (2013.01); *C07K 2317/565* (2013.01); *C07K 2317/734* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,192,880 A | 3/1993 | Dazai |
| 5,374,746 A | 12/1994 | Ok et al. |
| 5,552,534 A | 9/1996 | Hirschmann et al. |
| 5,736,523 A | 4/1998 | Attardo et al. |
| 6,143,724 A | 11/2000 | Ohira et al. |
| 7,160,865 B2 | 1/2007 | Lampidis et al. |
| 7,193,069 B2 | 3/2007 | Isogai et al. |
| 7,517,670 B2 | 4/2009 | Umaña et al. |
| 7,632,497 B2 | 12/2009 | Stavenhagen |
| 7,713,524 B2 | 5/2010 | Bourel et al. |
| 7,737,325 B2 | 6/2010 | Kanda et al. |
| 7,772,192 B2 | 8/2010 | Esko |
| 7,956,085 B2 | 6/2011 | Frick et al. |
| 8,101,583 B2 | 1/2012 | Glombik et al. |
| 8,242,167 B2 | 8/2012 | Lampidis et al. |
| 8,299,033 B2 | 10/2012 | Priebe et al. |
| 8,431,350 B2 | 4/2013 | Baldwin et al. |
| 8,586,006 B2 | 11/2013 | Hood et al. |
| 8,822,642 B2 | 9/2014 | Levin et al. |
| 8,969,518 B2 | 3/2015 | Brandt et al. |
| 9,061,059 B2 | 6/2015 | Chakraborty et al. |
| 9,089,604 B2 | 7/2015 | Chakraborty et al. |
| 9,220,755 B2 | 12/2015 | Chakraborty et al. |
| 9,327,014 B2 | 5/2016 | Gurney et al. |
| 9,499,596 B2 | 11/2016 | Clark et al. |
| 9,695,238 B2 | 7/2017 | Gao et al. |
| 9,713,641 B2 | 7/2017 | Hicklin et al. |
| 9,714,289 B2 | 7/2017 | White et al. |
| RE46,534 E | 9/2017 | Baldwin et al. |
| 9,756,085 B2 | 9/2017 | Chitty et al. |
| 9,782,462 B2 | 10/2017 | Bancel et al. |
| 9,833,500 B2 | 12/2017 | Gurney et al. |
| 9,873,740 B2 | 1/2018 | Grogan et al. |
| 9,913,866 B2 | 3/2018 | O'Shea et al. |
| 10,047,158 B2 | 8/2018 | Grogan et al. |
| 2002/0035082 A1 | 3/2002 | Grinstaff et al. |
| 2004/0067914 A1 | 4/2004 | Wechter et al. |
| 2004/0121370 A1 | 6/2004 | Baldwin et al. |
| 2004/0219521 A1 | 11/2004 | Tang et al. |
| 2004/0258678 A1 | 12/2004 | Bodary et al. |
| 2005/0272128 A1 | 12/2005 | Umana et al. |
| 2006/0105376 A1 | 5/2006 | Isogai et al. |
| 2006/0199181 A1 | 9/2006 | Bodary et al. |
| 2007/0054360 A1 | 3/2007 | Gao et al. |

(Continued)

FOREIGN PATENT DOCUMENTS

| | | |
|---|---|---|
| CN | 101555262 A | 10/2009 |
| EP | 335369 A2 | 10/1989 |

(Continued)

OTHER PUBLICATIONS

Chauvin et al., "TIGIT and PD-1 impair tumor antigen-specific CD8+ T cells in melanoma patients," The Journal of Clinical Investigation, vol. 125, No. 5, May 2015 pp. 2046-2058.

International Preliminary Report on Patentability (Chapter II of the PCT) and Article 34 Amendment for International Application No. PCT/US2018/020239, dated May 7, 2019 (13 pages).

International Search Report and Written Opinion of PCT/US2018/020239, dated Jun. 15, 2018 (9 pages).

Invitation to Pay Additional Fees from the International Searching Authority for International Application No. PCT/US2019/047607, dated Nov. 13, 2019 (12 pages).

(Continued)

*Primary Examiner* — Nelson B Moseley, II
(74) *Attorney, Agent, or Firm* — McNeill Baur PLLC

(57) ABSTRACT

Isolated antibodies that bind to human TIGIT (T-cell immunoreceptor with Ig and ITIM domains) are provided. In some embodiments, the antibody has a binding affinity ($K_D$) for human TIGIT of less than 5 nM. In some embodiments, the anti-TIGIT antibody blocks binding of CD155 and/or CD112 to TIGIT. In some embodiments, the antibodies are afucosylated.

122 Claims, 53 Drawing Sheets

Specification includes a Sequence Listing.

(56) References Cited

U.S. PATENT DOCUMENTS

| | | |
|---|---|---|
| 2007/0254339 A1 | 11/2007 | West et al. |
| 2008/0038264 A1 | 2/2008 | Bodary et al. |
| 2008/0050809 A1 | 2/2008 | Abuin et al. |
| 2009/0092605 A1 | 4/2009 | Bodary et al. |
| 2009/0156495 A1 | 6/2009 | Gao et al. |
| 2009/0162292 A1 | 6/2009 | Thompson et al. |
| 2009/0181024 A1 | 7/2009 | Baldwin et al. |
| 2009/0181380 A1 | 7/2009 | Belouchi et al. |
| 2009/0258013 A1 | 10/2009 | Clark et al. |
| 2010/0075377 A1 | 3/2010 | West et al. |
| 2010/0130434 A1 | 5/2010 | Priebe et al. |
| 2010/0196371 A1 | 8/2010 | Hanai et al. |
| 2010/0204165 A1 | 8/2010 | Crouse et al. |
| 2010/0316646 A1 | 12/2010 | Gao et al. |
| 2011/0003758 A1 | 1/2011 | Priebe et al. |
| 2011/0172114 A1 | 7/2011 | Bodary et al. |
| 2011/0183926 A1 | 7/2011 | Lampidis et al. |
| 2012/0039908 A1 | 2/2012 | Combs et al. |
| 2012/0064100 A1 | 3/2012 | Barry et al. |
| 2012/0100609 A1 | 4/2012 | Crawford et al. |
| 2012/0165279 A1 | 6/2012 | Lee et al. |
| 2012/0219540 A1 | 8/2012 | Gao et al. |
| 2012/0245347 A1 | 9/2012 | Biehl et al. |
| 2012/0276108 A1 | 11/2012 | Priebe |
| 2014/0010861 A1 | 1/2014 | Bancel et al. |
| 2014/0056890 A1 | 2/2014 | Gurney et al. |
| 2014/0106981 A1 | 4/2014 | Hood et al. |
| 2014/0171485 A1 | 6/2014 | Bancel et al. |
| 2014/0200264 A1 | 7/2014 | Bancel et al. |
| 2014/0206755 A1 | 7/2014 | Bancel et al. |
| 2014/0255467 A1 | 9/2014 | Bancel et al. |
| 2014/0255468 A1 | 9/2014 | Bancel et al. |
| 2015/0044277 A1 | 2/2015 | Bancel et al. |
| 2015/0132744 A1 | 5/2015 | Fromentin et al. |
| 2015/0152160 A1 | 6/2015 | Gao et al. |
| 2015/0175702 A1 | 6/2015 | Brandt et al. |
| 2015/0216970 A1 | 8/2015 | Grogan et al. |
| 2015/0216971 A1 | 8/2015 | Rotolo et al. |
| 2015/0322119 A1 | 11/2015 | Engelhardt et al. |
| 2016/0152720 A1 | 6/2016 | Kim et al. |
| 2016/0159905 A1 | 6/2016 | Abdiche et al. |
| 2016/0169869 A1 | 6/2016 | Cong et al. |
| 2016/0176963 A1 | 6/2016 | Maurer et al. |
| 2016/0320388 A1 | 11/2016 | Barry et al. |
| 2016/0355589 A1 | 12/2016 | Williams et al. |
| 2016/0376365 A1 | 12/2016 | Gurney et al. |
| 2017/0037127 A1 | 2/2017 | Grogan et al. |
| 2017/0044256 A1 | 2/2017 | Grogan et al. |
| 2017/0051061 A1* | 2/2017 | Snyder ............. G01N 33/57426 |
| 2017/0088607 A1 | 3/2017 | White et al. |
| 2017/0088613 A1* | 3/2017 | Grogan ................... A61P 37/02 |
| 2017/0095531 A1 | 4/2017 | Schreiber et al. |
| 2017/0107300 A1 | 4/2017 | Kuchroo et al. |
| 2017/0121409 A1 | 5/2017 | Verona et al. |
| 2017/0143825 A1 | 5/2017 | Grogan |
| 2017/0145093 A1 | 5/2017 | Clark et al. |
| 2017/0198042 A1 | 7/2017 | Williams et al. |
| 2017/0267763 A1 | 9/2017 | Gao et al. |
| 2017/0281764 A1 | 10/2017 | Tso et al. |
| 2017/0320959 A1 | 11/2017 | Swanson et al. |
| 2017/0340735 A1 | 11/2017 | Hicklin et al. |
| 2017/0369570 A1 | 12/2017 | Rubin-Bejerano et al. |
| 2018/0064787 A1 | 3/2018 | Schreiber et al. |
| 2018/0066055 A1 | 3/2018 | Williams et al. |
| 2018/0086807 A1 | 3/2018 | Bancel et al. |
| 2018/0169239 A1 | 6/2018 | Grogan |

FOREIGN PATENT DOCUMENTS

| | | | |
|---|---|---|---|
| EP | 275431 B1 | 9/1992 | |
| EP | 502661 A2 | 9/1992 | |
| EP | 577962 A1 | 1/1994 | |
| EP | 286926 B1 | 1/1995 | |
| EP | 761678 B1 | 3/1999 | |
| EP | 643140 B1 | 10/2001 | |
| EP | 1347046 A1 | 9/2003 | |
| EP | 1518864 A2 | 3/2005 | |
| EP | 1580263 A1 | 9/2005 | |
| EP | 1634887 A2 | 3/2006 | |
| EP | 1272527 B1 | 12/2008 | |
| EP | 2085096 A2 | 8/2009 | |
| EP | 2116551 A1 | 11/2009 | |
| EP | 1539228 B1 | 12/2010 | |
| EP | 2277532 A1 | 1/2011 | |
| EP | 1891107 B1 | 7/2011 | |
| EP | 2388265 A1 | 11/2011 | |
| EP | 2341078 B1 | 12/2011 | |
| EP | 2397493 A1 | 12/2011 | |
| EP | 2399932 B1 | 12/2011 | |
| EP | 2520935 A2 | 2/2013 | |
| EP | 2408934 B1 | 11/2014 | |
| EP | 2825649 A1 | 1/2015 | |
| EP | 2197489 B1 | 5/2017 | |
| EP | 2279412 B1 | 7/2017 | |
| EP | 3202419 A1 | 8/2017 | |
| EP | 3214095 A1 | 9/2017 | |
| EP | 3241846 A1 | 11/2017 | |
| EP | 3293271 A1 | 3/2018 | |
| EP | 2825649 A1 | 7/2019 | |
| EP | 3208612 B1 | 9/2019 | |
| EP | 1518864 B1 | 10/2019 | |
| JP | 1992290891 A | 10/1992 | |
| JP | 1996286368 A | 11/1996 | |
| JP | 3025056 B2 | 3/2000 | |
| JP | 1992283597 A | 3/2000 | |
| JP | 2009215217 A | 9/2009 | |
| JP | 5260093 B2 | 8/2013 | |
| PL | 182601 B1 | 2/2002 | |
| WO | 1991019725 A2 | 12/1991 | |
| WO | 1992001695 A1 | 2/1992 | |
| WO | 1992018640 A1 | 10/1992 | |
| WO | 1993008205 A1 | 4/1993 | |
| WO | 1995000527 A1 | 1/1995 | |
| WO | 1996007665 A1 | 3/1996 | |
| WO | 1998015573 A1 | 4/1998 | |
| WO | 1998025940 A1 | 6/1998 | |
| WO | 1998055490 A1 | 12/1998 | |
| WO | 2001077181 A2 | 10/2001 | |
| WO | 2002000669 A2 | 1/2002 | |
| WO | 2003068943 A2 | 8/2003 | |
| WO | 2003097657 A1 | 11/2003 | |
| WO | 2004024068 A2 | 3/2004 | |
| WO | 2004024072 A2 | 3/2004 | |
| WO | 2004091499 A2 | 10/2004 | |
| WO | 2003054152 A2 | 12/2004 | |
| WO | 2003072035 A2 | 7/2005 | |
| WO | 2005061523 A1 | 7/2005 | |
| WO | 2005049562 A2 | 10/2005 | |
| WO | 2006040558 A1 | 4/2006 | |
| WO | 2007073478 A2 | 6/2007 | |
| WO | 2006124667 A2 | 7/2007 | |
| WO | 2007124283 A2 | 11/2007 | |
| WO | 2008021290 A2 | 4/2008 | |
| WO | 2009046407 A2 | 4/2009 | |
| WO | WO 2009/13518 | * 5/2009 | .............. C12P 21/00 |
| WO | 2009102736 A1 | 8/2009 | |
| WO | 2009117728 A2 | 9/2009 | |
| WO | 2009126688 A2 | 10/2009 | |
| WO | 2009135181 A2 | 11/2009 | |
| WO | 2010105298 A1 | 9/2010 | |
| WO | 2011019419 A1 | 2/2011 | |
| WO | 2011100131 A2 | 10/2011 | |
| WO | 2011100131 A9 | 10/2011 | |
| WO | 2011137528 A1 | 11/2011 | |
| WO | 2011156356 A1 | 12/2011 | |
| WO | 2012019165 A2 | 2/2012 | |
| WO | 2012021400 A2 | 2/2012 | |
| WO | 2012163489 A1 | 12/2012 | |
| WO | 2013010641 A1 | 1/2013 | |
| WO | 2013138505 A1 | 9/2013 | |
| WO | 2013184912 A2 | 5/2014 | |
| WO | 2014089169 A2 | 9/2014 | |
| WO | 2015009856 A2 | 1/2015 | |
| WO | 2015073682 A1 | 5/2015 | |

(56) References Cited

FOREIGN PATENT DOCUMENTS

| | | |
|---|---|---|
| WO | 2016011264 A1 | 1/2016 |
| WO | 2016028656 A1 | 2/2016 |
| WO | 2016073704 A1 | 5/2016 |
| WO | 2016073879 A2 | 5/2016 |
| WO | 2016073906 A2 | 5/2016 |
| WO | 2016106302 A1 | 6/2016 |
| WO | 2016166139 A1 | 10/2016 |
| WO | 2016168771 A2 | 10/2016 |
| WO | 2016179288 A1 | 11/2016 |
| WO | 2016191643 A2 | 12/2016 |
| WO | 2016196389 A1 | 12/2016 |
| WO | 2016196912 A1 | 2/2017 |
| WO | 2017021526 A1 | 2/2017 |
| WO | 2017030823 A2 | 2/2017 |
| WO | 2017037707 A1 | 3/2017 |
| WO | 2017040660 A1 | 3/2017 |
| WO | 2017040666 A2 | 3/2017 |
| WO | 2017040945 A1 | 3/2017 |
| WO | 2017048824 A1 | 3/2017 |
| WO | 2017048878 A1 | 3/2017 |
| WO | 2017053748 A2 | 3/2017 |
| WO | 2017079112 A1 | 5/2017 |
| WO | 2017079115 A1 | 5/2017 |
| WO | 2017079116 A2 | 5/2017 |
| WO | 2016106302 A9 | 6/2017 |
| WO | 2017100428 A1 | 6/2017 |
| WO | 2017149538 A1 | 9/2017 |
| WO | 2017152088 A1 | 9/2017 |
| WO | 2017191274 A2 | 11/2017 |
| WO | 2017193059 A1 | 11/2017 |
| WO | 2017198631 A1 | 11/2017 |
| WO | 2017180587 A2 | 12/2017 |
| WO | 2017220990 A9 | 12/2017 |
| WO | 2017181148 A2 | 2/2018 |
| WO | 2017181152 A2 | 2/2018 |
| WO | 2018022945 A1 | 2/2018 |
| WO | 2018022946 A1 | 2/2018 |
| WO | 2018033798 A1 | 2/2018 |
| WO | 2018041120 A1 | 3/2018 |
| WO | 2018044866 A1 | 3/2018 |
| WO | 2018047178 A1 | 3/2018 |
| WO | 2018058111 A1 | 3/2018 |
| WO | 2018102746 A1 | 6/2018 |
| WO | 2018160704 A1 | 9/2018 |
| WO | 2018183889 A1 | 10/2018 |
| WO | 2017220989 A1 | 12/2018 |

OTHER PUBLICATIONS

Levin et al., "Vstm3 is a Member of the CD28 Family and an Important Modulator of T Cell Function," Eur J Immunol. Apr. 2011 ; 41(4): 902-915.

Lozano et al., "The TIGIT/CD226 axis regulates human T cell function," J Immunol. Apr. 15, 2012; 188(8): 3869-3875.

Piasecki et al., "Abstract 578: Discovery and characterization of novel antagonistic antibodies that bind with high affinity to human, cynomolgus, and murine TIGIT, an immune checkpoint receptor," ACCR Annual Meeting 2017, Washington DC, Cancer Research vol. 77, Issue 13, Jul. 2017 (3 pages).

Smith et al., "Abstract 4986: TIGIT directed human antibody modulates T-regulatory and effector cell function", Proceedings of the American Association for Cancer Research Annual Meeting 2019; Mar. 29-Apr. 3, 2019; Atlanta, GA. Philadelphia (PA): AACR; Cancer Res 2019;79(13 Suppl).

Stanietsky et al. "The interaction of TIGIT with PVR and PVRL2 inhibits human NK cell cytotoxicity," PNAS, vol. 106, No. 42, Oct. 20, 2009, pp. 17858-17863.

Partial Supplementary European Search Report issued in European Application No. 18760515.9, dated Jan. 19, 2021 (21 pages).

Extended European Search Report issued in European Application No. 18760515.9, dated Apr. 20, 2021 (20 pages).

Waight et al., "Selective FcγR Co-engagement on APCs Modulates the Activity of Therapeutic Antibodies Targeting T Cell Antigens," Cancer Cell, 33, pp. 1033-1047 (Jun. 11, 2018).

International Search Report and Written Opinion of PCT/US2019/047607, dated Feb. 18, 2020 (21 pages).

\* cited by examiner

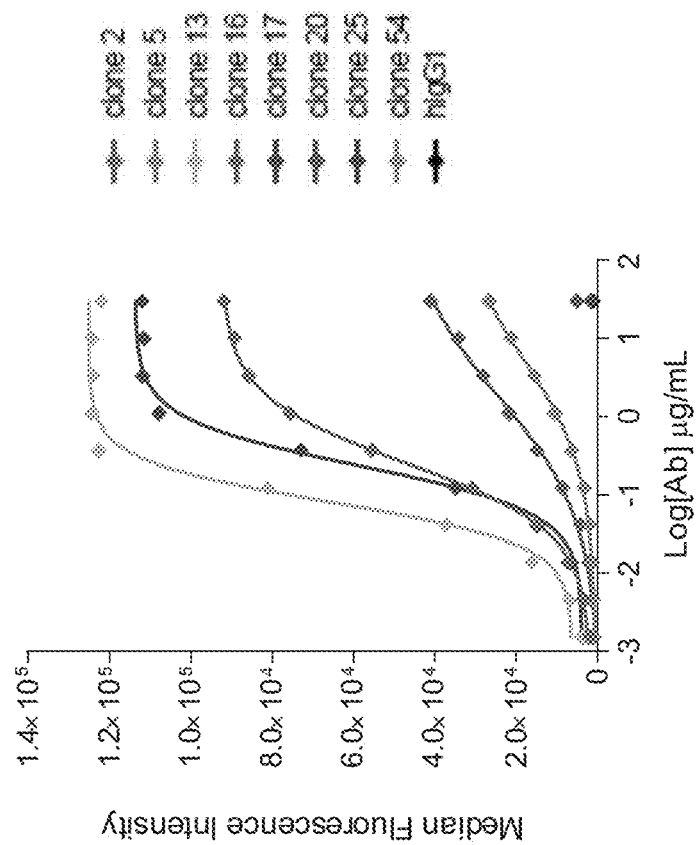
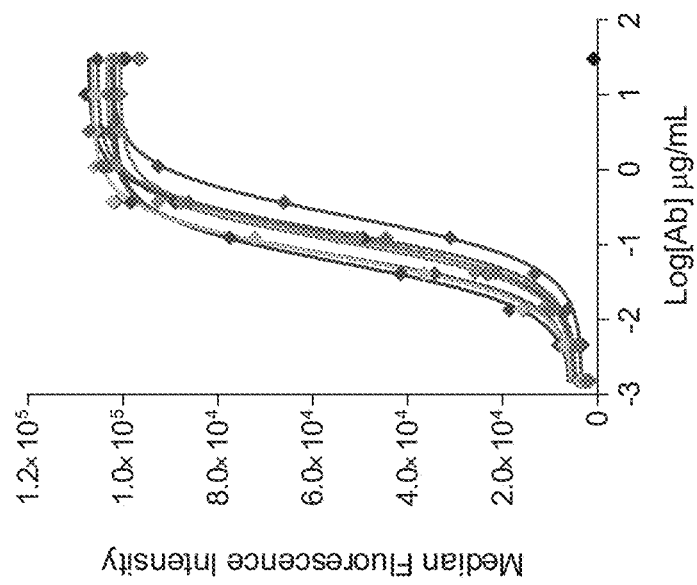
FIG. 3A
FIG. 3B

EC50s (µg/mL)

|  | clone 2 | clone 5 | clone 13 | clone 16 | clone 17 | clone 20 | clone 25 | clone 54 |
|---|---|---|---|---|---|---|---|---|
| human | 0.15 | 0.12 | 0.07 | 0.07 | 0.06 | 0.24 | 0.14 | 0.11 |
| mouse | 0.25 | 5.39 | 0.08 | 0.08 |  |  | 0.24 |  |
| cyno | 0.32 | 1.17 | 0.10 | 0.10 |  |  | 0.19 | 11.44 |

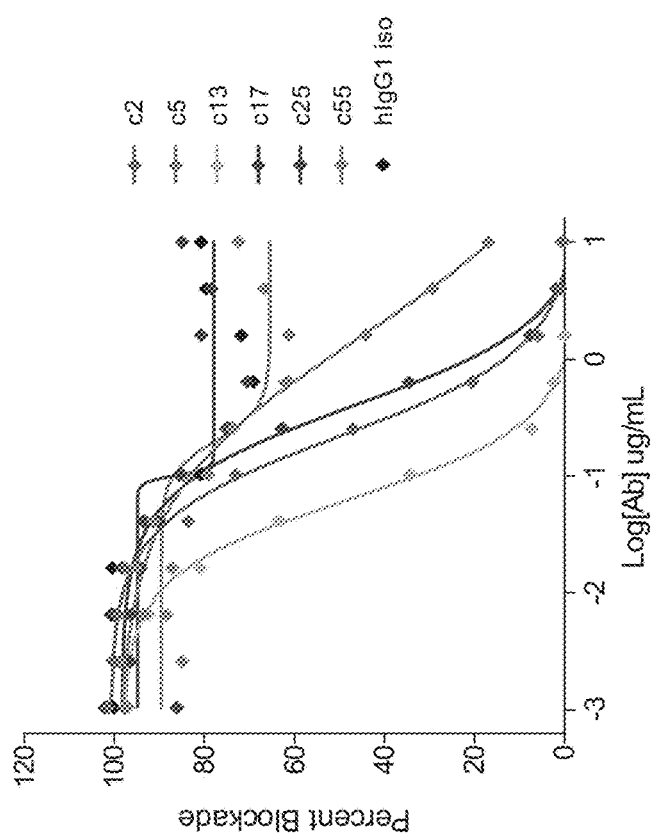
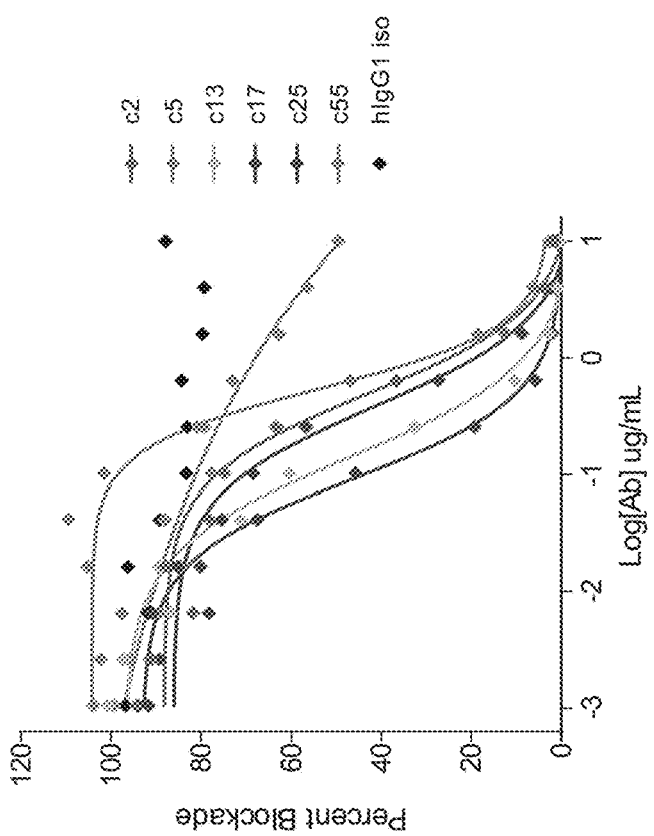
FIG. 5B
FIG. 5A

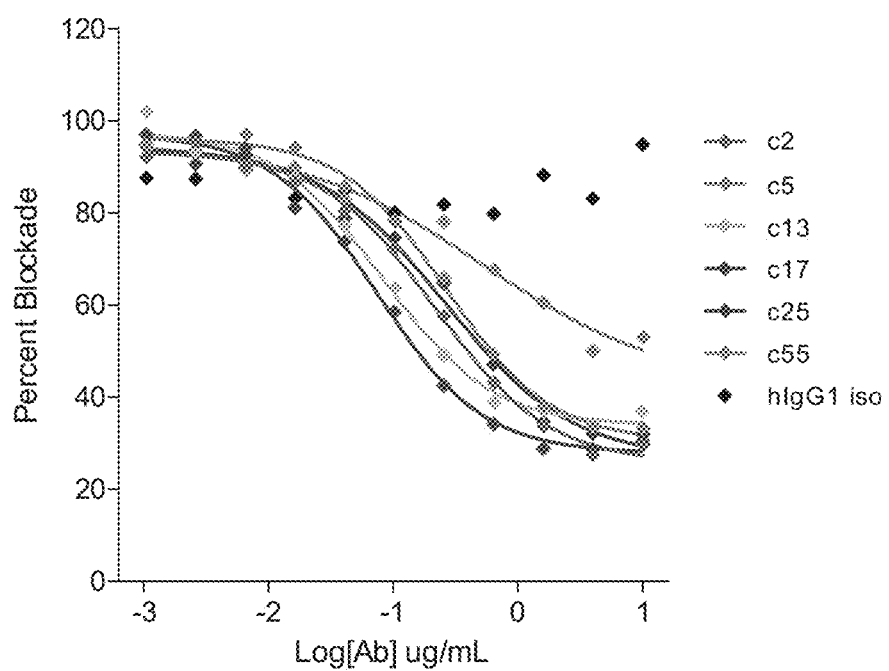

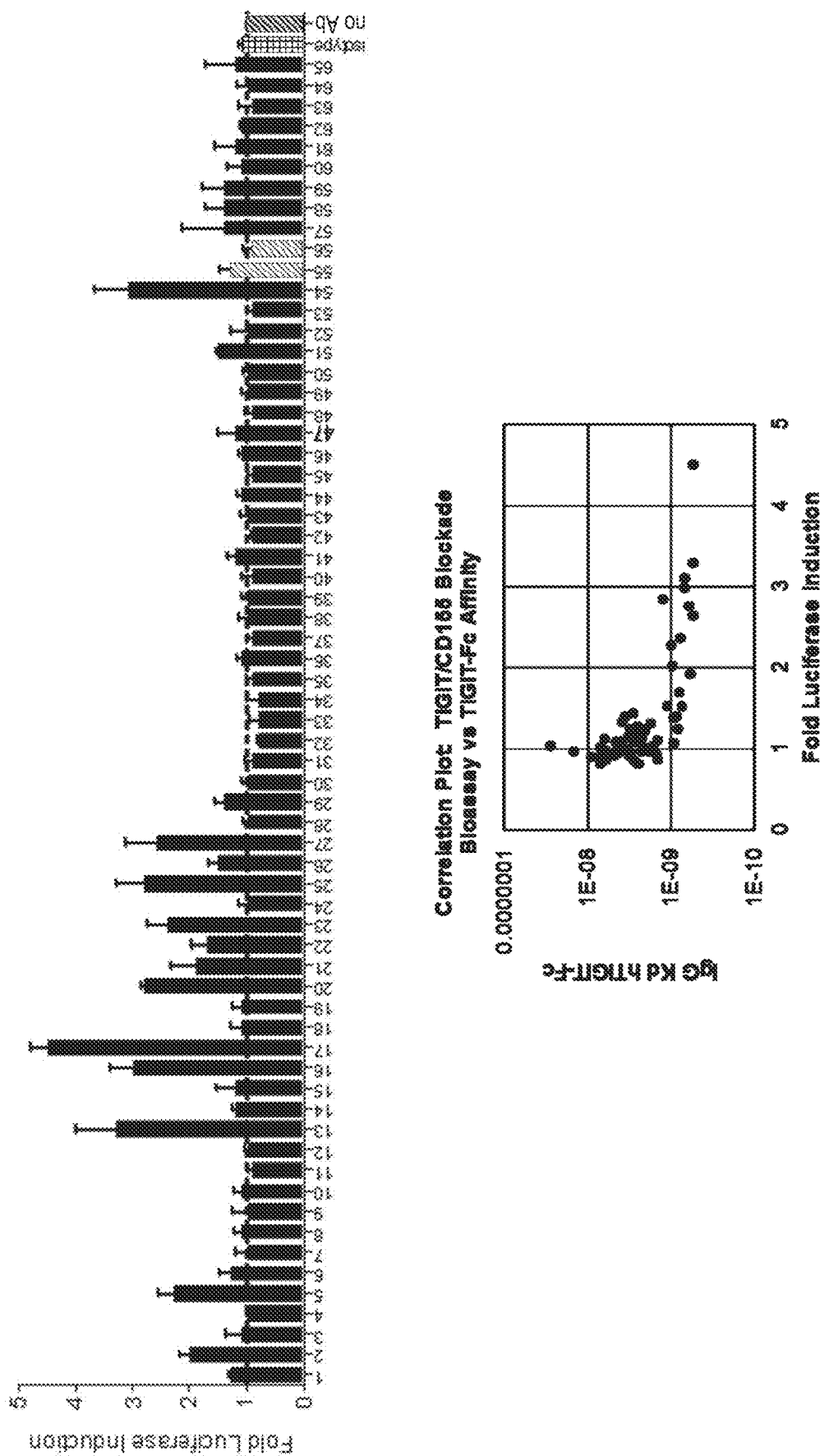

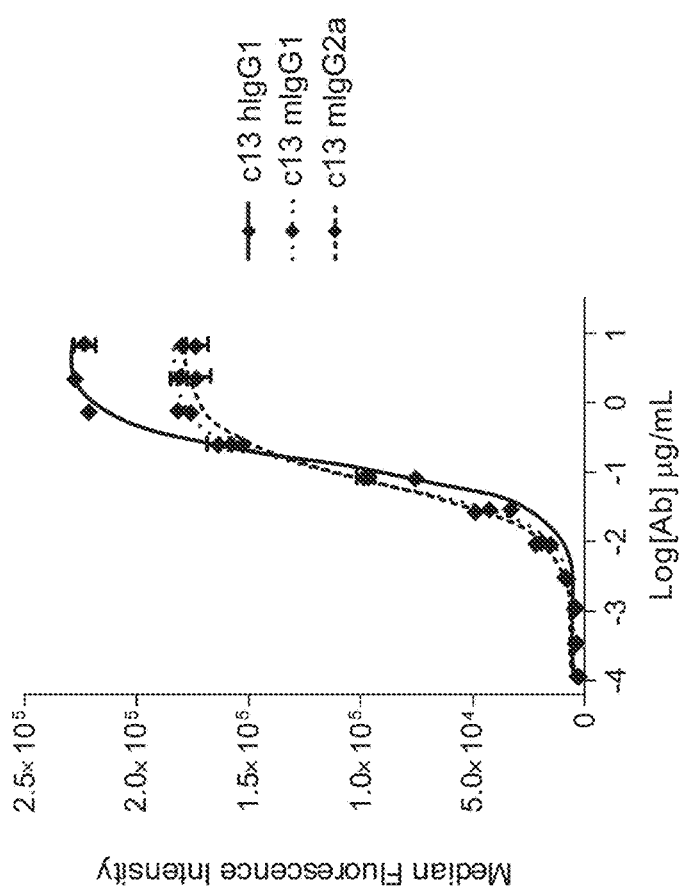

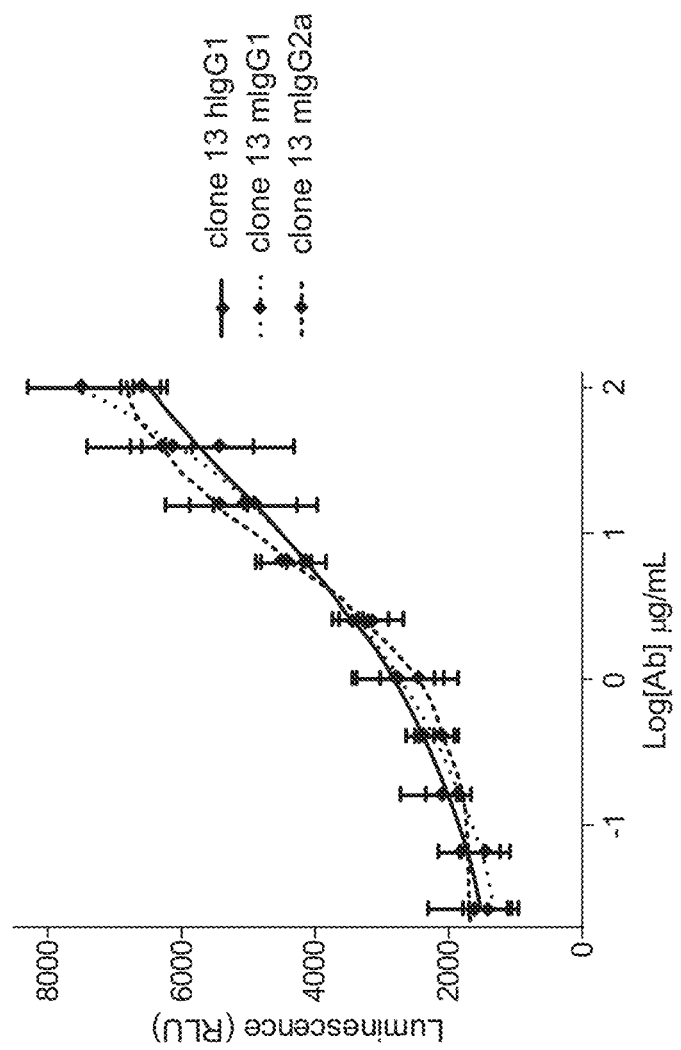

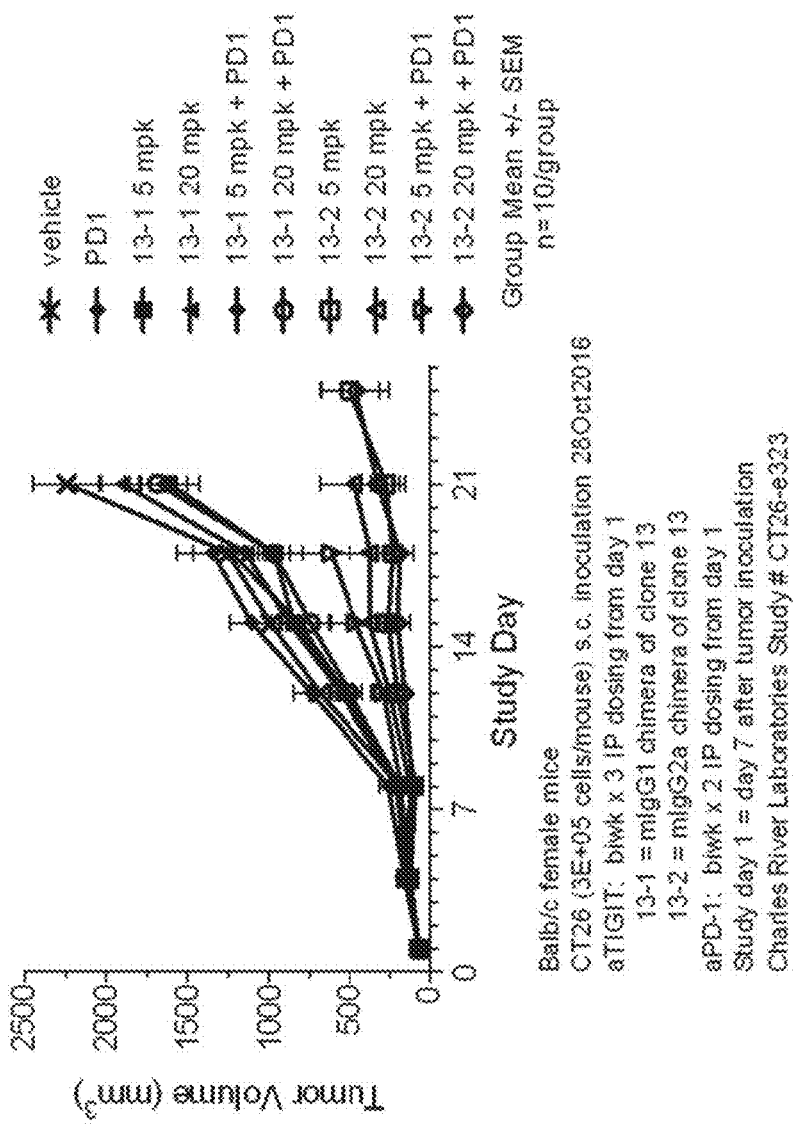

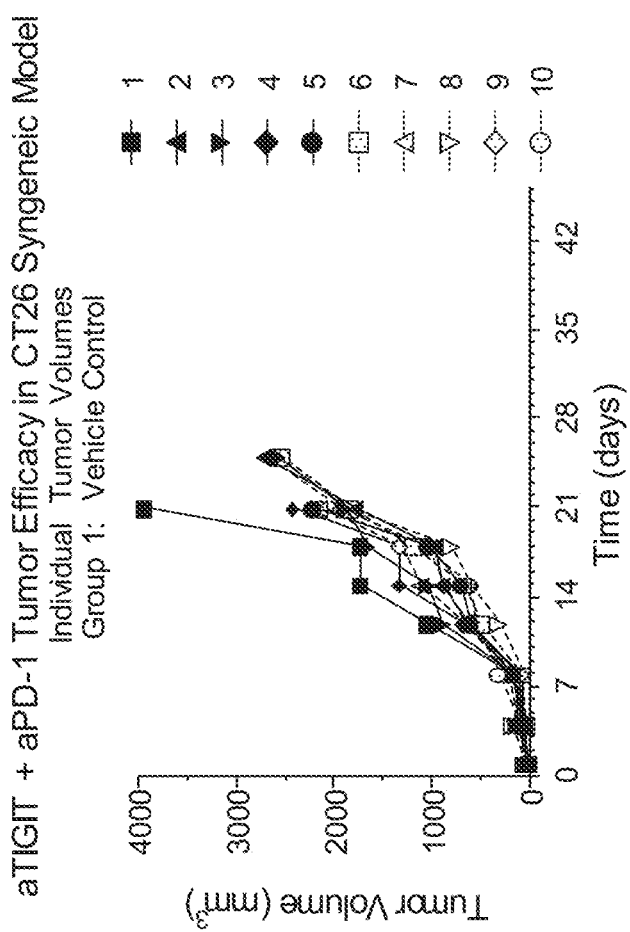

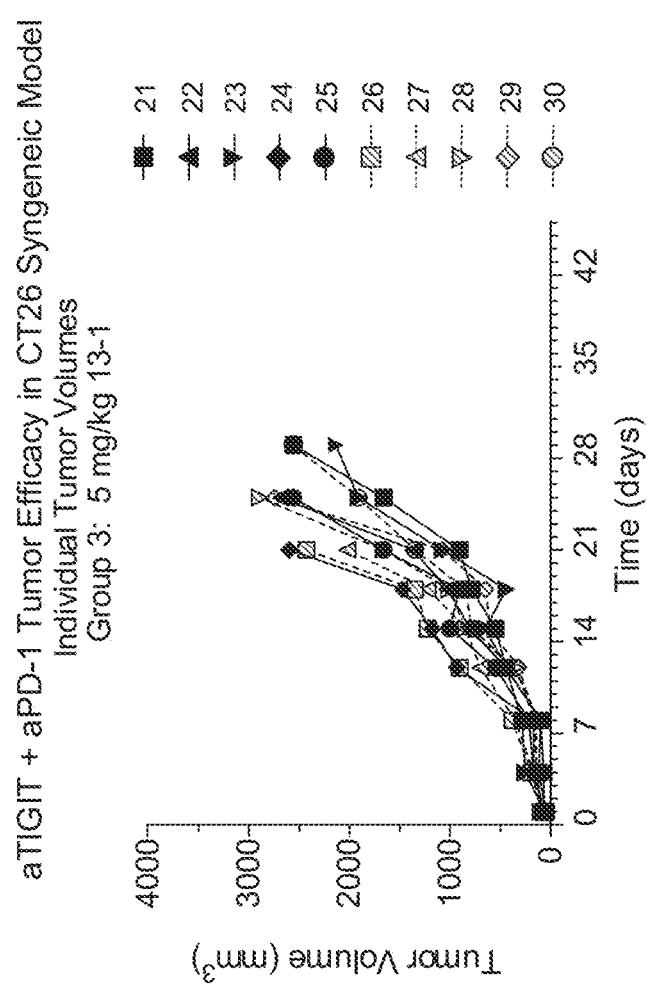

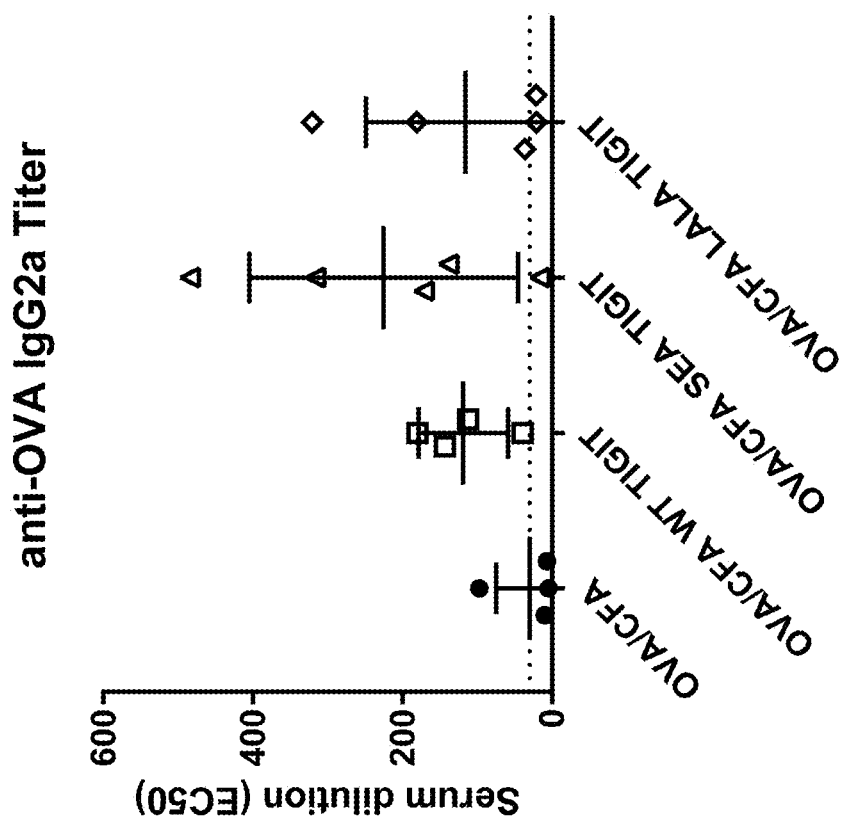
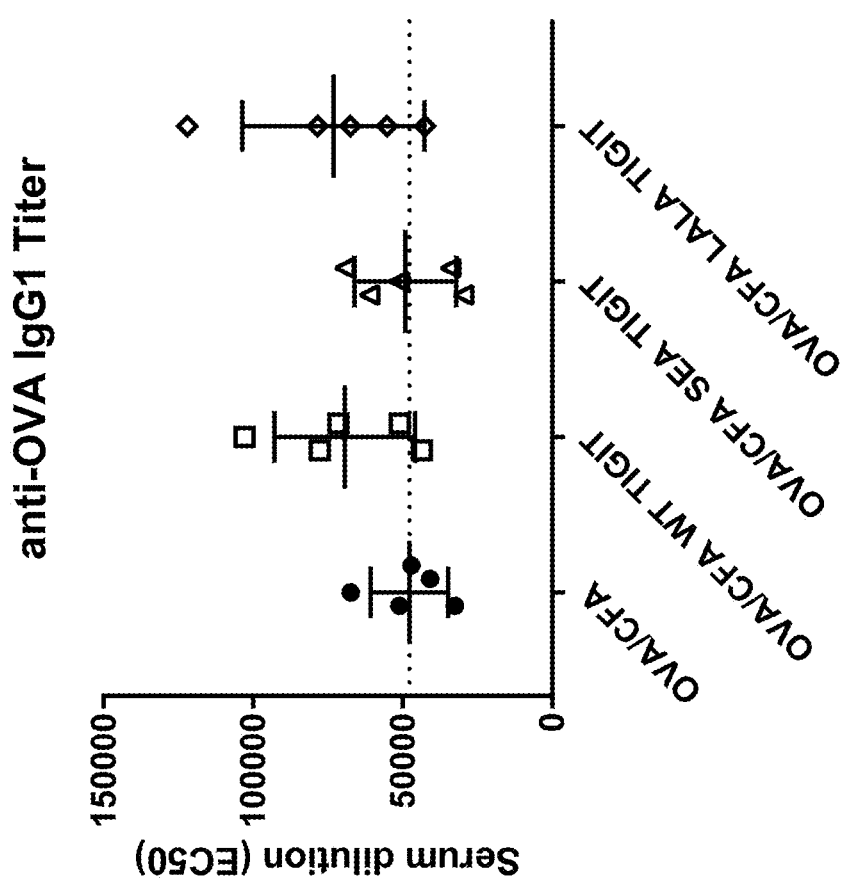
FIG. 32

SEQUENCE LISTING

<160> NUMBER OF SEQ ID NOS: 309

<210> SEQ ID NO 1
<211> LENGTH: 128
<212> TYPE: PRT
<213> ORGANISM: Artificial Sequence
<220> FEATURE:
<223> OTHER INFORMATION: Synthetic: Clone 2 VH Protein

<400> SEQUENCE: 1

Glu Val Gln Leu Val Glu Ser Gly Gly Gly Leu Val Gln Pro Gly Gly

```
                1               5                  10                 15
            Ser Leu Arg Leu Ser Cys Ala Ala Ser Gly Phe Thr Phe Ser Asp His
                        20                  25                  30

Tyr Met Asp Trp Val Arg Gln Ala Pro Gly Lys Gly Leu Glu Trp Val
                        35                  40                  45

Gly Arg Thr Arg Asn Lys Ala Asn Ser Tyr Thr Thr Glu Tyr Ala Ala
                        50                  55                  60

Ser Val Lys Gly Arg Phe Thr Ile Ser Arg Asp Asp Ser Lys Asn Ser
             65                  70                  75                  80

Leu Tyr Leu Gln Met Asn Ser Leu Lys Thr Glu Asp Thr Ala Val Tyr
                            85                  90                  95

Tyr Cys Ala Arg Gly Gln Tyr Tyr Tyr Gly Ser Ser Arg Gly Tyr
                        100                 105                 110

Tyr Tyr Met Asp Val Trp Gly Gln Gly Thr Thr Val Thr Val Ser Ser
                        115                 120                 125
```

<210> SEQ ID NO 2
<211> LENGTH: 384
<212> TYPE: DNA
<213> ORGANISM: Artificial Sequence
<220> FEATURE:
<223> OTHER INFORMATION: Synthetic: Clone 2 VH DNA

<400> SEQUENCE: 2

```
gaggtgcagc tggtggagtc tgggggaggc ttggtccagc ctggagggtc cctgagactc    60
tcctgtgcag cctctggatt caccttcagt gaccactaca tggactgggt ccgccaggct   120
ccagggaagg ggctggagtg ggttggccgt actagaaaca agctaacag ttacaccaca    180
gaatacgccg cgtctgtgaa aggcagattc accatctcaa gagatgattc aaagaactca   240
ctgtatctgc aaatgaacag cctgaaaacc gaggacacgg cggtgtacta ctgcgccaga   300
ggccagtact actacggcag cagcagcaga ggttactact acatggacgt atggggccag   360
ggaacaaccg tcaccgtctc ctca                                          384
```

<210> SEQ ID NO 3
<211> LENGTH: 26
<212> TYPE: PRT
<213> ORGANISM: Artificial Sequence
<220> FEATURE:
<223> OTHER INFORMATION: Synthetic: Clone 2 VH FR1

<400> SEQUENCE: 3

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly
            20                  25
```

<210> SEQ ID NO 4
<211> LENGTH: 9
<212> TYPE: PRT
<213> ORGANISM: Artificial Sequence
<220> FEATURE:
<223> OTHER INFORMATION: Synthetic: Clone 2 VH CDR1

<400> SEQUENCE: 4

```
Phe Thr Phe Ser Asp His Tyr Met Asp
 1               5
```

<210> SEQ ID NO 5
<211> LENGTH: 14

```
<212> TYPE: PRT
<213> ORGANISM: Artificial Sequence
<220> FEATURE:
<223> OTHER INFORMATION: Synthetic: Clone 2 VH FR2

<400> SEQUENCE: 5

Trp Val Arg Gln Ala Pro Gly Lys Gly Leu Glu Trp Val Gly
1               5                   10

<210> SEQ ID NO 6
<211> LENGTH: 19
<212> TYPE: PRT
<213> ORGANISM: Artificial Sequence
<220> FEATURE:
<223> OTHER INFORMATION: Synthetic: Clone 2 VH CDR2

<400> SEQUENCE: 6

Arg Thr Arg Asn Lys Ala Asn Ser Tyr Thr Thr Glu Tyr Ala Ala Ser
1               5                   10                  15

Val Lys Gly

<210> SEQ ID NO 7
<211> LENGTH: 30
<212> TYPE: PRT
<213> ORGANISM: Artificial Sequence
<220> FEATURE:
<223> OTHER INFORMATION: Synthetic: Clone 2 VH FR3

<400> SEQUENCE: 7

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys
            20                  25                  30

<210> SEQ ID NO 8
<211> LENGTH: 19
<212> TYPE: PRT
<213> ORGANISM: Artificial Sequence
<220> FEATURE:
<223> OTHER INFORMATION: Synthetic: Clone 2 VH CDR3

<400> SEQUENCE: 8

Ala Arg Gly Gln Tyr Tyr Tyr Gly Ser Ser Arg Gly Tyr Tyr Tyr
1               5                   10                  15

Met Asp Val

<210> SEQ ID NO 9
<211> LENGTH: 11
<212> TYPE: PRT
<213> ORGANISM: Artificial Sequence
<220> FEATURE:
<223> OTHER INFORMATION: Synthetic: Clone 2 VH FR4

<400> SEQUENCE: 9

Trp Gly Gln Gly Thr Thr Val Thr Val Ser Ser
1               5                   10

<210> SEQ ID NO 10
<211> LENGTH: 108
<212> TYPE: PRT
<213> ORGANISM: Artificial Sequence
<220> FEATURE:
<223> OTHER INFORMATION: Synthetic: Clones 2 and 2C VL Protein

<400> SEQUENCE: 10
```

-continued

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Val Pro Ser Pro
                85                  90                  95

Leu Thr Phe Gly Gly Gly Thr Lys Val Glu Ile Lys
            100                 105
```

<210> SEQ ID NO 11
<211> LENGTH: 324
<212> TYPE: DNA
<213> ORGANISM: Artificial Sequence
<220> FEATURE:
<223> OTHER INFORMATION: Synthetic: Clone 2 VL DNA

<400> SEQUENCE: 11

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag caggccgtcc ccagtcctct cacttttggc   300
ggagggacca aggttgagat caaa                                          324
```

<210> SEQ ID NO 12
<211> LENGTH: 23
<212> TYPE: PRT
<213> ORGANISM: Artificial Sequence
<220> FEATURE:
<223> OTHER INFORMATION: Synthetic: Clone 2 VL FR1

<400> SEQUENCE: 12

```
Glu Ile Val Leu Thr Gln Ser Pro Gly Thr Leu Ser Leu Ser Pro Gly
1               5                   10                  15

Glu Arg Ala Thr Leu Ser Cys
            20
```

<210> SEQ ID NO 13
<211> LENGTH: 12
<212> TYPE: PRT
<213> ORGANISM: Artificial Sequence
<220> FEATURE:
<223> OTHER INFORMATION: Synthetic: Clones 2 and 2C VL CDR1

<400> SEQUENCE: 13

```
Arg Ala Ser Gln Ser Val Ser Ser Ser Tyr Leu Ala
1               5                   10
```

<210> SEQ ID NO 14
<211> LENGTH: 15
<212> TYPE: PRT
<213> ORGANISM: Artificial Sequence
<220> FEATURE:
<223> OTHER INFORMATION: Synthetic: Clone 2 VL FR2

```
<400> SEQUENCE: 14

Trp Tyr Gln Gln Lys Pro Gly Gln Ala Pro Arg Leu Leu Ile Tyr
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Synthetic: Clones 2 and 2C VL CDR2

<400> SEQUENCE: 15

Gly Ala Ser Ser Arg Ala Thr
1               5

<210> SEQ ID NO 16
<211> LENGTH: 32
<212> TYPE: PRT
<213> ORGANISM: Artificial Sequence
<220> FEATURE:
<223> OTHER INFORMATION: Synthetic: Clone 2 VL FR3

<400> SEQUENCE: 16

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 17
<211> LENGTH: 9
<212> TYPE: PRT
<213> ORGANISM: Artificial Sequence
<220> FEATURE:
<223> OTHER INFORMATION: Synthetic: Clones 2 and 2CVL CDR3

<400> SEQUENCE: 17

Gln Gln Ala Val Pro Ser Pro Leu Thr
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic: Clone 2 VL FR4

<400> SEQUENCE: 18

Phe Gly Gly Gly Thr Lys Val Glu Ile Lys
1               5                   10

<210> SEQ ID NO 19
<211> LENGTH: 128
<212> TYPE: PRT
<213> ORGANISM: Artificial Sequence
<220> FEATURE:
<223> OTHER INFORMATION: Synthetic: Clone 3 VH Protein

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45
```

```
Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Gly Gln Tyr Tyr Gly Ser Ser Arg Gly Tyr
            100                 105                 110

Tyr Tyr Met Asp Val Trp Gly Gln Gly Thr Thr Val Thr Val Ser Ser
        115                 120                 125
```

<210> SEQ ID NO 20
<211> LENGTH: 384
<212> TYPE: DNA
<213> ORGANISM: Artificial Sequence
<220> FEATURE:
<223> OTHER INFORMATION: Synthetic: Clone 3 VH DNA

<400> SEQUENCE: 20

```
gaggtgcagc tggtggagtc tgggggaggc ttggtccagc ctggagggtc cctgagactc      60
tcctgtgcag cctctggatt caccttcagt gaccactaca tggactgggt ccgccaggct     120
ccagggaagg gctggagtg gttggccgt actagaaaca agctaacag ttacaccaca        180 gaatacgccg cgtctgtgaa aggcagattc accatctcaa gagatgattc aaagaactca     240
ctgtatctgc aaatgaacag cctgaaaacc gaggacacgg cggtgtacta ctgcgccaga     300
ggccagtact actacggcag cagcagcaga ggttactact acatggacgt atggggccag     360
ggaacaaccg tcaccgtctc ctca                                            384
```

<210> SEQ ID NO 21
<211> LENGTH: 26
<212> TYPE: PRT
<213> ORGANISM: Artificial Sequence
<220> FEATURE:
<223> OTHER INFORMATION: Synthetic: Clone 3 VH FR1

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25
```

<210> SEQ ID NO 22
<211> LENGTH: 9
<212> TYPE: PRT
<213> ORGANISM: Artificial Sequence
<220> FEATURE:
<223> OTHER INFORMATION: Synthetic: Clone 3 VH CDR1

<400> SEQUENCE: 22

```
Phe Thr Phe Ser Asp His Tyr Met Asp
1               5
```

<210> SEQ ID NO 23
<211> LENGTH: 14
<212> TYPE: PRT
<213> ORGANISM: Artificial Sequence
<220> FEATURE:
<223> OTHER INFORMATION: Synthetic: Clone 3 VH FR2

<400> SEQUENCE: 23

```
Trp Val Arg Gln Ala Pro Gly Lys Gly Leu Glu Trp Val Gly
1               5                   10
```

<210> SEQ ID NO 24
<211> LENGTH: 19
<212> TYPE: PRT
<213> ORGANISM: Artificial Sequence
<220> FEATURE:
<223> OTHER INFORMATION: Synthetic: Clone 3 VH CDR2

<400> SEQUENCE: 24

```
Arg Thr Arg Asn Lys Ala Asn Ser Tyr Thr Thr Glu Tyr Ala Ala Ser
1               5                   10                  15

Val Lys Gly
```

<210> SEQ ID NO 25
<211> LENGTH: 30
<212> TYPE: PRT
<213> ORGANISM: Artificial Sequence
<220> FEATURE:
<223> OTHER INFORMATION: Synthetic: Clone 3 VH FR3

<400> SEQUENCE: 25

```
Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys
            20                  25                  30
```

<210> SEQ ID NO 26
<211> LENGTH: 19
<212> TYPE: PRT
<213> ORGANISM: Artificial Sequence
<220> FEATURE:
<223> OTHER INFORMATION: Synthetic: Clone 3 VH CDR3

<400> SEQUENCE: 26

```
Ala Arg Gly Gln Tyr Tyr Tyr Gly Ser Ser Arg Gly Tyr Tyr Tyr
1               5                   10                  15

Met Asp Val
```

<210> SEQ ID NO 27
<211> LENGTH: 11
<212> TYPE: PRT
<213> ORGANISM: Artificial Sequence
<220> FEATURE:
<223> OTHER INFORMATION: Synthetic: Clone 3 VH FR4

<400> SEQUENCE: 27

```
Trp Gly Gln Gly Thr Thr Val Thr Val Ser Ser
1               5                   10
```

<210> SEQ ID NO 28
<211> LENGTH: 107
<212> TYPE: PRT
<213> ORGANISM: Artificial Sequence
<220> FEATURE:
<223> OTHER INFORMATION: Synthetic: Clone 3 VL Protein

<400> SEQUENCE: 28

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
```

```
                35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Val Gly Pro Pro Leu
                85                  90                  95
Thr Phe Gly Gly Gly Thr Lys Val Glu Ile Lys
            100                 105
```

<210> SEQ ID NO 29
<211> LENGTH: 321
<212> TYPE: DNA
<213> ORGANISM: Artificial Sequence
<220> FEATURE:
<223> OTHER INFORMATION: Synthetic: Clone 3 VL DNA

<400> SEQUENCE: 29

```
gaaattgtgt tgacgcagtc tccaggcacc ctgtctttgt ctccagggga aagagccacc    60
ctctcctgca gggccagtca gagtgttagg agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag caggtcggac cccccctcac ttttggcgga   300
gggaccaagg ttgagatcaa a                                             321
```

<210> SEQ ID NO 30
<211> LENGTH: 23
<212> TYPE: PRT
<213> ORGANISM: Artificial Sequence
<220> FEATURE:
<223> OTHER INFORMATION: Synthetic: Clone 3 VL FR1

<400> SEQUENCE: 30

```
Glu Ile Val Leu Thr Gln Ser Pro Gly Thr Leu Ser Leu Ser Pro Gly
 1               5                  10                  15
Glu Arg Ala Thr Leu Ser Cys
            20
```

<210> SEQ ID NO 31
<211> LENGTH: 12
<212> TYPE: PRT
<213> ORGANISM: Artificial Sequence
<220> FEATURE:
<223> OTHER INFORMATION: Synthetic: Clone 3 VL CDR1

<400> SEQUENCE: 31

```
Arg Ala Ser Gln Ser Val Arg Ser Ser Tyr Leu Ala
 1               5                  10
```

<210> SEQ ID NO 32
<211> LENGTH: 15
<212> TYPE: PRT
<213> ORGANISM: Artificial Sequence
<220> FEATURE:
<223> OTHER INFORMATION: Synthetic: Clone 3 VL FR2

<400> SEQUENCE: 32

```
Trp Tyr Gln Gln Lys Pro Gly Gln Ala Pro Arg Leu Leu Ile Tyr
 1               5                  10                  15
```

```
<210> SEQ ID NO 33
<211> LENGTH: 7
<212> TYPE: PRT
<213> ORGANISM: Artificial Sequence
<220> FEATURE:
<223> OTHER INFORMATION: Synthetic: Clone 3VL CDR2

<400> SEQUENCE: 33

Gly Ala Ser Ser Arg Ala Thr
1               5

<210> SEQ ID NO 34
<211> LENGTH: 32
<212> TYPE: PRT
<213> ORGANISM: Artificial Sequence
<220> FEATURE:
<223> OTHER INFORMATION: Synthetic: Clone 3 VL FR3

<400> SEQUENCE: 34

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 35
<211> LENGTH: 8
<212> TYPE: PRT
<213> ORGANISM: Artificial Sequence
<220> FEATURE:
<223> OTHER INFORMATION: Synthetic: Clone 3 VL CDR3

<400> SEQUENCE: 35

Gln Gln Val Gly Pro Pro Leu Thr
1               5

<210> SEQ ID NO 36
<211> LENGTH: 10
<212> TYPE: PRT
<213> ORGANISM: Artificial Sequence
<220> FEATURE:
<223> OTHER INFORMATION: Synthetic: Clone 3 VL FR4

<400> SEQUENCE: 36

Phe Gly Gly Gly Thr Lys Val Glu Ile Lys
1               5                   10

<210> SEQ ID NO 37
<211> LENGTH: 121
<212> TYPE: PRT
<213> ORGANISM: Artificial Sequence
<220> FEATURE:
<223> OTHER INFORMATION: Synthetic: Clone 5 VH Protein

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Gly Pro Arg Tyr Gln Asp Arg Ala Gly Met Asp Val Trp Gly
            100                 105                 110

Gln Gly Thr Thr Val Thr Val Ser Ser
        115                 120

<210> SEQ ID NO 38
<211> LENGTH: 363
<212> TYPE: DNA
<213> ORGANISM: Artificial Sequence
<220> FEATURE:
<223> OTHER INFORMATION: Synthetic: Clone 5 VH DNA

<400> SEQUENCE: 38
gaggtgcagc tgttggagtc tgggggaggc ttggtacagc ctgggggtc cctgagactc      60 tcctgtgcag cctctggatt cacctttagc acctatgcca tgagctgggt ccgccaggct    120
ccagggaagg ggctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac acggcggtgt actactgcgc caagggcccc    300
agataccaag acagggcagg aatggacgta tggggccagg gaacaactgt caccgtctcc    360
tca                                                                  363

<210> SEQ ID NO 39
<211> LENGTH: 26
<212> TYPE: PRT
<213> ORGANISM: Artificial Sequence
<220> FEATURE:
<223> OTHER INFORMATION: Synthetic: Clone 5 VH FR1

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 40
<211> LENGTH: 9
<212> TYPE: PRT
<213> ORGANISM: Artificial Sequence
<220> FEATURE:
<223> OTHER INFORMATION: Synthetic: Clone 5 VH CDR1

<400> SEQUENCE: 40

Phe Thr Phe Ser Thr Tyr Ala Met Ser
1               5

<210> SEQ ID NO 41
<211> LENGTH: 14
<212> TYPE: PRT
<213> ORGANISM: Artificial Sequence
<220> FEATURE:
<223> OTHER INFORMATION: Synthetic: Clone 5 VH FR2

<400> SEQUENCE: 41

Trp Val Arg Gln Ala Pro Gly Lys Gly Leu Glu Trp Val Ser
1               5                   10

<210> SEQ ID NO 42
<211> LENGTH: 17
<212> TYPE: PRT
```

```
<213> ORGANISM: Artificial Sequence
<220> FEATURE:
<223> OTHER INFORMATION: Synthetic: Clone 5 VH CDR2

<400> SEQUENCE: 42

Ala Ile Ser Gly Ser Gly Gly Ser Thr Tyr Tyr Ala Asp Ser Val Lys
1               5                   10                  15

Gly

<210> SEQ ID NO 43
<211> LENGTH: 30
<212> TYPE: PRT
<213> ORGANISM: Artificial Sequence
<220> FEATURE:
<223> OTHER INFORMATION: Synthetic: Clone 5 VH FR3

<400> SEQUENCE: 43

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 44
<211> LENGTH: 14
<212> TYPE: PRT
<213> ORGANISM: Artificial Sequence
<220> FEATURE:
<223> OTHER INFORMATION: Synthetic: Clone 5 VH CDR3

<400> SEQUENCE: 44

Ala Lys Gly Pro Arg Tyr Gln Asp Arg Ala Gly Met Asp Val
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic: Clone 5 VH FR4

<400> SEQUENCE: 45

Trp Gly Gln Gly Thr Thr Val Thr Val Ser Ser
1               5                   10

<210> SEQ ID NO 46
<211> LENGTH: 107
<212> TYPE: PRT
<213> ORGANISM: Artificial Sequence
<220> FEATURE:
<223> OTHER INFORMATION: Synthetic: Clone 5 VL Protein

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Ala Thr Pro Tyr
```

<210> SEQ ID NO 47
<211> LENGTH: 321
<212> TYPE: DNA
<213> ORGANISM: Artificial Sequence
<220> FEATURE:
<223> OTHER INFORMATION: Synthetic: Clone 5 VL DNA

<400> SEQUENCE: 47

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcaa agcctcgcca ctccttacac ttttggcgga   300
gggaccaagg ttgagatcaa a                                             321
```

<210> SEQ ID NO 48
<211> LENGTH: 23
<212> TYPE: PRT
<213> ORGANISM: Artificial Sequence
<220> FEATURE:
<223> OTHER INFORMATION: Synthetic: Clone 5 VL FR1

<400> SEQUENCE: 48

Asp Ile Gln Met Thr Gln Ser Pro Ser Ser Leu Ser Ala Ser Val Gly
1               5                   10                  15
Asp Arg Val Thr Ile Thr Cys
        20

<210> SEQ ID NO 49
<211> LENGTH: 11
<212> TYPE: PRT
<213> ORGANISM: Artificial Sequence
<220> FEATURE:
<223> OTHER INFORMATION: Synthetic: Clone 5 VL CDR1

<400> SEQUENCE: 49

Arg Ala Ser Gln Ser Ile Ser Ser Tyr Leu Asn
1               5                   10

<210> SEQ ID NO 50
<211> LENGTH: 15
<212> TYPE: PRT
<213> ORGANISM: Artificial Sequence
<220> FEATURE:
<223> OTHER INFORMATION: Synthetic: Clone 5 VL FR2

<400> SEQUENCE: 50

Trp Tyr Gln Gln Lys Pro Gly Lys Ala Pro Lys Leu Leu Ile Tyr
1               5                   10                  15

<210> SEQ ID NO 51
<211> LENGTH: 7
<212> TYPE: PRT
<213> ORGANISM: Artificial Sequence
<220> FEATURE:
<223> OTHER INFORMATION: Synthetic: Clone 5 VL CDR2

<400> SEQUENCE: 51

Ala Ala Ser Ser Leu Gln Ser
1               5

<210> SEQ ID NO 52
<211> LENGTH: 32
<212> TYPE: PRT
<213> ORGANISM: Artificial Sequence
<220> FEATURE:
<223> OTHER INFORMATION: Synthetic: Clone 5 VL FR3

<400> SEQUENCE: 52

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 53
<211> LENGTH: 9
<212> TYPE: PRT
<213> ORGANISM: Artificial Sequence
<220> FEATURE:
<223> OTHER INFORMATION: Synthetic: Clone 5 VL CDR3

<400> SEQUENCE: 53

Gln Gln Ser Leu Ala Thr Pro Tyr Thr
1               5

<210> SEQ ID NO 54
<211> LENGTH: 10
<212> TYPE: PRT
<213> ORGANISM: Artificial Sequence
<220> FEATURE:
<223> OTHER INFORMATION: Synthetic: Clone 5 VL FR4

<400> SEQUENCE: 54

Phe Gly Gly Gly Thr Lys Val Glu Ile Lys
1               5                   10

<210> SEQ ID NO 55
<211> LENGTH: 125
<212> TYPE: PRT
<213> ORGANISM: Artificial Sequence
<220> FEATURE:
<223> OTHER INFORMATION: Synthetic: Clone 13 VH Protein

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser
        115                 120                 125

<210> SEQ ID NO 56
<211> LENGTH: 375
<212> TYPE: DNA
<213> ORGANISM: Artificial Sequence
<220> FEATURE:
<223> OTHER INFORMATION: Synthetic: Clone 13 VH DNA

<400> SEQUENCE: 56

```
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagc atcatccca tctttggtac agcaaactac    180
gcacagaagt tccagggcag agtcacgatt accgcggacg aatccacgag cacagcctac   240
atggagctga gcagcctgag atctgaggac acggcggtgt actactgcgc cagaggccct   300
tctgaagtag gagcaatact cggatatgta tggttcgacc catggggaca gggtacattg   360
gtcaccgtct cctca                                                   375
```

<210> SEQ ID NO 57
<211> LENGTH: 26
<212> TYPE: PRT
<213> ORGANISM: Artificial Sequence
<220> FEATURE:
<223> OTHER INFORMATION: Synthetic: Clone 13 VH FR1

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 58
<211> LENGTH: 9
<212> TYPE: PRT
<213> ORGANISM: Artificial Sequence
<220> FEATURE:
<223> OTHER INFORMATION: Synthetic: Clone 13 VH CDR1

<400> SEQUENCE: 58

Gly Thr Phe Ser Ser Tyr Ala Ile Ser
1               5

<210> SEQ ID NO 59
<211> LENGTH: 14
<212> TYPE: PRT
<213> ORGANISM: Artificial Sequence
<220> FEATURE:
<223> OTHER INFORMATION: Synthetic: Clone 13 VH FR2

<400> SEQUENCE: 59

Trp Val Arg Gln Ala Pro Gly Gln Gly Leu Glu Trp Met Gly
1               5                   10

<210> SEQ ID NO 60
<211> LENGTH: 17
<212> TYPE: PRT
<213> ORGANISM: Artificial Sequence
<220> FEATURE:
<223> OTHER INFORMATION: Synthetic: Clone 13 VH CDR2

<400> SEQUENCE: 60

Ser Ile Ile Pro Ile Phe Gly Thr Ala Asn Tyr Ala Gln Lys Phe Gln
1               5                   10                  15

Gly

```
<210> SEQ ID NO 61
<211> LENGTH: 30
<212> TYPE: PRT
<213> ORGANISM: Artificial Sequence
<220> FEATURE:
<223> OTHER INFORMATION: Synthetic: Clone 13 VH FR3

<400> SEQUENCE: 61
```

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

```
<210> SEQ ID NO 62
<211> LENGTH: 18
<212> TYPE: PRT
<213> ORGANISM: Artificial Sequence
<220> FEATURE:
<223> OTHER INFORMATION: Synthetic: Clones 13 and 13A VH CDR3

<400> SEQUENCE: 62
```

Ala Arg Gly Pro Ser Glu Val Gly Ala Ile Leu Gly Tyr Val Trp Phe
1               5                   10                  15

Asp Pro

```
<210> SEQ ID NO 63
<211> LENGTH: 11
<212> TYPE: PRT
<213> ORGANISM: Artificial Sequence
<220> FEATURE:
<223> OTHER INFORMATION: Synthetic: Clone 13 VH FR4

<400> SEQUENCE: 63
```

Trp Gly Gln Gly Thr Leu Val Thr Val Ser Ser
1               5                   10

```
<210> SEQ ID NO 64
<211> LENGTH: 112
<212> TYPE: PRT
<213> ORGANISM: Artificial Sequence
<220> FEATURE:
<223> OTHER INFORMATION: Synthetic: Clones 13, 13A, 13B, 13C, and 13D VL
      Protein

<400> SEQUENCE: 64
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Arg Ile Pro Ile Thr Phe Gly Gly Gly Thr Lys Val Glu Ile Lys
            100                 105                 110

-continued

```
<210> SEQ ID NO 65
<211> LENGTH: 336
<212> TYPE: DNA
<213> ORGANISM: Artificial Sequence
<220> FEATURE:
<223> OTHER INFORMATION: Synthetic: Clone 13 VL DNA

<400> SEQUENCE: 65
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaggcaag acgaatccct    300
atcacttttg gcggagggac caaggttgag atcaaa                              336

<210> SEQ ID NO 66
<211> LENGTH: 23
<212> TYPE: PRT
<213> ORGANISM: Artificial Sequence
<220> FEATURE:
<223> OTHER INFORMATION: Synthetic: Clone 13 VL FR1

<400> SEQUENCE: 66

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 67
<211> LENGTH: 16
<212> TYPE: PRT
<213> ORGANISM: Artificial Sequence
<220> FEATURE:
<223> OTHER INFORMATION: Synthetic: Clones 13, 13A, 13B, 13C, and 13D VL
      CDR1

<400> SEQUENCE: 67

Arg Ser Ser Gln Ser Leu Leu His Ser Asn Gly Tyr Asn Tyr Leu Asp
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic: Clone 13 VL FR2

<400> SEQUENCE: 68

Trp Tyr Leu Gln Lys Pro Gly Gln Ser Pro Gln Leu Leu Ile Tyr
1               5                   10                  15

<210> SEQ ID NO 69
<211> LENGTH: 7
<212> TYPE: PRT
<213> ORGANISM: Artificial Sequence
<220> FEATURE:
<223> OTHER INFORMATION: Synthetic: Clones 13, 13A, 13B, 13C, and 13D VL
      CDR2

<400> SEQUENCE: 69

Leu Gly Ser Asn Arg Ala Ser
1               5
```

-continued

```
<210> SEQ ID NO 70
<211> LENGTH: 32
<212> TYPE: PRT
<213> ORGANISM: Artificial Sequence
<220> FEATURE:
<223> OTHER INFORMATION: Synthetic: Clone 13 VL FR3

<400> SEQUENCE: 70

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 71
<211> LENGTH: 9
<212> TYPE: PRT
<213> ORGANISM: Artificial Sequence
<220> FEATURE:
<223> OTHER INFORMATION: Synthetic: Clones 13, 13A, 13B, 13C, and 13D VL
      CDR3

<400> SEQUENCE: 71

Met Gln Ala Arg Arg Ile Pro Ile Thr
1               5

<210> SEQ ID NO 72
<211> LENGTH: 10
<212> TYPE: PRT
<213> ORGANISM: Artificial Sequence
<220> FEATURE:
<223> OTHER INFORMATION: Synthetic: Clone 13 VL FR4

<400> SEQUENCE: 72

Phe Gly Gly Gly Thr Lys Val Glu Ile Lys
1               5                   10

<210> SEQ ID NO 73
<211> LENGTH: 125
<212> TYPE: PRT
<213> ORGANISM: Artificial Sequence
<220> FEATURE:
<223> OTHER INFORMATION: Synthetic: Clone 14 VH Protein

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser
        115                 120                 125

<210> SEQ ID NO 74
<211> LENGTH: 375
```

<212> TYPE: DNA
<213> ORGANISM: Artificial Sequence
<220> FEATURE:
<223> OTHER INFORMATION: Synthetic: Clone 14 VH DNA

<400> SEQUENCE: 74

```
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagc atcatcccta tctttggtac agcaaactac    180
gcacagaagt tccagggcag agtcacgatt accgcggacg aatccacgag cacagcctac   240
atggagctga gcagcctgag atctgaggac acggcggtgt actactgcgc cagaggccct   300
tctgaagtag gagcaatact cggatatgta tggttcgacc catggggaca gggtacattg   360
gtcaccgtct cctca                                                    375
```

<210> SEQ ID NO 75
<211> LENGTH: 26
<212> TYPE: PRT
<213> ORGANISM: Artificial Sequence
<220> FEATURE:
<223> OTHER INFORMATION: Synthetic: Clone 14 VH FR1

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 76
<211> LENGTH: 9
<212> TYPE: PRT
<213> ORGANISM: Artificial Sequence
<220> FEATURE:
<223> OTHER INFORMATION: Synthetic: Clone 14 VH CDR1

<400> SEQUENCE: 76

Gly Thr Phe Ser Ser Tyr Ala Ile Ser
1               5

<210> SEQ ID NO 77
<211> LENGTH: 14
<212> TYPE: PRT
<213> ORGANISM: Artificial Sequence
<220> FEATURE:
<223> OTHER INFORMATION: Synthetic: Clone 14 VH FR2

<400> SEQUENCE: 77

Trp Val Arg Gln Ala Pro Gly Gln Gly Leu Glu Trp Met Gly
1               5                   10

<210> SEQ ID NO 78
<211> LENGTH: 17
<212> TYPE: PRT
<213> ORGANISM: Artificial Sequence
<220> FEATURE:
<223> OTHER INFORMATION: Synthetic: Clone 14 VH CDR2

<400> SEQUENCE: 78

Ser Ile Ile Pro Ile Phe Gly Thr Ala Asn Tyr Ala Gln Lys Phe Gln
1               5                   10                  15

Gly

<210> SEQ ID NO 79
<211> LENGTH: 30
<212> TYPE: PRT
<213> ORGANISM: Artificial Sequence
<220> FEATURE:
<223> OTHER INFORMATION: Synthetic: Clone 14 VH FR3

<400> SEQUENCE: 79

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 80
<211> LENGTH: 18
<212> TYPE: PRT
<213> ORGANISM: Artificial Sequence
<220> FEATURE:
<223> OTHER INFORMATION: Synthetic: Clone 14 VH CDR3

<400> SEQUENCE: 80

Ala Arg Gly Pro Ser Glu Val Gly Ala Ile Leu Gly Tyr Val Trp Phe
1               5                   10                  15

Asp Pro

<210> SEQ ID NO 81
<211> LENGTH: 11
<212> TYPE: PRT
<213> ORGANISM: Artificial Sequence
<220> FEATURE:
<223> OTHER INFORMATION: Synthetic: Clone 14 VH FR4

<400> SEQUENCE: 81

Trp Gly Gln Gly Thr Leu Val Thr Val Ser Ser
1               5                   10

<210> SEQ ID NO 82
<211> LENGTH: 112
<212> TYPE: PRT
<213> ORGANISM: Artificial Sequence
<220> FEATURE:
<223> OTHER INFORMATION: Synthetic: Clone 14 VL Protein

<400> SEQUENCE: 82

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Lys Arg Leu Pro Leu Thr Phe Gly Gly Gly Thr Lys Val Glu Ile Lys
            100                 105                 110

<210> SEQ ID NO 83
<211> LENGTH: 336
<212> TYPE: DNA
<213> ORGANISM: Artificial Sequence
<220> FEATURE:
<223> OTHER INFORMATION: Synthetic: Clone 14 VL DNA

<400> SEQUENCE: 83

```
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaggcaaa acgactccct    300
ctcactttg gcggagggac caaggttgag atcaaa                               336
```

<210> SEQ ID NO 84
<211> LENGTH: 23
<212> TYPE: PRT
<213> ORGANISM: Artificial Sequence
<220> FEATURE:
<223> OTHER INFORMATION: Synthetic: Clone 14 VL FR1

<400> SEQUENCE: 84

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 85
<211> LENGTH: 16
<212> TYPE: PRT
<213> ORGANISM: Artificial Sequence
<220> FEATURE:
<223> OTHER INFORMATION: Synthetic: Clone 14 VL CDR1

<400> SEQUENCE: 85

Arg Ser Ser Gln Ser Leu Leu His Ser Asn Gly Tyr Asn Tyr Leu Asp
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic: Clone 14 VL FR2

<400> SEQUENCE: 86

Trp Tyr Leu Gln Lys Pro Gly Gln Ser Pro Gln Leu Leu Ile Tyr
1               5                   10                  15

<210> SEQ ID NO 87
<211> LENGTH: 7
<212> TYPE: PRT
<213> ORGANISM: Artificial Sequence
<220> FEATURE:
<223> OTHER INFORMATION: Synthetic: Clone 14 VL CDR2

<400> SEQUENCE: 87

Leu Gly Ser Asn Arg Ala Ser
1               5

<210> SEQ ID NO 88
<211> LENGTH: 32
<212> TYPE: PRT
<213> ORGANISM: Artificial Sequence
<220> FEATURE:
<223> OTHER INFORMATION: Synthetic: Clone 14 VL FR3

-continued

<400> SEQUENCE: 88

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 89
<211> LENGTH: 9
<212> TYPE: PRT
<213> ORGANISM: Artificial Sequence
<220> FEATURE:
<223> OTHER INFORMATION: Synthetic: Clone 14 VL CDR3

<400> SEQUENCE: 89

Met Gln Ala Lys Arg Leu Pro Leu Thr
1               5

<210> SEQ ID NO 90
<211> LENGTH: 10
<212> TYPE: PRT
<213> ORGANISM: Artificial Sequence
<220> FEATURE:
<223> OTHER INFORMATION: Synthetic: Clone 14 VL FR4

<400> SEQUENCE: 90

Phe Gly Gly Gly Thr Lys Val Glu Ile Lys
1               5                   10

<210> SEQ ID NO 91
<211> LENGTH: 121
<212> TYPE: PRT
<213> ORGANISM: Artificial Sequence
<220> FEATURE:
<223> OTHER INFORMATION: Synthetic: Clone 16 VH Protein

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ser Thr Trp His Lys Leu Tyr Gly Thr Asp Val Trp Gly
            100                 105                 110

Gln Gly Thr Thr Val Thr Val Ser Ser
        115                 120

<210> SEQ ID NO 92
<211> LENGTH: 363
<212> TYPE: DNA
<213> ORGANISM: Artificial Sequence
<220> FEATURE:
<223> OTHER INFORMATION: Synthetic: Clone 16 VH DNA

<400> SEQUENCE: 92

```
caggtgcagc tggtgcagtc tggggctgag gtgaagaagc tgggtcctc ggtgaaggtc      60 tcctgcaagg cttctggagg caccttcagc agctatgcta tcagctgggt gcgacaggcc    120
cctggacaag ggcttgagtg gatgggaggg atcatcccta tctttggtac agcaagctac    180
gcacagaagt tccagggcag agtcacgatt accgcggacg aatccacgag cacagcctac    240
atggagctga gcagcctgag atctgaggac acggcggtgt actactgcgc aagacagagc    300
acctggcaca aattgtacgg aacggacgta tggggccagg gaacaactgt caccgtctcc    360
tca                                                                  363
```

```
<210> SEQ ID NO 93
<211> LENGTH: 26
<212> TYPE: PRT
<213> ORGANISM: Artificial Sequence
<220> FEATURE:
<223> OTHER INFORMATION: Synthetic: Clone 16 VH FR1

<400> SEQUENCE: 93

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 94
<211> LENGTH: 9
<212> TYPE: PRT
<213> ORGANISM: Artificial Sequence
<220> FEATURE:
<223> OTHER INFORMATION: Synthetic: Clone 16 VH CDR1

<400> SEQUENCE: 94

Gly Thr Phe Ser Ser Tyr Ala Ile Ser
1               5

<210> SEQ ID NO 95
<211> LENGTH: 14
<212> TYPE: PRT
<213> ORGANISM: Artificial Sequence
<220> FEATURE:
<223> OTHER INFORMATION: Synthetic: Clone 16 VH FR2

<400> SEQUENCE: 95

Trp Val Arg Gln Ala Pro Gly Gln Gly Leu Glu Trp Met Gly
1               5                   10

<210> SEQ ID NO 96
<211> LENGTH: 17
<212> TYPE: PRT
<213> ORGANISM: Artificial Sequence
<220> FEATURE:
<223> OTHER INFORMATION: Synthetic: Clone 16 VH CDR2

<400> SEQUENCE: 96

Gly Ile Ile Pro Ile Phe Gly Thr Ala Ser Tyr Ala Gln Lys Phe Gln
1               5                   10                  15

Gly

<210> SEQ ID NO 97
<211> LENGTH: 30
<212> TYPE: PRT
<213> ORGANISM: Artificial Sequence
<220> FEATURE:
<223> OTHER INFORMATION: Synthetic: Clone 16 VH FR3
```

<400> SEQUENCE: 97

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 98
<211> LENGTH: 14
<212> TYPE: PRT
<213> ORGANISM: Artificial Sequence
<220> FEATURE:
<223> OTHER INFORMATION: Synthetic: Clone 16 VH CDR3

<400> SEQUENCE: 98

Ala Arg Gln Ser Thr Trp His Lys Leu Tyr Gly Thr Asp Val
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Synthetic: Clone 16 VH FR4

<400> SEQUENCE: 99

Trp Gly Gln Gly Thr Thr Val Thr Val Ser Ser
1               5                   10

<210> SEQ ID NO 100
<211> LENGTH: 107
<212> TYPE: PRT
<213> ORGANISM: Artificial Sequence
<220> FEATURE:
<223> OTHER INFORMATION: Synthetic: Clones 16, 16C, 16D, and 16E VL
      Protein

<400> SEQUENCE: 100

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser Leu Pro Pro
                85                  90                  95

Thr Phe Gly Gly Gly Thr Lys Val Glu Ile Lys
            100                 105

<210> SEQ ID NO 101
<211> LENGTH: 321
<212> TYPE: DNA
<213> ORGANISM: Artificial Sequence
<220> FEATURE:
<223> OTHER INFORMATION: Synthetic: Clone 16 VL DNA

<400> SEQUENCE: 101
gacatccaga tgacccagtc tccatcttcc gtgtctgcat ctgtaggaga cagagtcacc      60
atcacttgtc gggcgagtca gggtattagc agctggttag cctggtatca gcagaaacca    120

```
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgtcagcag ggagacagtc tccctcctac ttttggcgga    300
gggaccaagg ttgagatcaa a                                              321
```

```
<210> SEQ ID NO 102
<211> LENGTH: 23
<212> TYPE: PRT
<213> ORGANISM: Artificial Sequence
<220> FEATURE:
<223> OTHER INFORMATION: Synthetic: Clone 16 VL FR1

<400> SEQUENCE: 102

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 103
<211> LENGTH: 11
<212> TYPE: PRT
<213> ORGANISM: Artificial Sequence
<220> FEATURE:
<223> OTHER INFORMATION: Synthetic: Clones 16, 16C, 16D, and 16E VL CDR1

<400> SEQUENCE: 103

Arg Ala Ser Gln Gly Ile Ser Ser Trp Leu Ala
1               5                   10

<210> SEQ ID NO 104
<211> LENGTH: 15
<212> TYPE: PRT
<213> ORGANISM: Artificial Sequence
<220> FEATURE:
<223> OTHER INFORMATION: Synthetic: Clone 16 VL FR2

<400> SEQUENCE: 104

Trp Tyr Gln Gln Lys Pro Gly Lys Ala Pro Lys Leu Leu Ile Tyr
1               5                   10                  15

<210> SEQ ID NO 105
<211> LENGTH: 7
<212> TYPE: PRT
<213> ORGANISM: Artificial Sequence
<220> FEATURE:
<223> OTHER INFORMATION: Synthetic: Clones 16, 16C, 16D, and 16E VL CDR2

<400> SEQUENCE: 105

Ala Ala Ser Ser Leu Gln Ser
1               5

<210> SEQ ID NO 106
<211> LENGTH: 32
<212> TYPE: PRT
<213> ORGANISM: Artificial Sequence
<220> FEATURE:
<223> OTHER INFORMATION: Synthetic: Clone 16 VL FR3

<400> SEQUENCE: 106

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 107
<211> LENGTH: 9
<212> TYPE: PRT
<213> ORGANISM: Artificial Sequence
<220> FEATURE:
<223> OTHER INFORMATION: Synthetic: Clones 16, 16C, 16D, and 16E VL CDR3

<400> SEQUENCE: 107

Gln Gln Gly Asp Ser Leu Pro Pro Thr
1               5

<210> SEQ ID NO 108
<211> LENGTH: 10
<212> TYPE: PRT
<213> ORGANISM: Artificial Sequence
<220> FEATURE:
<223> OTHER INFORMATION: Synthetic: Clone 16 VL FR4

<400> SEQUENCE: 108

Phe Gly Gly Gly Thr Lys Val Glu Ile Lys
1               5                   10

<210> SEQ ID NO 109
<211> LENGTH: 120
<212> TYPE: PRT
<213> ORGANISM: Artificial Sequence
<220> FEATURE:
<223> OTHER INFORMATION: Synthetic: Clone 18 VH Protein

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Arg Tyr Gly Tyr Ala Asp Gly Met Asp Val Trp Gly Gln
            100                 105                 110

Gly Thr Thr Val Thr Val Ser Ser
        115                 120

<210> SEQ ID NO 110
<211> LENGTH: 360
<212> TYPE: DNA
<213> ORGANISM: Artificial Sequence
<220> FEATURE:
<223> OTHER INFORMATION: Synthetic: Clone 18 VH DNA

<400> SEQUENCE: 110
caggtgcagc tggtgcagtc tggggctgag gtgaagaagc ctggggcctc agtgaaggtt      60
tcctgcaagg catctggata caccttcacc agctactata tgtcatgggt gcgacaggcc     120
cctggacaag gcttgagtg gatgggaata atcaacccta gtggtggtag cacaagctac      180
gcacagaagt tccagggcag agtcaccatg accagggaca cgtccacgag cacagtctac     240

```
atggagctga gcagcctgag atctgaggac acggcggtgt actactgcgc cagagtgagg      300
tacggatacg cagacggaat ggacgtatgg ggccagggaa caactgtcac cgtctcctca      360
```

<210> SEQ ID NO 111
<211> LENGTH: 26
<212> TYPE: PRT
<213> ORGANISM: Artificial Sequence
<220> FEATURE:
<223> OTHER INFORMATION: Synthetic: Clone 18 VH FR1

<400> SEQUENCE: 111

```
Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25
```

<210> SEQ ID NO 112
<211> LENGTH: 9
<212> TYPE: PRT
<213> ORGANISM: Artificial Sequence
<220> FEATURE:
<223> OTHER INFORMATION: Synthetic: Clone 18 VH CDR1

<400> SEQUENCE: 112

```
Tyr Thr Phe Thr Ser Tyr Tyr Met Ser
1               5
```

<210> SEQ ID NO 113
<211> LENGTH: 14
<212> TYPE: PRT
<213> ORGANISM: Artificial Sequence
<220> FEATURE:
<223> OTHER INFORMATION: Synthetic: Clone 18 VH FR2

<400> SEQUENCE: 113

```
Trp Val Arg Gln Ala Pro Gly Gln Gly Leu Glu Trp Met Gly
1               5                   10
```

<210> SEQ ID NO 114
<211> LENGTH: 17
<212> TYPE: PRT
<213> ORGANISM: Artificial Sequence
<220> FEATURE:
<223> OTHER INFORMATION: Synthetic: Clone 18 VH CDR2

<400> SEQUENCE: 114

```
Ile Ile Asn Pro Ser Gly Gly Ser Thr Ser Tyr Ala Gln Lys Phe Gln
1               5                   10                  15

Gly
```

<210> SEQ ID NO 115
<211> LENGTH: 30
<212> TYPE: PRT
<213> ORGANISM: Artificial Sequence
<220> FEATURE:
<223> OTHER INFORMATION: Synthetic: Clone 18 VH FR3

<400> SEQUENCE: 115

```
Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30
```

<210> SEQ ID NO 116

```
<211> LENGTH: 13
<212> TYPE: PRT
<213> ORGANISM: Artificial Sequence
<220> FEATURE:
<223> OTHER INFORMATION: Synthetic: Clone 18 VH CDR3

<400> SEQUENCE: 116

Ala Arg Val Arg Tyr Gly Tyr Ala Asp Gly Met Asp Val
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic: Clone 18 VH FR4

<400> SEQUENCE: 117

Trp Gly Gln Gly Thr Thr Val Thr Val Ser Ser
1               5                   10

<210> SEQ ID NO 118
<211> LENGTH: 107
<212> TYPE: PRT
<213> ORGANISM: Artificial Sequence
<220> FEATURE:
<223> OTHER INFORMATION: Synthetic: Clone 18 VL Protein

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr His Leu Pro Phe
                85                  90                  95

Thr Phe Gly Gly Gly Thr Lys Val Glu Ile Lys
            100                 105

<210> SEQ ID NO 119
<211> LENGTH: 321
<212> TYPE: DNA
<213> ORGANISM: Artificial Sequence
<220> FEATURE:
<223> OTHER INFORMATION: Synthetic: Clone 18 VL DNA

<400> SEQUENCE: 119
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatggt gcatccagtt tgcaaagtgg ggtcccatca     180
aggttcagtg gcagtggatc tgggacagat ttcactctca ccatcagcag tctgcaacct     240
gaagattttg caacttacta ctgtcagcaa gtataccacc tccctttcac ttttggcgga     300
gggaccaagg ttgagatcaa a                                                321

<210> SEQ ID NO 120
```

```
<211> LENGTH: 23
<212> TYPE: PRT
<213> ORGANISM: Artificial Sequence
<220> FEATURE:
<223> OTHER INFORMATION: Synthetic: Clone 18 VL FR1

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 121
<211> LENGTH: 11
<212> TYPE: PRT
<213> ORGANISM: Artificial Sequence
<220> FEATURE:
<223> OTHER INFORMATION: Synthetic: Clone 18 VL CDR1

<400> SEQUENCE: 121

Arg Ala Ser Gln Ser Ile Ser Ser Tyr Leu Asn
1               5                   10

<210> SEQ ID NO 122
<211> LENGTH: 15
<212> TYPE: PRT
<213> ORGANISM: Artificial Sequence
<220> FEATURE:
<223> OTHER INFORMATION: Synthetic: Clone 18 VL FR2

<400> SEQUENCE: 122

Trp Tyr Gln Gln Lys Pro Gly Lys Ala Pro Lys Leu Leu Ile Tyr
1               5                   10                  15

<210> SEQ ID NO 123
<211> LENGTH: 7
<212> TYPE: PRT
<213> ORGANISM: Artificial Sequence
<220> FEATURE:
<223> OTHER INFORMATION: Synthetic: Clone 18 VL CDR2

<400> SEQUENCE: 123

Gly Ala Ser Ser Leu Gln Ser
1               5

<210> SEQ ID NO 124
<211> LENGTH: 32
<212> TYPE: PRT
<213> ORGANISM: Artificial Sequence
<220> FEATURE:
<223> OTHER INFORMATION: Synthetic: Clone 18 VL FR3

<400> SEQUENCE: 124

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 125
<211> LENGTH: 9
<212> TYPE: PRT
<213> ORGANISM: Artificial Sequence
<220> FEATURE:
<223> OTHER INFORMATION: Synthetic: Clone 18 VL CDR3

<400> SEQUENCE: 125
```

Gln Gln Val Tyr His Leu Pro Phe Thr
1               5

<210> SEQ ID NO 126
<211> LENGTH: 10
<212> TYPE: PRT
<213> ORGANISM: Artificial Sequence
<220> FEATURE:
<223> OTHER INFORMATION: Synthetic: Clone 18 VL FR4

<400> SEQUENCE: 126

Phe Gly Gly Gly Thr Lys Val Glu Ile Lys
1               5                   10

<210> SEQ ID NO 127
<211> LENGTH: 121
<212> TYPE: PRT
<213> ORGANISM: Artificial Sequence
<220> FEATURE:
<223> OTHER INFORMATION: Synthetic: Clone 21 VH Protein

<400> SEQUENCE: 127

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Leu Tyr Gln Asp Ala Pro Phe Asp Tyr Trp Gly
            100                 105                 110

Gln Gly Thr Leu Val Thr Val Ser Ser
        115                 120

<210> SEQ ID NO 128
<211> LENGTH: 363
<212> TYPE: DNA
<213> ORGANISM: Artificial Sequence
<220> FEATURE:
<223> OTHER INFORMATION: Synthetic: Clone 21 VH DNA

<400> SEQUENCE: 128
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct attatagtgg gagcacctac     180
tacaacccgt ccctcaagag tcgagtcacc atatccgtag acacgtccaa gaaccagttc     240
tccctgaagc tgagttctgt gaccgccgca gacacggcgg tgtactactg cgccagagat     300
cctttgtacc aagacgctcc cttcgactat tggggacagg gtacattggt caccgtctcc     360
tca                                                                    363

<210> SEQ ID NO 129
<211> LENGTH: 26
<212> TYPE: PRT
<213> ORGANISM: Artificial Sequence

```
<220> FEATURE:
<223> OTHER INFORMATION: Synthetic: Clone 21 VH FR1

<400> SEQUENCE: 129

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 130
<211> LENGTH: 11
<212> TYPE: PRT
<213> ORGANISM: Artificial Sequence
<220> FEATURE:
<223> OTHER INFORMATION: Synthetic: Clone 21 VH CDR1

<400> SEQUENCE: 130

Gly Ser Ile Ser Ser Ser Ser Tyr Tyr Trp Gly
1               5                   10

<210> SEQ ID NO 131
<211> LENGTH: 14
<212> TYPE: PRT
<213> ORGANISM: Artificial Sequence
<220> FEATURE:
<223> OTHER INFORMATION: Synthetic: Clone 21 VH FR2

<400> SEQUENCE: 131

Trp Ile Arg Gln Pro Pro Gly Lys Gly Leu Glu Trp Ile Gly
1               5                   10

<210> SEQ ID NO 132
<211> LENGTH: 16
<212> TYPE: PRT
<213> ORGANISM: Artificial Sequence
<220> FEATURE:
<223> OTHER INFORMATION: Synthetic: Clone 21 VH CDR2

<400> SEQUENCE: 132

Ser Ile Tyr Tyr Ser Gly Ser Thr Tyr Tyr Asn Pro Ser Leu Lys Ser
1               5                   10                  15

<210> SEQ ID NO 133
<211> LENGTH: 30
<212> TYPE: PRT
<213> ORGANISM: Artificial Sequence
<220> FEATURE:
<223> OTHER INFORMATION: Synthetic: Clone 21 VH FR3

<400> SEQUENCE: 133

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 134
<211> LENGTH: 13
<212> TYPE: PRT
<213> ORGANISM: Artificial Sequence
<220> FEATURE:
<223> OTHER INFORMATION: Synthetic: Clone 21 VH CDR3

<400> SEQUENCE: 134

Ala Arg Asp Pro Leu Tyr Gln Asp Ala Pro Phe Asp Tyr
1               5                   10
```

<210> SEQ ID NO 135
<211> LENGTH: 11
<212> TYPE: PRT
<213> ORGANISM: Artificial Sequence
<220> FEATURE:
<223> OTHER INFORMATION: Synthetic: Clone 21 VH FR4

<400> SEQUENCE: 135

Trp Gly Gln Gly Thr Leu Val Thr Val Ser Ser
1               5                   10

<210> SEQ ID NO 136
<211> LENGTH: 106
<212> TYPE: PRT
<213> ORGANISM: Artificial Sequence
<220> FEATURE:
<223> OTHER INFORMATION: Synthetic: Clone 21 VL Protein

<400> SEQUENCE: 136

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Asn Phe Pro Thr
                85                  90                  95

Phe Gly Gly Gly Thr Lys Val Glu Ile Lys
            100                 105

<210> SEQ ID NO 137
<211> LENGTH: 318
<212> TYPE: DNA
<213> ORGANISM: Artificial Sequence
<220> FEATURE:
<223> OTHER INFORMATION: Synthetic: Clone 21 VL DNA

<400> SEQUENCE: 137
gaaattgtgt tgacacagtc tccagccacc ctgtctttgt ctccagggga agagccacc      60 ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag agagccaact cccctacttt tggcggaggg   300
accaaggttg agatcaaa                                                  318

<210> SEQ ID NO 138
<211> LENGTH: 23
<212> TYPE: PRT
<213> ORGANISM: Artificial Sequence
<220> FEATURE:
<223> OTHER INFORMATION: Synthetic: Clone 21 VL FR1

<400> SEQUENCE: 138

Glu Ile Val Leu Thr Gln Ser Pro Ala Thr Leu Ser Leu Ser Pro Gly
1               5                   10                  15

```
Glu Arg Ala Thr Leu Ser Cys
            20
```

<210> SEQ ID NO 139
<211> LENGTH: 11
<212> TYPE: PRT
<213> ORGANISM: Artificial Sequence
<220> FEATURE:
<223> OTHER INFORMATION: Synthetic: Clone 21 VL CDR1

<400> SEQUENCE: 139

```
Arg Ala Ser Gln Ser Val Ser Ser Tyr Leu Ala
1               5                   10
```

<210> SEQ ID NO 140
<211> LENGTH: 15
<212> TYPE: PRT
<213> ORGANISM: Artificial Sequence
<220> FEATURE:
<223> OTHER INFORMATION: Synthetic: Clone 21 VL FR2

<400> SEQUENCE: 140

```
Trp Tyr Gln Gln Lys Pro Gly Gln Ala Pro Arg Leu Leu Ile Tyr
1               5                   10                  15
```

<210> SEQ ID NO 141
<211> LENGTH: 7
<212> TYPE: PRT
<213> ORGANISM: Artificial Sequence
<220> FEATURE:
<223> OTHER INFORMATION: Synthetic: Clone 21 VL CDR2

<400> SEQUENCE: 141

```
Asp Ala Ser Asn Arg Ala Thr
1               5
```

<210> SEQ ID NO 142
<211> LENGTH: 32
<212> TYPE: PRT
<213> ORGANISM: Artificial Sequence
<220> FEATURE:
<223> OTHER INFORMATION: Synthetic: Clone 21 VL FR3

<400> SEQUENCE: 142

```
Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30
```

<210> SEQ ID NO 143
<211> LENGTH: 8
<212> TYPE: PRT
<213> ORGANISM: Artificial Sequence
<220> FEATURE:
<223> OTHER INFORMATION: Synthetic: Clone 21 VL CDR3

<400> SEQUENCE: 143

```
Gln Gln Arg Ala Asn Phe Pro Thr
1               5
```

<210> SEQ ID NO 144
<211> LENGTH: 10
<212> TYPE: PRT
<213> ORGANISM: Artificial Sequence
<220> FEATURE:
<223> OTHER INFORMATION: Synthetic: Clone 21 VL FR4

<400> SEQUENCE: 144

Phe Gly Gly Gly Thr Lys Val Glu Ile Lys
1               5                   10

<210> SEQ ID NO 145
<211> LENGTH: 124
<212> TYPE: PRT
<213> ORGANISM: Artificial Sequence
<220> FEATURE:
<223> OTHER INFORMATION: Synthetic: Clone 22 VH Protein

<400> SEQUENCE: 145

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Ala Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Tyr Tyr Gly Ser Ser Gly Ser Val Asp Phe Asp
            100                 105                 110

Leu Trp Gly Arg Gly Thr Leu Val Thr Val Ser Ser
        115                 120

<210> SEQ ID NO 146
<211> LENGTH: 372
<212> TYPE: DNA
<213> ORGANISM: Artificial Sequence
<220> FEATURE:
<223> OTHER INFORMATION: Synthetic: Clone 22 VH DNA

<400> SEQUENCE: 146
caggtgcagc tgcaggagtc gggcccagga ctggtgaagc cttcggagac cctgtccctc      60
acctgcgctg tctctggtta ctccatcagc agtggttact actgggcttg gatccggcag     120
cccccaggga aggggctgga gtggattggg agtatctatc atagtgggag cacctactac     180
aacccgtccc tcaagagtcg agtcaccata tcagtagaca cgtccaagaa ccagttctcc     240
ctgaagctga gttctgtgac cgccgcagac acggcggtgt actactgcgc caggcaggga     300
tactactacg gcagcagcgg cagtgtagac ttcgacctat gggggagagg taccttggtc     360
accgtctcct ca                                                        372

<210> SEQ ID NO 147
<211> LENGTH: 26
<212> TYPE: PRT
<213> ORGANISM: Artificial Sequence
<220> FEATURE:
<223> OTHER INFORMATION: Synthetic: Clone 22 VH FR1

<400> SEQUENCE: 147

Gln Val Gln Leu Gln Glu Ser Gly Pro Gly Leu Val Lys Pro Ser Glu
1               5                   10                  15

Thr Leu Ser Leu Thr Cys Ala Val Ser Gly
            20                  25

<210> SEQ ID NO 148
<211> LENGTH: 10
<212> TYPE: PRT
<213> ORGANISM: Artificial Sequence
<220> FEATURE:
<223> OTHER INFORMATION: Synthetic: Clone 22 VH CDR1

<400> SEQUENCE: 148

Tyr Ser Ile Ser Ser Gly Tyr Tyr Trp Ala
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Synthetic: Clone 22 VH FR2

<400> SEQUENCE: 149

Trp Ile Arg Gln Pro Pro Gly Lys Gly Leu Glu Trp Ile Gly
1               5                   10

<210> SEQ ID NO 150
<211> LENGTH: 16
<212> TYPE: PRT
<213> ORGANISM: Artificial Sequence
<220> FEATURE:
<223> OTHER INFORMATION: Synthetic: Clone 22 VH CDR2

<400> SEQUENCE: 150

Ser Ile Tyr His Ser Gly Ser Thr Tyr Tyr Asn Pro Ser Leu Lys Ser
1               5                   10                  15

<210> SEQ ID NO 151
<211> LENGTH: 30
<212> TYPE: PRT
<213> ORGANISM: Artificial Sequence
<220> FEATURE:
<223> OTHER INFORMATION: Synthetic: Clone 22 VH FR3

<400> SEQUENCE: 151

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 152
<211> LENGTH: 17
<212> TYPE: PRT
<213> ORGANISM: Artificial Sequence
<220> FEATURE:
<223> OTHER INFORMATION: Synthetic: Clone 22 VH CDR3

<400> SEQUENCE: 152

Ala Arg Gln Gly Tyr Tyr Tyr Gly Ser Ser Gly Ser Val Asp Phe Asp
1               5                   10                  15

Leu

<210> SEQ ID NO 153
<211> LENGTH: 11
<212> TYPE: PRT
<213> ORGANISM: Artificial Sequence
<220> FEATURE:
<223> OTHER INFORMATION: Synthetic: Clone 22 VH FR4

<400> SEQUENCE: 153

Trp Gly Arg Gly Thr Leu Val Thr Val Ser Ser
1               5                   10

<210> SEQ ID NO 154
<211> LENGTH: 108
<212> TYPE: PRT
<213> ORGANISM: Artificial Sequence
<220> FEATURE:
<223> OTHER INFORMATION: Synthetic: Clone 22 VL Protein

<400> SEQUENCE: 154

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Leu Pro Pro
                85                  90                  95

Trp Thr Phe Gly Gly Gly Thr Lys Val Glu Ile Lys
            100                 105

<210> SEQ ID NO 155
<211> LENGTH: 324
<212> TYPE: DNA
<213> ORGANISM: Artificial Sequence
<220> FEATURE:
<223> OTHER INFORMATION: Synthetic: Clone 22 VL DNA

<400> SEQUENCE: 155
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccaatt tgcaaagtgg ggtcccatca     180
aggttcagcg gcagtggatc tgggacagat tcactctca ccatcagcag cctgcagcct      240
gaagattttg caacttatta ctgtcaacag gcaaatagtc ccctccttg gacttttggc      300 ggagggacca aggttgagat caaa                                             324

<210> SEQ ID NO 156
<211> LENGTH: 23
<212> TYPE: PRT
<213> ORGANISM: Artificial Sequence
<220> FEATURE:
<223> OTHER INFORMATION: Synthetic: Clone 22 VL FR1

<400> SEQUENCE: 156

Asp Ile Gln Met Thr Gln Ser Pro Ser Ser Val Ser Ala Ser Val Gly
1               5                   10                  15

Asp Arg Val Thr Ile Thr Cys
                20

<210> SEQ ID NO 157
<211> LENGTH: 11
<212> TYPE: PRT
<213> ORGANISM: Artificial Sequence
<220> FEATURE:

-continued

<223> OTHER INFORMATION: Synthetic: Clone 22 VL CDR1

<400> SEQUENCE: 157

Arg Ala Ser Gln Gly Ile Ser Ser Trp Leu Ala
1               5                   10

<210> SEQ ID NO 158
<211> LENGTH: 15
<212> TYPE: PRT
<213> ORGANISM: Artificial Sequence
<220> FEATURE:
<223> OTHER INFORMATION: Synthetic: Clone 22 VL FR2

<400> SEQUENCE: 158

Trp Tyr Gln Gln Lys Pro Gly Lys Ala Pro Lys Leu Leu Ile Tyr
1               5                   10                  15

<210> SEQ ID NO 159
<211> LENGTH: 7
<212> TYPE: PRT
<213> ORGANISM: Artificial Sequence
<220> FEATURE:
<223> OTHER INFORMATION: Synthetic: Clone 22 VL CDR2

<400> SEQUENCE: 159

Ala Ala Ser Asn Leu Gln Ser
1               5

<210> SEQ ID NO 160
<211> LENGTH: 32
<212> TYPE: PRT
<213> ORGANISM: Artificial Sequence
<220> FEATURE:
<223> OTHER INFORMATION: Synthetic: Clone 22 VL FR3

<400> SEQUENCE: 160

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 161
<211> LENGTH: 10
<212> TYPE: PRT
<213> ORGANISM: Artificial Sequence
<220> FEATURE:
<223> OTHER INFORMATION: Synthetic: Clone 22 VL CDR3

<400> SEQUENCE: 161

Gln Gln Ala Asn Ser Leu Pro Pro Trp Thr
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Synthetic: Clone 22 VL FR4

<400> SEQUENCE: 162

Phe Gly Gly Gly Thr Lys Val Glu Ile Lys
1               5                   10

<210> SEQ ID NO 163
<211> LENGTH: 125
<212> TYPE: PRT

```
<213> ORGANISM: Artificial Sequence
<220> FEATURE:
<223> OTHER INFORMATION: Synthetic: Clone 25 VH Protein

<400> SEQUENCE: 163

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Ser Ser Phe Trp Ser Gly Asp Val Leu Gly Ala Phe
            100                 105                 110

Asp Ile Trp Gly Gln Gly Thr Met Val Thr Val Ser Ser
        115                 120                 125

<210> SEQ ID NO 164
<211> LENGTH: 375
<212> TYPE: DNA
<213> ORGANISM: Artificial Sequence
<220> FEATURE:
<223> OTHER INFORMATION: Synthetic: Clone 25 VH DNA

<400> SEQUENCE: 164
caggttcagc tggtgcagtc tggagctgag gtgaagaagc ctggggcctc agtgaaggtc     60
tcctgcaagg cttctggtta cacctttacc agctatgcca tcagctgggt gcgacaggcc    120
cctggacaag gcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggcggtgt actactgcgc aagggatttg    300
tctagcttct ggagcggaga cgtgttagga gccttcgaca tatgggtca gggtacaatg    360 gtcaccgtct cctca                                                    375

<210> SEQ ID NO 165
<211> LENGTH: 26
<212> TYPE: PRT
<213> ORGANISM: Artificial Sequence
<220> FEATURE:
<223> OTHER INFORMATION: Synthetic: Clone 25 VH FR1

<400> SEQUENCE: 165

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 166
<211> LENGTH: 9
<212> TYPE: PRT
<213> ORGANISM: Artificial Sequence
<220> FEATURE:
<223> OTHER INFORMATION: Synthetic: Clones 25 and 25A VH CDR1

<400> SEQUENCE: 166
```

Tyr Thr Phe Thr Ser Tyr Ala Ile Ser
1               5

<210> SEQ ID NO 167
<211> LENGTH: 14
<212> TYPE: PRT
<213> ORGANISM: Artificial Sequence
<220> FEATURE:
<223> OTHER INFORMATION: Synthetic: Clone 25 VH FR2

<400> SEQUENCE: 167

Trp Val Arg Gln Ala Pro Gly Gln Gly Leu Glu Trp Met Gly
1               5                   10

<210> SEQ ID NO 168
<211> LENGTH: 17
<212> TYPE: PRT
<213> ORGANISM: Artificial Sequence
<220> FEATURE:
<223> OTHER INFORMATION: Synthetic: Clones 25 and 25E VH CDR2

<400> SEQUENCE: 168

Trp Ile Ser Ala Tyr Asn Gly Asn Thr Asn Tyr Ala Gln Lys Leu Gln
1               5                   10                  15

Gly

<210> SEQ ID NO 169
<211> LENGTH: 30
<212> TYPE: PRT
<213> ORGANISM: Artificial Sequence
<220> FEATURE:
<223> OTHER INFORMATION: Synthetic: Clone 25 VH FR3

<400> SEQUENCE: 169

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys
            20                  25                  30

<210> SEQ ID NO 170
<211> LENGTH: 18
<212> TYPE: PRT
<213> ORGANISM: Artificial Sequence
<220> FEATURE:
<223> OTHER INFORMATION: Synthetic: Clones 25, 25A, and 25B VH CDR3

<400> SEQUENCE: 170

Ala Arg Asp Leu Ser Ser Phe Trp Ser Gly Asp Val Leu Gly Ala Phe
1               5                   10                  15

Asp Ile

<210> SEQ ID NO 171
<211> LENGTH: 11
<212> TYPE: PRT
<213> ORGANISM: Artificial Sequence
<220> FEATURE:
<223> OTHER INFORMATION: Synthetic: Clone 25 VH FR4

<400> SEQUENCE: 171

Trp Gly Gln Gly Thr Met Val Thr Val Ser Ser
1               5                   10

<210> SEQ ID NO 172
<211> LENGTH: 106

<212> TYPE: PRT
<213> ORGANISM: Artificial Sequence
<220> FEATURE:
<223> OTHER INFORMATION: Synthetic: Clones 25, 25A, 25B, 25C, 25D, and 25E VL Protein

<400> SEQUENCE: 172

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Val Pro Pro Arg Thr
                85                  90                  95
Phe Gly Gly Gly Thr Lys Val Glu Ile Lys
            100                 105

<210> SEQ ID NO 173
<211> LENGTH: 318
<212> TYPE: DNA
<213> ORGANISM: Artificial Sequence
<220> FEATURE:
<223> OTHER INFORMATION: Synthetic: Clone 25 VL DNA

<400> SEQUENCE: 173
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa agcgtccccc ccaggacttt tggcggaggg     300
accaaggttg agatcaaa                                                   318

<210> SEQ ID NO 174
<211> LENGTH: 23
<212> TYPE: PRT
<213> ORGANISM: Artificial Sequence
<220> FEATURE:
<223> OTHER INFORMATION: Synthetic: Clone 25 VL FR1

<400> SEQUENCE: 174

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 175
<211> LENGTH: 11
<212> TYPE: PRT
<213> ORGANISM: Artificial Sequence
<220> FEATURE:
<223> OTHER INFORMATION: Synthetic: Clones 25, 25A, 25B, 25C, 25D, and 25E VL CDR1

<400> SEQUENCE: 175

Arg Ala Ser Gln Ser Ile Ser Ser Tyr Leu Asn

```
<210> SEQ ID NO 176
<211> LENGTH: 15
<212> TYPE: PRT
<213> ORGANISM: Artificial Sequence
<220> FEATURE:
<223> OTHER INFORMATION: Synthetic: Clone 25 VL FR2

<400> SEQUENCE: 176

Trp Tyr Gln Gln Lys Pro Gly Lys Ala Pro Lys Leu Leu Ile Tyr
1               5                   10                  15

<210> SEQ ID NO 177
<211> LENGTH: 7
<212> TYPE: PRT
<213> ORGANISM: Artificial Sequence
<220> FEATURE:
<223> OTHER INFORMATION: Synthetic: Clones 25, 25A, 25B, 25C, 25D, and
      25E VL CDR2

<400> SEQUENCE: 177

Ala Ala Ser Ser Leu Gln Ser
1               5

<210> SEQ ID NO 178
<211> LENGTH: 32
<212> TYPE: PRT
<213> ORGANISM: Artificial Sequence
<220> FEATURE:
<223> OTHER INFORMATION: Synthetic: Clone 25 VL FR3

<400> SEQUENCE: 178

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 179
<211> LENGTH: 8
<212> TYPE: PRT
<213> ORGANISM: Artificial Sequence
<220> FEATURE:
<223> OTHER INFORMATION: Synthetic: Clones 25, 25A, 25B, 25C, 25D, and
      25E VL CDR3

<400> SEQUENCE: 179

Gln Gln Ser Val Pro Pro Arg Thr
1               5

<210> SEQ ID NO 180
<211> LENGTH: 10
<212> TYPE: PRT
<213> ORGANISM: Artificial Sequence
<220> FEATURE:
<223> OTHER INFORMATION: Synthetic: Clone 25 VL FR4

<400> SEQUENCE: 180

Phe Gly Gly Gly Thr Lys Val Glu Ile Lys
1               5                   10

<210> SEQ ID NO 181
<211> LENGTH: 125
<212> TYPE: PRT
<213> ORGANISM: Artificial Sequence
<220> FEATURE:
<223> OTHER INFORMATION: Synthetic: Clone 27 VH Protein
```

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Ser Ser Phe Trp Ser Gly Asp Val Leu Gly Ala Phe
            100                 105                 110

Asp Ile Trp Gly Gln Gly Thr Met Val Thr Val Ser Ser
        115                 120                 125

<210> SEQ ID NO 182
<211> LENGTH: 375
<212> TYPE: DNA
<213> ORGANISM: Artificial Sequence
<220> FEATURE:
<223> OTHER INFORMATION: Synthetic: Clone 27 VH DNA

<400> SEQUENCE: 182
caggttcagc tggtgcagtc tggagctgag gtgaagaagc ctggggcctc agtgaaggtc      60
tcctgcaagg cttctggtta cacctttacc agctatgcca tcagctgggt gcgacaggcc     120
cctggacaag gcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggcggtgt actactgcgc aagggatttg     300
tctagcttct ggagcggaga cgtgttagga gccttcgaca tatggggtca gggtacaatg     360
gtcaccgtct cctca                                                      375

<210> SEQ ID NO 183
<211> LENGTH: 26
<212> TYPE: PRT
<213> ORGANISM: Artificial Sequence
<220> FEATURE:
<223> OTHER INFORMATION: Synthetic: Clone 27 VH FR1

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 184
<211> LENGTH: 9
<212> TYPE: PRT
<213> ORGANISM: Artificial Sequence
<220> FEATURE:
<223> OTHER INFORMATION: Synthetic: Clone 27 VH CDR1

<400> SEQUENCE: 184

Tyr Thr Phe Thr Ser Tyr Ala Ile Ser
1               5

<210> SEQ ID NO 185
<211> LENGTH: 14
<212> TYPE: PRT
<213> ORGANISM: Artificial Sequence
<220> FEATURE:
<223> OTHER INFORMATION: Synthetic: Clone 27 VH FR2

<400> SEQUENCE: 185

Trp Val Arg Gln Ala Pro Gly Gln Gly Leu Glu Trp Met Gly
1               5                   10

<210> SEQ ID NO 186
<211> LENGTH: 17
<212> TYPE: PRT
<213> ORGANISM: Artificial Sequence
<220> FEATURE:
<223> OTHER INFORMATION: Synthetic: Clone 27 VH CDR2

<400> SEQUENCE: 186

Trp Ile Ser Ala Tyr Asn Gly Asn Thr Asn Tyr Ala Gln Lys Leu Gln
1               5                   10                  15

Gly

<210> SEQ ID NO 187
<211> LENGTH: 30
<212> TYPE: PRT
<213> ORGANISM: Artificial Sequence
<220> FEATURE:
<223> OTHER INFORMATION: Synthetic: Clone 27 VH FR3

<400> SEQUENCE: 187

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys
            20                  25                  30

<210> SEQ ID NO 188
<211> LENGTH: 18
<212> TYPE: PRT
<213> ORGANISM: Artificial Sequence
<220> FEATURE:
<223> OTHER INFORMATION: Synthetic: Clone 27 VH CDR3

<400> SEQUENCE: 188

Ala Arg Asp Leu Ser Ser Phe Trp Ser Gly Asp Val Leu Gly Ala Phe
1               5                   10                  15

Asp Ile

<210> SEQ ID NO 189
<211> LENGTH: 11
<212> TYPE: PRT
<213> ORGANISM: Artificial Sequence
<220> FEATURE:
<223> OTHER INFORMATION: Synthetic: Clone 27 VH FR4

<400> SEQUENCE: 189

Trp Gly Gln Gly Thr Met Val Thr Val Ser Ser
1               5                   10

<210> SEQ ID NO 190
<211> LENGTH: 106
<212> TYPE: PRT
<213> ORGANISM: Artificial Sequence
<220> FEATURE:

<223> OTHER INFORMATION: Synthetic: Clone 27 VL Protein

<400> SEQUENCE: 190

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Ala Asn His Ile Thr
                85                  90                  95

Phe Gly Gly Gly Thr Lys Val Glu Ile Lys
            100                 105

<210> SEQ ID NO 191
<211> LENGTH: 318
<212> TYPE: DNA
<213> ORGANISM: Artificial Sequence
<220> FEATURE:
<223> OTHER INFORMATION: Synthetic: Clone 27 VL DNA

<400> SEQUENCE: 191
gaaatagtga tgacgcagtc tccagccacc ctgtctgtgt ctccagggga aagagccacc      60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag cacgccaatc acatcacttt tggcggaggg    300
accaaggttg agatcaaa                                                  318

<210> SEQ ID NO 192
<211> LENGTH: 23
<212> TYPE: PRT
<213> ORGANISM: Artificial Sequence
<220> FEATURE:
<223> OTHER INFORMATION: Synthetic: Clone 27 VL FR1

<400> SEQUENCE: 192

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 193
<211> LENGTH: 11
<212> TYPE: PRT
<213> ORGANISM: Artificial Sequence
<220> FEATURE:
<223> OTHER INFORMATION: Synthetic: Clone 27 VL CDR1

<400> SEQUENCE: 193

Arg Ala Ser Gln Ser Val Ser Ser Asn Leu Ala
1               5                   10

<210> SEQ ID NO 194
<211> LENGTH: 15

```
<212> TYPE: PRT
<213> ORGANISM: Artificial Sequence
<220> FEATURE:
<223> OTHER INFORMATION: Synthetic: Clone 27 VL FR2

<400> SEQUENCE: 194

Trp Tyr Gln Gln Lys Pro Gly Gln Ala Pro Arg Leu Leu Ile Tyr
1               5                   10                  15

<210> SEQ ID NO 195
<211> LENGTH: 7
<212> TYPE: PRT
<213> ORGANISM: Artificial Sequence
<220> FEATURE:
<223> OTHER INFORMATION: Synthetic: Clone 27 VL CDR2

<400> SEQUENCE: 195

Gly Ala Ser Thr Arg Ala Thr
1               5

<210> SEQ ID NO 196
<211> LENGTH: 32
<212> TYPE: PRT
<213> ORGANISM: Artificial Sequence
<220> FEATURE:
<223> OTHER INFORMATION: Synthetic: Clone 27 VL FR3

<400> SEQUENCE: 196

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 197
<211> LENGTH: 8
<212> TYPE: PRT
<213> ORGANISM: Artificial Sequence
<220> FEATURE:
<223> OTHER INFORMATION: Synthetic: Clone 27 VL CDR3

<400> SEQUENCE: 197

Gln Gln His Ala Asn His Ile Thr
1               5

<210> SEQ ID NO 198
<211> LENGTH: 10
<212> TYPE: PRT
<213> ORGANISM: Artificial Sequence
<220> FEATURE:
<223> OTHER INFORMATION: Synthetic: Clone 27 VL FR4

<400> SEQUENCE: 198

Phe Gly Gly Gly Thr Lys Val Glu Ile Lys
1               5                   10

<210> SEQ ID NO 199
<211> LENGTH: 124
<212> TYPE: PRT
<213> ORGANISM: Artificial Sequence
<220> FEATURE:
<223> OTHER INFORMATION: Synthetic: Clone 54 VH Protein

<400> SEQUENCE: 199

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
            20                  25                  30
Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ser Asp Ser Tyr Gly Val Gly Leu Tyr Tyr Gly Met Asp
            100                 105                 110

Val Trp Gly Gln Gly Thr Thr Val Thr Val Ser Ser
            115                 120

<210> SEQ ID NO 200
<211> LENGTH: 372
<212> TYPE: DNA
<213> ORGANISM: Artificial Sequence
<220> FEATURE:
<223> OTHER INFORMATION: Synthetic: Clone 54 VH DNA

<400> SEQUENCE: 200
caggtgcagc tggtgcagtc tggggctgag gtgaagaagc ctggggcctc agtgaaggtt      60
tcctgcaagg catctggata ccttcacc agctactata tgcactgggt gcgacaggcc      120
cctggacaag gcttgagtg gatgggaata tcaaccccta gtggtggtag cacaagctac      180
gcacagaagt tccagggcag agtcaccatg accaggggaca cgtccacgag cacagtctac      240
atggagctga gcagcctgag atctgaggac acggcggtgt actactgcgc tagggcatct      300
gactcctacg gagtgggcct ctactacgga atggacgtat ggggccaggg aacaactgtc      360
accgtctcct ca                                                          372

<210> SEQ ID NO 201
<211> LENGTH: 26
<212> TYPE: PRT
<213> ORGANISM: Artificial Sequence
<220> FEATURE:
<223> OTHER INFORMATION: Synthetic: Clone 54 VH FR1

<400> SEQUENCE: 201

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 202
<211> LENGTH: 9
<212> TYPE: PRT
<213> ORGANISM: Artificial Sequence
<220> FEATURE:
<223> OTHER INFORMATION: Synthetic: Clone 54 VH CDR1

<400> SEQUENCE: 202

Tyr Thr Phe Thr Ser Tyr Tyr Met His
1               5

<210> SEQ ID NO 203
<211> LENGTH: 14
<212> TYPE: PRT
<213> ORGANISM: Artificial Sequence
<220> FEATURE:
```

```
<223> OTHER INFORMATION: Synthetic: Clone 54 VH FR2

<400> SEQUENCE: 203

Trp Val Arg Gln Ala Pro Gly Gln Gly Leu Glu Trp Met Gly
1               5                   10

<210> SEQ ID NO 204
<211> LENGTH: 17
<212> TYPE: PRT
<213> ORGANISM: Artificial Sequence
<220> FEATURE:
<223> OTHER INFORMATION: Synthetic: Clone 54 VH CDR2

<400> SEQUENCE: 204

Ile Ile Asn Pro Ser Gly Gly Ser Thr Ser Tyr Ala Gln Lys Phe Gln
1               5                   10                  15

Gly

<210> SEQ ID NO 205
<211> LENGTH: 30
<212> TYPE: PRT
<213> ORGANISM: Artificial Sequence
<220> FEATURE:
<223> OTHER INFORMATION: Synthetic: Clone 54 VH FR3

<400> SEQUENCE: 205

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 206
<211> LENGTH: 17
<212> TYPE: PRT
<213> ORGANISM: Artificial Sequence
<220> FEATURE:
<223> OTHER INFORMATION: Synthetic: Clone 54 VH CDR3

<400> SEQUENCE: 206

Ala Arg Ala Ser Asp Ser Tyr Gly Val Gly Leu Tyr Tyr Gly Met Asp
1               5                   10                  15

Val

<210> SEQ ID NO 207
<211> LENGTH: 11
<212> TYPE: PRT
<213> ORGANISM: Artificial Sequence
<220> FEATURE:
<223> OTHER INFORMATION: Synthetic: Clone 54 VH FR4

<400> SEQUENCE: 207

Trp Gly Gln Gly Thr Thr Val Thr Val Ser Ser
1               5                   10

<210> SEQ ID NO 208
<211> LENGTH: 108
<212> TYPE: PRT
<213> ORGANISM: Artificial Sequence
<220> FEATURE:
<223> OTHER INFORMATION: Synthetic: Clone 54 VL Protein

<400> SEQUENCE: 208

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Val Ser Pro
                85                  90                  95

Leu Thr Phe Gly Gly Gly Thr Lys Val Glu Ile Lys
            100                 105

<210> SEQ ID NO 209
<211> LENGTH: 324
<212> TYPE: DNA
<213> ORGANISM: Artificial Sequence
<220> FEATURE:
<223> OTHER INFORMATION: Synthetic: Clone 54 VL DNA

<400> SEQUENCE: 209
gaaattgtgt tgacgcagtc tccaggcacc ctgtctttgt ctccagggga aagagccacc        60
ctctcctgca gggccagtca gagtgttagg agcagctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtactacg tcagtcctct cacttttggc       300
ggagggacca aggttgagat caaa                                              324

<210> SEQ ID NO 210
<211> LENGTH: 23
<212> TYPE: PRT
<213> ORGANISM: Artificial Sequence
<220> FEATURE:
<223> OTHER INFORMATION: Synthetic: Clone 54 VL FR1

<400> SEQUENCE: 210

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 211
<211> LENGTH: 12
<212> TYPE: PRT
<213> ORGANISM: Artificial Sequence
<220> FEATURE:
<223> OTHER INFORMATION: Synthetic: Clone 54 VL CDR1

<400> SEQUENCE: 211

Arg Ala Ser Gln Ser Val Arg Ser Ser Tyr Leu Ala
1               5                   10

<210> SEQ ID NO 212
<211> LENGTH: 15
<212> TYPE: PRT
<213> ORGANISM: Artificial Sequence
<220> FEATURE:
<223> OTHER INFORMATION: Synthetic: Clone 54 VL FR2

<400> SEQUENCE: 212
```

Trp Tyr Gln Gln Lys Pro Gly Gln Ala Pro Arg Leu Leu Ile Tyr
1               5                   10                  15

<210> SEQ ID NO 213
<211> LENGTH: 7
<212> TYPE: PRT
<213> ORGANISM: Artificial Sequence
<220> FEATURE:
<223> OTHER INFORMATION: Synthetic: Clone 54 VL CDR2

<400> SEQUENCE: 213

Gly Ala Ser Ser Arg Ala Thr
1               5

<210> SEQ ID NO 214
<211> LENGTH: 32
<212> TYPE: PRT
<213> ORGANISM: Artificial Sequence
<220> FEATURE:
<223> OTHER INFORMATION: Synthetic: Clone 54 VL FR3

<400> SEQUENCE: 214

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 215
<211> LENGTH: 9
<212> TYPE: PRT
<213> ORGANISM: Artificial Sequence
<220> FEATURE:
<223> OTHER INFORMATION: Synthetic: Clone 54 VL CDR3

<400> SEQUENCE: 215

Gln Gln Tyr Tyr Val Ser Pro Leu Thr
1               5

<210> SEQ ID NO 216
<211> LENGTH: 10
<212> TYPE: PRT
<213> ORGANISM: Artificial Sequence
<220> FEATURE:
<223> OTHER INFORMATION: Synthetic: Clone 54 VL FR4

<400> SEQUENCE: 216

Phe Gly Gly Gly Thr Lys Val Glu Ile Lys
1               5                   10

<210> SEQ ID NO 217
<211> LENGTH: 2978
<212> TYPE: DNA
<213> ORGANISM: Homo sapiens
<220> FEATURE:
<221> NAME/KEY: misc_feature
<223> OTHER INFORMATION: Human TIGIT cDNA sequence

<400> SEQUENCE: 217
cgtcctatct gcagtcggct actttcagtg gcagaagagg ccacatctgc ttcctgtagg      60
ccctctgggc agaagcatgc gctggtgtct cctcctgatc tgggcccagg ggctgaggca     120
ggctcccctc gcctcaggaa tgatgacagg cacaatagaa caacgggga acatttctgc     180 agagaaaggt ggctctatca tcttacaatg tcacctctcc tccaccacgg cacaagtgac    240
ccaggtcaac tgggagcagc aggaccagct tctggccatt gtaatgctg acttggggtg    300

```
gcacatctcc ccatccttca aggatcgagt ggccccaggt cccggcctgg gcctcaccct    360
ccagtcgctg accgtgaacg atacagggga gtacttctgc atctatcaca cctaccctga    420
tgggacgtac actgggagaa tcttcctgga ggtcctagaa agctcagtgg ctgagcacgg    480
tgccaggttc cagattccat tgcttggagc catggccgcg acgctggtgg tcatctgcac    540
agcagtcatc gtggtggtcg cgttgactag aaagaagaaa gccctcagaa tccattctgt    600
ggaaggtgac ctcaggagaa aatcagctgg acaggaggaa tggagcccca gtgctccctc    660 accccagga agctgtgtcc aggcagaagc tgcacctgct gggctctgtg agagcagcg     720 gggagaggac tgtgccgagc tgcatgacta cttcaatgtc ctgagttaca aagcctggg    780 taactgcagc ttcttcacag agactggtta gcaaccagag gcatcttctg gaagatacac    840
ttttgtcttt gctattatag atgaatatat aagcagctgt actctccatc agtgctgcgt    900
gtgtgtgtgt gtgtgtatgt gtgtgtgtgt tcagttgagt gaataaatgt catcctcttc    960
tccatcttca ttccttggc cttttcgttc tattccattt tgcattatgg caggcctagg    1020
gtgagtaacg tggatcttga tcataaatgc aaaattaaaa aatatcttga cctggtttta    1080
aatctggcag tttgagcaga tcctatgtct ctgagagaca cattcctcat aatggccagc    1140
attttgggct acaaggtttt gtggttgatg atgaggatgg catgactgca gagccatcct    1200
catctcattt tttcacgtca ttttcagtaa cttttcactca ttcaaaggca ggttataagt    1260
aagtcctggt agcagcctct atggggagat ttgagagtga ctaaatcttg gtatctgccc    1320
tcaagaactt acagttaaat ggggagacaa tgttgtcatg aaaaggtatt atagtaagga    1380
gagaaggaga catacacagg ccttcaggaa gagacgacag tttggggtga ggtagttggc    1440
ataggcttat ctgtgatgaa gtggcctggg agcaccaagg ggatgttgag gctagtctgg    1500
gaggagcagg agttttgtct agggaacttg taggaaattc ttggagctga aagtcccaca    1560
aagaaggccc tggcaccaag ggagtcagca aacttcagat tttattctct gggcaggcat    1620
ttcaagtttc cttttgctgt gacatactca tccattagac agcctgatac aggcctgtag    1680
cctcttccgg ccgtgtgtgc tggggaagcc ccaggaaacg cacatgccca cacagggagc    1740
caagtcgtag catttgggcc ttgatctacc ttttctgcat caatacactc ttgagccttt    1800 gaaaaagaa cgtttcccac taaaagaaa atgtggattt ttaaaatagg gactcttcct    1860 agggaaaaa gggggctgg gagtgataga gggtttaaaa aataaacacc ttcaaactaa    1920
cttcttcgaa ccctttttatt cactccctga cgactttgtg ctggggttgg ggtaactgaa    1980
ccgcttattt ctgtttaatt gcattcaggc tggatcttag aagactttta tccttccacc    2040
atctctctca gaggaatgag cggggaggtt ggatttactg gtgactgatt ttctttcatg    2100
ggccaaggaa ctgaaagaga atgtgaagca aggttgtgtc ttgcgcatgg ttaaaaataa    2160
agcattgtcc tgcttcctaa gacttagact ggggttgaca attgttttag caacaagaca    2220
attcaactat ttctcctagg attttttatta ttattatttt ttcactttc taccaaatgg    2280 gttacatagg aagaatgaac tgaaatctgt ccagagctcc aagtcctttg gaagaaagat    2340
tagatgaacg taaaaatgtt gttgtttgct gtggcagttt acagcatttt tcttgcaaaa    2400
ttagtgcaaa tctgttggaa atagaacaca attcacaaat tggaagtgaa ctaaaatgta    2460
atgacgaaaa gggagtagtg ttttgatttg gaggaggtgt atattcggca gaggttggac    2520
tgagagttgg gtgttatttta acataattat ggtaattggg aaacatttat aaacactatt    2580
gggatggtga taaaatacaa aagggcctat agatgttaga aatgggtcag gttactgaaa    2640
tgggattcaa tttgaaaaaa attttttttaa atagaactca ctgaactaga ttctcctctg    2700
```

```
agaaccagag aagaccattt catagttgga ttcctggaga catgcgctat ccaccacgta    2760
gccactttcc acatgtggcc atcaaccact taagatgggg ttagtttaaa tcaagatgtg    2820
ctgttataat tggtataagc ataaaatcac actagattct ggagatttaa tatgaataat    2880
aagaatacta tttcagtagt tttggtatat tgtgtgtcaa aaatgataat attttggatg    2940
tattgggtga ataaaatat taacattaaa aaaaaaa                              2978
```

```
<210> SEQ ID NO 218
<211> LENGTH: 244
<212> TYPE: PRT
<213> ORGANISM: Homo sapiens
<220> FEATURE:
<221> NAME/KEY: misc_feature
<223> OTHER INFORMATION: Human TIGIT protein

<400> SEQUENCE: 218
```

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly
```

```
<210> SEQ ID NO 219
<211> LENGTH: 312
<212> TYPE: PRT
<213> ORGANISM: Macaca fascicularis
<220> FEATURE:
<221> NAME/KEY: misc_feature
<223> OTHER INFORMATION: Cynomolgus monkey TIGIT protein

<400> SEQUENCE: 219
```

```
Met Ala Phe Leu Val Ala Pro Pro Met Gln Phe Val Tyr Leu Leu Lys
1               5                   10                  15

Thr Leu Cys Val Phe Asn Met Val Phe Ala Lys Pro Gly Phe Ser Glu
            20                  25                  30

Thr Val Phe Ser His Arg Leu Ser Phe Thr Val Leu Ser Ala Val Gly
        35                  40                  45

Tyr Phe Arg Trp Gln Lys Arg Pro His Leu Leu Pro Val Ser Pro Leu
    50                  55                  60

Gly Arg Ser Met Arg Trp Cys Leu Phe Leu Ile Trp Ala Gln Gly Leu
65                  70                  75                  80

Arg Gln Ala Pro Leu Ala Ser Gly Met Met Thr Gly Thr Ile Glu Thr
                85                  90                  95

Thr Gly Asn Ile Ser Ala Lys Lys Gly Gly Ser Val Ile Leu Gln Cys
            100                 105                 110

His Leu Ser Ser Thr Met Ala Gln Val Thr Gln Val Asn Trp Glu Gln
        115                 120                 125

His Asp His Ser Leu Leu Ala Ile Arg Asn Ala Glu Leu Gly Trp His
    130                 135                 140

Ile Tyr Pro Ala Phe Lys Asp Arg Val Ala Pro Gly Pro Gly Leu Gly
145                 150                 155                 160

Leu Thr Leu Gln Ser Leu Thr Met Asn Asp Thr Gly Glu Tyr Phe Cys
                165                 170                 175

Thr Tyr His Thr Tyr Pro Asp Gly Thr Tyr Arg Gly Arg Ile Phe Leu
            180                 185                 190

Glu Val Leu Glu Ser Ser Val Ala Glu His Ser Ala Arg Phe Gln Ile
        195                 200                 205

Pro Leu Leu Gly Ala Met Ala Met Met Leu Val Val Ile Cys Ile Ala
    210                 215                 220

Val Ile Val Val Val Val Leu Ala Arg Lys Lys Lys Ser Leu Arg Ile
225                 230                 235                 240

His Ser Val Glu Ser Gly Leu Gln Arg Lys Ser Thr Gly Gln Glu Glu
                245                 250                 255

Gln Ile Pro Ser Ala Pro Ser Pro Pro Gly Ser Cys Val Gln Ala Glu
            260                 265                 270

Ala Ala Pro Ala Gly Leu Cys Gly Glu Gln Gln Gly Asp Asp Cys Ala
        275                 280                 285

Glu Leu His Asp Tyr Phe Asn Val Leu Ser Tyr Arg Ser Leu Gly Ser
    290                 295                 300

Cys Ser Phe Phe Thr Glu Thr Gly
305                 310

<210> SEQ ID NO 220
<211> LENGTH: 241
<212> TYPE: PRT
<213> ORGANISM: Mus musculus
<220> FEATURE:
<221> NAME/KEY: misc_feature
<223> OTHER INFORMATION: Mouse TIGIT protein

<400> SEQUENCE: 220

Met His Gly Trp Leu Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
            20                  25                  30

Asn Ile Ser Ala Glu Glu Gly Gly Ser Val Ile Leu Gln Cys His Phe
```

-continued

```
                35                  40                  45
Ser Ser Asp Thr Ala Glu Val Thr Gln Val Asp Trp Lys Gln Gln Asp
 50                  55                  60
Gln Leu Leu Ala Ile Tyr Ser Val Asp Leu Gly Trp His Val Ala Ser
 65                  70                  75                  80
Val Phe Ser Asp Arg Val Val Pro Gly Pro Ser Leu Gly Leu Thr Phe
                 85                  90                  95
Gln Ser Leu Thr Met Asn Asp Thr Gly Glu Tyr Phe Cys Thr Tyr His
                100                 105                 110
Thr Tyr Pro Gly Gly Ile Tyr Lys Gly Arg Ile Phe Leu Lys Val Gln
                115                 120                 125
Glu Ser Ser Val Ala Gln Phe Gln Thr Ala Pro Leu Gly Gly Thr Met
130                 135                 140
Ala Ala Val Leu Gly Leu Ile Cys Leu Met Val Thr Gly Val Thr Val
145                 150                 155                 160
Leu Ala Arg Lys Lys Ser Ile Arg Met His Ser Ile Glu Ser Gly Leu
                165                 170                 175
Gly Arg Thr Glu Ala Glu Pro Gln Glu Trp Asn Leu Arg Ser Leu Ser
                180                 185                 190
Ser Pro Gly Ser Pro Val Gln Thr Gln Thr Ala Pro Ala Gly Pro Cys
                195                 200                 205
Gly Glu Gln Ala Glu Asp Asp Tyr Ala Asp Pro Gln Glu Tyr Phe Asn
210                 215                 220
Val Leu Ser Tyr Arg Ser Leu Glu Ser Phe Ile Ala Val Ser Lys Thr
225                 230                 235                 240
Gly

<210> SEQ ID NO 221
<211> LENGTH: 9
<212> TYPE: PRT
<213> ORGANISM: Artificial Sequence
<220> FEATURE:
<223> OTHER INFORMATION: Synthetic: Clone 2C VH CDR1

<400> SEQUENCE: 221

Phe Thr Phe Thr Asp Tyr Tyr Met Asp
 1               5

<210> SEQ ID NO 222
<211> LENGTH: 19
<212> TYPE: PRT
<213> ORGANISM: Artificial Sequence
<220> FEATURE:
<223> OTHER INFORMATION: Synthetic: Clone 2C VH CDR2

<400> SEQUENCE: 222

Arg Thr Arg Asn Lys Val Asn Ser Tyr Tyr Thr Glu Tyr Ala Ala Ser
 1               5                  10                  15

Val Lys Gly

<210> SEQ ID NO 223
<211> LENGTH: 19
<212> TYPE: PRT
<213> ORGANISM: Artificial Sequence
<220> FEATURE:
<223> OTHER INFORMATION: Synthetic: Clone 2C VH CDR3

<400> SEQUENCE: 223

Ala Arg Gly Gln Tyr Tyr Tyr Gly Ser Asp Arg Arg Gly Tyr Tyr Tyr
```

-continued

```
1               5                   10                  15

Met Asp Val

<210> SEQ ID NO 224
<211> LENGTH: 9
<212> TYPE: PRT
<213> ORGANISM: Artificial Sequence
<220> FEATURE:
<223> OTHER INFORMATION: Synthetic: Clones 13A, 13C, and 13D VH CDR1

<400> SEQUENCE: 224

Gly Thr Phe Leu Ser Ser Ala Ile Ser
1               5

<210> SEQ ID NO 225
<211> LENGTH: 17
<212> TYPE: PRT
<213> ORGANISM: Artificial Sequence
<220> FEATURE:
<223> OTHER INFORMATION: Synthetic: Clone 13A VH CDR2

<400> SEQUENCE: 225

Ser Leu Ile Pro Tyr Phe Gly Thr Ala Asn Tyr Ala Gln Lys Phe Gln
1               5                   10                  15

Gly

<210> SEQ ID NO 226
<211> LENGTH: 9
<212> TYPE: PRT
<213> ORGANISM: Artificial Sequence
<220> FEATURE:
<223> OTHER INFORMATION: Synthetic: Clone 13B VH CDR1

<400> SEQUENCE: 226

Gly Thr Phe Ser Ala Trp Ala Ile Ser
1               5

<210> SEQ ID NO 227
<211> LENGTH: 17
<212> TYPE: PRT
<213> ORGANISM: Artificial Sequence
<220> FEATURE:
<223> OTHER INFORMATION: Synthetic: Clones 13B and 13D VH CDR2

<400> SEQUENCE: 227

Ser Ile Ile Pro Tyr Phe Gly Lys Ala Asn Tyr Ala Gln Lys Phe Gln
1               5                   10                  15

Gly

<210> SEQ ID NO 228
<211> LENGTH: 18
<212> TYPE: PRT
<213> ORGANISM: Artificial Sequence
<220> FEATURE:
<223> OTHER INFORMATION: Synthetic: Clone 13B VH CDR3

<400> SEQUENCE: 228

Ala Arg Gly Pro Ser Glu Val Ser Gly Ile Leu Gly Tyr Val Trp Phe
1               5                   10                  15

Asp Pro

<210> SEQ ID NO 229
<211> LENGTH: 17
<212> TYPE: PRT
```

```
<213> ORGANISM: Artificial Sequence
<220> FEATURE:
<223> OTHER INFORMATION: Synthetic: Clone 13C VH CDR2

<400> SEQUENCE: 229

Ser Ile Ile Pro Leu Phe Gly Lys Ala Asn Tyr Ala Gln Lys Phe Gln
1               5                   10                  15

Gly

<210> SEQ ID NO 230
<211> LENGTH: 18
<212> TYPE: PRT
<213> ORGANISM: Artificial Sequence
<220> FEATURE:
<223> OTHER INFORMATION: Synthetic: Clones 13C and 13D VH CDR3

<400> SEQUENCE: 230

Ala Arg Gly Pro Ser Glu Val Lys Gly Ile Leu Gly Tyr Val Trp Phe
1               5                   10                  15

Asp Pro

<210> SEQ ID NO 231
<211> LENGTH: 9
<212> TYPE: PRT
<213> ORGANISM: Artificial Sequence
<220> FEATURE:
<223> OTHER INFORMATION: Synthetic: Clone 16C VH CDR1

<400> SEQUENCE: 231

Gly Thr Phe Arg Glu Tyr Ala Ile Ser
1               5

<210> SEQ ID NO 232
<211> LENGTH: 17
<212> TYPE: PRT
<213> ORGANISM: Artificial Sequence
<220> FEATURE:
<223> OTHER INFORMATION: Synthetic: Clone 16C VH CDR2

<400> SEQUENCE: 232

Gly Ile His Pro Ile Phe Gly Thr Ala Arg Tyr Ala Gln Lys Phe Gln
1               5                   10                  15

Gly

<210> SEQ ID NO 233
<211> LENGTH: 9
<212> TYPE: PRT
<213> ORGANISM: Artificial Sequence
<220> FEATURE:
<223> OTHER INFORMATION: Synthetic: Clones 16D and 16E VH CDR1

<400> SEQUENCE: 233

Gly Thr Phe Ser Asp Tyr Pro Ile Ser
1               5

<210> SEQ ID NO 234
<211> LENGTH: 17
<212> TYPE: PRT
<213> ORGANISM: Artificial Sequence
<220> FEATURE:
<223> OTHER INFORMATION: Synthetic: Clones 16B, 16D, and 16E VH CDR2

<400> SEQUENCE: 234

Gly Ile Ile Pro Ile Val Gly Gly Ala Asn Tyr Ala Gln Lys Phe Gln
1               5                   10                  15
```

Gly

<210> SEQ ID NO 235
<211> LENGTH: 14
<212> TYPE: PRT
<213> ORGANISM: Artificial Sequence
<220> FEATURE:
<223> OTHER INFORMATION: Synthetic: Clone 16C VH CDR3

<400> SEQUENCE: 235

Thr Arg Gln Ser Thr Trp His Lys Leu Tyr Gly Thr Asp Val
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Synthetic: Clone 16D VH CDR3

<400> SEQUENCE: 236

Thr Arg Gln Ser Thr Trp His Lys Leu Phe Gly Thr Asp Val
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Synthetic: Clone 16E VH CDR3

<400> SEQUENCE: 237

Ala Arg Gln Ser Thr Trp His Lys Val Tyr Gly Thr Asp Val
1               5                   10

<210> SEQ ID NO 238
<211> LENGTH: 17
<212> TYPE: PRT
<213> ORGANISM: Artificial Sequence
<220> FEATURE:
<223> OTHER INFORMATION: Synthetic: Clone 25A VH CDR2

<400> SEQUENCE: 238

Trp Ile Ser Ala Tyr Asn Gly Asn Thr Lys Tyr Ala Gln Lys Leu Gln
1               5                   10                  15

Gly

<210> SEQ ID NO 239
<211> LENGTH: 9
<212> TYPE: PRT
<213> ORGANISM: Artificial Sequence
<220> FEATURE:
<223> OTHER INFORMATION: Synthetic: Clones 25B, 25C, and 25D VH CDR1

<400> SEQUENCE: 239

Tyr Thr Phe Thr Ser Tyr Pro Ile Gly
1               5

<210> SEQ ID NO 240
<211> LENGTH: 17
<212> TYPE: PRT
<213> ORGANISM: Artificial Sequence
<220> FEATURE:
<223> OTHER INFORMATION: Synthetic: Clones 25B, 25C, and 25D VH CDR2

<400> SEQUENCE: 240

```
Trp Ile Ser Ser Tyr Asn Gly Asn Thr Asn Tyr Ala Gln Lys Leu Gln
1               5                   10                  15

Gly

<210> SEQ ID NO 241
<211> LENGTH: 18
<212> TYPE: PRT
<213> ORGANISM: Artificial Sequence
<220> FEATURE:
<223> OTHER INFORMATION: Synthetic: Clone 25C VH CDR3

<400> SEQUENCE: 241

Ala Arg Gly Ala Ser Ser Phe Trp Ser Gly Asp Val Leu Gly Ala Phe
1               5                   10                  15

Asp Ile

<210> SEQ ID NO 242
<211> LENGTH: 18
<212> TYPE: PRT
<213> ORGANISM: Artificial Sequence
<220> FEATURE:
<223> OTHER INFORMATION: Synthetic: Clone 25D VH CDR3

<400> SEQUENCE: 242

Ala Arg Asp Leu Lys Ser Phe Trp Ser Gly Asp Val Leu Gly Ala Phe
1               5                   10                  15

Asp Ile

<210> SEQ ID NO 243
<211> LENGTH: 9
<212> TYPE: PRT
<213> ORGANISM: Artificial Sequence
<220> FEATURE:
<223> OTHER INFORMATION: Synthetic: Clone 25E VH CDR1

<400> SEQUENCE: 243

Tyr Thr Phe Thr Ser Tyr Ala Ile Ala
1               5

<210> SEQ ID NO 244
<211> LENGTH: 18
<212> TYPE: PRT
<213> ORGANISM: Artificial Sequence
<220> FEATURE:
<223> OTHER INFORMATION: Synthetic: Clone 25E VH CDR3

<400> SEQUENCE: 244

Ala Arg Ser Gly Ser Ser Phe Trp Ser Gly Asp Val Leu Gly Ala Phe
1               5                   10                  15

Asp Ile

<210> SEQ ID NO 245
<211> LENGTH: 128
<212> TYPE: PRT
<213> ORGANISM: Artificial Sequence
<220> FEATURE:
<223> OTHER INFORMATION: Synthetic: Clone 2C VH

<400> SEQUENCE: 245

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30
```

Tyr Met Asp Trp Val Arg Gln Ala Pro Gly Lys Gly Leu Glu Trp Val
            35                  40                  45

Gly Arg Thr Arg Asn Lys Val Asn Ser Tyr Tyr Thr Glu Tyr Ala Ala
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Gly Gln Tyr Tyr Gly Ser Asp Arg Arg Gly Tyr
                100                 105                 110

Tyr Tyr Met Asp Val Trp Gly Gln Gly Thr Thr Val Thr Val Ser Ser
            115                 120                 125

<210> SEQ ID NO 246
<211> LENGTH: 125
<212> TYPE: PRT
<213> ORGANISM: Artificial Sequence
<220> FEATURE:
<223> OTHER INFORMATION: Synthetic: Clone 13A VH

<400> SEQUENCE: 246

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Leu Ser Ser
                20                  25                  30

Ala Ile Ser Trp Val Arg Gln Ala Pro Gly Gln Gly Leu Glu Trp Met
            35                  40                  45

Gly Ser Leu Ile Pro Tyr Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
                100                 105                 110

Asp Pro Trp Gly Gln Gly Thr Leu Val Thr Val Ser Ser
            115                 120                 125

<210> SEQ ID NO 247
<211> LENGTH: 125
<212> TYPE: PRT
<213> ORGANISM: Artificial Sequence
<220> FEATURE:
<223> OTHER INFORMATION: Synthetic: Clone 13B VH

<400> SEQUENCE: 247

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Trp
                20                  25                  30

Ala Ile Ser Trp Val Arg Gln Ala Pro Gly Gln Gly Leu Glu Trp Met
            35                  40                  45

Gly Ser Ile Ile Pro Tyr Phe Gly Lys Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys 85                  90                  95

Ala Arg Gly Pro Ser Glu Val Ser Gly Ile Leu Gly Tyr Val Trp Phe
                100                 105                 110

Asp Pro Trp Gly Gln Gly Thr Leu Val Thr Val Ser Ser
        115                 120                 125

<210> SEQ ID NO 248
<211> LENGTH: 125
<212> TYPE: PRT
<213> ORGANISM: Artificial Sequence
<220> FEATURE:
<223> OTHER INFORMATION: Synthetic: Clone 13C VH

<400> SEQUENCE: 248

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Leu Ser Ser
                20                  25                  30

Ala Ile Ser Trp Val Arg Gln Ala Pro Gly Gln Gly Leu Glu Trp Met
            35                  40                  45

Gly Ser Ile Ile Pro Leu Phe Gly Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Lys Gly Ile Leu Gly Tyr Val Trp Phe
                100                 105                 110

Asp Pro Trp Gly Gln Gly Thr Leu Val Thr Val Ser Ser
        115                 120                 125

<210> SEQ ID NO 249
<211> LENGTH: 125
<212> TYPE: PRT
<213> ORGANISM: Artificial Sequence
<220> FEATURE:
<223> OTHER INFORMATION: Synthetic: Clone 13D VH

<400> SEQUENCE: 249

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Leu Ser Ser
                20                  25                  30

Ala Ile Ser Trp Val Arg Gln Ala Pro Gly Gln Gly Leu Glu Trp Met
            35                  40                  45

Gly Ser Ile Ile Pro Tyr Phe Gly Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Lys Gly Ile Leu Gly Tyr Val Trp Phe
                100                 105                 110

Asp Pro Trp Gly Gln Gly Thr Leu Val Thr Val Ser Ser
        115                 120                 125

<210> SEQ ID NO 250
<211> LENGTH: 121

```
<212> TYPE: PRT
<213> ORGANISM: Artificial Sequence
<220> FEATURE:
<223> OTHER INFORMATION: Synthetic: Clone 16C VH

<400> SEQUENCE: 250

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Glu Tyr
            20                  25                  30

Ala Ile Ser Trp Val Arg Gln Ala Pro Gly Gln Gly Leu Glu Trp Met
        35                  40                  45

Gly Gly Ile His Pro Ile Phe Gly Thr Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gln Ser Thr Trp His Lys Leu Tyr Gly Thr Asp Val Trp Gly
            100                 105                 110

Gln Gly Thr Thr Val Thr Val Ser Ser
        115                 120

<210> SEQ ID NO 251
<211> LENGTH: 121
<212> TYPE: PRT
<213> ORGANISM: Artificial Sequence
<220> FEATURE:
<223> OTHER INFORMATION: Synthetic: Clone 16D VH

<400> SEQUENCE: 251

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Pro Ile Ser Trp Val Arg Gln Ala Pro Gly Gln Gly Leu Glu Trp Met
        35                  40                  45

Gly Gly Ile Ile Pro Ile Val Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gln Ser Thr Trp His Lys Leu Phe Gly Thr Asp Val Trp Gly
            100                 105                 110

Gln Gly Thr Thr Val Thr Val Ser Ser
        115                 120

<210> SEQ ID NO 252
<211> LENGTH: 121
<212> TYPE: PRT
<213> ORGANISM: Artificial Sequence
<220> FEATURE:
<223> OTHER INFORMATION: Synthetic: Clone 16E VH

<400> SEQUENCE: 252

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
```

-continued

```
                20                  25                  30
Pro Ile Ser Trp Val Arg Gln Ala Pro Gly Gln Gly Leu Glu Trp Met
            35                  40                  45
Gly Gly Ile Ile Pro Ile Val Gly Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gln Ser Thr Trp His Lys Val Tyr Gly Thr Asp Val Trp Gly
            100                 105                 110
Gln Gly Thr Thr Val Thr Val Ser Ser
        115                 120
```

<210> SEQ ID NO 253
<211> LENGTH: 125
<212> TYPE: PRT
<213> ORGANISM: Artificial Sequence
<220> FEATURE:
<223> OTHER INFORMATION: Synthetic: Clone 25A VH

<400> SEQUENCE: 253

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Ala Ile Ser Trp Val Arg Gln Ala Pro Gly Gln Gly Leu Glu Trp Met
            35                  40                  45
Gly Trp Ile Ser Ala Tyr Asn Gly Asn Thr Lys Tyr Ala Gln Lys Leu
        50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Leu Ser Ser Phe Trp Ser Gly Asp Val Leu Gly Ala Phe
            100                 105                 110
Asp Ile Trp Gly Gln Gly Thr Met Val Thr Val Ser Ser
        115                 120                 125
```

<210> SEQ ID NO 254
<211> LENGTH: 125
<212> TYPE: PRT
<213> ORGANISM: Artificial Sequence
<220> FEATURE:
<223> OTHER INFORMATION: Synthetic: Clone 25B VH

<400> SEQUENCE: 254

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Pro Ile Gly Trp Val Arg Gln Ala Pro Gly Gln Gly Leu Glu Trp Met
            35                  40                  45
Gly Trp Ile Ser Ser Tyr Asn Gly Asn Thr Asn Tyr Ala Gln Lys Leu
        50                  55                  60
Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
             85                  90                  95

Ala Arg Asp Leu Ser Ser Phe Trp Ser Gly Asp Val Leu Gly Ala Phe
            100                 105                 110

Asp Ile Trp Gly Gln Gly Thr Met Val Thr Val Ser Ser
        115                 120                 125

<210> SEQ ID NO 255
<211> LENGTH: 125
<212> TYPE: PRT
<213> ORGANISM: Artificial Sequence
<220> FEATURE:
<223> OTHER INFORMATION: Synthetic: Clone 25C VH

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Pro Ile Gly Trp Val Arg Gln Ala Pro Gly Gln Gly Leu Glu Trp Met
        35                  40                  45

Gly Trp Ile Ser Ser Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ala Ser Ser Phe Trp Ser Gly Asp Val Leu Gly Ala Phe
            100                 105                 110

Asp Ile Trp Gly Gln Gly Thr Met Val Thr Val Ser Ser
        115                 120                 125

<210> SEQ ID NO 256
<211> LENGTH: 125
<212> TYPE: PRT
<213> ORGANISM: Artificial Sequence
<220> FEATURE:
<223> OTHER INFORMATION: Synthetic: Clone 25D VH

<400> SEQUENCE: 256

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Pro Ile Gly Trp Val Arg Gln Ala Pro Gly Gln Gly Leu Glu Trp Met
        35                  40                  45

Gly Trp Ile Ser Ser Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Lys Ser Phe Trp Ser Gly Asp Val Leu Gly Ala Phe
            100                 105                 110

Asp Ile Trp Gly Gln Gly Thr Met Val Thr Val Ser Ser
        115                 120                 125

<210> SEQ ID NO 257
```

```
<211> LENGTH: 125
<212> TYPE: PRT
<213> ORGANISM: Artificial Sequence
<220> FEATURE:
<223> OTHER INFORMATION: Synthetic: Clone 25E VH

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ala Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gly Ser Ser Phe Trp Ser Gly Asp Val Leu Gly Ala Phe
            100                 105                 110

Asp Ile Trp Gly Gln Gly Thr Met Val Thr Val Ser Ser
        115                 120                 125

<210> SEQ ID NO 258
<211> LENGTH: 15
<212> TYPE: PRT
<213> ORGANISM: Homo sapiens
<220> FEATURE:
<221> NAME/KEY: misc_feature
<223> OTHER INFORMATION: hTIGIT 68-82 epitope

<400> SEQUENCE: 258

Ile Cys Asn Ala Asp Leu Gly Trp His Ile Ser Pro Ser Phe Lys
1               5                   10                  15

<210> SEQ ID NO 259
<211> LENGTH: 1365
<212> TYPE: DNA
<213> ORGANISM: Artificial Sequence
<220> FEATURE:
<223> OTHER INFORMATION: Synthetic: Clone 13 heavy chain hIgG1 (and
      hIgG1 afucosylated) nucleotide sequence

<400> SEQUENCE: 259
caggtgcagc tggtgcagtc tggggctgag gtgaagaagc ctgggtcctc tgtgaaggtc    60
tcctgcaagg cttctggagg caccttcagc agctatgcta tcagctgggt gcgacaggcc   120
cctggacaag gcttgagtg gatgggaagc atcatcccta tctttggtac agcaaactac   180
gcacagaagt tccagggcag agtcaccatt actgctgatg aatccaccag cacagcctac   240
atggagctga gcagcctgag atctgaggac actgctgtgt actactgtgc cagaggccct   300
tctgaagtag gagcaatact gggatatgta tggtttgacc catggggaca gggtacattg   360
gtcaccgtct cctcagctag caccaagggc ccatctgtct tccccctggc accctcctcc   420
aagagcacct ctgggggcac agctgccctg ggctgcctgg tcaaggacta cttccctgaa   480
cctgtgacag tgtcctggaa ctcaggagcc ctgaccagcg gcgtgcacac cttcccggct   540
gtcctacagt cctcaggact ctactccctc agcagcgtgg tgaccgtgcc ctccagcagc   600
ttgggcaccc agacctacat ctgcaacgtg aatcacaagc ccagcaacac caaggtggac   660
```

```
aagaaagttg agcccaaatc ttgtgacaaa actcacacat gcccaccgtg cccagcacct    720
gaactcctgg gggaccgtc  agtcttcctc ttccccccaa acccaagga  caccctcatg    780 atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc agcccccatc   1020
gagaaaacca tctccaaagc caaagggcag ccccgagaac acaggtttta cccctgccc   1080 ccatcccggg atgagctgac caagaaccag gtcagcctga cctgcctggt caaaggcttc   1140
tatcccagcg acatcgccgt ggagtgggag agcaatgggc agccggagaa caactacaag   1200
accacgcctc ccgtgctgga ctccgacggc tccttcttcc tctacagcaa gctcaccgtg   1260
gacaagagca ggtggcagca ggggaacgtc ttctcatgct ccgtgatgca tgaggctctg   1320
cacaaccact acacacagaa gagcctctcc ctgtctccgg gcaaa                   1365
```

<210> SEQ ID NO 260
<211> LENGTH: 455
<212> TYPE: PRT
<213> ORGANISM: Artificial Sequence
<220> FEATURE:
<223> OTHER INFORMATION: Synthetic: Clone 13 heavy chain hIgG1 (and
      hIgG1 afucosylated) amino acid sequence <400> SEQUENCE: 260

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240
```

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 261
<211> LENGTH: 1365
<212> TYPE: DNA
<213> ORGANISM: Artificial Sequence
<220> FEATURE:
<223> OTHER INFORMATION: Synthetic: Clone 13 heavy chain hIgG1 LALA-PG
      nucleotide sequence

<400> SEQUENCE: 261
caggtgcagc tggtgcagtc tggggctgag gtgaagaagc ctgggtcctc tgtgaaggtc      60
tcctgcaagg cttctggagg cacttcagc agctatgcta tcagctgggt gcgacaggcc     120
cctggacaag ggcttgagtg gatgggaagc atcatcccta tctttggtac agcaaactac     180
gcacagaagt tccagggcag agtcaccatt actgctgatg aatccaccag cacagcctac     240
atggagctga gcagcctgag atctgaggac actgctgtgt actactgtgc cagaggccct     300
tctgaagtag gagcaatact gggatatgta tggtttgacc catggggaca gggtacattg     360
gtcaccgtct cctcagctag caccaagggc ccatctgtct tccccctggc accctcctcc     420
aagagcacct ctgggggcac agctgccctg ggctgcctgg tcaaggacta cttccctgaa     480
cctgtgacag tgtcctggaa ctcaggagcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaagctgctg gggaccgtc agtcttcctc ttccccccaa aacccaagga caccctcatg     780

-continued

```
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctcgg ggcccccatc   1020
gagaaaacca tctccaaagc caagggcag ccccgagaac acaggttta caccctgccc     1080
```

```
ccatcccggg atgagctgac caagaaccag gtcagcctga cctgcctggt caaaggcttc   1140
tatcccagcg acatcgccgt ggagtgggag agcaatgggc agccggagaa caactacaag   1200
accacgcctc ccgtgctgga ctccgacggc tccttcttcc tctacagcaa gctcaccgtg   1260
gacaagagca ggtggcagca ggggaacgtc ttctcatgct ccgtgatgca tgaggctctg   1320
cacaaccact acacacagaa gagcctctcc ctgtctccgg gcaaa               1365
```

<210> SEQ ID NO 262
<211> LENGTH: 455
<212> TYPE: PRT
<213> ORGANISM: Artificial Sequence
<220> FEATURE:
<223> OTHER INFORMATION: Synthetic: Clone 13 heavy chain hIgG1 LALA-PG
      amino acid sequence

<400> SEQUENCE: 262

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

```
Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Gly Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 263
<211> LENGTH: 1356
<212> TYPE: DNA
<213> ORGANISM: Artificial Sequence
<220> FEATURE:
<223> OTHER INFORMATION: Synthetic: Clone 13 heavy chain hIgG4 S228P
      nucleotide sequence

<400> SEQUENCE: 263
caggtgcagc tggtgcagtc tggggctgag gtgaagaagc ctgggtcctc tgtgaaggtc    60
tcctgcaagg cttctggagg caccttcagc agctatgcta tcagctgggt gcgacaggcc   120
cctggacaag gcttgagtg gatgggaagc atcatcccta tctttggtac agcaaactac   180
gcacagaagt tccagggcag agtcaccatt actgctgatg aatccaccag cacagcctac   240
atggagctga gcagcctgag atctgaggac actgctgtgt actactgtgc cagaggccct   300
tctgaagtag gagcaatact gggatatgta tggtttgacc catggggaca gggtacattg   360
gtcaccgtct cctcagctag caccaagggc ccatctgtct tccccctggc cccttgctcc   420
agaagcacat ctgagagcac agcggccctg ggatgcctgg tcaaggacta tttccctgag   480
ccggtgaccg taagctggaa ctctggagcc ctgaccagcg gcgtgcacac cttcccagct   540
gtcctgcagt cttcagggct ctactccctc agcagtgtgg tgactgtacc ctccagcagc   600
ttgggcacca agacctacac ctgcaacgta atcacaagc ccagcaacac caaggtggac   660
aagagagttg agtccaaata tggtccccca tgcccaccct gcccagcacc agagttcctg   720
gggggaccat ctgtcttcct cttcccccca aaacccaagg ataccctcat gatctcccgg   780
acccctgagg tcacatgtgt ggtggtggac gtgagccagg aggaccccga ggtccagttc   840
```

```
aactggtatg tggatggcgt ggaagtgcat aatgctaaga caaagccacg ggaggagcag    900
ttcaacagca cctaccgtgt ggtcagcgtc ctcacagtgc tgcaccagga ctggctgaat    960
ggcaaggagt acaaatgcaa ggtctccaac aaaggcctcc catcctccat cgagaaaacc   1020
atctccaaag ccaaagggca accccgggaa ccacaggtat acaccctgcc tccatcccaa   1080
gaagagatga ccaagaacca ggtcagcctg acctgcctgg tcaaaggctt ctacccctct   1140
gacattgccg tggagtggga gagcaatggg cagccagaga caactacaa gaccacacct    1200 cccgtgctgg actccgatgg ctccttcttc ctgtactccc ggctcacagt ggacaagagc   1260
aggtggcagg agggaaatgt cttctcctgc tccgtgatgc atgaggctct gcacaaccac   1320
tacacacaga gagcctctc cctgtctctg ggcaaa                              1356
```

<210> SEQ ID NO 264
<211> LENGTH: 452
<212> TYPE: PRT
<213> ORGANISM: Artificial Sequence
<220> FEATURE:
<223> OTHER INFORMATION: Synthetic: Clone 13 heavy chain hIgG4 S228P
   amino acid sequence

<400> SEQUENCE: 264

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 265
<211> LENGTH: 1365
<212> TYPE: DNA
<213> ORGANISM: Artificial Sequence
<220> FEATURE:
<223> OTHER INFORMATION: Synthetic: Clone 13A heavy chain hIgG1 (and
      hIgG1 afucosylated) nucleotide sequence

<400> SEQUENCE: 265
caggtgcagc tggtgcagtc tggggctgag gtgaagaagc ctgggtcctc tgtgaaggtc      60
tcctgcaagg cttctggagg caccttcctt agctctgcta tcagctgggt gcgacaggcc    120
cctggacaag gcttgagtg gatgggatct ctcatccctt attttggtac agcaaactac     180
gcacagaagt tccagggcag agtcaccatt actgctgatg aatccaccag cacagcctac    240
atggagctga gcagcctgag atctgaggac actgctgtgt actactgtgc cagaggccct    300
tctgaagtag gagcaatact gggatatgta tggtttgacc catggggaca gggtacattg    360
gtcaccgtct cctcagctag caccaagggc ccatctgtct tccccctggc accctcctcc    420
aagagcacct ctgggggcac agctgccctg ggctgcctgg tcaaggacta cttccctgaa    480
cctgtgacag tgtcctggaa ctcaggagcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagaaagttg agcccaaatc ttgtgacaaa actcacacat gcccaccgtg cccagcacct    720
gaactcctgg ggggaccgtc agtcttcctc ttccccccaa aacccaagga caccctcatg    780
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960

-continued

```
tggctgaatg caaggagta caagtgcaag gtctccaaca aagccctccc agcccccatc   1020
gagaaaacca tctccaaagc caaagggcag ccccgagaac acaggttta cccctgccc    1080 ccatcccggg atgagctgac caagaaccag tcagcctga cctgcctggt caaaggcttc   1140
tatcccagcg acatcgccgt ggagtgggag agcaatgggc agccggagaa caactacaag   1200
accacgcctc ccgtgctgga ctccgacggc tccttcttcc tctacagcaa gctcaccgtg   1260
gacaagagca ggtggcagca ggggaacgtc ttctcatgct ccgtgatgca tgaggctctg   1320
cacaaccact acacacagaa gagcctctcc ctgtctccgg gcaaa                  1365
```

<210> SEQ ID NO 266
<211> LENGTH: 455
<212> TYPE: PRT
<213> ORGANISM: Artificial Sequence
<220> FEATURE:
<223> OTHER INFORMATION: Synthetic: Clone 13A heavy chain hIgG1 (and hIgG1 afucosylated) amino acid sequence

<400> SEQUENCE: 266

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Leu Ser Ser
            20                  25                  30

Ala Ile Ser Trp Val Arg Gln Ala Pro Gly Gln Gly Leu Glu Trp Met
        35                  40                  45

Gly Ser Leu Ile Pro Tyr Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285
```

Gly Val Glu Val His Asn Ala Lys Thr Lys Pro Arg Glu Glu Gln Tyr
     290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 267
<211> LENGTH: 1365
<212> TYPE: DNA
<213> ORGANISM: Artificial Sequence
<220> FEATURE:
<223> OTHER INFORMATION: Synthetic: Clone 13B heavy chain hIgG1 (and
      hIgG1 afucosylated) nucleotide sequence

<400> SEQUENCE: 267
caggtgcagc tggtgcagtc tggggctgag gtgaagaagc ctgggtcctc tgtgaaggtc      60
tcctgcaagg cttctggagg caccttctct gcctgggcta tcagctgggt gcgacaggcc     120
cctggacaag gcttgagtg gatgggatcc atcatccctt attttggtaa ggcaaactac     180
gcacagaagt tccagggcag agtcaccatt actgctgatg aatccaccag cacagcctac     240
atggagctga gcagcctgag atctgaggac actgctgtgt actactgtgc cagaggccct     300
tctgaagtaa gtggtatact gggatatgta tggtttgacc catgggggaca gggtacattg     360 gtcaccgtct cctcagctag caccaagggc ccatctgtct tccccctggc accctcctcc     420
aagagcacct ctgggggcac agctgccctg ggctgcctgg tcaaggacta cttccctgaa     480
cctgtgacag tgtcctggaa ctcaggagcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaactcctgg ggggaccgtc agtcttcctc ttccccccaa aacccaagga caccctcatg     780 atctccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020

```
gagaaaacca tctccaaagc caagggcag ccccgagaac cacaggttta caccctgccc    1080
ccatcccggg atgagctgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacacagaa gagcctctcc ctgtctccgg gcaaa                   1365
```

<210> SEQ ID NO 268
<211> LENGTH: 455
<212> TYPE: PRT
<213> ORGANISM: Artificial Sequence
<220> FEATURE:
<223> OTHER INFORMATION: Synthetic: Clone 13B heavy chain hIgG1 (and
      hIgG1 afucosylated) amino acid sequence

<400> SEQUENCE: 268

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Trp
            20                  25                  30

Ala Ile Ser Trp Val Arg Gln Ala Pro Gly Gln Gly Leu Glu Trp Met
        35                  40                  45

Gly Ser Ile Ile Pro Tyr Phe Gly Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Ser Gly Ile Leu Gly Tyr Val Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300
```

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Asp Glu Leu Thr Lys
    355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
435                 440                 445

Leu Ser Leu Ser Pro Gly Lys
    450                 455

<210> SEQ ID NO 269
<211> LENGTH: 1365
<212> TYPE: DNA
<213> ORGANISM: Artificial Sequence
<220> FEATURE:
<223> OTHER INFORMATION: Synthetic: Clone 13C heavy chain hIgG1 (and
      hIgG1 afucosylated) nucleotide sequence

<400> SEQUENCE: 269
caggtgcagc tggtgcagtc tggggctgag gtgaagaagc ctgggtcctc tgtgaaggtc     60
tcctgcaagg cttctggagg caccttcctt agctctgcta tcagctgggt gcgacaggcc    120
cctggacaag gcttgagtg gatgggaagt atcatccctc tgtttggtaa ggcaaactac    180
gcacagaagt tccagggcag agtcaccatt actgctgatg aatccaccag cacagcctac    240
atggagctga gcagcctgag atctgaggac actgctgtgt actactgtgc cagaggccct    300
tctgaagtaa agggtatact gggatatgta tggtttgacc catggggaca gggtacattg    360
gtcaccgtct cctcagctag caccaagggc ccatctgtct tccccctggc accctcctcc    420
aagagcacct ctgggggcac agctgccctg ggctgcctgg tcaaggacta cttccctgaa    480
cctgtgacag tgtcctggaa ctcaggagcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagaaagttg agcccaaatc ttgtgacaaa actcacacat gcccaccgtg cccagcacct    720
gaactcctgg ggggaccgtc agtcttcctc ttccccccaa aacccaagga caccctcatg    780
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc agcccccatc   1020
gagaaaacca tctccaaagc caagggcag ccccgagaac acaggtttta cccctgccc    1080 ccatcccggg atgagctgac caagaaccag gtcagcctga cctgcctggt caaaggcttc   1140

```
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacacagaa gagcctctcc ctgtctccgg gcaaa                    1365
```

<210> SEQ ID NO 270
<211> LENGTH: 455
<212> TYPE: PRT
<213> ORGANISM: Artificial Sequence
<220> FEATURE:
<223> OTHER INFORMATION: Synthetic: Clone 13C heavy chain hIgG1 (and
      hIgG1 afucosylated) amino acid sequence

<400> SEQUENCE: 270

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Leu Ser Ser
            20                  25                  30

Ala Ile Ser Trp Val Arg Gln Ala Pro Gly Gln Gly Leu Glu Trp Met
        35                  40                  45

Gly Ser Ile Ile Pro Leu Phe Gly Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Lys Gly Ile Leu Gly Tyr Val Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320
```

```
Trp Leu Asn Gly Lys Glu Tyr Lys Cys Lys Val Ser Asn Lys Ala Leu
            325                 330                 335
Pro Ala Pro Ile Glu Lys Thr Ile Ser Lys Ala Lys Gly Gln Pro Arg
        340                 345                 350
Glu Pro Gln Val Tyr Thr Leu Pro Pro Ser Arg Asp Glu Leu Thr Lys
    355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
            405                 410                 415
Lys Leu Thr Val Asp Lys Ser Arg Trp Gln Gln Gly Asn Val Phe Ser
        420                 425                 430
Cys Ser Val Met His Glu Ala Leu His Asn His Tyr Thr Gln Lys Ser
    435                 440                 445
Leu Ser Leu Ser Pro Gly Lys
    450                 455
```

<210> SEQ ID NO 271
<211> LENGTH: 1365
<212> TYPE: DNA
<213> ORGANISM: Artificial Sequence
<220> FEATURE:
<223> OTHER INFORMATION: Synthetic: Clone 13D heavy chain hIgG1 (and
      hIgG1 afucosylated) nucleotide sequence

<400> SEQUENCE: 271

```
caggtgcagc tggtgcagtc tggggctgag gtgaagaagc ctgggtcctc tgtgaaggtc    60
tcctgcaagg cttctggagg caccttcctt agctctgcta tcagctgggt gcgacaggcc   120
cctggacaag gcttgagtg gatgggatcc atcatccctt attttggtaa ggcaaactac    180
gcacagaagt tccagggcag agtcaccatt actgctgatg aatccaccag cacagcctac   240
atggagctga gcagcctgag atctgaggac actgctgtgt actactgtgc cagaggccct   300
tctgaagtaa agggtatact gggatatgta tggtttgacc catggggaca gggtacattg   360
gtcaccgtct cctcagctag caccaagggc ccatctgtct tccccctggc acctcctcc    420
aagagcacct ctgggggcac agctgccctg ggctgcctgg tcaaggacta cttcctgaa    480
cctgtgacag tgtcctggaa ctcaggagcc ctgaccagcg gcgtgcacac cttcccggct   540
gtcctacagt cctcaggact ctactccctc agcagcgtgg tgaccgtgcc ctccagcagc   600
ttgggcaccc agacctacat ctgcaacgtg aatcacaagc ccagcaacac caaggtggac   660
aagaaagttg agcccaaatc ttgtgacaaa actcacacat gcccaccgtg cccagcacct   720
gaactcctgg ggggaccgtc agtcttcctc ttccccccaa acccaaggac accctcatg    780
atctccggga cccctgaggt cacatgcgtg gtggtggacg tgagccacga agaccctgag   840
gtcaagttca actggtacgt ggacggcgtg gaggtgcata atgccaagac aaagccgcgg   900
gaggagcagt acaacagcac gtaccgtgtg gtcagcgtcc tcaccgtcct gcaccaggac   960
tggctgaatg gcaaggagta caagtgcaag gtctccaaca aagccctccc agcccccatc  1020
gagaaaacca tctccaaagc caagggcag ccccgagaac acaggtttta caccctgccc   1080
ccatccggg atgagctgac caagaaccag gtcagcctga cctgcctggt caaaggcttc  1140
tatcccagcg acatcgccgt ggagtgggag agcaatgggc agccggagaa caactacaag  1200
```

```
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacacagaa gagcctctcc ctgtctccgg gcaaa                    1365
```

<210> SEQ ID NO 272
<211> LENGTH: 455
<212> TYPE: PRT
<213> ORGANISM: Artificial Sequence
<220> FEATURE:
<223> OTHER INFORMATION: Synthetic: Clone 13D heavy chain hIgG1 (and hIgG1 afucosylated) amino acid sequence

<400> SEQUENCE: 272

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Leu Ser Ser
            20                  25                  30

Ala Ile Ser Trp Val Arg Gln Ala Pro Gly Gln Gly Leu Glu Trp Met
        35                  40                  45

Gly Ser Ile Ile Pro Tyr Phe Gly Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Lys Gly Ile Leu Gly Tyr Val Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335
```

```
Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 273
<211> LENGTH: 657
<212> TYPE: DNA
<213> ORGANISM: Artificial Sequence
<220> FEATURE:
<223> OTHER INFORMATION: Synthetic: Clone 13, 13A, 13B, 13C, and 13D
      light chain hkappa (and afucosylated) nucleotide sequence

<400> SEQUENCE: 273
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaggcaag acgaatccct    300
atcacttttg gcggagggac caaggttgag atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657

<210> SEQ ID NO 274
<211> LENGTH: 219
<212> TYPE: PRT
<213> ORGANISM: Artificial Sequence
<220> FEATURE:
<223> OTHER INFORMATION: Synthetic: Clone 13, 13A, 13B, 13C, and 13D
      light chain hkappa (and afucosylated) amino acid sequence

<400> SEQUENCE: 274

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
```

```
              50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Arg Arg Ile Pro Ile Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 275
<211> LENGTH: 1365
<212> TYPE: DNA
<213> ORGANISM: Artificial Sequence
<220> FEATURE:
<223> OTHER INFORMATION: Synthetic: Clone 13 heavy chain mIgG2a (and afucosylated) nucleotide sequence

<400> SEQUENCE: 275

```
caggtgcagc tggtgcagtc tggggctgag gtgaagaagc ctgggtcctc tgtgaaggtc      60
tcctgcaagg cttctggagg caccttcagc agctatgcta tcagctgggt gcgacaggcc    120
cctggacaag gcttgagtg gatgggaagc atcatcccta tctttggtac agcaaactac    180
gcacagaagt tccagggcag agtcaccatt actgctgatg aatccaccag cacagcctac    240
atggagctga gcagcctgag atctgaggac actgctgtgt actactgtgc cagaggccct    300
tctgaagtag gagcaatact gggatatgta tggtttgacc catggggaca gggtacattg    360
gtcaccgtct cctcagctaa acaacagcc ccatcggtct atccgctagc cctgtgtgt     420
ggagatacaa ctggctcctc ggtgactcta ggatgcctgg tcaagggtta tttccctgag    480
ccagtgacct tgacctggaa ctctggatcc ctgtccagtg gtgtgcacac cttcccagct    540
gtcctgcagt ctgacctcta caccctcagc agctcagtga ctgtaacctc tagcacctgg    600
cccagccagt ccatcacctg caatgtggcc acccggcaa gcagcaccaa ggtggacaag    660
aaaattgagc ccagagggcc acaatcaag ccctgtcctc catgcaaatg cccagcacct    720
aacgctgctg gtggaccatc cgtcttcatc ttccctccaa agatcaagga tgtactcatg    780
atctccctga gccccatagt cacatgtgtg gtggtggatg tgagcgagga tgacccagat    840
gtccagatca gctggttgt gaacaacgtg aagtacaca cagctcagac acaaacccat    900
agagaggatt acaacagtac tctccgggtg gtcagtgccc tccccatcca gcaccaggac    960
tggatgagtg gcaaggagtt caatgcaag gtcaacaaca aagacctcgg ggcgcccatc   1020
gagagaacca tctcaaaaacc caaaggctca gtaagagctc cacaggtata tgtcttgcct   1080
```

```
ccaccagaag aagagatgac taagaaacag gtcactctga cctgcatggt cacagacttc    1140
atgcctgaag acatttacgt ggagtggacc aacaacggga aaacagagct aaactacaag    1200
aacactgaac cagtcctgga ctctgatggt tcttacttca tgtacagcaa gctgagagtg    1260
gaaaagaaga actgggtgga agaaatagc tactcctgtt cagtggtcca cgagggtctg    1320
cacaatcacc acacgactaa gagcttctcc cggactccgg gcaaa                    1365
```

<210> SEQ ID NO 276
<211> LENGTH: 455
<212> TYPE: PRT
<213> ORGANISM: Artificial Sequence
<220> FEATURE:
<223> OTHER INFORMATION: Synthetic: Clone 13 heavy chain mIgG2a (and afucosylated) amino acid sequence

<400> SEQUENCE: 276

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser Ala Lys Thr
        115                 120                 125

Thr Ala Pro Ser Val Tyr Pro Leu Ala Pro Val Cys Gly Asp Thr Thr
    130                 135                 140

Gly Ser Ser Val Thr Leu Gly Cys Leu Val Lys Gly Tyr Phe Pro Glu
145                 150                 155                 160

Pro Val Thr Leu Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Thr Ser Ser Thr Trp Pro Ser Gln Ser Ile Thr Cys Asn
        195                 200                 205

Val Ala His Pro Ala Ser Ser Thr Lys Val Asp Lys Lys Ile Glu Pro
    210                 215                 220

Arg Gly Pro Thr Ile Lys Pro Cys Pro Pro Cys Lys Cys Pro Ala Pro
225                 230                 235                 240

Asn Ala Ala Gly Gly Pro Ser Val Phe Ile Phe Pro Pro Lys Ile Lys
                245                 250                 255

Asp Val Leu Met Ile Ser Leu Ser Pro Ile Val Thr Cys Val Val Val
            260                 265                 270

Asp Val Ser Glu Asp Asp Pro Asp Val Gln Ile Ser Trp Phe Val Asn
        275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
```

```
                305                 310                 315                 320
        Trp Met Ser Gly Lys Glu Phe Lys Cys Lys Val Asn Asn Lys Asp Leu
                        325                 330                 335
        Gly Ala Pro Ile Glu Arg Thr Ile Ser Lys Pro Lys Gly Ser Val Arg
                        340                 345                 350
        Ala Pro Gln Val Tyr Val Leu Pro Pro Glu Glu Met Thr Lys
                        355                 360                 365
        Lys Gln Val Thr Leu Thr Cys Met Val Thr Asp Phe Met Pro Glu Asp
                370                 375                 380
        Ile Tyr Val Glu Trp Thr Asn Asn Gly Lys Thr Glu Leu Asn Tyr Lys
        385                 390                 395                 400
        Asn Thr Glu Pro Val Leu Asp Ser Asp Gly Ser Tyr Phe Met Tyr Ser
                        405                 410                 415
        Lys Leu Arg Val Glu Lys Lys Asn Trp Val Arg Asn Ser Tyr Ser
                        420                 425                 430
        Cys Ser Val Val His Glu Gly Leu His Asn His His Thr Thr Lys Ser
                        435                 440                 445
        Phe Ser Arg Thr Pro Gly Lys
            450                 455

<210> SEQ ID NO 277
<211> LENGTH: 1365
<212> TYPE: DNA
<213> ORGANISM: Artificial Sequence
<220> FEATURE:
<223> OTHER INFORMATION: Synthetic: Clone 13 heavy chain mIgG2a LALA-PG
      nucleotide sequence

<400> SEQUENCE: 277
caggtgcagc tggtgcagtc tgggctgag gtgaagaagc ctgggtcctc tgtgaaggtc      60
tcctgcaagg cttctggagg caccttcagc agctatgcta tcagctgggt gcgacaggcc    120
cctggacaag gcttgagtg gatgggaagc atcatcccta tctttggtac agcaaactac    180
gcacagaagt tccagggcag agtcaccatt actgctgatg aatccaccag cacagcctac    240
atggagctga gcagcctgag atctgaggac actgctgtgt actactgtgc cagaggccct    300
tctgaagtag gagcaatact gggatatgta tggtttgacc atggggacag ggtacattg     360
gtcaccgtct cctcagctaa acaacagcc catcggtct atccgctagc cctgtgtgt      420
ggagatacaa ctggctcctc ggtgactcta ggatgcctgg tcaagggtta tttccctgag   480
ccagtgacct tgacctggaa ctctggatcc ctgtccagtg tgtgcacac cttcccagct    540
gtcctgcagt ctgacctcta caccctcagc agctcagtga ctgtaacctc tagcacctgg   600
cccagccagt ccatcacctg caatgtggcc caccggcaa gcagcaccaa ggtggacaag    660
aaaattgagc ccagagggcc cacaatcaag ccctgtcctc catgcaaatg cccagcacct   720
aacgctgctg gtggaccatc cgtcttcatc ttccctccaa agatcaagga tgtactcatg   780
atctccctga gccccatagt cacatgtgtg gtggtggatg tgagcgagga tgacccagat   840
gtccagatca gctggtttgt gaacaacgtg gaagtacaca cagctcagac aaaacccat    900
agagaggatt acaacagtac tctccgggtg gtcagtgccc tccccatcca gcaccaggac   960
tggatgagtg gcaaggagtt caatgcaag gtcaacaaca aagacctcgg ggcgcccatc    1020
gagagaacca tctcaaaacc caaggctcaa gtaagagctc cacaggtata tgtcttgcct   1080
ccaccagaag aagagatgac taagaaacag gtcactctga cctgcatggt cacagacttc   1140
atgcctgaag acatttacgt ggagtggacc aacaacggga aaacagagct aaactacaag   1200
```
aacactgaac cagtcctgga ctctgatggt tcttacttca tgtacagcaa gctgagagtg    1260
gaaaagaaga actgggtgga agaaatagc tactcctgtt cagtggtcca cgagggtctg     1320
cacaatcacc acacgactaa gagcttctcc cggactccgg gcaaa                    1365

<210> SEQ ID NO 278
<211> LENGTH: 455
<212> TYPE: PRT
<213> ORGANISM: Artificial Sequence
<220> FEATURE:
<223> OTHER INFORMATION: Synthetic: Clone 13 heavy chain mIgG2a LALA-PG
      amino acid sequence

<400> SEQUENCE: 278

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser Ala Lys Thr
        115                 120                 125

Thr Ala Pro Ser Val Tyr Pro Leu Ala Pro Val Cys Gly Asp Thr Thr
    130                 135                 140

Gly Ser Ser Val Thr Leu Gly Cys Leu Val Lys Gly Tyr Phe Pro Glu
145                 150                 155                 160

Pro Val Thr Leu Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Thr Ser Ser Thr Trp Pro Ser Gln Ser Ile Thr Cys Asn
        195                 200                 205

Val Ala His Pro Ala Ser Ser Thr Lys Val Asp Lys Lys Ile Glu Pro
    210                 215                 220

Arg Gly Pro Thr Ile Lys Pro Cys Pro Pro Cys Lys Cys Pro Ala Pro
225                 230                 235                 240

Asn Ala Ala Gly Gly Pro Ser Val Phe Ile Phe Pro Pro Lys Ile Lys
                245                 250                 255

Asp Val Leu Met Ile Ser Leu Ser Pro Ile Val Thr Cys Val Val Val
            260                 265                 270

Asp Val Ser Glu Asp Asp Pro Asp Val Gln Ile Ser Trp Phe Val Asn
        275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Lys Asp Leu

```
                325                 330                 335
Gly Ala Pro Ile Glu Arg Thr Ile Ser Lys Pro Lys Gly Ser Val Arg
            340                 345                 350
Ala Pro Gln Val Tyr Val Leu Pro Pro Glu Glu Met Thr Lys
        355                 360                 365
Lys Gln Val Thr Leu Thr Cys Met Val Thr Asp Phe Met Pro Glu Asp
    370                 375                 380
Ile Tyr Val Glu Trp Thr Asn Asn Gly Lys Thr Glu Leu Asn Tyr Lys
385                 390                 395                 400
Asn Thr Glu Pro Val Leu Asp Ser Asp Gly Ser Tyr Phe Met Tyr Ser
                405                 410                 415
Lys Leu Arg Val Glu Lys Lys Asn Trp Val Glu Arg Asn Ser Tyr Ser
            420                 425                 430
Cys Ser Val Val His Glu Gly Leu His Asn His Thr Thr Lys Ser
        435                 440                 445
Phe Ser Arg Thr Pro Gly Lys
    450                 455

<210> SEQ ID NO 279
<211> LENGTH: 1347
<212> TYPE: DNA
<213> ORGANISM: Artificial Sequence
<220> FEATURE:
<223> OTHER INFORMATION: Synthetic: Clone 13 heavy chain mIgG1
      nucleotide sequence

<400> SEQUENCE: 279
```

| | | | | | |
|---|---|---|---|---|---|
| caggtgcagc | tggtgcagtc | tggggctgag | gtgaagaagc | ctgggtcctc | tgtgaaggtc | 60 |
| tcctgcaagg | cttctggagg | caccttcagc | agctatgcta | tcagctgggt | gcgacaggcc | 120 |
| cctggacaag | ggcttgagtg | gatgggaagc | atcatcccta | tctttggtac | agcaaactac | 180 |
| gcacagaagt | tccagggcag | agtcaccatt | actgctgatg | aatccaccag | cacagcctac | 240 |
| atggagctga | gcagcctgag | atctgaggac | actgctgtgt | actactgtgc | cagaggccct | 300 |
| tctgaagtag | gagcaatact | gggatatgta | tggtttgacc | catggggaca | gggtacattg | 360 |
| gtcaccgtct | cctcagccaa | aacgacaccc | ccatctgtct | atccgctagc | ccctggatct | 420 |
| gctgcccaaa | ctaactccat | ggtgaccctg | ggatgcctgg | tcaagggcta | tttccctgag | 480 |
| ccagtgacag | tgacctggaa | ctctggatcc | ctgtccagcg | gtgtgcacac | cttcccagct | 540 |
| gtcctggagt | ctgacctcta | cactctgagc | agctcagtga | ctgtcccctc | agccctcgg | 600 |
| cccagcgaga | ccgtcacctg | caacgttgcc | cacccggcca | gcagcaccaa | ggtggacaag | 660 |
| aaaattgtgc | ccagggattg | tggttgtaag | ccttgcatct | gtacagtccc | agaagtatca | 720 |
| tctgtcttca | tcttcccccc | aaagcccaag | gatgtgctca | ccattactct | gactcctaag | 780 |
| gtcacgtgtg | ttgtggtaga | catcagcaag | gatgatcccg | aggtccagtt | cagctggttt | 840 |
| gtagatgatg | tggaggtgca | cacagctcag | acgcaacccc | gggaggagca | gttcaacagc | 900 |
| actttccgct | cagtcagtga | acttcccatc | atgcaccagg | actggctcaa | tggcaaggag | 960 |
| ttcaaatgca | gggtcaacag | tgcagctttc | cctgcccca | tcgagaaaac | catctccaaa | 1020 |
| accaaaggca | gaccgaaggc | tccacaggtg | tacaccattc | cacctcccaa | ggagcagatg | 1080 |
| gccaaggata | aagtcagtct | gacctgcatg | ataacagact | tcttccctga | agacattact | 1140 |
| gtggagtggc | agtggaatgg | gcagccagcg | gagaactaca | agaacactca | gcccatcatg | 1200 |
| aacacgaatg | gctcttactt | cgtctacagc | aagctcaatg | tgcagaagag | caactgggag | 1260 |

```
gcaggaaata ctttcacctg ctctgtgtta catgagggcc tgcacaacca ccatactgag    1320
aagagcctct cccactctcc tggcaaa                                        1347
```

<210> SEQ ID NO 280
<211> LENGTH: 449
<212> TYPE: PRT
<213> ORGANISM: Artificial Sequence
<220> FEATURE:
<223> OTHER INFORMATION: Synthetic: Clone 13 heavy chain mIgG1 amino
      acid sequence

<400> SEQUENCE: 280

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Glu Ser Asp Leu Tyr Thr Leu Ser Ser Ser
            180                 185                 190

Val Thr Val Pro Ser Ser Pro Arg Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
```

```
                340              345             350
Ile Pro Pro Lys Glu Gln Met Ala Lys Asp Lys Val Ser Leu Thr
           355                360               365

Cys Met Ile Thr Asp Phe Phe Pro Glu Asp Ile Thr Val Glu Trp Gln
    370                375                380

Trp Asn Gly Gln Pro Ala Glu Asn Tyr Lys Asn Thr Gln Pro Ile Met
385                390                395                400

Asn Thr Asn Gly Ser Tyr Phe Val Tyr Ser Lys Leu Asn Val Gln Lys
                405                410                415

Ser Asn Trp Glu Ala Gly Asn Thr Phe Thr Cys Ser Val Leu His Glu
            420                425                430

Gly Leu His Asn His His Thr Glu Lys Ser Leu Ser His Ser Pro Gly
            435                440                445

Lys

<210> SEQ ID NO 281
<211> LENGTH: 657
<212> TYPE: DNA
<213> ORGANISM: Artificial Sequence
<220> FEATURE:
<223> OTHER INFORMATION: Synthetic: Clone 13 light chain mKappa
      nucleotide sequence

<400> SEQUENCE: 281
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaggcaag acgaatccct    300
atcacttttg gcggagggac caaggttgag atcaaacgtg cagatgcggc cccaactgta    360
tccatcttcc caccatccag tgagcagtta acatctggag gtgcctcagt cgtgtgcttc    420
ttgaacaact ctaccccaa agacatcaat gtcaagtgga gattgatgg cagtgaacga      480 caaaatggcg tcctgaacag ttggactgat caggacagca agacagcac ctacagcatg      540 agcagcaccc tcacgttgac caaggacgag tatgaacgac ataacagcta tacctgtgag    600
gccactcaca gacatcaac ttcacccatt gtcaagagct tcaacaggaa tgagtgt        657

<210> SEQ ID NO 282
<211> LENGTH: 219
<212> TYPE: PRT
<213> ORGANISM: Artificial Sequence
<220> FEATURE:
<223> OTHER INFORMATION: Synthetic: Clone 13 light chain mKappa amino
      acid sequence

<400> SEQUENCE: 282

Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Met Gln Ala
                    85                  90                  95

Arg Arg Ile Pro Ile Thr Phe Gly Gly Gly Thr Lys Val Glu Ile Lys
                100                 105                 110

Arg Ala Asp Ala Ala Pro Thr Val Ser Ile Phe Pro Pro Ser Ser Glu
                115                 120                 125

Gln Leu Thr Ser Gly Gly Ala Ser Val Val Cys Phe Leu Asn Asn Phe
            130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
        210                 215
```

<210> SEQ ID NO 283
<211> LENGTH: 8
<212> TYPE: PRT
<213> ORGANISM: Artificial Sequence
<220> FEATURE:
<223> OTHER INFORMATION: Synthetic

<400> SEQUENCE: 283

```
Gly Gly Thr Phe Ser Ser Tyr Ala
1               5
```

<210> SEQ ID NO 284
<211> LENGTH: 5
<212> TYPE: PRT
<213> ORGANISM: Artificial Sequence
<220> FEATURE:
<223> OTHER INFORMATION: Synthetic

<400> SEQUENCE: 284

```
Ser Tyr Ala Ile Ser
1               5
```

<210> SEQ ID NO 285
<211> LENGTH: 8
<212> TYPE: PRT
<213> ORGANISM: Artificial Sequence
<220> FEATURE:
<223> OTHER INFORMATION: Synthetic

<400> SEQUENCE: 285

```
Ile Ile Pro Ile Phe Gly Thr Ala
1               5
```

<210> SEQ ID NO 286
<211> LENGTH: 16
<212> TYPE: PRT
<213> ORGANISM: Artificial Sequence
<220> FEATURE:
<223> OTHER INFORMATION: Synthetic

<400> SEQUENCE: 286

```
Gly Pro Ser Glu Val Gly Ala Ile Leu Gly Tyr Val Trp Phe Asp Pro
```

```
<210> SEQ ID NO 287
<211> LENGTH: 11
<212> TYPE: PRT
<213> ORGANISM: Artificial Sequence
<220> FEATURE:
<223> OTHER INFORMATION: Synthetic

<400> SEQUENCE: 287

Gln Ser Leu Leu His Ser Asn Gly Tyr Asn Tyr
1               5                   10

<210> SEQ ID NO 288
<211> LENGTH: 3
<212> TYPE: PRT
<213> ORGANISM: Artificial Sequence
<220> FEATURE:
<223> OTHER INFORMATION: Synthetic

<400> SEQUENCE: 288

Leu Gly Ser
1

<210> SEQ ID NO 289
<211> LENGTH: 8
<212> TYPE: PRT
<213> ORGANISM: Artificial Sequence
<220> FEATURE:
<223> OTHER INFORMATION: Synthetic

<400> SEQUENCE: 289

Gly Gly Thr Phe Ser Ala Trp Ala
1               5

<210> SEQ ID NO 290
<211> LENGTH: 5
<212> TYPE: PRT
<213> ORGANISM: Artificial Sequence
<220> FEATURE:
<223> OTHER INFORMATION: Synthetic

<400> SEQUENCE: 290

Ala Trp Ala Ile Ser
1               5

<210> SEQ ID NO 291
<211> LENGTH: 8
<212> TYPE: PRT
<213> ORGANISM: Artificial Sequence
<220> FEATURE:
<223> OTHER INFORMATION: Synthetic

<400> SEQUENCE: 291

Ile Ile Pro Tyr Phe Gly Lys Ala
1               5

<210> SEQ ID NO 292
<211> LENGTH: 16
<212> TYPE: PRT
<213> ORGANISM: Artificial Sequence
<220> FEATURE:
<223> OTHER INFORMATION: Synthetic

<400> SEQUENCE: 292

Gly Pro Ser Glu Val Ser Gly Ile Leu Gly Tyr Val Trp Phe Asp Pro
1               5                   10                  15
```

```
<210> SEQ ID NO 293
<211> LENGTH: 8
<212> TYPE: PRT
<213> ORGANISM: Artificial Sequence
<220> FEATURE:
<223> OTHER INFORMATION: Synthetic

<400> SEQUENCE: 293

Gly Gly Thr Phe Leu Ser Ser Ala
1               5

<210> SEQ ID NO 294
<211> LENGTH: 5
<212> TYPE: PRT
<213> ORGANISM: Artificial Sequence
<220> FEATURE:
<223> OTHER INFORMATION: Synthetic

<400> SEQUENCE: 294

Ser Ser Ala Ile Ser
1               5

<210> SEQ ID NO 295
<211> LENGTH: 8
<212> TYPE: PRT
<213> ORGANISM: Artificial Sequence
<220> FEATURE:
<223> OTHER INFORMATION: Synthetic

<400> SEQUENCE: 295

Ile Ile Pro Leu Phe Gly Lys Ala
1               5

<210> SEQ ID NO 296
<211> LENGTH: 16
<212> TYPE: PRT
<213> ORGANISM: Artificial Sequence
<220> FEATURE:
<223> OTHER INFORMATION: Synthetic

<400> SEQUENCE: 296

Gly Pro Ser Glu Val Lys Gly Ile Leu Gly Tyr Val Trp Phe Asp Pro
1               5                   10                  15

<210> SEQ ID NO 297
<211> LENGTH: 8
<212> TYPE: PRT
<213> ORGANISM: Artificial Sequence
<220> FEATURE:
<223> OTHER INFORMATION: Synthetic

<400> SEQUENCE: 297

Leu Ile Pro Tyr Phe Gly Thr Ala
1               5

<210> SEQ ID NO 298
<211> LENGTH: 13
<212> TYPE: PRT
<213> ORGANISM: Artificial Sequence
<220> FEATURE:
<223> OTHER INFORMATION: Synthetic

<400> SEQUENCE: 298

Ile Leu Gln Cys His Leu Ser Ser Thr Ala Gln Val
1               5                   10
```

```
<210> SEQ ID NO 299
<211> LENGTH: 15
<212> TYPE: PRT
<213> ORGANISM: Artificial Sequence
<220> FEATURE:
<223> OTHER INFORMATION: Synthetic

<400> SEQUENCE: 299

Cys Ile Tyr His Thr Tyr Pro Asp Gly Thr Tyr Thr Gly Arg Ile
1               5                   10                  15

<210> SEQ ID NO 300
<211> LENGTH: 11
<212> TYPE: PRT
<213> ORGANISM: Artificial Sequence
<220> FEATURE:
<223> OTHER INFORMATION: Synthetic

<400> SEQUENCE: 300

Ser Phe Lys Asp Arg Val Ala Pro Gly Pro Gly
1               5                   10

<210> SEQ ID NO 301
<211> LENGTH: 7
<212> TYPE: PRT
<213> ORGANISM: Artificial Sequence
<220> FEATURE:
<223> OTHER INFORMATION: Synthetic

<400> SEQUENCE: 301

Thr Thr Ala Gln Val Thr Gln
1               5

<210> SEQ ID NO 302
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa is Cys-acm
<220> FEATURE:
<221> NAME/KEY: misc_feature
<222> LOCATION: (19)..(19)
<223> OTHER INFORMATION: Xaa is Cys-acm

<400> SEQUENCE: 302

Cys Ile Leu Gln Xaa His Leu Ser Ser Thr Thr Ala Gln Val Thr Gln
1               5                   10                  15

Cys Ile Xaa Asn Ala Asp Leu Gly Trp His Ile Ser Pro Ser Phe Lys
            20                  25                  30

Cys

<210> SEQ ID NO 303
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: Xaa is Cys-acm

<400> SEQUENCE: 303
```

```
Cys Lys Asp Arg Val Ala Pro Gly Pro Gly Leu Gly Leu Thr Leu Gln
1               5                   10                  15

Cys Ile Xaa Asn Ala Asp Leu Gly Trp His Ile Ser Pro Ser Phe Lys
            20                  25                  30

Cys

<210> SEQ ID NO 304
<211> LENGTH: 7
<212> TYPE: PRT
<213> ORGANISM: Artificial Sequence
<220> FEATURE:
<223> OTHER INFORMATION: Synthetic

<400> SEQUENCE: 304

Ala Asp His Ile Gln Arg Tyr
1               5

<210> SEQ ID NO 305
<211> LENGTH: 5
<212> TYPE: PRT
<213> ORGANISM: Artificial Sequence
<220> FEATURE:
<223> OTHER INFORMATION: Synthetic

<400> SEQUENCE: 305

Thr Ala Gln Val Thr
1               5

<210> SEQ ID NO 306
<211> LENGTH: 4
<212> TYPE: PRT
<213> ORGANISM: Artificial Sequence
<220> FEATURE:
<223> OTHER INFORMATION: Synthetic

<400> SEQUENCE: 306

Gly Trp His Ile
1

<210> SEQ ID NO 307
<211> LENGTH: 7
<212> TYPE: PRT
<213> ORGANISM: Artificial Sequence
<220> FEATURE:
<223> OTHER INFORMATION: Synthetic

<400> SEQUENCE: 307

Pro Gly Pro Gly Leu Gly Leu
1               5

<210> SEQ ID NO 308
<211> LENGTH: 5
<212> TYPE: PRT
<213> ORGANISM: Artificial Sequence
<220> FEATURE:
<223> OTHER INFORMATION: Synthetic

<400> SEQUENCE: 308

Lys Asp Arg Val Ala
1               5

<210> SEQ ID NO 309
<211> LENGTH: 5
<212> TYPE: PRT
<213> ORGANISM: Artificial Sequence
<220> FEATURE:
```

```
<223> OTHER INFORMATION: Synthetic

<400> SEQUENCE: 309

Gly Gly Ser Gly Gly
1               5
```

ANTI-TIGIT ANTIBODIES

CROSS-REFERENCE TO RELATED APPLICATIONS

This application claims the benefit of priority of U.S. Provisional Application No. 62/722,063, filed Aug. 23, 2018; U.S. Provisional Application No. 62/734,130, filed Sep. 20, 2018; and U.S. Provisional Application No. 62/822,674, filed Mar. 22, 2019; each of which is incorporated by reference herein in its entirety for any purpose.

FIELD

Provided herein are antibodies that bind to human TIGIT (T-cell immunoreceptor with Ig and ITIM domains), and uses thereof.

BACKGROUND

TIGIT ("T-cell immunoreceptor with Ig and ITIM domains") is an immune receptor that is expressed on subsets of T cells, such as activated, memory, and regulatory T cells and natural killer (NK) cells. TIGIT is a member of the CD28 family within the Ig superfamily of proteins, and serves as a co-inhibitory molecule that limits T cell proliferation and activation and NK cell function. TIGIT mediates its immunosuppressive effect by competing with CD226 (also known as DNAX Accessory Molecule-1, or "DNAM-1") for the same set of ligands: CD155 (also known as poliovirus receptor or "PVR") and CD112 (also known as poliovirus receptor-related 2 or "PVRL2"). See, Levin et al., *Eur. J. Immunol.*, 2011, 41:902-915. Because the affinity of CD155 for TIGIT is higher than its affinity for CD226, in the presence of TIGIT CD226 signaling is inhibited, thereby limiting T cell proliferation and activation.

In patients with melanoma, TIGIT expression is upregulated on tumor antigen (TA)-specific $CD8^+$ T cells and $CD8^+$ tumor-infiltrating lymphocytes (TILs). Blockade of TIGIT in the presence of TIGIT ligand (CD155)-expressing cells increased the proliferation, cytokine production, and degranulation of both TA-specific $CD8^+$ T cells and $CD8^+$ TILs See, Chauvin et al., *J Clin Invest.*, 2015, 125:2046-2058. Thus, TIGIT represents a potential therapeutic target for stimulating anti-tumor T cell responses in patients, although there remains a need for improved methods of blocking TIGIT and promoting anti-tumor responses.

BRIEF SUMMARY

Embodiment 1

A composition comprising isolated antibodies that bind to human TIGIT (T-cell immunoreceptor with Ig and ITIM domains), wherein the antibodies have a binding affinity ($K_D$) for human TIGIT of less than 5 nM, and wherein at least 90%, at least 91%, at least 92%, at least 93%, at least 94%, at least 95%, at least 96%, at least 97%, at least 98%, or at least 99% of the antibodies in the composition are afucosylated.

Embodiment 2

The composition of embodiment 1, wherein the antibodies have a $K_D$ for human TIGIT of less than 1 nM.

Embodiment 3

The composition of embodiment 1, wherein the antibodies have a $K_D$ for human TIGIT of less than 100 pM.

Embodiment 4

The composition of any one of embodiments 1 to 3, wherein the antibodies exhibit cross-reactivity with cynomolgus monkey TIGIT and/or mouse TIGIT.

Embodiment 5

The composition of embodiment 4, wherein the antibodies exhibit cross-reactivity with both cynomolgus monkey TIGIT and mouse TIGIT.

Embodiment 6

The composition of any one of embodiments 1 to 5, wherein the antibodies block binding of CD155 to TIGIT.

Embodiment 7

The composition of any one of embodiments 1 to 5, wherein the antibodies block binding of CD112 to TIGIT.

Embodiment 8

The composition of any one of embodiments 1 to 5, wherein the antibodies block binding of both CD155 and CD112 to TIGIT.

Embodiment 9

The composition of any one of embodiments 1 to 8, wherein the antibodies compete for binding to human TIGIT with an antibody comprising a heavy chain variable region comprising the amino acid sequence of SEQ ID NO: 55 and a light chain variable region comprising the amino acid sequence of SEQ ID NO: 64.

Embodiment 10

The composition of any one of embodiments 1 to 9, wherein the antibodies when bound to human TIGIT bind one or both of amino acid positions 81 and 82.

Embodiment 11

The composition of embodiment 10, wherein the antibodies bind both of amino acid positions 81 and 82.

Embodiment 12

The composition of embodiment 10 or embodiment 11, wherein amino acid positions 81 and 82 are Phe81 and Lys82.

Embodiment 13

The composition of any one of embodiments 1 to 12, wherein the antibodies bind to an epitope on human TIGIT that comprises one or both of amino acid positions 81 and 82.

Embodiment 14

A composition comprising isolated antibodies that binds to human TIGIT, wherein the antibodies when bound to human TIGIT bind one or both of amino acid positions 81 and 82, and wherein at least 90%, at least 91%, at least 92%, at least 93%, at least 94%, at least 95%, at least 96%, at least 97%, at least 98%, or at least 99% of the antibodies in the composition are afucosylated.

Embodiment 15

The composition of embodiment 14, wherein the antibodies bind both of amino acid positions 81 and 82.

Embodiment 16

The composition of embodiment 14 or embodiment 15, wherein amino acid positions 81 and 82 are Phe81 and Lys82.

Embodiment 17

A composition comprising isolated antibodies that binds to human TIGIT, wherein the antibodies bind to an epitope on human TIGIT that comprises one or both of amino acid positions 81 and 82, and wherein at least 90%, at least 91%, at least 92%, at least 93%, at least 94%, at least 95%, at least 96%, at least 97%, at least 98%, or at least 99% of the antibodies in the composition are afucosylated.

Embodiment 18

The composition of embodiment 13 or embodiment 17, wherein the epitope comprises Phe at position 81.

Embodiment 19

The composition of any one of embodiments 13, 17, and 18, wherein the epitope comprises Lys or Ser at position 82.

Embodiment 20

The composition of any one of embodiments 13, and 17 to 19, wherein the epitope comprises Phe at position 81 and Lys or Ser at position 82.

Embodiment 21

The composition of embodiment 20, wherein the epitope comprises Phe81 and Lys82.

Embodiment 22

The composition of any one of embodiments 13 and 17 to 21, wherein the epitope is a discontinuous epitope.

Embodiment 23

The composition of any one of embodiments 13 and 17 to 22, wherein the antibodies bind to an epitope on human TIGIT that further comprises one or more of amino acid positions 51, 52, 53, 54, 55, 73, 74, 75, 76, 77, 79, 83, 84, 85, 86, 87, 88, 89, 90, 91, 92, or 93.

Embodiment 24

The composition of embodiment 23, wherein the epitope further comprises one or more amino acid residues selected from the group consisting of Thr51, Ala52, Gln53, Val54, Thr55, Leu73, Gly74, Trp75, His76, Ile77, Pro79, Asp83, Arg84, Val85, Ala86, Pro87, Gly88, Pro89, Gly90, Leu91, Gly92, and Leu93.

Embodiment 25

The composition of embodiment 24, wherein the epitope comprises the amino acid residues Thr51, Ala52, Gln53, Val54, Thr55, Gly74, Trp75, His76, Ile77, Phe81, Lys82, Pro87, Gly88, Pro89, Gly90, Leu91, Gly92, and Leu93.

Embodiment 26

The composition of embodiment 24, wherein the epitope comprises the amino acid residues Ala52, Gln53, Leu73, Gly74, Trp75, Pro79, Phe81, Lys82, Asp83, Arg84, Val85, and Ala86.

Embodiment 27

The composition of any one of embodiments 13 and 17 to 26, wherein the epitope comprises the sequence ICNADLGWHISPSFK (SEQ ID NO: 258).

Embodiment 28

The composition of any one of embodiments 1 to 27, wherein human TIGIT comprises the sequence of SEQ ID NO: 218.

Embodiment 29

The composition of any one of embodiments 1 to 28, wherein each of the antibodies comprises one or more of:
(a) a heavy chain CDR1 comprising a sequence selected from SEQ ID NO:4, SEQ ID NO:22, SEQ ID NO:40, SEQ ID NO:58, SEQ ID NO:76, SEQ ID NO:94, SEQ ID NO:112, SEQ ID NO:130, SEQ ID NO:148, SEQ ID NO:166, SEQ ID NO:184, SEQ ID NO:202, SEQ ID NO:221, SEQ ID NO:224, SEQ ID NO:226, SEQ ID NO:231, SEQ ID NO:233, SEQ ID NO:239, SEQ ID NO:243, SEQ ID NO:283, SEQ ID NO:284, SEQ ID NO:293, SEQ ID NO:294, SEQ ID NO:289, and SEQ ID NO:290;
(b) a heavy chain CDR2 comprising a sequence selected from SEQ ID NO:6, SEQ ID NO:24, SEQ ID NO:42, SEQ ID NO:60, SEQ ID NO:78, SEQ ID NO:96, SEQ ID NO:114, SEQ ID NO:132, SEQ ID NO:150, SEQ ID NO:168, SEQ ID NO:186, SEQ ID NO:204, SEQ ID NO:222, SEQ ID NO:225, SEQ ID NO:227, SEQ ID NO:229, SEQ ID NO:232, SEQ ID NO:234, SEQ ID NO:238, SEQ ID NO:240, SEQ ID NO:285, SEQ ID NO:297, SEQ ID NO:291, and SEQ ID NO:295;
(c) a heavy chain CDR3 comprising a sequence selected from SEQ ID NO:8, SEQ ID NO:26, SEQ ID NO:44, SEQ ID NO:62, SEQ ID NO:80, SEQ ID NO:98, SEQ ID NO:116, SEQ ID NO:134, SEQ ID NO:152, SEQ ID NO:170, SEQ ID NO:188, SEQ ID NO:206, SEQ ID NO:223, SEQ ID NO:228, SEQ ID NO:230, SEQ ID NO:235, SEQ ID NO:236, SEQ ID NO:237, SEQ ID NO:241, SEQ ID NO:242, SEQ ID NO:244, SEQ ID NO:286, SEQ ID NO:292, and SEQ ID NO:296;
(d) a light chain CDR1 comprising a sequence selected from SEQ ID NO:13, SEQ ID NO:31, SEQ ID NO:49, SEQ ID NO:67, SEQ ID NO:85, SEQ ID NO:103, SEQ ID NO:121, SEQ ID NO:139, SEQ ID NO:157, SEQ ID NO:175, SEQ ID NO:193, SEQ ID NO:211, and SEQ ID NO:287;
(e) a light chain CDR2 comprising a sequence selected from SEQ ID NO:15, SEQ ID NO:33, SEQ ID NO:51, SEQ ID NO:69, SEQ ID NO:87, SEQ ID NO:105, SEQ ID NO:123, SEQ ID NO:141, SEQ ID NO:159, SEQ ID NO:177, SEQ ID NO:195, SEQ ID NO:213, and SEQ ID NO:288; or
(f) a light chain CDR3 comprising a sequence selected from SEQ ID NO:17, SEQ ID NO:35, SEQ ID NO:53, SEQ ID NO:71, SEQ ID NO:89, SEQ ID NO:107, SEQ ID NO:125, SEQ ID NO:143, SEQ ID NO:161, SEQ ID NO:179, SEQ ID NO:197, and SEQ ID NO:215.

Embodiment 30

The composition of embodiment 29, wherein each of the antibodies comprises:
(a) a heavy chain CDR1 sequence comprising an amino acid sequence selected from SEQ ID NO:58, SEQ ID NO:283, SEQ ID NO:284, SEQ ID NO:224, SEQ ID NO:293, SEQ ID NO:294, SEQ ID NO:226, SEQ ID NO:289, and SEQ ID NO:290;
(b) a heavy chain CDR2 sequence comprising an amino acid sequence selected from SEQ ID NO:60, SEQ ID NO:285, SEQ ID NO:225, SEQ ID NO:297, SEQ ID NO:227, SEQ ID NO:291, SEQ ID NO:229, and SEQ ID NO:295;
(c) a heavy chain CDR3 sequence comprising an amino acid sequence selected from SEQ ID NO:62, SEQ ID NO:286, SEQ ID NO:228, SEQ ID NO:292, SEQ ID NO:230, and SEQ ID NO:296;
(d) a light chain CDR1 sequence comprising an amino acid sequence selected from SEQ ID NO:67 and SEQ ID NO:287;
(e) a light chain CDR2 sequence comprising an amino acid sequence selected from SEQ ID NO:69 and SEQ ID NO:288; and/or
(f) a light chain CDR3 sequence comprising the amino acid sequence of SEQ ID NO:71.

Embodiment 31

The composition of embodiment 29 or embodiment 30, wherein each of the antibodies comprises a heavy chain CDR1, CDR2, and CDR3 and a light chain CDR1, CDR, and CDR3 comprising the sequences of:
(a) SEQ ID NOs: 4, 6, 8, 13, 15, and 17, respectively; or
(b) SEQ ID NOs: 22, 24, 26, 31, 33, and 35, respectively; or
(c) SEQ ID NOs: 40, 42, 44, 49, 51, and 53, respectively; or
(d) SEQ ID NOs: 58, 60, 62, 67, 69, and 71, respectively; or
(e) SEQ ID NOs: 283, 285, 62, 287, 288, and 71, respectively; or
(f) SEQ ID NOs: 284, 60, 286, 67, 69, and 71, respectively; or
(g) SEQ ID NOs: 76, 78, 80, 85, 87, and 89, respectively; or
(h) SEQ ID NOs: 94, 96, 98, 103, 105, and 107, respectively; or
(i) SEQ ID NOs: 112, 114, 116, 121, 123, and 125, respectively; or
(j) SEQ ID NOs: 130, 132, 134, 139, 141, and 143, respectively; or
(k) SEQ ID NOs: 148, 150, 152, 157, 159, and 161, respectively; or
(l) SEQ ID NOs: 166, 168, 170, 175, 177, and 179, respectively; or
(m) SEQ ID NOs: 184, 186, 188, 193, 195, and 197, respectively; or
(n) SEQ ID NOs: 202, 204, 206, 211, 213, and 215, respectively; or
(o) SEQ ID NOs: 221, 222, 223, 13, 15, and 17, respectively; or
(p) SEQ ID NOs: 224, 225, 62, 67, 69, and 71, respectively; or
(q) SEQ ID NOs: 293, 297, 62, 287, 288, and 71, respectively; or
(r) SEQ ID NOs: 294, 225, 286, 67, 69, and 71, respectively; or
(s) SEQ ID NOs: 226, 227, 228, 67, 69, and 71, respectively; or
(t) SEQ ID NOs: 289, 291, 228, 287, 288, and 71, respectively; or
(u) SEQ ID NOs: 290, 227, 292, 67, 69, and 71, respectively; or
(v) SEQ ID NOs: 224, 229, 230, 67, 69, and 71, respectively; or
(w) SEQ ID NOs: 293, 295, 230, 287, 288, and 71, respectively; or
(x) SEQ ID NOs: 294, 229, 296, 67, 69, and 71, respectively; or
(y) SEQ ID NOs: 224, 227, 230, 67, 69, and 71, respectively; or
(z) SEQ ID NOs: 293, 290, 230, 287, 288, and 71, respectively; or
(aa) SEQ ID NOs: 294, 290, 230, 67, 69, and 71, respectively; or
(bb) SEQ ID NOs: 231, 232, 235, 103, 105, and 107, respectively; or
(cc) SEQ ID NOs: 233, 234, 236, 103, 105, and 107, respectively; or
(dd) SEQ ID NOs: 233, 234, 237, 103, 105, and 107, respectively; or
(ee) SEQ ID NOs: 166, 238, 170, 175, 177, and 179, respectively; or
(ff) SEQ ID NOs: 239, 240, 170, 175, 177, and 179, respectively; or
(gg) SEQ ID NOs: 239, 240, 241, 175, 177, and 179, respectively; or
(hh) SEQ ID NOs: 239, 240, 242, 175, 177, and 179, respectively; or
(ii) SEQ ID NOs: 243, 168, 244, 175, 177, and 179, respectively.

Embodiment 32

The composition of any one of embodiments 1 to 31, wherein each of the antibodies comprises a heavy chain CDR1, CDR2, and CDR3 and a light chain CDR1, CDR, and CDR3 comprising the sequences of:
(a) SEQ ID NOs: 58, 60, 62, 67, 69, and 71, respectively; or
(b) SEQ ID NOs: 283, 285, 62, 287, 288, and 71, respectively; or
(c) SEQ ID NOs: 284, 60, 286, 67, 69, and 71, respectively.

Embodiment 33

The composition of any one of embodiments 1 to 32, wherein each of the antibodies comprises:

(a) a heavy chain variable region comprising an amino acid sequence that has at least 90% sequence identity to SEQ ID NO:1, SEQ ID NO:19, SEQ ID NO:37, SEQ ID NO:55, SEQ ID NO:73, SEQ ID NO:91, SEQ ID NO:109, SEQ ID NO:127, SEQ ID NO:145, SEQ ID NO:163, SEQ ID NO:181, SEQ ID NO:199, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, or SEQ ID NO:257; and/or (b) a light chain variable region comprising an amino acid sequence that has at least 90% sequence identity to SEQ ID NO:10, SEQ ID NO:28, SEQ ID NO:46, SEQ ID NO:64, SEQ ID NO:82, SEQ ID NO:100, SEQ ID NO:118, SEQ ID NO:136, SEQ ID NO:154, SEQ ID NO:172, SEQ ID NO:190, or SEQ ID NO:208.

Embodiment 34

The composition of any one of embodiments 1 to 33, wherein each of the antibodies comprises:
(a) a heavy chain variable region comprising an amino acid sequence that has at least 90% sequence identity to SEQ ID NO:1 or SEQ ID NO:245 and a light chain variable region comprising an amino acid sequence that has at least 90% sequence identity to SEQ ID NO:10; or
(b) a heavy chain variable region comprising an amino acid sequence that has at least 90% sequence identity to SEQ ID NO:19 and a light chain variable region comprising an amino acid sequence that has at least 90% sequence identity to SEQ ID NO:28; or
(c) a heavy chain variable region comprising an amino acid sequence that has at least 90% sequence identity to SEQ ID NO:37 and a light chain variable region comprising an amino acid sequence that has at least 90% sequence identity to SEQ ID NO:46; or
(d) a heavy chain variable region comprising an amino acid sequence that has at least 90% sequence identity to any one of SEQ ID NO:55, SEQ ID NO:246, SEQ ID NO:247, SEQ ID NO:248, or SEQ ID NO:249 and a light chain variable region comprising an amino acid sequence that has at least 90% sequence identity to SEQ ID NO:64; or
(e) a heavy chain variable region comprising an amino acid sequence that has at least 90% sequence identity to SEQ ID NO:73 and a light chain variable region comprising an amino acid sequence that has at least 90% sequence identity to SEQ ID NO:82; or
(f) a heavy chain variable region comprising an amino acid sequence that has at least 90% sequence identity to any one of SEQ ID NO:91, SEQ ID NO:250, SEQ ID NO:251, or SEQ ID NO:252 and a light chain variable region comprising an amino acid sequence that has at least 90% sequence identity to SEQ ID NO:100; or
(g) a heavy chain variable region comprising an amino acid sequence that has at least 90% sequence identity to SEQ ID NO:109 and a light chain variable region comprising an amino acid sequence that has at least 90% sequence identity to SEQ ID NO:118; or
(h) a heavy chain variable region comprising an amino acid sequence that has at least 90% sequence identity to SEQ ID NO:127 and a light chain variable region comprising an amino acid sequence that has at least 90% sequence identity to SEQ ID NO:136; or (i) a heavy chain variable region comprising an amino acid sequence that has at least 90% sequence identity to SEQ ID NO:145 and a light chain variable region comprising an amino acid sequence that has at least 90% sequence identity to SEQ ID NO:154; or
(j) a heavy chain variable region comprising an amino acid sequence that has at least 90% sequence identity to any one of SEQ ID NO:163, SEQ ID NO:253, SEQ ID NO:254, SEQ ID NO:255, SEQ ID NO:256, or SEQ ID NO:257 and a light chain variable region comprising an amino acid sequence that has at least 90% sequence identity to SEQ ID NO:172; or
(k) a heavy chain variable region comprising an amino acid sequence that has at least 90% sequence identity to SEQ ID NO:181 and a light chain variable region comprising an amino acid sequence that has at least 90% sequence identity to SEQ ID NO:190; or
(l) a heavy chain variable region comprising an amino acid sequence that has at least 90% sequence identity to SEQ ID NO:199 and a light chain variable region comprising an amino acid sequence that has at least 90% sequence identity to SEQ ID NO:208.

Embodiment 35

The composition of embodiment 34, wherein each of the antibodies comprises:
(a) a heavy chain variable region comprising the amino acid sequence of SEQ ID NO:1 or SEQ ID NO:245 and a light chain variable region comprising the amino acid sequence of SEQ ID NO:10; or
(b) a heavy chain variable region comprising the amino acid sequence of SEQ ID NO:19 and a light chain variable region comprising the amino acid sequence of SEQ ID NO:28; or
(c) a heavy chain variable region comprising the amino acid sequence of SEQ ID NO:37 and a light chain variable region comprising the amino acid sequence of SEQ ID NO:46; or
(d) a heavy chain variable region comprising the amino acid sequence of any one of SEQ ID NO:55, SEQ ID NO:246, SEQ ID NO:247, SEQ ID NO:248, or SEQ ID NO:249 and a light chain variable region comprising the amino acid sequence of SEQ ID NO:64; or
(e) a heavy chain variable region comprising the amino acid sequence of SEQ ID NO:73 and a light chain variable region comprising the amino acid sequence of SEQ ID NO:82; or
(f) a heavy chain variable region comprising the amino acid sequence of any one of SEQ ID NO:91, SEQ ID NO:250, SEQ ID NO:251, or SEQ ID NO:252 and a light chain variable region comprising the amino acid sequence of SEQ ID NO:100; or
(g) a heavy chain variable region comprising the amino acid sequence of SEQ ID NO:109 and a light chain variable region comprising the amino acid sequence of SEQ ID NO:118; or
(h) a heavy chain variable region comprising the amino acid sequence of SEQ ID NO:127 and a light chain variable region comprising the amino acid sequence of SEQ ID NO:136; or
(i) a heavy chain variable region comprising the amino acid sequence of SEQ ID NO:145 and a light chain variable region comprising the amino acid sequence of SEQ ID NO:154; or
(j) a heavy chain variable region comprising the amino acid sequence of any one of SEQ ID NO:163, SEQ ID NO:253, SEQ ID NO:254, SEQ ID NO:255, SEQ ID NO:256, or SEQ ID NO:257 and a light chain variable region comprising the amino acid sequence of SEQ ID NO:172; or (k) a heavy chain variable region comprising the amino acid sequence of SEQ ID NO:181 and a light chain variable region comprising the amino acid sequence of SEQ ID NO:190; or (l) a heavy chain variable region comprising the amino acid sequence of SEQ ID NO:199 and a light chain variable region comprising the amino acid sequence of SEQ ID NO:208.

Embodiment 36

The composition of any one of embodiments 1 to 35, wherein each of the antibodies comprises a heavy chain variable region comprising the amino acid sequence of SEQ ID NO:55, and a light chain variable region comprising the amino acid sequence of SEQ ID NO:64.

Embodiment 37

The composition of any one of embodiments 1 to 36, wherein the antibodies are IgG antibodies.

Embodiment 38

The composition of embodiment 37, wherein the antibodies are IgG1 antibodies or IgG3 antibodies.

Embodiment 39

The composition of any one of embodiments 1 to 38, wherein each of the antibodies comprises a heavy chain comprising an amino acid sequence selected from SEQ ID NOs: 260, 262, 264, 266, 268, 270, and 272; and a light chain comprising the amino acid sequence of SEQ ID NO: 274.

Embodiment 40

The composition of embodiment 39, wherein each of the antibodies comprises a heavy chain comprising the amino acid sequence of SEQ ID NOs: 260; and a light chain comprising the amino acid sequence of SEQ ID NO: 274.

Embodiment 41

The composition of embodiment 39, wherein each of the antibodies comprises a heavy chain consisting of the amino acid sequence of SEQ ID NOs: 260; and a light chain consisting of the amino acid sequence of SEQ ID NO: 274.

Embodiment 42

A composition comprising isolated antibodies that bind to human TIGIT, wherein at least 90%, at least 91%, at least 92%, at least 93%, at least 94%, at least 95%, at least 96%, at least 97%, at least 98%, or at least 99% of the antibodies in the composition are afucosylated, and wherein each of the antibodies comprises a heavy chain comprising the amino acid sequence of SEQ ID NOs: 260; and a light chain comprising the amino acid sequence of SEQ ID NO: 274.

Embodiment 43

A composition comprising isolated antibodies that bind to human TIGIT, wherein at least 90%, at least 91%, at least 92%, at least 93%, at least 94%, at least 95%, at least 96%, at least 97%, at least 98%, or at least 99% of the antibodies in the composition are afucosylated, and wherein each of the antibodies comprises a heavy chain consisting of the amino acid sequence of SEQ ID NOs: 260; and a light chain consisting of the amino acid sequence of SEQ ID NO: 274.

Embodiment 44

The composition of any one of embodiments 1 to 43, wherein the antibodies exhibit synergy with an anti-PD-1 antibody or an anti-PD-L1 antibody.

Embodiment 45

The composition of embodiment 44, wherein synergy is determined using an assay that comprises contacting a co-culture comprising (i) Jurkat effector cells that express PD-1, TIGIT and CD226, wherein the Jurkat effector cells comprise a luciferase reporter gene driven by the IL-2 promoter; and (ii) CHO-K1 artificial antigen presenting cells (aAPCs) expressing a TCR activator, PD-L1 and CD155; with the composition and an anti-PD-1 antibody or an anti-PD-L1 antibody.

Embodiment 46

The composition of any one of embodiments 1 to 45, wherein regulatory T (Treg) cells are depleted from human PBMCs contacted with the composition.

Embodiment 47

The composition of any one of embodiments 1 to 46, expression of MCP1, IL-8, and MIP1α is increased in human PBMCs contacted with the composition.

Embodiment 48

The composition of any one of embodiments 1 to 47, wherein monocyte/macrophages are activated when contacted with the composition.

Embodiment 49

The composition of any one of embodiments 1 to 48, wherein CD86 and WWII are upregulated when CD14+ monocyte/macrophages are contacted with the composition.

Embodiment 50

The composition of any one of embodiments 1 to 49, wherein CD14+ monocyte/macrophages contacted with the composition mature into antigen presenting cells.

Embodiment 51

The composition of any one of embodiments 1 to 50, wherein the memory T cells contacted with the composition show increasd IFNγ production in response to antigen.

Embodiment 52

The composition of any one of embodiments 1 to 51, wherein the memory T cells contacted with the composition demonstrate enhanced response to antigen.

Embodiment 53

The composition of any one of embodiments 1 to 52, wherein effector memory CD8+ T cells and/or effector memory CD4+ T cells are increased in tumors contacted with the composition.

Embodiment 54

The composition of any one of embodiments 1 to 53, wherein the composition enhances a Th1 response in an animal administered the composition.

Embodiment 55

The composition of any one of embodiments 1 to 54, wherein the antibodies of the composition have lower binding affinity for FcγRIIa and/or FcγRIIb compared to the same anti-TIGIT antibodies that are not afucosylated.

Embodiment 56

The composition of any one of embodiments 1 to 55, wherein the composition mediates antibody-dependent cellular phagocytosis (ADCP) of cells that express TIGIT in the presence of monocyte macrophages.

Embodiment 57

The composition of any one of embodiments 1 to 56, wherein the antibodies are monoclonal.

Embodiment 58

The composition of any one of embodiments 1 to 57, wherein the antibodies are fully human antibodies.

Embodiment 59

The composition of any one of embodiments 1 to 58, wherein the antibodies are chimeric antibodies.

Embodiment 60

The composition of any one of embodiments 1 to 28 and 44 to 59, wherein the antibodies are humanized.

Embodiment 61

The composition of any one of embodiments 1 to 60, wherein the antibodies are antibody fragments.

Embodiment 62

The composition of embodiment 61, wherein the antibody fragments are Fab, Fab', F(ab')$_2$, scFv, or diabodies.

Embodiment 63

The composition of any one of embodiments 1 to 62, wherein the antibodies are bispecific antibodies.

Embodiment 64

The composition of any one of embodiments 1 to 63, wherein the antibodies are antibody-drug conjugates.

Embodiment 65

An antibody that binds to human TIGIT (T-cell immunoreceptor with Ig and ITIM domains), wherein the antibody has a binding affinity ($K_D$) for human TIGIT of less than 5 nM, and wherein the antibody is afucosylated.

Embodiment 66

The antibody of embodiment 65, wherein the antibody has a $K_D$ for human TIGIT of less than 1 nM.

Embodiment 67

The antibody of embodiment 66, wherein antibody has a $K_D$ for human TIGIT of less than 100 pM.

Embodiment 68

The antibody of any one of embodiments 65 to 67, wherein antibody exhibits cross-reactivity with cynomolgus monkey TIGIT and/or mouse TIGIT.

Embodiment 69

The antibody of embodiment 68, wherein the antibody exhibits cross-reactivity with both cynomolgus monkey TIGIT and mouse TIGIT.

Embodiment 70

The antibody of any one of embodiments 65 to 69, wherein the antibody blocks binding of CD155 to TIGIT.

Embodiment 71

The antibody of any one of embodiments 65 to 70, wherein the antibody blocks binding of CD112 to TIGIT.

Embodiment 72

The antibody of any one of embodiments 65 to 71, wherein the antibody blocks binding of both CD155 and CD112 to TIGIT.

Embodiment 73

The antibody of any one of embodiments 65 to 72, wherein the antibody competes for binding to human TIGIT with an antibody comprising a heavy chain variable region comprising the amino acid sequence of SEQ ID NO: 55 and a light chain variable region comprising the amino acid sequence of SEQ ID NO: 64.

Embodiment 74

The antibody of any one of embodiments 65 to 73, wherein when bound to human TIGIT binds one or both of amino acid positions 81 and 82.

Embodiment 75

The antibody of embodiment 74, wherein the antibody binds both of amino acid positions 81 and 82.

Embodiment 76

The antibody of embodiment 74 or embodiment 75, wherein amino acid positions 81 and 82 are Phe81 and Lys82.

Embodiment 77

The antibody of any one of embodiments 65 to 76, wherein the antibody binds to an epitope on human TIGIT that comprises one or both of amino acid positions 81 and 82.

Embodiment 78

An antibody that binds to human TIGIT, wherein when bound to human TIGIT binds one or both of amino acid positions 81 and 82, and wherein the antibody is afucosylated.

Embodiment 79

The antibody of embodiment 78, wherein the antibody binds both of amino acid positions 81 and 82.

Embodiment 80

The antibody of embodiment 78 or embodiment 79, wherein amino acid positions 81 and 82 are Phe81 and Lys82.

Embodiment 81

An antibody that binds to human TIGIT, wherein the antibody binds to an epitope on human TIGIT that comprises one or both of amino acid positions 81 and 82, and wherein the antibody is afucosylated.

Embodiment 82

The antibody of embodiment 77 or embodiment 81, wherein the epitope comprises Phe at position 81.

Embodiment 83

The antibody of any one of embodiments 77, 81, and 82, wherein the epitope comprises Lys or Ser at position 82.

Embodiment 84

The antibody of any one of embodiments 77 and 81 to 83, wherein the epitope comprises Phe at position 81 and Lys or Ser at position 82.

Embodiment 85

The antibody of embodiment 84, wherein the epitope comprises Phe81 and Lys82.

Embodiment 86

The antibody of any one of embodiments 77 and 81 to 85, wherein the epitope is a discontinuous epitope.

Embodiment 87

The antibody of any one of embodiments 77 and 81 to 86, wherein the antibody binds to an epitope on human TIGIT that further comprises one or more of amino acid positions 51, 52, 53, 54, 55, 73, 74, 75, 76, 77, 79, 83, 84, 85, 86, 87, 88, 89, 90, 91, 92, or 93.

Embodiment 88

The antibody of embodiment 87, wherein the epitope further comprises one or more amino acid residues selected from the group consisting of Thr51, Ala52, Gln53, Val54, Thr55, Leu73, Gly74, Trp75, His76, Ile77, Pro79, Asp83, Arg84, Val85, Ala86, Pro87, Gly88, Pro89, Gly90, Leu91, Gly92, and Leu93.

Embodiment 89

The antibody of embodiment 88, wherein the epitope comprises the amino acid residues Thr51, Ala52, Gln53, Val54, Thr55, Gly74, Trp75, His76, Ile77, Phe81, Lys82, Pro87, Gly88, Pro89, Gly90, Leu91, Gly92, and Leu93.

Embodiment 90

The antibody of embodiment 88, wherein the epitope comprises the amino acid residues Ala52, Gln53, Leu73, Gly74, Trp75, Pro79, Phe81, Lys82, Asp83, Arg84, Val85, and Ala86.

Embodiment 91

The antibody of any one of embodiments 77 and 81 to 90, wherein the epitope comprises the sequence ICNADLGWHISPSFK (SEQ ID NO: 258).

Embodiment 92

The antibody of any one of embodiments 65 to 91, wherein human TIGIT comprises the sequence of SEQ ID NO: 218.

Embodiment 93

The antibody of any one of embodiments 65 to 92, wherein the antibody comprises one or more of:
(a) a heavy chain CDR1 comprising a sequence selected from SEQ ID NO:4, SEQ ID NO:22, SEQ ID NO:40, SEQ ID NO:58, SEQ ID NO:76, SEQ ID NO:94, SEQ ID NO:112, SEQ ID NO:130, SEQ ID NO:148, SEQ ID NO:166, SEQ ID NO:184, SEQ ID NO:202, SEQ ID NO:221, SEQ ID NO:224, SEQ ID NO:226, SEQ ID NO:231, SEQ ID NO:233, SEQ ID NO:239, SEQ ID NO:243, SEQ ID NO:283, SEQ ID NO:284, SEQ ID NO:293, SEQ ID NO:294, SEQ ID NO:289, and SEQ ID NO:290;
(b) a heavy chain CDR2 comprising a sequence selected from SEQ ID NO:6, SEQ ID NO:24, SEQ ID NO:42, SEQ ID NO:60, SEQ ID NO:78, SEQ ID NO:96, SEQ ID NO:114, SEQ ID NO:132, SEQ ID NO:150, SEQ ID NO:168, SEQ ID NO:186, SEQ ID NO:204, SEQ ID NO:222, SEQ ID NO:225, SEQ ID NO:227, SEQ ID NO:229, SEQ ID NO:232, SEQ ID NO:234, SEQ ID NO:238, SEQ ID NO:240, SEQ ID NO:285, SEQ ID NO:297, SEQ ID NO:291, and SEQ ID NO:295;
(c) a heavy chain CDR3 comprising a sequence selected from SEQ ID NO:8, SEQ ID NO:26, SEQ ID NO:44, SEQ ID NO:62, SEQ ID NO:80, SEQ ID NO:98, SEQ ID NO:116, SEQ ID NO:134, SEQ ID NO:152, SEQ ID NO:170, SEQ ID NO:188, SEQ ID NO:206, SEQ ID NO:223, SEQ ID NO:228, SEQ ID NO:230, SEQ ID NO:235, SEQ ID NO:236, SEQ ID NO:237, SEQ ID NO:241, SEQ ID NO:242, SEQ ID NO:244, SEQ ID NO:286, SEQ ID NO:292, and SEQ ID NO:296;
(d) a light chain CDR1 comprising a sequence selected from SEQ ID NO:13, SEQ ID NO:31, SEQ ID NO:49, SEQ ID NO:67, SEQ ID NO:85, SEQ ID NO:103, SEQ ID NO:121, SEQ ID NO:139, SEQ ID NO:157, SEQ ID NO:175, SEQ ID NO:193, SEQ ID NO:211, and SEQ ID NO:287;
(e) a light chain CDR2 comprising a sequence selected from SEQ ID NO:15, SEQ ID NO:33, SEQ ID NO:51, SEQ ID NO:69, SEQ ID NO:87, SEQ ID NO:105, SEQ ID NO:123, SEQ ID NO:141, SEQ ID NO:159, SEQ ID NO:177, SEQ ID NO:195, SEQ ID NO:213, and SEQ ID NO:288; or
(f) a light chain CDR3 comprising a sequence selected from SEQ ID NO:17, SEQ ID NO:35, SEQ ID NO:53, SEQ ID NO:71, SEQ ID NO:89, SEQ ID NO:107, SEQ ID NO:125, SEQ ID NO:143, SEQ ID NO:161, SEQ ID NO:179, SEQ ID NO:197, and SEQ ID NO:215.

Embodiment 94

The antibody of embodiment 93, wherein the antibody comprises:
(d) a heavy chain CDR1 sequence comprising an amino acid sequence selected from SEQ ID NO:58, SEQ ID NO:283, SEQ ID NO:284, SEQ ID NO:224, SEQ ID NO:293, SEQ ID NO:294, SEQ ID NO:226, SEQ ID NO:289, and SEQ ID NO:290;
(e) a heavy chain CDR2 sequence comprising an amino acid sequence selected from SEQ ID NO:60, SEQ ID NO:285, SEQ ID NO:225, SEQ ID NO:297, SEQ ID NO:227, SEQ ID NO:291, SEQ ID NO:229, and SEQ ID NO:295;
(f) a heavy chain CDR3 sequence comprising an amino acid sequence selected from SEQ ID NO:62, SEQ ID NO:286, SEQ ID NO:228, SEQ ID NO:292, SEQ ID NO:230, and SEQ ID NO:296;
(g) a light chain CDR1 sequence comprising an amino acid sequence selected from SEQ ID NO:67 and SEQ ID NO:287;
(h) a light chain CDR2 sequence comprising an amino acid sequence selected from SEQ ID NO:69 and SEQ ID NO:288; and/or
(i) a light chain CDR3 sequence comprising the amino acid sequence of SEQ ID NO:71.

Embodiment 95

The antibody of embodiment 94, wherein the antibody comprises a heavy chain CDR1, CDR2, and CDR3 and a light chain CDR1, CDR, and CDR3 comprising the sequences of:
(a) SEQ ID NOs: 4, 6, 8, 13, 15, and 17, respectively; or
(b) SEQ ID NOs: 22, 24, 26, 31, 33, and 35, respectively; or
(c) SEQ ID NOs: 40, 42, 44, 49, 51, and 53, respectively; or
(d) SEQ ID NOs: 58, 60, 62, 67, 69, and 71, respectively; or
(e) SEQ ID NOs: 76, 78, 80, 85, 87, and 89, respectively; or
(f) SEQ ID NOs: 94, 96, 98, 103, 105, and 107, respectively; or
(g) SEQ ID NOs: 112, 114, 116, 121, 123, and 125, respectively; or
(h) SEQ ID NOs: 130, 132, 134, 139, 141, and 143, respectively; or
(i) SEQ ID NOs: 148, 150, 152, 157, 159, and 161, respectively; or
(j) SEQ ID NOs: 166, 168, 170, 175, 177, and 179, respectively; or
(k) SEQ ID NOs: 184, 186, 188, 193, 195, and 197, respectively; or
(l) SEQ ID NOs: 202, 204, 206, 211, 213, and 215, respectively; or
(m) SEQ ID NOs: 221, 222, 223, 13, 15, and 17, respectively; or
(n) SEQ ID NOs: 224, 225, 62, 67, 69, and 71, respectively; or
(o) SEQ ID NOs: 226, 227, 228, 67, 69, and 71, respectively; or
(p) SEQ ID NOs: 224, 229, 230, 67, 69, and 71, respectively; or
(q) SEQ ID NOs: 224, 227, 230, 67, 69, and 71, respectively; or
(r) SEQ ID NOs: 231, 232, 235, 103, 105, and 107, respectively; or
(s) SEQ ID NOs: 233, 234, 236, 103, 105, and 107, respectively; or
(t) SEQ ID NOs: 233, 234, 237, 103, 105, and 107, respectively; or
(u) SEQ ID NOs: 166, 238, 170, 175, 177, and 179, respectively; or
(v) SEQ ID NOs: 239, 240, 170, 175, 177, and 179, respectively; or
(w) SEQ ID NOs: 239, 240, 241, 175, 177, and 179, respectively; or
(x) SEQ ID NOs: 239, 240, 242, 175, 177, and 179, respectively; or
(y) SEQ ID NOs: 243, 168, 244, 175, 177, and 179, respectively.

Embodiment 96

The antibody of any one of embodiments 65 to 95, wherein the antibody comprises a heavy chain CDR1, CDR2, and CDR3 and a light chain CDR1, CDR, and CDR3 comprising the sequences of:
(j) SEQ ID NOs: 58, 60, 62, 67, 69, and 71, respectively; or
(k) SEQ ID NOs: 283, 285, 62, 287, 288, and 71, respectively; or
(l) SEQ ID NOs: 284, 60, 286, 67, 69, and 71, respectively.

Embodiment 97

The antibody of any one of embodiments 65 to 96, wherein the antibody comprises:
(a) a heavy chain variable region comprising an amino acid sequence that has at least 90% sequence identity to SEQ ID NO:1, SEQ ID NO:19, SEQ ID NO:37, SEQ ID NO:55, SEQ ID NO:73, SEQ ID NO:91, SEQ ID NO:109, SEQ ID NO:127, SEQ ID NO:145, SEQ ID NO:163, SEQ ID NO:181, SEQ ID NO:199, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, or SEQ ID NO:257; and/or
(b) a light chain variable region comprising an amino acid sequence that has at least 90% sequence identity to SEQ ID NO:10, SEQ ID NO:28, SEQ ID NO:46, SEQ ID NO:64, SEQ ID NO:82, SEQ ID NO:100, SEQ ID NO:118, SEQ ID NO:136, SEQ ID NO:154, SEQ ID NO:172, SEQ ID NO:190, or SEQ ID NO:208.

Embodiment 98

The antibody of any one of embodiments 65 to 97, wherein the antibody comprises:

(a) a heavy chain variable region comprising an amino acid sequence that has at least 90% sequence identity to SEQ ID NO:1 or SEQ ID NO:245 and a light chain variable region comprising an amino acid sequence that has at least 90% sequence identity to SEQ ID NO:10; or
(b) a heavy chain variable region comprising an amino acid sequence that has at least 90% sequence identity to SEQ ID NO:19 and a light chain variable region comprising an amino acid sequence that has at least 90% sequence identity to SEQ ID NO:28; or
(c) a heavy chain variable region comprising an amino acid sequence that has at least 90% sequence identity to SEQ ID NO:37 and a light chain variable region comprising an amino acid sequence that has at least 90% sequence identity to SEQ ID NO:46; or
(d) a heavy chain variable region comprising an amino acid sequence that has at least 90% sequence identity to any one of SEQ ID NO:55, SEQ ID NO:246, SEQ ID NO:247, SEQ ID NO:248, or SEQ ID NO:249 and a light chain variable region comprising an amino acid sequence that has at least 90% sequence identity to SEQ ID NO:64; or
(e) a heavy chain variable region comprising an amino acid sequence that has at least 90% sequence identity to SEQ ID NO:73 and a light chain variable region comprising an amino acid sequence that has at least 90% sequence identity to SEQ ID NO:82; or
(f) a heavy chain variable region comprising an amino acid sequence that has at least 90% sequence identity to any one of SEQ ID NO:91, SEQ ID NO:250, SEQ ID NO:251, or SEQ ID NO:252 and a light chain variable region comprising an amino acid sequence that has at least 90% sequence identity to SEQ ID NO:100; or
(g) a heavy chain variable region comprising an amino acid sequence that has at least 90% sequence identity to SEQ ID NO:109 and a light chain variable region comprising an amino acid sequence that has at least 90% sequence identity to SEQ ID NO:118; or
(h) a heavy chain variable region comprising an amino acid sequence that has at least 90% sequence identity to SEQ ID NO:127 and a light chain variable region comprising an amino acid sequence that has at least 90% sequence identity to SEQ ID NO:136; or
(i) a heavy chain variable region comprising an amino acid sequence that has at least 90% sequence identity to SEQ ID NO:145 and a light chain variable region comprising an amino acid sequence that has at least 90% sequence identity to SEQ ID NO:154; or
(j) a heavy chain variable region comprising an amino acid sequence that has at least 90% sequence identity to any one of SEQ ID NO:163, SEQ ID NO:253, SEQ ID NO:254, SEQ ID NO:255, SEQ ID NO:256, or SEQ ID NO:257 and a light chain variable region comprising an amino acid sequence that has at least 90% sequence identity to SEQ ID NO:172; or
(k) a heavy chain variable region comprising an amino acid sequence that has at least 90% sequence identity to SEQ ID NO:181 and a light chain variable region comprising an amino acid sequence that has at least 90% sequence identity to SEQ ID NO:190; or
(l) a heavy chain variable region comprising an amino acid sequence that has at least 90% sequence identity to SEQ ID NO:199 and a light chain variable region comprising an amino acid sequence that has at least 90% sequence identity to SEQ ID NO:208.

Embodiment 99

The antibody of embodiment 98, wherein the antibody comprises:
(a) a heavy chain variable region comprising the amino acid sequence of SEQ ID NO:1 or SEQ ID NO:245 and a light chain variable region comprising the amino acid sequence of SEQ ID NO:10; or
(b) a heavy chain variable region comprising the amino acid sequence of SEQ ID NO:19 and a light chain variable region comprising the amino acid sequence of SEQ ID NO:28; or
(c) a heavy chain variable region comprising the amino acid sequence of SEQ ID NO:37 and a light chain variable region comprising the amino acid sequence of SEQ ID NO:46; or
(d) a heavy chain variable region comprising the amino acid sequence of any one of SEQ ID NO:55, SEQ ID NO:246, SEQ ID NO:247, SEQ ID NO:248, or SEQ ID NO:249 and a light chain variable region comprising the amino acid sequence of SEQ ID NO:64; or
(e) a heavy chain variable region comprising the amino acid sequence of SEQ ID NO:73 and a light chain variable region comprising the amino acid sequence of SEQ ID NO:82; or
(f) a heavy chain variable region comprising the amino acid sequence of any one of SEQ ID NO:91, SEQ ID NO:250, SEQ ID NO:251, or SEQ ID NO:252 and a light chain variable region comprising the amino acid sequence of SEQ ID NO:100; or
(g) a heavy chain variable region comprising the amino acid sequence of SEQ ID NO:109 and a light chain variable region comprising the amino acid sequence of SEQ ID NO:118; or
(h) a heavy chain variable region comprising the amino acid sequence of SEQ ID NO:127 and a light chain variable region comprising the amino acid sequence of SEQ ID NO:136; or
(i) a heavy chain variable region comprising the amino acid sequence of SEQ ID NO:145 and a light chain variable region comprising the amino acid sequence of SEQ ID NO:154; or
(j) a heavy chain variable region comprising the amino acid sequence of any one of SEQ ID NO:163, SEQ ID NO:253, SEQ ID NO:254, SEQ ID NO:255, SEQ ID NO:256, or SEQ ID NO:257 and a light chain variable region comprising the amino acid sequence of SEQ ID NO:172; or
(k) a heavy chain variable region comprising the amino acid sequence of SEQ ID NO:181 and a light chain variable region comprising the amino acid sequence of SEQ ID NO:190; or
(l) a heavy chain variable region comprising the amino acid sequence of SEQ ID NO:199 and a light chain variable region comprising the amino acid sequence of SEQ ID NO:208.

Embodiment 100

The antibody of any one of embodiments 65 to 99, wherein the antibody comprises a heavy chain variable region comprising the amino acid sequence of SEQ ID NO:55, and a light chain variable region comprising the amino acid sequence of SEQ ID NO:64.

Embodiment 101

The antibody of any one of embodiments 65 to 100, wherein the antibody is an IgG antibody.

Embodiment 102

The antibody of embodiment 101, wherein the antibody is an IgG1 antibody or an IgG3 antibody.

Embodiment 103

The antibody of any one of embodiments 65 to 102, wherein the antibody comprises a heavy chain comprising an amino acid sequence selected from SEQ ID NOs: 260, 262, 264, 266, 268, 270, and 272; and a light chain comprising the amino acid sequence of SEQ ID NO: 274.

Embodiment 104

The antibody of embodiment 103, wherein the antibody comprises a heavy chain comprising the amino acid sequence of SEQ ID NOs: 260; and a light chain comprising the amino acid sequence of SEQ ID NO: 274.

Embodiment 105

The antibody of embodiment 103, wherein the antibody comprises a heavy chain consisting of the amino acid sequence of SEQ ID NOs: 260; and a light chain consisting of the amino acid sequence of SEQ ID NO: 274.

Embodiment 106

An antibody that binds to human TIGIT, wherein the antibody comprises a heavy chain comprising an amino acid sequence selected from SEQ ID NOs: 260, 262, 264, 266, 268, 270, and 272; and a light chain comprising the amino acid sequence of SEQ ID NO: 274.

Embodiment 107

An antibody that binds to human TIGIT, wherein the antibody comprises a heavy chain comprising the amino acid sequence of SEQ ID NOs: 260; and a light chain comprising the amino acid sequence of SEQ ID NO: 274.

Embodiment 108

An antibody that binds to human TIGIT, wherein the antibody comprises a heavy chain consisting of the amino acid sequence of SEQ ID NOs: 260; and a light chain consisting of the amino acid sequence of SEQ ID NO: 274.

Embodiment 109

The antibody of any one of embodiments 65 to 108, wherein the antibody exhibits synergy with an anti-PD-1 antibody or an anti-PD-L1 antibody.

Embodiment 110

The antibody of embodiment 109, wherein synergy is determined using an assay that comprises contacting a co-culture comprising (i) Jurkat effector cells that express PD-1, TIGIT and CD226, wherein the Jurkat effector cells comprise a luciferase reporter gene driven by the IL-2 promoter; and (ii) CHO-K1 artificial antigen presenting cells (aAPCs) expressing a TCR activator, PD-L1 and CD155; with the composition and an anti-PD-1 antibody or an anti-PD-L1 antibody.

Embodiment 111

The antibody of any one of embodiments 65 to 110, wherein regulatory T (Treg) cells are depleted from human PBMCs contacted with the antibody.

Embodiment 112

The antibody of any one of embodiments 65 to 111, expression of MCP1, IL-8, and MIP1α is increased in human PBMCs contacted with the antibody.

Embodiment 113

The antibody of any one of embodiments 65 to 112, wherein monocyte/macrophages are activated when contacted with the antibody.

Embodiment 114

The antibody of any one of embodiments 65 to 113, wherein CD86 and WWII are upregulated when CD14+ monocyte/macrophages are contacted with the antibody.

Embodiment 115

The antibody of any one of embodiments 65 to 114, wherein CD14+ monocyte/macrophages contacted with the antibody mature into antigen presenting cells.

Embodiment 116

The antibody of any one of embodiments 65 to 115, wherein the memory T cells contacted with the antibody show increasd IFNγ production in response to antigen.

Embodiment 117

The antibody of any one of embodiments 65 to 116, wherein the memory T cells contacted with the antibody demonstrate enhanced response to antigen.

Embodiment 118

The antibody of any one of embodiments 65 to 117, wherein effector memory CD8+ T cells and/or effector memory CD4+ T cells are increased in tumors contacted with the antibody.

Embodiment 119

The antibody of any one of embodiments 65 to 118, wherein the antibody enhances a Th1 response in an animal administered the antibody.

Embodiment 120

The antibody of any one of embodiments 65 to 119, wherein the antibody has lower binding affinity for FcγRIIa and/or FcγRIIb compared to the same anti-TIGIT antibody that is not afucosylated.

Embodiment 121

The antibody of any one of embodiments 65 to 120, wherein the composition mediates antibody-dependent cellular phagocytosis (ADCP) of cells that express TIGIT in the presence of monocyte macrophages.

Embodiment 122

The antibody of any one of embodiments 65 to 121, wherein the antibody is monoclonal.

Embodiment 123

The antibody of any one of embodiments 65 to 122, wherein the antibody is a fully human antibody.

Embodiment 124

The antibody of any one of embodiments 65 to 123, wherein the antibody is a chimeric antibody.

Embodiment 125

The antibody of any one of embodiments 65 to 92 and 109 to 124, wherein the antibody is humanized.

Embodiment 126

The antibody of any one of embodiments 65 to 125, wherein the antibody is an antibody fragment.

Embodiment 127

The antibody of embodiment 126, wherein the antibody fragment is a Fab, a Fab', a F(ab')$_2$, a scFv, or a diabody.

Embodiment 128

The antibody of any one of embodiments 65 to 127, wherein the antibody is a bispecific antibody.

Embodiment 129

The antibody of any one of embodiments 65 to 128, wherein the antibody is an antibody-drug conjugate.

Embodiment 130

A pharmaceutical formulation comprising the composition of any one of embodiments 1 to 64 or the antibody of any one of embodiments 65 to 129 and a pharmaceutically acceptable carrier.

Embodiment 131

An isolated polynucleotide that encodes (i) the heavy chain of the antibody of any one of embodiments 106 to 108; (ii) the light chain of the antibody of any one of embodiments 106 to 108; or (iii) the heavy chain and the light chain of the antibody of any one of embodiments 106 to 108.

Embodiment 132

The isolated polynucleotide of embodiment 131, wherein the polynucleotide comprises (i) a nucleotide sequence selected from SEQ ID NOs: 259, 261, 163, 265, 267, 269, and 271; or (ii) a nucleotide sequence of SEQ ID NO: 273; or (iii) a nucleotide sequence selected from SEQ ID NOs: 259, 261, 263, 265, 267, 269, and 271, and a nucleotide sequence of SEQ ID NO: 273.

Embodiment 133

A vector comprising the polynucleotide of embodiment 131 or embodiment 132.

Embodiment 134

An isolated host cell comprising the isolated polynucleotide of embodiment 131 or embodiment 132, or the vector of embodiment 133.

Embodiment 135

An isolated host cell that expresses the antibody of any one of embodiments 106-108.

Embodiment 136

The host cell of embodiment 134 or embodiment 135, which is engineered to produce afucosylated antibodies.

Embodiment 137

A method of producing an antibody that binds to human TIGIT, comprising incubating the host cell of any one of embodiments 134 to 136 under conditions suitable for producing the antibody.

Embodiment 138

The method of embodiment 137, wherein the host cell is engineered to produce afucosylated antibodies.

Embodiment 139

The method of embodiment 137, wherein the host cell is cultured in the presence of a fucose analogue under conditions suitable for producing afucosylated antibodies.

Embodiment 140

The method of any one of embodiments 137 to 139, further comprising isolating the antibodies.

Embodiment 141

A composition of isolated antibodies that bind to human TIGIT, wherein at least 90%, at least 91%, at least 92%, at least 93%, at least 94%, at least 95%, at least 96%, at least 97%, at least 98%, or at least 99% of the antibodies in the composition are afucosylated, wherein the antibodies are produced by the method of any one of embodiments 138 to 140.

Embodiment 142

A composition of isolated antibodies that bind to human TIGIT, wherein at least 90%, at least 91%, at least 92%, at least 93%, at least 94%, at least 95%, at least 96%, at least 97%, at least 98%, or at least 99% of the antibodies in the composition are afucosylated, wherein the antibodies are produced by the method comprising incubating the host cell of embodiment 134 or embodiment 135 under conditions suitable for producing afucosylated antibodies, and isolating the antibodies to form the composition of isolated antibodies.

Embodiment 143

The composition of embodiment 142, wherein the host cell is engineered to produce afucosylated antibodies.

Embodiment 144

The composition of embodiment 142, wherein the host cell is cultured in the presence of a fucose analogue under conditions suitable for producing afucosylated antibodies.

Embodiment 145

A host cell comprising a polynucleotide comprising a nucleotide sequence encoding the (i) antibodies of the composition of any one of embodiments 1 to 63, or (ii) the antibody of any one of embodiments 65 to 128, wherein the host cell is engineered to produce afucosylated antibodies.

Embodiment 146

The host cell of embodiment 145, wherein the polynucleotide is a vector.

Embodiment 147

A host cell that expresses (i) the antibodies of the composition of any one of embodiments 1 to 63, or (ii) the antibody of any one of embodiments 65 to 128, wherein the host cell is engineered to produce afucosylated antibodies.

Embodiment 148

The host cell of any one of embodiments 145 to 147, wherein the host cell comprises:
(a) the nucleotide sequence of SEQ ID NO:2, SEQ ID NO:20, SEQ ID NO:38, SEQ ID NO:56, SEQ ID NO:74, SEQ ID NO:92, SEQ ID NO:110, SEQ ID NO:128, SEQ ID NO:146, SEQ ID NO:164, SEQ ID NO:182, SEQ ID NO:200, SEQ ID NO:259, SEQ ID NO:265, SEQ ID NO:267, SEQ ID NO:269, or SEQ ID NO:271; and/or
(b) the nucleotide sequence of SEQ ID NO:11, SEQ ID NO:29, SEQ ID NO:47, SEQ ID NO:65, SEQ ID NO:83, SEQ ID NO:101, SEQ ID NO:119, SEQ ID NO:137, SEQ ID NO:155, SEQ ID NO:173, SEQ ID NO:191, SEQ ID NO:209, or SEQ ID NO:273.

Embodiment 149

A method of producing afucosylated antibodies that bind TIGIT, comprising culturing the host cell of any one of embodiments 145 to 148 under conditions suitable for producing the afucosylated antibodies.

Embodiment 150

A method of producing afucosylated antibodies that bind TIGIT, comprising culturing a host cell in the presence of a fucose analogue under conditions suitable for producing afucosylated antibodies, wherein the host cell comprises a polynucleotide comprising a nucleotide sequence encoding the (i) antibodies of the composition of any one of embodiments 1 to 63, or (ii) the antibody of any one of embodiments 65 to 128.

Embodiment 151

The method of embodiment 150, wherein the polynucleotide is a vector.

Embodiment 152

A method of producing afucosylated antibodies that bind TIGIT, comprising culturing a host cell in the presence of a fucose analogue under conditions suitable for producing afucosylated antibodies, wherein the host cell expresses (i) the antibodies of the composition of any one of embodiments 1 to 63, or (ii) the antibody of any one of embodiments 65 to 128.

Embodiment 153

The method of any one of embodiments 150 to 152, wherein the host cell comprises:
(a) the nucleotide sequence of SEQ ID NO:2, SEQ ID NO:20, SEQ ID NO:38, SEQ ID NO:56, SEQ ID NO:74, SEQ ID NO:92, SEQ ID NO:110, SEQ ID NO:128, SEQ ID NO:146, SEQ ID NO:164, SEQ ID NO:182, SEQ ID NO:200, SEQ ID NO:259, SEQ ID NO:265, SEQ ID NO:267, SEQ ID NO:269, or SEQ ID NO:271; and/or
(b) the nucleotide sequence of SEQ ID NO:11, SEQ ID NO:29, SEQ ID NO:47, SEQ ID NO:65, SEQ ID NO:83, SEQ ID NO:101, SEQ ID NO:119, SEQ ID NO:137, SEQ ID NO:155, SEQ ID NO:173, SEQ ID NO:191, SEQ ID NO:209, or SEQ ID NO:273.

Embodiment 154

The method of any one of embodiments 150 to 153, wherein the fucose analogue is 2-fluorofucose.

Embodiment 155

The method of any one of embodiments 149 to 154, further comprising isolating the afucosylated antibodies.

Embodiment 156

A composition of isolated antibodies that bind to human TIGIT, wherein at least 90%, at least 91%, at least 92%, at least 93%, at least 94%, at least 95%, at least 96%, at least 97%, at least 98%, or at least 99% of the antibodies in the composition are afucosylated, wherein the antibodies are produced by the method of any one of embodiments 149 to 155.

Embodiment 157

A composition of isolated antibodies that bind to human TIGIT, wherein at least 90%, at least 91%, at least 92%, at least 93%, at least 94%, at least 95%, at least 96%, at least 97%, at least 98%, or at least 99% of the antibodies in the composition are afucosylated, wherein the antibodies are produced by a method comprising incubating the host cell of any one of embodiments 145 to 147 under conditions suitable for producing afucosylated antibodies, and isolating the antibodies to form the composition of isolated antibodies.

Embodiment 158

A composition of isolated antibodies that bind to human TIGIT, wherein at least 90%, at least 91%, at least 92%, at least 93%, at least 94%, at least 95%, at least 96%, at least 97%, at least 98%, or at least 99% of the antibodies in the composition are afucosylated, wherein the antibodies are produced by a method comprising culturing a host cell in the presence of a fucose analogue under conditions suitable for producing afucosylated antibodies, wherein the host cell comprises a polynucleotide comprising a nucleotide sequence encoding the (i) antibodies of the composition of any one of embodiments 1 to 63, or (ii) the antibody of any one of embodiments 65 to 128.

Embodiment 159

A composition of isolated antibodies that bind to human TIGIT, wherein at least 90%, at least 91%, at least 92%, at least 93%, at least 94%, at least 95%, at least 96%, at least 97%, at least 98%, or at least 99% of the antibodies in the composition are afucosylated, wherein the antibodies are produced by a method comprising culturing a host cell in the presence of a fucose analogue under conditions suitable for producing afucosylated antibodies, wherein the host cell expresses (i) the antibodies of the composition of any one of embodiments 1 to 63, or (ii) the antibody of any one of embodiments 65 to 128.

Embodiment 160

A kit comprising:
the composition of any one of embodiments 1 to 64, the antibody of any one of embodiments 65 to 129, or the pharmaceutical composition of embodiment 130; and an additional therapeutic agent.

Embodiment 161

The kit of embodiment 160, wherein the additional therapeutic is an anti-cancer agent.

Embodiment 162

The kit of embodiment 160 or embodiment 161, wherein the additional therapeutic agent is an antibody.

Embodiment 163

The kit of any one of embodiments 160 to 162, wherein the additional therapeutic agent is an antagonist or an inhibitor of a T cell coinhibitor; an agonist of a T cell coactivator; an immune stimulatory cytokine; or SGN-2FF.

Embodiment 164

The kit of any one of embodiments 160 to 163, wherein the additional therapeutic agent binds a protein selected from CD25, PD-1, PD-L1, Tim3, Lag3, CTLA4, 41BB, OX40, CD3, CD40, CD47M, GM-CSF, CSF1R, TLR, STING, RIGI, TAM receptor kinase, NKG2A, NKG2D, GD2, HER2, EGFR, PDGFRa, SLAMF7, VEGF, CTLA-4, CD20, cCLB8, KIR, and CD52.

Embodiment 165

The kit of embodiment any one of embodiments 160 to 164, wherein the additional therapeutic agent is selected from an anti-CD25 antibody, anti-PD-1 antibody, anti-PD-L1 antibody, anti-Tim3 antibody, anti-Lag3 antibody, anti-CTLA4 antibody, anti-41BB antibody, anti-OX40 antibody, anti-CD3 antibody, anti-CD40 antibody, anti-CD47M antibody, anti-CSF1R antibody, anti-TLR antibody, anti-STING antibody, anti-RIGI antibody, anti-TAM receptor kinase antibody, anti-NKG2A antibody, an anti-NKG2D antibody, an anti-GD2 antibody, an anti-HER2 antibody, an anti-EGFR antibody, an anti-PDGFR-α-antibody, an anti-SLAMF7 antibody, an anti-VEGF antibody, an anti-CTLA-4 antibody, an anti-CD20 antibody, an anti-cCLB8 antibody, an anti-KIR antibody, and an anti-CD52 antibody.

Embodiment 166

The kit of any one of embodiments 160 to 165, wherein the additional therapeutic agent comprises a cytokine selected from IL-15, IL-21, IL-2, GM-CSF, M-CSF, G-CSF, IL-1, IL-3, IL-12, and IFNγ.

Embodiment 167

The kit of any one of embodiments 160 to 165, wherein the additional therapeutic agent is selected from SEA-CD40, avelumab, durvalumab, nivolumab, pembrolizumab, pidilizumab, atezolizumab, Hu14.18K322A, Hu3F8, dinituximab, trastuzumab, cetuximab, olaratumab, necitumumab, elotuzumab, ramucirumab, pertuzumab, ipilimumab, bevacizumab, rituximab, obinutuzumab, siltuximab, ofatumumab, lirilumab, and alemtuzumab.

Embodiment 168

The kit of embodiment 160 or embodiment 161, wherein the additional therapeutic agent is selected from an alkylating agent (e.g., cyclophosphamide, ifosfamide, chlorambucil, busulfan, melphalan, mechlorethamine, uramustine, thiotepa, nitrosoureas, or temozolomide), an anthracycline (e.g., doxorubicin, adriamycin, daunorubicin, epirubicin, or mitoxantrone), a cytoskeletal disruptor (e.g., paclitaxel or docetaxel), a histone deacetylase inhibitor (e.g., vorinostat or romidepsin), an inhibitor of topoisomerase (e.g., irinotecan, topotecan, amsacrine, etoposide, or teniposide), a kinase inhibitor (e.g., bortezomib, erlotinib, gefitinib, imatinib, vemurafenib, or vismodegib), a nucleoside analog or precursor analog (e.g., azacitidine, azathioprine, capecitabine, cytarabine, fluorouracil, gemcitabine, hydroxyurea, mercaptopurine, methotrexate, or thioguanine), a peptide antibiotic (e.g., actinomycin or bleomycin), a platinum-based agent (e.g., cisplatin, oxaloplatin, or carboplatin), or a plant alkaloid (e.g., vincristine, vinblastine, vinorelbine, vindesine, podophyllotoxin, paclitaxel, or docetaxel), galardin, thalidomide, lenalidomide, and pomalidomide.

Embodiment 169

A method of treating a cancer in a subject, comprising administering to the subject a therapeutically effective amount of the composition of any one of embodiments 1 to 64, the antibody of any one of embodiments 65 to 129, or the pharmaceutical composition of embodiment 130.

Embodiment 170

The method of embodiment 169, wherein the cancer is a cancer that is enriched for expression of CD112 or CD155.

Embodiment 171

The method of embodiment 169 or embodiment 170, wherein the cancer is a cancer that is enriched for T cells or natural killer (NK) cells that express TIGIT.

Embodiment 172

The method of any one of embodiments 169 to 171, wherein the cancer is bladder cancer, breast cancer, uterine cancer, cervical cancer, ovarian cancer, prostate cancer, testicular cancer, esophageal cancer, gastrointestinal cancer, gastric cancer, pancreatic cancer, colorectal cancer, colon cancer, kidney cancer, clear cell renal carcinoma, head and neck cancer, lung cancer, lung adenocarcinoma, stomach cancer, germ cell cancer, bone cancer, liver cancer, thyroid cancer, skin cancer, melanoma, neoplasm of the central nervous system, mesothelioma, lymphoma, leukemia, chronic lymphocytic leukemia, diffuse large B cell lymphoma, follicular lymphoma, Hodgkin lymphoma, myeloma, or sarcoma.

Embodiment 173

The method of embodiment 172, wherein the cancer is lymphoma, leukemia, chronic lymphocytic leukemia, diffuse large B cell lymphoma, follicular lymphoma, or Hodgkin lymphoma.

Embodiment 174

The method of any one of embodiments 169 to 173, further comprising administering to the subject a therapeutically effective amount of an additional therapeutic agent.

Embodiment 175

The method of embodiment 174, wherein the additional therapeutic is an anti-cancer agent.

Embodiment 176

The method of embodiment 174 or embodiment 175, wherein the additional therapeutic agent is an antibody.

Embodiment 177

The method of any one of embodiments 174 to 176, wherein the additional therapeutic agent is an antagonist or an inhibitor of a T cell coinhibitor; an agonist of a T cell coactivator; or an immune stimulatory cytokine; or SGN-2FF.

Embodiment 178

The method of any one of embodiments 174 to 177, wherein the additional therapeutic agent binds a protein selected from CD25, PD-1, PD-L1, Tim3, Lag3, CTLA4, 41BB, OX40, CD3, CD40, CD47M, GM-CSF, CSF1R, TLR, STING, RIGI, TAM receptor kinase, NKG2A, NKG2D, GD2, HER2, EGFR, PDGFRa, SLAMF7, VEGF, CTLA-4, CD20, cCLB8, KIR, and CD52.

Embodiment 179

The method of embodiment 178, wherein the additional therapeutic agent is selected from an anti-CD25 antibody, anti-PD-1 antibody, anti-PD-L1 antibody, anti-Tim3 antibody, anti-Lag3 antibody, anti-CTLA4 antibody, anti-41BB antibody, anti-OX40 antibody, anti-CD3 antibody, anti-CD40 antibody, anti-CD47M antibody, anti-CSF1R antibody, anti-TLR antibody, anti-STING antibody, anti-RIGI antibody, anti-TAM receptor kinase antibody, anti-NKG2A antibody, an anti-NKG2D antibody, an anti-GD2 antibody, an anti-HER2 antibody, an anti-EGFR antibody, an anti-PDGFR-α-antibody, an anti-SLAMF7 antibody, an anti-VEGF antibody, an anti-CTLA-4 antibody, an anti-CD20 antibody, an anti-cCLB8 antibody, an anti-KIR antibody, and an anti-CD52 antibody.

Embodiment 180

The method of embodiment 174 or embodiment 175, wherein the additional therapeutic agent comprises a cytokine selected from IL-15, IL-21, IL-2, GM-CSF, M-CSF, G-CSF, IL-1, IL-3, IL-12, and IFNγ.

Embodiment 181

The method of any one of embodiments 174 to 179, wherein the additional therapeutic agent is selected from SEA-CD40, avelumab, durvalumab, nivolumab, pembrolizumab, pidilizumab, atezolizumab, Hu14.18K322A, Hu3F8, dinituximab, trastuzumab, cetuximab, olaratumab, necitumumab, elotuzumab, ramucirumab, pertuzumab, ipilimumab, bevacizumab, rituximab, obinutuzumab, siltuximab, ofatumumab, lirilumab, and alemtuzumab.

Embodiment 182

The method of embodiment 174 or embodiment 175, wherein the additional therapeutic agent is selected from an alkylating agent (e.g., cyclophosphamide, ifosfamide, chlorambucil, busulfan, melphalan, mechlorethamine, uramustine, thiotepa, nitrosoureas, or temozolomide), an anthracycline (e.g., doxorubicin, adriamycin, daunorubicin, epirubicin, or mitoxantrone), a cytoskeletal disruptor (e.g., paclitaxel or docetaxel), a histone deacetylase inhibitor (e.g., vorinostat or romidepsin), an inhibitor of topoisomerase (e.g., irinotecan, topotecan, amsacrine, etoposide, or teniposide), a kinase inhibitor (e.g., bortezomib, erlotinib, gefitinib, imatinib, vemurafenib, or vismodegib), a nucleoside analog or precursor analog (e.g., azacitidine, azathioprine, capecitabine, cytarabine, fluorouracil, gemcitabine, hydroxyurea, mercaptopurine, methotrexate, or thioguanine), a peptide antibiotic (e.g., actinomycin or bleomycin), a platinum-based agent (e.g., cisplatin, oxaloplatin, or carboplatin), or a plant alkaloid (e.g., vincristine, vinblastine, vinorelbine, vindesine, podophyllotoxin, paclitaxel, or docetaxel), galardin, thalidomide, lenalidomide, and pomalidomide.

Embodiment 183

The method of any one of embodiments 174 to 182, wherein the composition, the antibody, or the pharmaceutical composition is administered concurrently with the additional therapeutic agent.

Embodiment 184

The method of any one of embodiments 174 to 183, wherein the composition, the antibody, or the pharmaceutical composition is administered sequentially to the additional therapeutic agent.

BRIEF DESCRIPTION OF THE DRAWINGS

FIG. 3A-3D. (A-C) Binding titration values of eight anti-TIGIT antibody clones (clones 2, 5, 13, 16, 17, 20, 25, and 54) to human (A), mouse (B), and cynomolgus monkey (C) TIGIT expressed on HEK 293 cells. Results are shown for singlicate wells. (D) EC50 values of eight anti-TIGIT antibody clones (clones 2, 5, 13, 16, 17, 20, 25, and 54) to human, mouse, and cynomolgus monkey TIGIT expressed on HEK 293 cells.

FIG. 5A-5B. Anti-TIGIT antibodies blocked CD155 interaction with TIGIT expressed on HEK 293 cells, for both human CD155 binding to HEK 293 cells expressing human TIGIT (A) and mouse CD155 binding to HEK 293 cells expressing mouse TIGIT (B). Results are shown for singlicate wells.

FIG. 6. Anti-TIGIT antibodies blocked human CD112 interaction with human TIGIT expressed on HEK 293 cells. Results are shown for singlicate wells.

FIG. 7A-7B. (A) Upper panel: Select anti-TIGIT antibodies effectively blocked TIGIT-CD155 engagement, resulting in T cell activation, as measured by a >1.5-fold induction in luciferase activity. About 12 clones showed >1.5-fold induction in the bioassay. Two clones did not block TIGIT-CD155 interaction in ForteBio assay (pink bars). Fold induction was measured over no Ab control. Mean and SD are of duplicate experiments; antibodies were at 20 µg/mL. Gray bar=hIgG1 isotype control. Black bar=no antibody control (defined as baseline). Lower panel: Correlation plot of TIGIT/CD155 blockade bioassay versus TIGIT-Fc affinity. The activity in the bioassay correlated with affinity for recombinant protein. (B) Dose response of 12 selected anti-TIGIT clones in TIGIT/CD155 blockade bioassay. Clones 13 and 25, which showed strong binding to all three species, showed good activity in the bioassay. Mean and SD are of triplicate wells.

FIG. 9A-9H. (A-D) Binding titration (A-C) and EC50 values (D) for binding to human (A), mouse (B), and cynomolgus monkey (C) TIGIT expressed on HEK 293 cells for fully human anti-TIGIT clone 13 ("c13 hIgG1") and mouse IgG1 ("c13 mIgG1") and mouse IgG2a ("c13 mIgG2a") chimeras of clone 13. Mean and SD are of duplicate wells. (E-F) Antibodies c13 hIgG1, c13 mIgG1, and c13 mIgG2a blocked CD155 interaction with TIGIT expressed on HEK 293 cells, for both human CD155 binding to HEK 293 cells expressing human TIGIT (E) and mouse CD155 binding to HEK 293 cells expressing mouse TIGIT (F). Results are for singlicate wells. (G) Antibodies c13 hIgG1, c13 mIgG1, and c13 mIgG2a blocked human CD112 interaction with human TIGIT expressed on HEK 293 cells. Results are for singlicate wells. (H) Dose response of parental and chimeric anti-TIGIT antibody clones c13 hIgG1, c13 mIgG1, and c13 mIgG2a in TIGIT/CD155 blockade bioassay. Mean and SD are of triplicate wells.

FIG. 10A-10K. Anti-TIGIT antibodies that can engage activating Fcgamma receptors mediated anti-tumor efficacy in a CT26 syngeneic tumor model in mice. (A) Group mean tumor volume. (B-K) Individual animal tumor volume for groups 1 through 10. PR=Partial Response (tumor volume is 50% or less of its day 1 volume for three consecutive measurements and equal to or greater than 13.5 mm$^3$ for one or more of these three measurements). CR=Complete Response (tumor volume is less than 13.5 mm$^3$ for three consecutive measurements).

FIG. 8A shows the effect of clone 13 IgG2a wild-type, clone 13 IgG2a afucosylated, and clone 13 IgG2a LALA-PG on the tumor volume in the A20 syngeneic lymphoma model. FIG. 8B shows the effect of clone 13 IgG2a wild-type, clone 13 IgG2a afucosylated, and clone 13 IgG2a LALA-PG on the tumor volume in CT26 syngeneic colon cancer model. FIG. 8C shows the effect of clone 13 IgG2a wild-type, clone 13 IgG2a afucosylated, and clone 13 IgG2a LALA-PG on the tumor volume in MC38 syngeneic colon cancer model. In all 3 models, clone 13 mIgG2a wild-type (black circles) and clone 13 mIGg2a afucosylated (black diamonds) were more effective at controlling tumor size when compared to clone 13 IgG2a LALPG (black squares) or untreated animals (gray triangles).

FIG. 29A shows the effect of 5 mg/kg clone 13 IgG2a wild-type ("TIGIT") and 0.1 mg/kg, 1 mg·kg, and 5 mg/kg clone 13 IgG2a afucosylated ("SEA TIGIT") on the tumor volume in the EMT6 syngeneic breast cancer model. FIG. 29B shows the effect of 5 mg/kg clone 13 IgG2a wild-type ("TIGIT") and 0.1 mg/kg, 1 mg·kg, and 5 mg/kg clone 13 IgG2a afucosylated ("SEA TIGIT") on the tumor volume in E0771 syngeneic breast cancer model. FIG. 29C shows the effect of 1 mg/ml clone 13 IgG2a wild-type on the tumor volume in an externally maintained CT26 syngeneic colon cancer model.

FIG. 32. Anti-OVA IgG1 (left panel) and IgG2a (right panel) levels in mice following vaccination with OVA and treatment with 1 mg/kg clone 13 IgG2a wild-type ("WT TIGIT"), clone 13 mIgG2a afucosylated ("SEA TIGIT"), or clone 13 mIgG2a LALA-PG ("LALA TIGIT") antibody.

FIG. 38A IL-2 expression (FIG. 38A) or IL-10 expression (FIG. 38B) following contact with superantigen staphylococcal enterotoxin B peptide and anti-TIGIT antibodies clone 13 IgG1 wild-type ("WT Clone 13"), clone 13 IgG1 afucosylated ("SEA clone 13"), clone 13 IgG1 DLE ("DLE"), or clone H5/L4 IgG1.

Figure 1:
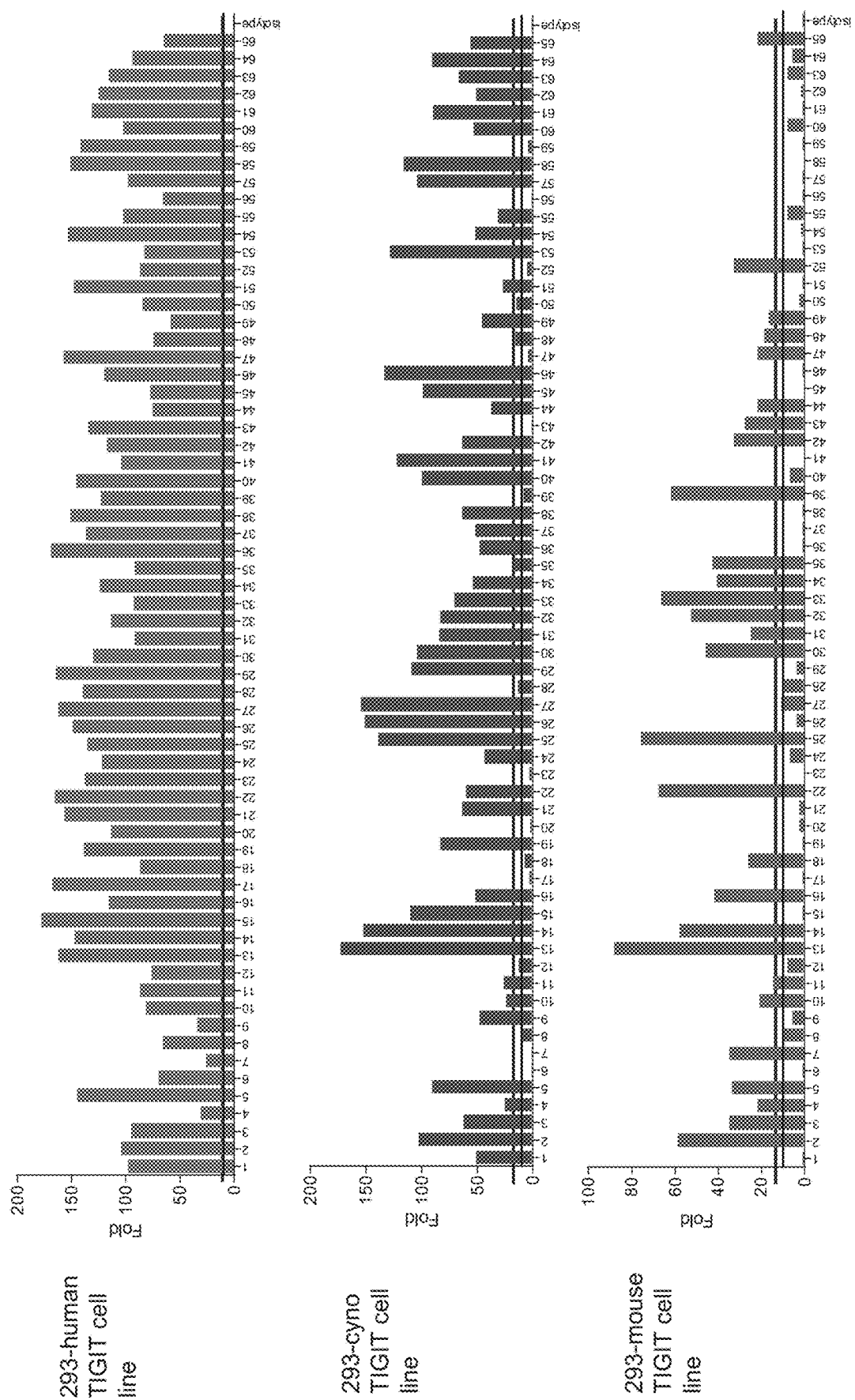
FIG. 1. Binding of 65 anti-TIGIT antibody clones and an irrelevant isotype control antibody to HEK 293 cells engineered to express human TIGIT (top panel), cynomolgus monkey TIGIT (middle panel), and mouse TIGIT (bottom panel).

DLE ("Clone 13 DLE"), or clone H5/L4 IgG1; and by anti-CD47 antibody hB6h12.3.

DETAILED DESCRIPTION

I. Introduction

Provided herein are antibodies having high affinity for human TIGIT (T-cell immunoreceptor with Ig and ITIM domains), and further having cross-reactivity with either or both of mouse TIGIT and cynomolgus monkey TIGIT, have been identified that inhibit the interaction between TIGIT and CD155. These antibodies also exhibit synergy with anti-PD-1 antibodies. Thus, the anti-TIGIT antibodies described herein may be used in a number of therapeutic applications, such as for the treatment of various cancers, either as a single agent or in combination with another therapeutic agent. In some embodiments, the anti-TIGIT antibodies are afucosylated.

Accordingly, in some embodiments, the present invention provides compositions, kits, and methods of treatment comprising an antibody that binds to human TIGIT, wherein the antibody is afucosylated.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention.

As used herein, the singular forms "a", "an" and "the" include plural referents unless the content clearly dictates otherwise. Thus, for example, reference to "an antibody" optionally includes a combination of two or more such molecules, and the like.

The term "about," as used herein, refers to the usual error range for the respective value readily known to the skilled person in this technical field.

As used herein, the term "TIGIT" refers to "T-cell immunoreceptor with Ig and ITIM domains." The protein encoded by the TIGIT gene is a member of the CD28 family within the Ig superfamily of proteins. TIGIT is expressed on several classes of T cells and on natural killer (NK) cells and mediates its immunosuppressive effect by competing with CD226 for the ligands CD155 and CD112. See, Levin et al., *Eur. J. Immunol.*, 2011, 41:902-915. TIGIT is also referred to in the art as WUCAM (Washington University Cell Adhesion Molecule) and VSTM3 (HUGO designation). See, Levin et al., *Eur J Immunol*, 2011, 41:902-915. Accordingly, reference to "TIGIT" throughout this application also includes a reference to WUCAM and/or VSTM3 unless otherwise stated or apparent from context. Human TIGIT nucleotide and protein sequences are set forth in, e.g., Genbank Accession Nos. NM173799 (SEQ ID NO:217) and NP776160 (SEQ ID NO:218), respectively.

The term "antibody" includes intact antibodies and antigen-binding fragments thereof, wherein the antigen-binding fragments comprise the antigen-binding region and at least a portion of the heavy chain constant region comprising asparagine (N) 297, located in CH2. Typically, the "variable region" contains the antigen-binding region of the antibody and is involved in specificity and affinity of binding. See, *Fundamental Immunology* 7$^{th}$ *Edition*, Paul, ed., Wolters Kluwer Health/Lippincott Williams & Wilkins (2013). Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively.

The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

The term "antibody" includes an antibody by itself (naked antibody) or an antibody conjugated to a cytotoxic or cytostatic drug.

A "monoclonal antibody" refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, for example, U.S. Pat. No. 4,816,567). The "monoclonal antibodies" may also be isolated from phage antibody libraries using the techniques described in Clackson et al. (1991) Nature, 352:624-628 and Marks et al. (1991) J. Mol. Biol., 222:581-597, for example or may be made by other methods. The antibodies described herein are monoclonal antibodies.

Specific binding of a monoclonal antibody to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, J. Mol. Biol. 196:901-917 (1987); Chothia et al., Nature 342:878-883 (1989), or a composite of Kabat and Chothia, or IMGT (ImMunoGeneTics information system), AbM or Contact or other conventional definition of CDRs. Kabat also provides a widely used numbering convention (Kabat numbering) in which corresponding residues between different heavy chains or between different light chains are assigned the same number. Unless otherwise apparent from the context, Kabat numbering is used to designate the position of amino acids in the variable regions. Unless otherwise apparent from the context EU numbering is used to designated positions in constant regions.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *PNAS USA*, 81:6851-6855 (1984); Morrison and Oi, *Adv. Immunol.*, 44:65-92 (1988); Verhoeyen et al., *Science*, 239:1534-1536 (1988); Padlan, *Molec. Immun.*, 28:489-498 (1991); Padlan, *Molec. Immun.*, 31(3):169-217 (1994).

As used herein, the term "chimeric antibody" refers to an antibody molecule in which (a) the constant region, or a portion thereof, is replaced so that the antigen binding site (variable region, CDR, or portion thereof) is linked to a constant region of a different species.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The phrase "specifically binds" refers to a molecule (e.g., antibody or antibody fragment) that binds to a target with greater affinity, avidity, more readily, and/or with greater duration to that target in a sample than it binds to a non-target compound. In some embodiments, an antibody that specifically binds a target is an antibody that binds to the target with at least 2-fold greater affinity than non-target compounds, such as, for example, at least 4-fold, 5-fold, 6-fold, 7-fold, 8-fold, 9-fold, 10-fold, 20-fold, 25-fold, 50-fold, or 100-fold greater affinity. For example, an antibody that specifically binds TIGIT will typically bind to TIGIT with at least a 2-fold greater affinity than to a non-TIGIT target. It will be understood by a person of ordinary skill in the art reading this definition, for example, that an antibody (or moiety or epitope) that specifically or preferentially binds to a first target may or may not specifically or preferentially bind to a second target. As such, "specific binding" does not necessarily require (although it can include) exclusive binding.

The term "binding affinity" is herein used as a measure of the strength of a non-covalent interaction between two molecules, e.g., an antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation using, as a nonlimiting example, the surface plasmon resonance (SPR) method (Biacore™). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D = k_d/k_a$. The value of the dissociation constant can be determined directly by well-known methods, and can be computed even for complex mixtures by methods such as those, for example, set forth in Caceci et al. (1984, *Byte* 9: 340-362). For example, the $K_D$ may be established using a double-filter nitrocellulose filter binding assay such as that disclosed by Wong & Lohman (1993, *Proc. Natl. Acad. Sci. USA* 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art or as described in the Examples section below, such as Surface Plasmon Resonance (SPR), e.g. by using a Biacore™ system; kinetic exclusion assays such as KinExA®; and BioLayer interferometry (e.g., using the ForteBio® Octet platform). In some embodiments, binding affinity is determined using a BioLayer interferometry assay. See, e.g., Wilson et al., *Biochemistry and Molecular Biology Education*, 38:400-407 (2010); Dysinger et al., *J. Immunol. Methods*, 379:30-41 (2012); and Estep et al., *Mabs*, 2013, 5:270-278.

The term "cross-reacts," as used herein, refers to the ability of an antibody to bind to an antigen other than the antigen against which the antibody was raised. In some embodiments, cross-reactivity refers to the ability of an antibody to bind to an antigen from another species than the antigen against which the antibody was raised. As a non-limiting example, an anti-TIGIT antibody as described herein that is raised against a human TIGIT antigen can exhibit cross-reactivity with TIGIT from a different species (e.g., mouse or monkey).

An "isolated" antibody refers to an antibody that has been identified and separated and/or recovered from components of its natural environment and/or an antibody that is recombinantly produced. A "purified antibody" is an antibody that is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Interfering proteins and other contaminants can include, for example, cellular components of the cells from which an antibody is isolated or recombinantly produced. Sometimes monoclonal antibodies are at least 60%, 70%, 80%, 90%, 95 or 99% w/w pure of interfering proteins and contaminants from production or purification. The antibodies described herein, including rat, chimeric, veneered and humanized antibodies can be provided in isolated and/or purified form.

The term "immuno-oncology agent" refers to an agent that enhances, stimulates, or upregulates an immune response against a cancer in a subject (e.g., in stimulating an immune response for inhibiting tumor growth). In some embodiments, an immuno-oncology agent is a small molecule, antibody, peptide, protein, circular peptide, peptidomimetic, polynucleotide, inhibitory RNA, aptamer, drug compound, or other compound. In some embodiments, an immuno-oncology agent is an antagonist or inhibitor of PD-1 or the PD-1 pathway.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision.

The terms "therapy," "treatment," and "amelioration" refer to any reduction in the severity of symptoms. In the case of treating cancer, treatment can refer to reducing, e.g., tumor size, number of cancer cells, growth rate, metastatic activity, cell death of non-cancer cells, etc. As used herein, the terms "treat" and "prevent" are not intended to be absolute terms. Treatment and prevention can refer to any delay in onset, amelioration of symptoms, improvement in patient survival, increase in survival time or rate, etc. Treatment and prevention can be complete (no detectable symptoms remaining) or partial, such that symptoms are less frequent or severe than in a patient without the treatment described herein. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects, the severity of disease is reduced by at least 25%, 50%, 75%, 80%, or 90%, or in some cases, no longer detectable using standard diagnostic techniques.

As used herein, a "therapeutic amount" or "therapeutically effective amount" of an agent (e.g., an antibody as described herein) is an amount of the agent that prevents, alleviates, abates, ameliorates, or reduces the severity of symptoms of a disease (e.g., a cancer) in a subject.

The terms "administer," "administered," or "administering" refer to methods of delivering agents, compounds, or compositions to the desired site of biological action. These methods include, but are not limited to, topical delivery, parenteral delivery, intravenous delivery, intradermal delivery, intramuscular delivery, colonic delivery, rectal delivery, or intraperitoneal delivery. Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

III. Antibodies Against TIGIT

In one aspect, antibodies that bind to human TIGIT (T-cell immunoreceptor with Ig and ITIM domains) are provided. As described herein, in some embodiments, the anti-TIGIT antibody inhibits interaction between TIGIT and one or both of the ligands CD155 and CD112. In some embodiments, the anti-TIGIT antibody inhibits the interaction between TIGIT and CD155 in a functional bioassay, allowing CD155-CD226 signaling to occur. In some embodiments, the anti-TIGIT antibody exhibits synergy with an anti-PD-1 agent (e.g., an anti-PD-1 antibody) or an anti-PD-L1 agent (e.g., an anti-PD-L1 antibody).

The present inventors found that, surprisingly, anti-TIGIT antibodies with enhanced effector function, such as may be achieved with afucosylated IgG1 antibodies, deplete Treg cells and show improved efficacy in vivo. Accordingly, in various embodiments, afucosylated anti-TIGIT antibodies are provided.

Exemplary Characteristics of Anti-TIGIT Antibodies

In some embodiments, an anti-TIGIT antibody, such as an afucosylated anti-TIGIT antibody, binds to human TIGIT protein (SEQ ID NO:218) or a portion thereof with high affinity. In some embodiments, the antibody has a binding affinity ($K_D$) for human TIGIT of less than 5 nM, less than 1 nM, less than 500 pM, less than 250 pM, less than 150 pM, less than 100 pM, less than 50 pM, less than 40 pM, less than 30 pM, less than 20 pM, or less than about 10 pM. In some embodiments, the antibody has a binding affinity ($K_D$) for human TIGIT of less than 50 pM. In some embodiments, the antibody has a $K_D$ for human TIGIT in the range of about 1 pM to about 5 nM, e.g., about 1 pM to about 1 nM, about 1 pM to about 500 pM, about 5 pM to about 250 pM, or about 10 pM to about 100 pM.

In some embodiments, in addition to binding to human TIGIT with high affinity, an afucosylated anti-TIGIT antibody exhibits cross-reactivity with cynomolgus monkey ("cyno") TIGIT (e.g., a cyno TIGIT protein having the sequence of SEQ ID NO:219) and/or mouse TIGIT (e.g., a mouse TIGIT protein having the sequence of SEQ ID NO:220). In some embodiments, the anti-TIGIT antibody binds to mouse TIGIT (e.g., a mouse TIGIT having the sequence of SEQ ID NO:220) with a binding affinity ($K_D$) of 100 nM or less. In some embodiments, the anti-TIGIT antibody binds to human TIGIT with a $K_D$ of 5 nM or less, and cross-reacts with mouse TIGIT with a $K_D$ of 100 nM or less. In some embodiments, an anti-TIGIT antibody that binds to a human TIGIT also exhibits cross-reactivity with both cynomolgus monkey TIGIT and mouse TIGIT.

In some embodiments, antibody cross-reactivity is determined by detecting specific binding of the anti-TIGIT antibody to TIGIT that is expressed on a cell (e.g., a cell line that expresses human TIGIT, cyno TIGIT, or mouse TIGIT, or a primary cell that endogenously expresses TIGIT, e.g., primary T cells that endogenously express human TIGIT, cyno TIGIT, or mouse TIGIT). In some embodiments, antibody binding and antibody cross-reactivity is determined by detecting specific binding of the anti-TIGIT antibody to purified or recombinant TIGIT (e.g., purified or recombinant human TIGIT, purified or recombinant cyno TIGIT, or purified or recombinant mouse TIGIT) or a chimeric protein comprising TIGIT (e.g., an Fc-fusion protein comprising human TIGIT, cyno TIGIT, or mouse TIGIT, or a His-tagged protein comprising human TIGIT, cyno TIGIT, or mouse TIGIT).

Methods for analyzing binding affinity, binding kinetics, and cross-reactivity are known in the art. See, e.g., Ernst et al., Determination of Equilibrium Dissociation Constants, *Therapeutic Monoclonal Antibodies* (Wiley & Sons ed. 2009). These methods include, but are not limited to, solid-phase binding assays (e.g., ELISA assay), immunoprecipitation, surface plasmon resonance (SPR, e.g., Biacore™ (GE Healthcare, Piscataway, N.J.)), kinetic exclusion assays (e.g. KinExA®), flow cytometry, fluorescence-activated cell sorting (FACS), BioLayer interferometry (e.g., Octet™ (ForteBio, Inc., Menlo Park, Calif.)), and Western blot analysis. SPR techniques are reviewed, e.g., in Hahnfeld et al. Determination of Kinetic Data Using SPR Biosensors, *Molecular Diagnosis of Infectious Diseases* (2004). In a typical SPR experiment, one interactant (target or targeting agent) is immobilized on an SPR-active, gold-coated glass slide in a flow cell, and a sample containing the other interactant is introduced to flow across the surface. When light of a given wavelength is shined on the surface, the changes to the optical reflectivity of the gold indicate binding, and the kinetics of binding. In some embodiments, kinetic exclusion assays are used to determine affinity. This technique is described, e.g., in Darling et al., *Assay and Drug Development Technologies* Vol. 2, number 6 647-657 (2004). In some embodiments, BioLayer interferometry assays are used to determine affinity. This technique is described, e.g., in Wilson et al., *Biochemistry and Molecular Biology Education*, 38:400-407 (2010); Dysinger et al., *J. Immunol. Methods*, 379:30-41 (2012).

In some embodiments, the anti-TIGIT antibodies provided herein inhibit interaction between TIGIT and the ligand CD155. In some embodiments, the anti-TIGIT antibodies provided herein inhibit interaction between TIGIT and the ligand CD112. In some embodiments, the anti-TIGIT antibodies provided herein inhibit interaction between TIGIT and both of the ligands CD155 and CD112.

In some embodiments, the ability of an anti-TIGIT antibody to inhibit interactions between TIGIT and CD155 and/or CD112 is evaluated by measuring whether physical interactions between TIGIT and CD155 or CD112 decrease in a binding assay. In some embodiments, the binding assay is a competitive binding assay. The assay may be performed in various formats, such as but not limited to an ELISA assay, flow cytometry, a surface plasmon resonance (SPR) assay (e.g., Biacore™), or BioLayer interferometry (e.g., ForteBio Octet™) See, e.g., Duff et al., *Biochem J.*, 2009, 419:577-584; Dysinger et al., *J. Immunol. Methods*, 379:30-41 (2012); and Estep et al, *Mabs*, 2013, 5:270-278.

In some embodiments, the anti-TIGIT antibody inhibits the interaction between TIGIT and CD155 in a functional bioassay, such as a functional cellular assay in which inhibition of TIGIT/CD155 interaction is evaluated by measuring activation of CD155-CD226 signaling in the cell (e.g., via activation of a downstream reporter). A non-limiting exemplary functional cellular assay is described in the Examples section below. In this exemplary functional assay, luciferase expression requires TCR engagement and a co-stimulatory signal from CD155-CD226. A first cell (also referred to as a "T effector cell") expresses a TCR complex, TIGIT, and CD226 on the cell surface and contains a luciferase gene. A second cell (also referred to as an "artificial antigen presenting cell") expresses a TCR activator and CD155. Co-culture of the cells in the absence of anti-TIGIT antibody results in a TIGIT-CD155 interaction that inhibits co-stimulation of the effector cell by CD155-CD226, preventing expression of luciferase by the effector cell. In the presence of an anti-TIGIT antibody that inhibits the interaction between TIGIT and CD155, CD155 and CD226 are able to interact and produce a co-stimulatory signal that drives luciferase expression in the first cell. Such functional cellular assays are described in the art, e.g., Cong et al., *Genetic Engineering and Biotechnology News*, 2015, 35(10):16-17, and are also commercially available (e.g., TIGIT/CD155 Blockade Bioassay Kit, Promega Corp., Madison, Wis.). In some embodiments, an anti-TIGIT antibody that inhibits the interaction between TIGIT and CD155 increases the level or amount of activation of CD155-CD226 signaling (e.g., as measured in a cellular assay such as the TIGIT/CD155 Blockade Bioassay Kit) by at least 10%, at least 20%, at least 30%, at least 40%, at least 50%, at least 60%, at least 70%, at least 80%, at least 90%, or more as compared to the level or amount of CD155-CD226 signaling in the absence of the anti-TIGIT antibody. In some embodiments, an anti-TIGIT antibody that inhibits the interaction between TIGIT and CD155 increases the level or amount of activation of CD155-CD226 signaling (e.g., as measured in a cellular assay such as the TIGIT/CD155 Blockade Bioassay Kit) by at least about 1.2-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold or more as compared to the level or amount of CD155-CD226 signaling in the absence of the anti-TIGIT antibody.

In some embodiments, an anti-TIGIT antibody that binds to human TIGIT (and optionally exhibits cross-reactivity with cynomolgus monkey and/or mouse TIGIT and/or optionally inhibits interaction between TIGIT and CD155 and/or CD112) exhibits synergy with an anti-PD-1 agent (e.g., an anti-PD-1 antibody). In some embodiments, the anti-TIGIT antibody enhances the effect of the anti-PD-1 agent (e.g., anti-PD-1 antibody) by at least about 1.2-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold or more.

In some embodiments, the anti-TIGIT antibody exhibits synergy with an anti-PD-1 agent (e.g., an anti-PD-1 antibody) in a functional bioassay, such as a functional cellular assay in which inhibition of TIGIT signaling and inhibition of PD-1 signaling is evaluated by measuring the activation of signaling in an effector cell. A non-limiting exemplary functional cellular assay is described in the Examples section below. In this exemplary functional assay, a first cell (also referred to as a "T effector cell") expresses a TCR complex, TIGIT, CD226, and PD-1 on the cell surface and contains a luciferase gene. A second cell (also referred to as an "artificial antigen presenting cell") expresses a TCR activator, CD155, and PD-L1. Expression of the luciferase gene by the effector cell is activated by either or both of (1) blockade of TIGIT-CD155 interaction, thereby allowing CD155-CD226 interaction and subsequent co-stimulation of luciferase expression by the effector cell, or (2) blockade of PD-1/PD-L1 interaction, thereby relieving the inhibition of luciferase expression by the effector cell. The level of luciferase expression in the absence or presence of anti-TIGIT antibodies and anti-PD-1 agents or anti-PD-L1 agents can be measured and quantified for determining whether an anti-TIGIT antibody exhibits synergy with the anti-PD-1 agent or the anti-PD-L1 agent. Such functional cellular assays are described in the art (e.g., Cong et al., *Genetic Engineering and Biotechnology News*, 2015, 35(10):16-17), and are also commercially available (e.g., PD-1/TIGIT Combination Bioassay Kit, Promega Corp., Madison, Wis.).

In some embodiments, the efficacy of an anti-TIGIT antibody, as well as whether the anti-TIGIT antibody inhibits synergistically with an anti-PD-1 agent (e.g., an anti-PD-1 antibody) or an anti-PD-L1 agent (e.g., an anti-PD-L1 antibody), can be measured using an in vivo model, e.g., an in vivo tumor model. For example, the efficacy of an anti-TIGIT antibody as described herein, or the efficacy of an anti-TIGIT antibody as described herein when administered in combination with an anti-PD-1 agent or an anti-PD-L1 agent can be evaluated using a syngeneic mouse tumor model. Suitable syngeneic tumor models are described in the art. See, e.g., Rios-Doria et al., *Neoplasia*, 2015, 17:661-670; and Moynihan et al., *Nature Medicine*, 2016, doi:10.1038/nm.4200. In some embodiments, an anti-TIGIT antibody reduces the size of a tumor or the overall number of tumors in an in vivo model by at least 10%, at least 20%, at least 30%, at least 40%, at least 50%, at least 60%, at least 70%, at least 80%, at least 90% or more as compared to a control or reference value (e.g., as compared to tumor size or overall number of tumors in an untreated control).

In some embodiments, an anti-TIGIT antibody recognizes an epitope of human TIGIT that comprises one or both of amino acid positions 81 and 82, as numbered with reference to SEQ ID NO:218. In some embodiments, an anti-TIGIT antibody recognizes an epitope that comprises Phe at position 81. In some embodiments, an anti-TIGIT antibody recognizes an epitope that comprises Lys or Ser at position 82. In some embodiments, an anti-TIGIT antibody recognizes an epitope that comprises Phe at position 81 and Lys at position 82. In some embodiments, an anti-TIGIT antibody recognizes an epitope that comprises Phe at position 81 and Ser at position 82.

In some embodiments, an anti-TIGIT antibody recognizes a linear epitope that comprises one or both of amino acid positions 81 and 82 (e.g., a linear epitope that comprises Phe at position 81 and Lys or Ser at position 82). In some embodiments, an anti-TIGIT antibody recognizes a discontinuous epitope that comprises one or both of amino acid positions 81 and 82 (e.g., a discontinuous epitope that comprises Phe at position 81 and Lys or Ser at position 82).

In some embodiments, an anti-TIGIT antibody binds to an epitope on human TIGIT that further comprises one or more (e.g., 1, 2, 3, 4, 5, 6, 7, 8, 9, 10, 12, 13, 14, 15 or more) of amino acid positions 51, 52, 53, 54, 55, 73, 74, 75, 76, 77, 79, 83, 84, 85, 86, 87, 88, 89, 90, 91, 92, or 93. In some embodiments, an anti-TIGIT antibody binds to an epitope on human TIGIT that further comprises one or more (e.g., 1, 2, 3, 4, 5, 6, 7, 8, 9, 10, 12, 13, 14, 15 or more) of the following: Thr at position 51, Ala at position 52, Glu or Gln at position 53, Val at position 54, Thr at position 55, Leu at position 73, Gly at position 74, Trp at position 75, His at position 76, Val or Ile at position 77, Ser or Pro at position 79, Asp at position 83, Arg at position 84, Val at position 85, Val or Ala at position 86, Pro at position 87, Gly at position 88, Pro at position 89, Ser or Gly at position 90, Leu at position 91, Gly at position 92, or Leu at position 93. In some embodiments, an anti-TIGIT antibody binds to an epitope on human TIGIT that further comprises one or more (e.g., 1, 2, 3, 4, 5, 6, 7, 8, 9, 10, 12, 13, 14, 15 or more) of the amino acid residues Thr51, Ala52, Gln53, Val54, Thr55, Leu73, Gly74, Trp75, His76, Ile77, Pro79, Asp83, Arg84, Val85, Ala86, Pro87, Gly88, Pro89, Gly90, Leu91, Gly92, and Leu93.

In some embodiments, an anti-TIGIT antibody recognizes an epitope that comprises Phe at position 81 and Lys or Ser at position 82, and further comprises Thr at position 51, Ala at position 52, Glu or Gln at position 53, Val at position 54, and/or Thr at position 55. In some embodiments, an anti-TIGIT antibody recognizes an epitope that comprises Phe at position 81 and Lys or Ser at position 82, and further comprises Gly at position 74, Trp at position 75, His at position 76, and/or Val or Ile at position 77. In some embodiments, an anti-TIGIT antibody recognizes an epitope that comprises Phe at position 81 and Lys or Ser at position 82, and further comprises Pro at position 87, Gly at position 88, Pro at position 89, Ser or Gly at position 90, Leu at position 91, Gly at position 92, and/or Leu at position 93. In some embodiments, an anti-TIGIT antibody recognizes an epitope comprising the amino acid residues Thr51, Ala52, Gln53, Val54, Thr55, Gly74, Trp75, His76, Ile77, Phe81, Lys82, Pro87, Gly88, Pro89, Gly90, Leu91, Gly92, and Leu93.

In some embodiments, an anti-TIGIT antibody recognizes an epitope that comprises Phe at position 81 and Lys or Ser at position 82, and further comprises Ala at position 52 and/or Glu or Gln at position 53. In some embodiments, an anti-TIGIT antibody recognizes an epitope that comprises Phe at position 81 and Lys or Ser at position 82, and further comprises Leu at position 73, Gly at position 74, and/or Trp at position 75. In some embodiments, an anti-TIGIT antibody recognizes an epitope that comprises Phe at position 81 and Lys or Ser at position 82, and further comprises Asp at position 83, Arg at position 84, Val at position 85, and/or Val or Ala at position 86. In some embodiments, an anti-TIGIT antibody recognizes an epitope comprising the amino acid residues Ala52, Gln53, Leu73, Gly74, Trp75, Pro79, Phe81, Lys82, Asp83, Arg84, Val85, and Ala86.

In some embodiments, an anti-TIGIT antibody recognizes an epitope of human TIGIT comprising the sequence ICNADLGWHISPSFK (SEQ ID NO:258), which corresponds to residues 68-82 of human TIGIT (SEQ ID NO:218). In some embodiments, an anti-TIGIT antibody recognizes an epitope of human TIGIT consisting of the sequence ICNADLGWHISPSFK (SEQ ID NO:258).

Certain Anti-TIGIT Antibody Sequences

In some embodiments, an anti-TIGIT antibody that binds to human TIGIT and that optionally exhibits cross-reactivity with cynomolgus monkey TIGIT and/or mouse TIGIT comprises a light chain variable region sequence, or a portion thereof, and/or a heavy chain variable region sequence, or a portion thereof, derived from any of the following antibodies described herein: Clone 2, Clone 2C, Clone 3, Clone 5, Clone 13, Clone 13A, Clone 13B, Clone 13C, Clone 13D, Clone 14, Clone 16, Clone 16C, Clone 16D, Clone 16E, Clone 18, Clone 21, Clone 22, Clone 25, Clone 25A, Clone 25B, Clone 25C, Clone 25D, Clone 25E, Clone 27, or Clone 54. The amino acid sequences of the CDR, light chain variable domain (VL), and heavy chain variable domain (VH) of the anti-TIGIT antibodies Clone 2, Clone 2C, Clone 3, Clone 5, Clone 13, Clone 13A, Clone 13B, Clone 13C, Clone 13D, Clone 14, Clone 16, Clone 16C, Clone 16D, Clone 16E, Clone 18, Clone 21, Clone 22, Clone 25, Clone 25A, Clone 25B, Clone 25C, Clone 25D, Clone 25E, Clone 27, and Clone 54 are set forth in the Sequence Table below.

In some embodiments, an anti-TIGIT antibody comprises a heavy chain variable region (VH) comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:1, SEQ ID NO:19, SEQ ID NO:37, SEQ ID NO:55, SEQ ID NO:73, SEQ ID NO:91, SEQ ID NO:109, SEQ ID NO:127, SEQ ID NO:145, SEQ ID NO:163, SEQ ID NO:181, SEQ ID NO:199, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, or SEQ ID NO:257. In some embodiments, an anti-TIGIT antibody comprises a VH comprising the amino acid sequence of SEQ ID NO:1, SEQ ID NO:19, SEQ ID NO:37, SEQ ID NO:55, SEQ ID NO:73, SEQ ID NO:91, SEQ ID NO:109, SEQ ID NO:127, SEQ ID NO:145, SEQ ID NO:163, SEQ ID NO:181, SEQ ID NO:199, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, or SEQ ID NO:257. In some embodiments, a VH sequence having at least 90% sequence identity to a reference sequence (e.g., SEQ ID NO:1, SEQ ID NO:19, SEQ ID NO:37, SEQ ID NO:55, SEQ ID NO:73, SEQ ID NO:91, SEQ ID NO:109, SEQ ID NO:127, SEQ ID NO:145, SEQ ID NO:163, SEQ ID NO:181, SEQ ID NO:199, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, or SEQ ID NO:257) contains one, two, three, four, five, six, seven, eight, nine, ten or more substitutions (e.g., conservative substitutions), insertions, or deletions relative to the reference sequence but retains the ability to bind to human TIGIT and optionally, retains the ability to block binding of CD155 and/or CD112 to TIGIT.

In some embodiments, an anti-TIGIT antibody comprises a light chain variable region (VL) comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:10, SEQ ID NO:28, SEQ ID NO:46, SEQ ID NO:64, SEQ ID NO:82, SEQ ID NO:100, SEQ ID NO:118, SEQ ID NO:136, SEQ ID NO:154, SEQ ID NO:172, SEQ ID NO:190, or SEQ ID NO:208. In some embodiments, an anti-TIGIT antibody comprises a VL comprising the amino acid sequence of SEQ ID NO:10, SEQ ID NO:28, SEQ ID NO:46, SEQ ID NO:64, SEQ ID NO:82, SEQ ID NO:100, SEQ ID NO:118, SEQ ID NO:136, SEQ ID NO:154, SEQ ID NO:172, SEQ ID NO:190, or SEQ ID NO:208. In some embodiments, a VL sequence having at least 90% sequence identity to a reference sequence (e.g., SEQ ID NO:10, SEQ ID NO:28, SEQ ID NO:46, SEQ ID NO:64, SEQ ID NO:82, SEQ ID NO:100, SEQ ID NO:118, SEQ ID NO:136, SEQ ID NO:154, SEQ ID NO:172, SEQ ID NO:190, or SEQ ID NO:208) contains one, two, three, four, five, six, seven, eight, nine, ten or more substitutions (e.g., conservative substitutions), insertions, or deletions relative to the reference sequence but retains the ability to bind to human TIGIT and optionally, retains the ability to block binding of CD155 and/or CD112 to TIGIT.

In some embodiments, an anti-TIGIT antibody comprises a heavy chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:1, SEQ ID NO:19, SEQ ID NO:37, SEQ ID NO:55, SEQ ID NO:73, SEQ ID NO:91, SEQ ID NO:109, SEQ ID NO:127, SEQ ID NO:145, SEQ ID NO:163, SEQ ID NO:181, SEQ ID NO:199, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, or SEQ ID NO:257, and further comprises a light chain variable region comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:10, SEQ ID NO:28, SEQ ID NO:46, SEQ ID NO:64, SEQ ID NO:82, SEQ ID NO:100, SEQ ID NO:118, SEQ ID NO:136, SEQ ID NO:154, SEQ ID NO:172, SEQ ID NO:190, or SEQ ID NO:208. In some embodiments, an anti-TIGIT antibody comprises a heavy chain variable region comprising the amino acid sequence of SEQ ID NO:1, SEQ ID NO:19, SEQ ID NO:37, SEQ ID NO:55, SEQ ID NO:73, SEQ ID NO:91, SEQ ID NO:109, SEQ ID NO:127, SEQ ID NO:145, SEQ ID NO:163, SEQ ID NO:181, SEQ ID NO:199, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, or SEQ ID NO:257 and further comprises a light chain variable region comprising the amino acid sequence of SEQ ID NO:10, SEQ ID NO:28, SEQ ID NO:46, SEQ ID NO:64, SEQ ID NO:82, SEQ ID NO:100, SEQ ID NO:118, SEQ ID NO:136, SEQ ID NO:154, SEQ ID NO:172, SEQ ID NO:190, or SEQ ID NO:208.

In some embodiments, an anti-TIGIT antibody comprises:
(a) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:1 or SEQ ID NO:245 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:10;
(b) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:19 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:28;
(c) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:37 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:46;
(d) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NO:55, SEQ ID NO:246, SEQ ID NO:247, SEQ ID NO:248, or SEQ ID NO:249 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:64;
(e) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:73 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:82;
(f) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NO:91, SEQ ID NO:250, SEQ ID NO:251, or SEQ ID NO:252 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:100;
(g) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:109 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:118;
(h) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:127 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:136;
(i) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:145 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:154;
(j) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to any one of SEQ ID NO:163, SEQ ID NO:253, SEQ ID NO:254, SEQ ID NO:255, SEQ ID NO:256, or SEQ ID NO:257 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:172;
(k) a VH comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:181 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:190; or
(l) a VH comprising an amino acid sequence that has at least 90% sequence identity (e.g., at least 91%, at least 92%, at least 93%, at least 94%, at least 95%, at least 96%, at least 9'7%, at least 98%, or at least 99% sequence identity) to SEQ ID NO:199 and a VL comprising an amino acid sequence that has at least 90% sequence identity (e.g., at least 91%, at least 92%, at least 93%, at least 94%, at least 95%, at least 96%, at least 97%, at least 98%, or at least 99% sequence identity) to SEQ ID NO:208.

In some embodiments, an anti-TIGIT antibody comprises:
(a) a VH comprising the amino acid sequence of SEQ ID NO:1 and a VL comprising the amino acid sequence of SEQ ID NO:10;
(b) a VH comprising the amino acid sequence of SEQ ID NO:19 and a VL comprising the amino acid sequence of SEQ ID NO:28;
(c) a VH comprising the amino acid sequence of SEQ ID NO:37 and a VL comprising the amino acid sequence of SEQ ID NO:46;
(d) a VH comprising the amino acid sequence of SEQ ID NO:55 and a VL comprising the amino acid sequence of SEQ ID NO:64;
(e) a VH comprising the amino acid sequence of SEQ ID NO:73 and a VL comprising the amino acid sequence of SEQ ID NO:82;
(f) a VH comprising the amino acid sequence of SEQ ID NO:91 and a VL comprising the amino acid sequence of SEQ ID NO:100;
(g) a VH comprising the amino acid sequence of SEQ ID NO:109 and a VL comprising the amino acid sequence of SEQ ID NO:118;
(h) a VH comprising the amino acid sequence of SEQ ID NO:127 and a VL comprising the amino acid sequence of SEQ ID NO:136;

(i) a VH comprising the amino acid sequence of SEQ ID NO:145 and a VL comprising the amino acid sequence of SEQ ID NO:154;

(j) a VH comprising the amino acid sequence of SEQ ID NO:163 and a VL comprising the amino acid sequence of SEQ ID NO:172;

(k) a VH comprising the amino acid sequence of SEQ ID NO:181 and a VL comprising the amino acid sequence of SEQ ID NO:190;

(l) a VH comprising the amino acid sequence of SEQ ID NO:199 and a VL comprising the amino acid sequence of SEQ ID NO:208; or (m) a VH comprising the amino acid sequence of SEQ ID NO:245 and a VL comprising the amino acid sequence of SEQ ID NO:10; or (n) a VH comprising the amino acid sequence of SEQ ID NO:246 and a VL comprising the amino acid sequence of SEQ ID NO:64; or (o) a VH comprising the amino acid sequence of SEQ ID NO:247 and a VL comprising the amino acid sequence of SEQ ID NO:64; or (p) a VH comprising the amino acid sequence of SEQ ID NO:248 and a VL comprising the amino acid sequence of SEQ ID NO:64;

(q) a VH comprising the amino acid sequence of SEQ ID NO:249 and a VL comprising the amino acid sequence of SEQ ID NO:64; or (r) a VH comprising the amino acid sequence of SEQ ID NO:250 and a VL comprising the amino acid sequence of SEQ ID NO:100; or (s) a VH comprising the amino acid sequence of SEQ ID NO:251 and a VL comprising the amino acid sequence of SEQ ID NO:100; or (t) a VH comprising the amino acid sequence of SEQ ID NO:252 and a VL comprising the amino acid sequence of SEQ ID NO:100; or (u) a VH comprising the amino acid sequence of SEQ ID NO:253 and a VL comprising the amino acid sequence of SEQ ID NO:172; or (v) a VH comprising the amino acid sequence of SEQ ID NO:254 and a VL comprising the amino acid sequence of SEQ ID NO:172; or (w) a VH comprising the amino acid sequence of SEQ ID NO:255 and a VL comprising the amino acid sequence of SEQ ID NO:172; or (x) a VH comprising the amino acid sequence of SEQ ID NO:256 and a VL comprising the amino acid sequence of SEQ ID NO:172; or (y) a VH comprising the amino acid sequence of SEQ ID NO:257 and a VL comprising the amino acid sequence of SEQ ID NO:172.

In some embodiments, an anti-TIGIT antibody comprises heavy chain CDR1, CDR2, and CDR3, and light chain CDR1, CDR2, and CDR3, wherein one or more (e.g., one, two, three, four, five, or six) of the CDRs are selected from the heavy chain CDR1, CDR2, and CDR3, and light chain CDR1, CDR2, and CDR3 shown in Tables A, B, C, D, and E.

TABLE A

Clone 13 alternative CDR definitions

| CDR definition | Heavy chain (HC) CDR1 | SEQ ID NO | HC CDR2 | SEQ ID NO | HC CDR3 | SEQ ID NO |
|---|---|---|---|---|---|---|
| Composite | GTFSSYAIS | 58 | SIIPIFGTANYAQKFQG | 60 | ARGPSEVGAILGYVWFDP | 62 |
| IMGT | GGTFSSYA | 283 | IIPIFGTA | 285 | ARGPSEVGAILGYVWFDP | 62 |
| Kabat | SYAIS | 284 | SIIPIFGTANYAQKFQG | 60 | GPSEVGAILGYVWFDP | 286 |

| CDR definition | Light chain (LC) CDR1 | SEQ ID NO | LC CDR2 | SEQ ID NO | LC CDR3 | SEQ ID NO |
|---|---|---|---|---|---|---|
| Composite | RSSQSLLHSNGYNYLD | 67 | LGSNRAS | 69 | MQARRIPIT | 71 |
| IMGT | QSLLHSNGYNY | 287 | LGS | 288 | MQARRIPIT | 71 |
| Kabat | RSSQSLLHSNGYNYLD | 67 | LGSNRAS | 69 | MQARRIPIT | 71 |

TABLE B

Clone 13A alternative CDR definitions

| CDR definition | Heavy chain (HC) CDR1 | SEQ ID NO | HC CDR2 | SEQ ID NO | HC CDR3 | SEQ ID NO |
|---|---|---|---|---|---|---|
| Composite | GTFLSSAIS | 224 | SLIPYFGTANYAQKFQG | 225 | ARGPSEVGAILGYVWFDP | 62 |
| IMGT | GGTFLSSA | 293 | LIPYFGTA | 297 | ARGPSEVGAILGYVWFDP | 62 |
| Kabat | SSAIS | 294 | SLIPYFGTANYAQKFQG | 225 | GPSEVGAILGYVWFDP | 286 |

TABLE B-continued

Clone 13A alternative CDR definitions

| CDR definition | Light chain (LC) CDR1 | SEQ ID NO | LC CDR2 | SEQ ID NO | LC CDR3 | SEQ ID NO |
|---|---|---|---|---|---|---|
| Composite | RSSQSLLHSNGYNYLD | 67 | LGSNRAS | 69 | MQARRIPIT | 71 |
| IMGT | QSLLHSNGYNY | 287 | LGS | 288 | MQARRIPIT | 71 |
| Kabat | RSSQSLLHSNGYNYLD | 67 | LGSNRAS | 69 | MQARRIPIT | 71 |

TABLE C

Clone 13B alternative CDR definitions

| CDR definition | Heavy chain (HC) CDR1 | SEQ ID NO | HC CDR2 | SEQ ID NO | HC CDR3 | SEQ ID NO |
|---|---|---|---|---|---|---|
| Composite | GTFSAWAIS | 226 | SIIPYFGKANYAQKFQG | 227 | ARGPSEVSGILGYVWFDP | 228 |
| IMGT | GGTFSAWA | 289 | IIPYFGKA | 291 | ARGPSEVSGILGYVWFDP | 228 |
| Kabat | AWAIS | 290 | SIIPYFGKANYAQKFQG | 227 | GPSEVSGILGYVWFDP | 292 |

| CDR definition | Light chain (LC) CDR1 | SEQ ID NO | LC CDR2 | SEQ ID NO | LC CDR3 | SEQ ID NO |
|---|---|---|---|---|---|---|
| Composite | RSSQSLLHSNGYNYLD | 67 | LGSNRAS | 69 | MQARRIPIT | 71 |
| IMGT | QSLLHSNGYNY | 287 | LGS | 288 | MQARRIPIT | 71 |
| Kabat | RSSQSLLHSNGYNYLD | 67 | LGSNRAS | 69 | MQARRIPIT | 71 |

TABLE D

Clone 13C alternative CDR definitions

| CDR definition | Heavy chain (HC) CDR1 | SEQ ID NO | HC CDR2 | SEQ ID NO | HC CDR3 | SEQ ID NO |
|---|---|---|---|---|---|---|
| Composite | GTFLSSAIS | 224 | SIIPLFGKANYAQKFQG | 229 | ARGPSEVKGILGYVWFDP | 230 |
| IMGT | GGTFLSSA | 293 | IIPLFGKA | 295 | ARGPSEVKGILGYVWFDP | 230 |
| Kabat | SSAIS | 294 | SIIPLFGKANYAQKFQG | 229 | GPSEVKGILGYVWFDP | 296 |

| CDR definition | Light chain (LC) CDR1 | SEQ ID NO | LC CDR2 | SEQ ID NO | LC CDR3 | SEQ ID NO |
|---|---|---|---|---|---|---|
| Composite | RSSQSLLHSNGYNYLD | 67 | LGSNRAS | 69 | MQARRIPIT | 71 |
| IMGT | QSLLHSNGYNY | 287 | LGS | 288 | MQARRIPIT | 71 |
| Kabat | RSSQSLLHSNGYNYLD | 67 | LGSNRAS | 69 | MQARRIPIT | 71 |

TABLE E

Clone 13D alternative CDR definitions

| CDR definition | Heavy chain (HC) CDR1 | SEQ ID NO | HC CDR2 | SEQ ID NO | HC CDR3 | SEQ ID NO |
|---|---|---|---|---|---|---|
| Composite | GTFLSSAIS | 224 | SIIPYFGKANYAQKFQG | 227 | ARGPSEVKGILGYVWFDP | 230 |
| IMGT | GGTFLSSA | 293 | IIPYFGKA | 290 | ARGPSEVKGILGYVWFDP | 230 |
| Kabat | SSAIS | 294 | SIIPYFGKANYAQKFQG | 227 | GPSEVKGILGYVWFDP | 296 |

| CDR definition | Light chain (LC) CDR1 | SEQ ID NO | LC CDR2 | SEQ ID NO | LC CDR3 | SEQ ID NO |
|---|---|---|---|---|---|---|
| Composite | RSSQSLLHSNGYNYLD | 67 | LGSNRAS | 69 | MQARRIPIT | 71 |
| IMGT | QSLLHSNGYNY | 287 | LGS | 288 | MQARRIPIT | 71 |
| Kabat | RSSQSLLHSNGYNYLD | 67 | LGSNRAS | 69 | MQARRIPIT | 71 |

In some embodiments, an anti-TIGIT antibody comprises one or more (e.g., one, two, three, four, five, or six) of:
a heavy chain CDR1 sequence comprising an amino acid sequence selected from SEQ ID NO:58, SEQ ID NO:283, SEQ ID NO:284, SEQ ID NO:224, SEQ ID NO:293, SEQ ID NO:294, SEQ ID NO:226, SEQ ID NO:289, and SEQ ID NO:290;
a heavy chain CDR2 sequence comprising an amino acid sequence selected from SEQ ID NO:60, SEQ ID NO:285, SEQ ID NO:225, SEQ ID NO:297, SEQ ID NO:227, SEQ ID NO:291, SEQ ID NO:229, and SEQ ID NO:295;
a heavy chain CDR3 sequence comprising an amino acid sequence selected from SEQ ID NO:62, SEQ ID NO:286, SEQ ID NO:228, SEQ ID NO:292, SEQ ID NO:230, and SEQ ID NO:296;
a light chain CDR1 sequence comprising an amino acid sequence selected from SEQ ID NO:67 and SEQ ID NO:287;
a light chain CDR2 sequence comprising an amino acid sequence selected from SEQ ID NO:69 and SEQ ID NO:288; and/or
a light chain CDR3 sequence comprising the amino acid sequence of SEQ ID NO:71.

In some embodiments, an anti-TIGIT antibody comprises a heavy chain CDR1 sequence comprising the amino acid sequence of any of SEQ ID NO:58, SEQ ID NO:283, SEQ ID NO:284, SEQ ID NO:224, SEQ ID NO:293, SEQ ID NO:294, SEQ ID NO:226, SEQ ID NO:289, or SEQ ID NO:290; a heavy chain CDR2 sequence comprising the amino acid sequence of any of SEQ ID NO:60, SEQ ID NO:285, SEQ ID NO:225, SEQ ID NO:297, SEQ ID NO:227, SEQ ID NO:291, SEQ ID NO:229, or SEQ ID NO:295; a heavy chain CDR3 sequence comprising the amino acid sequence of any of SEQ ID NO:62, SEQ ID NO:286, SEQ ID NO:228, SEQ ID NO:292, SEQ ID NO:230, or SEQ ID NO:296; a light chain CDR1 sequence comprising the amino acid sequence of any of SEQ ID NO:67 or SEQ ID NO:287; a light chain CDR2 sequence comprising the amino acid sequence of any of SEQ ID NO:69 or SEQ ID NO:288; and a light chain CDR3 sequence comprising the amino acid sequence of SEQ ID NO:71.

In some embodiments, an anti-TIGIT antibody comprises a heavy chain CDR1 sequence comprising the amino acid sequence of any of SEQ ID NO:58, SEQ ID NO:283, SEQ ID NO:284, SEQ ID NO:224, SEQ ID NO:293, SEQ ID NO:294, SEQ ID NO:226, SEQ ID NO:289, or SEQ ID NO:290; a heavy chain CDR2 sequence comprising the amino acid sequence of any of SEQ ID NO:60, SEQ ID NO:285, SEQ ID NO:225, SEQ ID NO:297, SEQ ID NO:227, SEQ ID NO:291, SEQ ID NO:229, or SEQ ID NO:295; and a heavy chain CDR3 sequence comprising the amino acid sequence of any of SEQ ID NO:62, SEQ ID NO:286, SEQ ID NO:228, SEQ ID NO:292, SEQ ID NO:230, or SEQ ID NO:296.

In some embodiments, an anti-TIGIT antibody comprises a light chain CDR1 sequence comprising the amino acid sequence of any of SEQ ID NO:67 or SEQ ID NO:287; a light chain CDR2 sequence comprising the amino acid sequence of any of SEQ ID NO:69 or SEQ ID NO:288; and a light chain CDR3 sequence comprising the amino acid sequence of SEQ ID NO:71.

In some embodiments, an anti-TIGIT antibody comprises: (i) a heavy chain CDR1 sequence comprising the amino acid sequence of SEQ ID NO:58, SEQ ID NO:283, or SEQ ID NO:284; (ii) a heavy chain CDR2 sequence comprising the amino acid sequence of SEQ ID NO:60 or SEQ ID NO:285; (iii) a heavy chain CDR3 sequence comprising the amino acid sequence of SEQ ID NO:62 or SEQ ID NO:286; (iv) a light chain CDR1 sequence comprising the amino acid sequence of SEQ ID NO:67 or SEQ ID NO:287; (v) a light chain CDR2 sequence comprising the amino acid sequence of SEQ ID NO:69 or SEQ ID NO:288; and (vi) a light chain CDR3 sequence comprising the amino acid sequence of SEQ ID NO:71.

In some embodiments, an anti-TIGIT antibody comprises: (i) a heavy chain CDR1 sequence comprising the amino acid sequence of SEQ ID NO:224, SEQ ID NO:293, or SEQ ID NO:294; (ii) a heavy chain CDR2 sequence comprising the amino acid sequence of SEQ ID NO:225 or SEQ ID NO:297; (iii) a heavy chain CDR3 sequence comprising the amino acid sequence of SEQ ID NO:62 or SEQ ID NO:286; (iv) a light chain CDR1 sequence comprising the amino acid sequence of SEQ ID NO:67 or SEQ ID NO:287; (v) a light chain CDR2 sequence comprising the amino acid sequence of SEQ ID NO:69 or SEQ ID NO:288; and (vi) a light chain CDR3 sequence comprising the amino acid sequence of SEQ ID NO:71.

In some embodiments, an anti-TIGIT antibody comprises: (i) a heavy chain CDR1 sequence comprising the amino acid sequence of SEQ ID NO:226, SEQ ID NO:289, or SEQ ID NO:290; (ii) a heavy chain CDR2 sequence comprising the amino acid sequence of SEQ ID NO:227 or SEQ ID NO:291; (iii) a heavy chain CDR3 sequence comprising the amino acid sequence of SEQ ID NO:228 or SEQ ID NO:292; (iv) a light chain CDR1 sequence comprising the amino acid sequence of SEQ ID NO:67 or SEQ ID NO:287; (v) a light chain CDR2 sequence comprising the amino acid sequence of SEQ ID NO:69 or SEQ ID NO:288; and (vi) a light chain CDR3 sequence comprising the amino acid sequence of SEQ ID NO:71.

In some embodiments, an anti-TIGIT antibody comprises: (i) a heavy chain CDR1 sequence comprising the amino acid sequence of SEQ ID NO:224, SEQ ID NO:293, or SEQ ID NO:294; (ii) a heavy chain CDR2 sequence comprising the amino acid sequence of SEQ ID NO:229 or SEQ ID NO:295; (iii) a heavy chain CDR3 sequence comprising the amino acid sequence of SEQ ID NO:230 or SEQ ID NO:296; (iv) a light chain CDR1 sequence comprising the amino acid sequence of SEQ ID NO:67 or SEQ ID NO:287; (v) a light chain CDR2 sequence comprising the amino acid sequence of SEQ ID NO:69 or SEQ ID NO:288; and (vi) a light chain CDR3 sequence comprising the amino acid sequence of SEQ ID NO:71.

In some embodiments, an anti-TIGIT antibody comprises: (i) a heavy chain CDR1 sequence comprising the amino acid sequence of SEQ ID NO:224, SEQ ID NO:293, or SEQ ID NO:294; (ii) a heavy chain CDR2 sequence comprising the amino acid sequence of SEQ ID NO:227 or SEQ ID NO:290; (iii) a heavy chain CDR3 sequence comprising the amino acid sequence of SEQ ID NO:230 or SEQ ID NO:296; (iv) a light chain CDR1 sequence comprising the amino acid sequence of SEQ ID NO:67 or SEQ ID NO:287; (v) a light chain CDR2 sequence comprising the amino acid sequence of SEQ ID NO:69 or SEQ ID NO:288; and (vi) a light chain CDR3 sequence comprising the amino acid sequence of SEQ ID NO:71.

In some embodiments, an anti-TIGIT antibody comprises one or more (e.g., one, two, three, four, five, or six) of:
  a heavy chain CDR1 sequence comprising the amino acid sequence of any of SEQ ID NO:4, SEQ ID NO:22, SEQ ID NO:40, SEQ ID NO:58, SEQ ID NO:76, SEQ ID NO:94, SEQ ID NO:112, SEQ ID NO:130, SEQ ID NO:148, SEQ ID NO:166, SEQ ID NO:184, SEQ ID NO:202, SEQ ID NO:221, SEQ ID NO:224, SEQ ID NO:226, SEQ ID NO:231, SEQ ID NO:233, SEQ ID NO:239, SEQ ID NO:243, SEQ ID NO:283, SEQ ID NO:284, SEQ ID NO:293, SEQ ID NO:294, SEQ ID NO:289, or SEQ ID NO:290;
  a heavy chain CDR2 sequence comprising the amino acid sequence of any of SEQ ID NO:6, SEQ ID NO:24, SEQ ID NO:42, SEQ ID NO:60, SEQ ID NO:78, SEQ ID NO:96, SEQ ID NO:114, SEQ ID NO:132, SEQ ID NO:150, SEQ ID NO:168, SEQ ID NO:186, SEQ ID NO:204, SEQ ID NO:222, SEQ ID NO:225, SEQ ID NO:227, SEQ ID NO:229, SEQ ID NO:232, SEQ ID NO:234, SEQ ID NO:238, SEQ ID NO:240, SEQ ID NO:285, SEQ ID NO:297, SEQ ID NO:291, or SEQ ID NO:295;
  a heavy chain CDR3 sequence comprising the amino acid sequence of any of SEQ ID NO:8, SEQ ID NO:26, SEQ ID NO:44, SEQ ID NO:62, SEQ ID NO:80, SEQ ID NO:98, SEQ ID NO:116, SEQ ID NO:134, SEQ ID NO:152, SEQ ID NO:170, SEQ ID NO:188, SEQ ID NO:206, SEQ ID NO:223, SEQ ID NO:228, SEQ ID NO:230, SEQ ID NO:235, SEQ ID NO:236, SEQ ID NO:237, SEQ ID NO:241, SEQ ID NO:242, SEQ ID NO:244, SEQ ID NO:286, SEQ ID NO:292, or SEQ ID NO:296;
  a light chain CDR1 sequence comprising the amino acid sequence of any of SEQ ID NO:13, SEQ ID NO:31, SEQ ID NO:49, SEQ ID NO:67, SEQ ID NO:85, SEQ ID NO:103, SEQ ID NO:121, SEQ ID NO:139, SEQ ID NO:157, SEQ ID NO:175, SEQ ID NO:193, SEQ ID NO:211, or SEQ ID NO:287;
  a light chain CDR2 sequence comprising the amino acid sequence of any of SEQ ID NO:15, SEQ ID NO:33, SEQ ID NO:51, SEQ ID NO:69, SEQ ID NO:87, SEQ ID NO:105, SEQ ID NO:123, SEQ ID NO:141, SEQ ID NO:159, SEQ ID NO:177, SEQ ID NO:195, SEQ ID NO:213, or SEQ ID NO:288; and/or
  a light chain CDR3 sequence comprising the amino acid sequence of any of SEQ ID NO:17, SEQ ID NO:35, SEQ ID NO:53, SEQ ID NO:71, SEQ ID NO:89, SEQ ID NO:107, SEQ ID NO:125, SEQ ID NO:143, SEQ ID NO:161, SEQ ID NO:179, SEQ ID NO:197, or SEQ ID NO:215.

In some embodiments, an anti-TIGIT antibody comprises a heavy chain CDR1 sequence comprising the amino acid sequence of any of SEQ ID NO:4, SEQ ID NO:22, SEQ ID NO:40, SEQ ID NO:58, SEQ ID NO:76, SEQ ID NO:94, SEQ ID NO:112, SEQ ID NO:130, SEQ ID NO:148, SEQ ID NO:166, SEQ ID NO:184, SEQ ID NO:202, SEQ ID NO:221, SEQ ID NO:224, SEQ ID NO:226, SEQ ID NO:231, SEQ ID NO:233, SEQ ID NO:239, SEQ ID NO:243, SEQ ID NO:283, SEQ ID NO:284, SEQ ID NO:293, SEQ ID NO:294, SEQ ID NO:289, or SEQ ID NO:290; a heavy chain CDR2 sequence comprising the amino acid sequence of any of SEQ ID NO:6, SEQ ID NO:24, SEQ ID NO:42, SEQ ID NO:60, SEQ ID NO:78, SEQ ID NO:96, SEQ ID NO:114, SEQ ID NO:132, SEQ ID NO:150, SEQ ID NO:168, SEQ ID NO:186, SEQ ID NO:204, SEQ ID NO:222, SEQ ID NO:225, SEQ ID NO:227, SEQ ID NO:229, SEQ ID NO:232, SEQ ID NO:234, SEQ ID NO:238, SEQ ID NO:240, SEQ ID NO:285, SEQ ID NO:297, SEQ ID NO:291, or SEQ ID NO:295; and a heavy chain CDR3 sequence comprising the amino acid sequence of any of SEQ ID NO:8, SEQ ID NO:26, SEQ ID NO:44, SEQ ID NO:62, SEQ ID NO:80, SEQ ID NO:98, SEQ ID NO:116, SEQ ID NO:134, SEQ ID NO:152, SEQ ID NO:170, SEQ ID NO:188, SEQ ID NO:206, SEQ ID NO:223, SEQ ID NO:228, SEQ ID NO:230, SEQ ID NO:235, SEQ ID NO:236, SEQ ID NO:237, SEQ ID NO:241, SEQ ID NO:242, SEQ ID NO:244, SEQ ID NO:286, SEQ ID NO:292, or SEQ ID NO:296.

In some embodiments, an anti-TIGIT antibody comprises a light chain CDR1 sequence comprising the amino acid sequence of any of SEQ ID NO:13, SEQ ID NO:31, SEQ ID NO:49, SEQ ID NO:67, SEQ ID NO:85, SEQ ID NO:103, SEQ ID NO:121, SEQ ID NO:139, SEQ ID NO:157, SEQ ID NO:175, SEQ ID NO:193, SEQ ID NO:211, or SEQ ID NO:287; a light chain CDR2 sequence comprising the amino acid sequence of any of SEQ ID NO:15, SEQ ID NO:33, SEQ ID NO:51, SEQ ID NO:69, SEQ ID NO:87, SEQ ID NO:105, SEQ ID NO:123, SEQ ID NO:141, SEQ ID NO:159, SEQ ID NO:177, SEQ ID NO:195, SEQ ID NO:213, or SEQ ID NO:288; and a light chain CDR3 sequence comprising the amino acid sequence of any of SEQ ID NO:17, SEQ ID NO:35, SEQ ID NO:53, SEQ ID NO:71, SEQ ID NO:89, SEQ ID NO:107, SEQ ID NO:125, SEQ ID NO:143, SEQ ID NO:161, SEQ ID NO:179, SEQ ID NO:197, or SEQ ID NO:215.

In some embodiments, an anti-TIGIT antibody comprises:
(i) a heavy chain CDR1 sequence comprising the amino acid sequence of any of SEQ ID NO:4, SEQ ID NO:22, SEQ ID NO:40, SEQ ID NO:58, SEQ ID NO:76, SEQ ID NO:94, SEQ ID NO:112, SEQ ID NO:130, SEQ ID NO:148, SEQ ID NO:166, SEQ ID NO:184, SEQ ID NO:202, SEQ ID NO:221, SEQ ID NO:224, SEQ ID NO:226, SEQ ID NO:231, SEQ ID NO:233, SEQ ID NO:239, SEQ ID NO:243, SEQ ID NO:283, SEQ ID NO:284, SEQ ID NO:293, SEQ ID NO:294, SEQ ID NO:289, or SEQ ID NO:290; and
(ii) a heavy chain CDR2 sequence comprising the amino acid sequence of any of SEQ ID NO:6, SEQ ID NO:24, SEQ ID NO:42, SEQ ID NO:60, SEQ ID NO:78, SEQ ID NO:96, SEQ ID NO:114, SEQ ID NO:132, SEQ ID NO:150, SEQ ID NO:168, SEQ ID NO:186, SEQ ID NO:204, SEQ ID NO:222, SEQ ID NO:225, SEQ ID NO:227, SEQ ID NO:229, SEQ ID NO:232, SEQ ID NO:234, SEQ ID NO:238, SEQ ID NO:240, SEQ ID NO:285, SEQ ID NO:297, SEQ ID NO:291, or SEQ ID NO:295; and
(iii) a heavy chain CDR3 sequence comprising the amino acid sequence of any of SEQ ID NO:8, SEQ ID NO:26, SEQ ID NO:44, SEQ ID NO:62, SEQ ID NO:80, SEQ ID NO:98, SEQ ID NO:116, SEQ ID NO:134, SEQ ID NO:152, SEQ ID NO:170, SEQ ID NO:188, SEQ ID NO:206, SEQ ID NO:223, SEQ ID NO:228, SEQ ID NO:230, SEQ ID NO:235, SEQ ID NO:236, SEQ ID NO:237, SEQ ID NO:241, SEQ ID NO:242, SEQ ID NO:244, SEQ ID NO:286, SEQ ID NO:292, or SEQ ID NO:296; and
(iv) a light chain CDR1 sequence comprising the amino acid sequence of any of SEQ ID NO:13, SEQ ID NO:31, SEQ ID NO:49, SEQ ID NO:67, SEQ ID NO:85, SEQ ID NO:103, SEQ ID NO:121, SEQ ID NO:139, SEQ ID NO:157, SEQ ID NO:175, SEQ ID NO:193, SEQ ID NO:211, or SEQ ID NO:287; and
(v) a light chain CDR2 sequence comprising the amino acid sequence of any of SEQ ID NO:15, SEQ ID NO:33, SEQ ID NO:51, SEQ ID NO:69, SEQ ID NO:87, SEQ ID NO:105, SEQ ID NO:123, SEQ ID NO:141, SEQ ID NO:159, SEQ ID NO:177, SEQ ID NO:195, SEQ ID NO:213, or SEQ ID NO:288; and
(vi) a light chain CDR3 sequence comprising the amino acid sequence of any of SEQ ID NO:17, SEQ ID NO:35, SEQ ID NO:53, SEQ ID NO:71, SEQ ID NO:89, SEQ ID NO:107, SEQ ID NO:125, SEQ ID NO:143, SEQ ID NO:161, SEQ ID NO:179, SEQ ID NO:197, or SEQ ID NO:215.

In some embodiments, an anti-TIGIT antibody comprises: (i) a heavy chain CDR1 sequence comprising the amino acid sequence of SEQ ID NO:4 or SEQ ID NO:221; (ii) a heavy chain CDR2 sequence comprising the amino acid sequence of SEQ ID NO:6 or SEQ ID NO:222; (iii) a heavy chain CDR3 sequence comprising the amino acid sequence of SEQ ID NO:8 or SEQ ID NO:223; (iv) a light chain CDR1 sequence comprising the amino acid sequence of SEQ ID NO:13; (v) a light chain CDR2 sequence comprising the amino acid sequence of SEQ ID NO:15; and (vi) a light chain CDR3 sequence comprising the amino acid sequence of SEQ ID NO:17.

In some embodiments, an anti-TIGIT antibody comprises: (i) a heavy chain CDR1 sequence comprising the amino acid sequence of any of SEQ ID NO:58, SEQ ID NO:224, or SEQ ID NO:226; (ii) a heavy chain CDR2 sequence comprising the amino acid sequence of SEQ ID NO:60, SEQ ID NO:225, SEQ ID NO:227, or SEQ ID NO:229; (iii) a heavy chain CDR3 sequence comprising the amino acid sequence of any of SEQ ID NO:62, SEQ ID NO:228, or SEQ ID NO:230; (iv) a light chain CDR1 sequence comprising the amino acid sequence of SEQ ID NO:67; (v) a light chain CDR2 sequence comprising the amino acid sequence of SEQ ID NO:69; and (vi) a light chain CDR3 sequence comprising the amino acid sequence of SEQ ID NO:71.

In some embodiments, an anti-TIGIT antibody comprises: (i) a heavy chain CDR1 sequence comprising the amino acid sequence of any of SEQ ID NO:94, SEQ ID NO:231, or SEQ ID NO:233; (ii) a heavy chain CDR2 sequence comprising the amino acid sequence of any of SEQ ID NO:96, SEQ ID NO:232, or SEQ ID NO:234; (iii) a heavy chain CDR3 sequence comprising the amino acid sequence of any of SEQ ID NO:98, SEQ ID NO:235, SEQ ID NO:236, or SEQ ID NO:237; (iv) a light chain CDR1 sequence comprising the amino acid sequence of SEQ ID NO:103; (v) a light chain CDR2 sequence comprising the amino acid sequence of SEQ ID NO:105; and (vi) a light chain CDR3 sequence comprising the amino acid sequence of SEQ ID NO:107.

In some embodiments, an anti-TIGIT antibody comprises: (i) a heavy chain CDR1 sequence comprising the amino acid sequence of any of SEQ ID NO:166, SEQ ID NO:239, or SEQ ID NO:243; (ii) a heavy chain CDR2 sequence comprising the amino acid sequence of any of SEQ ID NO:168, SEQ ID NO:238, or SEQ ID NO:240; (iii) a heavy chain CDR3 sequence comprising the amino acid sequence of any of SEQ ID NO:170, SEQ ID NO:241, SEQ ID NO:242, or SEQ ID NO:244; (iv) a light chain CDR1 sequence comprising the amino acid sequence of SEQ ID NO:175; (v) a light chain CDR2 sequence comprising the amino acid sequence of SEQ ID NO:177; and (vi) a light chain CDR3 sequence comprising the amino acid sequence of SEQ ID NO:179.

In some embodiments, an anti-TIGIT antibody comprises a heavy chain CDR1-3 and a light chain CDR1-3 comprising the amino acid sequences of:
(a) SEQ ID NOs: 4, 6, 8, 13, 15, and 17, respectively;
(b) SEQ ID NOs: 22, 24, 26, 31, 33, and 35, respectively;
(c) SEQ ID NOs: 40, 42, 44, 49, 51, and 53, respectively;
(d) SEQ ID NOs: 58, 60, 62, 67, 69, and 71, respectively;
(e) SEQ ID NOs: 76, 78, 80, 85, 87, and 89, respectively;
(f) SEQ ID NOs: 94, 96, 98, 103, 105, and 107, respectively;
(g) SEQ ID NOs: 112, 114, 116, 121, 123, and 125, respectively;
(h) SEQ ID NOs: 130, 132, 134, 139, 141, and 143, respectively;
(i) SEQ ID NOs: 148, 150, 152, 157, 159, and 161, respectively;
(j) SEQ ID NOs: 166, 168, 170, 175, 177, and 179, respectively;
(k) SEQ ID NOs: 184, 186, 188, 193, 195, and 197, respectively;
(l) SEQ ID NOs: 202, 204, 206, 211, 213, and 215, respectively; or
(m) SEQ ID NOs: 221, 222, 223, 13, 15, and 17, respectively; or
(n) SEQ ID NOs: 224, 225, 62, 67, 69, and 71, respectively; or
(o) SEQ ID NOs: 226, 227, 228, 67, 69, and 71, respectively; or
(p) SEQ ID NOs: 224, 229, 230, 67, 69, and 71, respectively; or (q) SEQ ID NOs: 224, 227, 230, 67, 69, and 71, respectively; or
(r) SEQ ID NOs: 231, 232, 235, 103, 105, and 107, respectively; or
(s) SEQ ID NOs: 233, 234, 236, 103, 105, and 107, respectively; or
(t) SEQ ID NOs: 233, 234, 237, 103, 105, and 107, respectively; or
(u) SEQ ID NOs: 166, 238, 170, 175, 177, and 179, respectively; or
(v) SEQ ID NOs: 239, 240, 170, 175, 177, and 179, respectively; or
(w) SEQ ID NOs: 239, 240, 241, 175, 177, and 179, respectively; or
(x) SEQ ID NOs: 239, 240, 242, 175, 177, and 179, respectively; or
(y) SEQ ID NOs: 243, 168, 244, 175, 177, and 179, respectively.

In some embodiments, an anti-TIGIT antibody comprises one or more heavy chain framework regions (FR1, FR2, FR3, and/or FR4) comprising an amino acid sequence of SEQ ID NO:3, SEQ ID NO:5, SEQ ID NO:7, SEQ ID NO:9, SEQ ID NO:21, SEQ ID NO:23, SEQ ID NO:25, SEQ ID NO:27, SEQ ID NO:39, SEQ ID NO:41, SEQ ID NO:43, SEQ ID NO:45, SEQ ID NO:57, SEQ ID NO:59, SEQ ID NO:61, SEQ ID NO:63, SEQ ID NO:75, SEQ ID NO:77, SEQ ID NO:79, SEQ ID NO:81, SEQ ID NO:93, SEQ ID NO:95, SEQ ID NO:97, SEQ ID NO:99, SEQ ID NO:111, SEQ ID NO:113, SEQ ID NO:115, SEQ ID NO:117, SEQ ID NO:129, SEQ ID NO:131, SEQ ID NO:133, SEQ ID NO:135, SEQ ID NO:147, SEQ ID NO:149, SEQ ID NO:151, SEQ ID NO:153, SEQ ID NO:165, SEQ ID NO:167, SEQ ID NO:169, SEQ ID NO:171, SEQ ID NO:183, SEQ ID NO:185, SEQ ID NO:187, SEQ ID NO:189, SEQ ID NO:201, SEQ ID NO:203, SEQ ID NO:205, or SEQ ID NO:207.

In some embodiments, an anti-TIGIT antibody comprises one or more light chain framework regions (FR1, FR2, FR3, and/or FR4) comprising an amino acid sequence of SEQ ID NO:12, SEQ ID NO:14, SEQ ID NO:16, SEQ ID NO:18, SEQ ID NO:30, SEQ ID NO:32, SEQ ID NO:34, SEQ ID NO:36, SEQ ID NO:48, SEQ ID NO:50, SEQ ID NO:52, SEQ ID NO:54, SEQ ID NO:66, SEQ ID NO:68, SEQ ID NO:70, SEQ ID NO:72, SEQ ID NO:84, SEQ ID NO:86, SEQ ID NO:88, SEQ ID NO:90, SEQ ID NO:102, SEQ ID NO:104, SEQ ID NO:106, SEQ ID NO:108, SEQ ID NO:120, SEQ ID NO:122, SEQ ID NO:124, SEQ ID NO:126, SEQ ID NO:138, SEQ ID NO:140, SEQ ID NO:142, SEQ ID NO:144, SEQ ID NO:156, SEQ ID NO:158, SEQ ID NO:160, SEQ ID NO:162, SEQ ID NO:174, SEQ ID NO:176, SEQ ID NO:178, SEQ ID NO:180, SEQ ID NO:192, SEQ ID NO:194, SEQ ID NO:196, SEQ ID NO:198, SEQ ID NO:210, SEQ ID NO:212, SEQ ID NO:214, or SEQ ID NO:216.

In some embodiments, an anti-TIGIT antibody comprises a heavy chain comprising an amino acid sequence selected from SEQ ID NOs: 260, 266, 268, 270, and 272; and a light chain comprising the amino acid sequence of SEQ ID NO: 274.

In some embodiments, the anti-TIGIT antibodies of the instant disclosure do not compete for binding with the antibodies described in US 2009/0258013, US 2016/0176963, US 2016/0376365, or WO 2016/028656. In some embodiments, the anti-TIGIT antibodies of the instant disclosure do not bind to the same epitope as antibodies described in US 2009/0258013, US 2016/0176963, US 2016/0376365, or WO 2016/028656.

Preparation of Antibodies

For preparing an antibody that binds to TIGIT, many techniques known in the art can be used. See, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2nd ed. 1986)).

The genes encoding the heavy and light chains of an antibody of interest can be cloned from a cell, e.g., the genes encoding a monoclonal antibody can be cloned from a hybridoma that expresses the antibody and used to produce a recombinant monoclonal antibody. Gene libraries encoding heavy and light chains of monoclonal antibodies can also be made from hybridoma or plasma cells. Additionally, phage or yeast display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992); Lou et al. (2010) *PEDS* 23:311; and Chao et al., *Nature Protocols*, 1:755-768 (2006)). Alternatively, antibodies and antibody sequences may be isolated and/or identified using a yeast-based antibody presentation system, such as that disclosed in, e.g., Xu et al., *Protein Eng Des Sel*, 2013, 26:663-670; WO 2009/036379; WO 2010/105256; and WO 2012/009568. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can also be adapted to produce antibodies. Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or antibodies covalently bound to immunotoxins (see, e.g., U.S. Pat. No. 4,676,980, WO 91/00360; and WO 92/200373).

Antibodies can be produced using any number of expression systems, including prokaryotic and eukaryotic expression systems. In some embodiments, the expression system is a mammalian cell, such as a hybridoma, or a CHO cell. Many such systems are widely available from commercial suppliers. In embodiments in which an antibody comprises both a heavy chain and light chain, the heavy chain and heavy chain and light chain may be expressed using a single vector, e.g., in a di-cistronic expression unit, or be under the control of different promoters. In other embodiments, the heavy chain and light chain region may be expressed using separate vectors. Heavy chains and light chains as described herein may optionally comprise a methionine at the N-terminus.

In some embodiments, antibody fragments (such as a Fab, a Fab', a F(ab')$_2$, a scFv, or a diabody) are generated. Various techniques have been developed for the production of antibody fragments. Traditionally, these fragments were derived via proteolytic digestion of intact antibodies (see, e.g., Morimoto et al., *J. Biochem. Biophys. Meth.*, 24:107-117 (1992); and Brennan et al., *Science*, 229:81 (1985)). However, these fragments can now be produced directly using recombinant host cells. For example, antibody fragments can be isolated from antibody phage libraries. Alternatively, Fab'-SH fragments can be directly recovered from *E. coli* cells and chemically coupled to form F(ab')$_2$ fragments (see, e.g., Carter et al., *BioTechnology*, 10:163-167 (1992)). According to another approach, F(ab')$_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870.

In some embodiments, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227, 2007).

In some embodiments, multispecific antibodies comprising an anti-TIGIT antibody as described herein are provided, e.g., a bispecific antibody. Multispecific antibodies are antibodies that have binding specificities for at least two different sites. In some embodiments, the multispecific antibody has a binding specificity for TIGIT (e.g., human TIGIT) and has a binding specificity for at least one other antigen. Methods for making multispecific antibodies include, but are not limited to, recombinant co-expression of two pairs of heavy chain and light chain in a host cell (see, e.g., Zuo et al., *Protein Eng Des Sel*, 2000, 13:361-367); "knobs-into-holes" engineering (see, e.g., Ridgway et al., *Protein Eng Des Sel*, 1996, 9:617-721); "diabody" technology (see, e.g., Hollinger et al., *PNAS* (USA), 1993, 90:6444-6448); and intramolecular trimerization (see, e.g., Alvarez-Cienfuegos et al., *Scientific Reports*, 2016, doi:/10.1038/srep28643; See also, Spiess et al., *Molecular Immunology*, 2015, 67(2), Part A:95-106.

In some embodiments, antibody-drug conjugates comprising an anti-TIGIT antibody as described herein are provided. In antibody-drug conjugates, a monoclonal antibody having a binding specificity for an antigen (e.g., TIGIT) is covalently linked to a cytotoxic drug. Methods for making antibody-drug conjugates are described, e.g., in Chudasama et al., *Nature Chemistry*, 2016, 8:114-119; WO 2013/068874; and U.S. Pat. No. 8,535,678.

Selection of Constant Region

Heavy and light chain variable regions of the anti-TIGIT antibodies described herein can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have strong complement-dependent cytotoxicity, human isotype IgG2 weak complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')$_2$, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

Exemplary substitution include the amino acid substitution of the native amino acid to a cysteine residue is introduced at amino acid position 234, 235, 237, 239, 267, 298, 299, 326, 330, or 332, preferably an S239C mutation in a human IgG1 isotype (numbering is according to the EU index (Kabat, *Sequences of Proteins of Immunological Interest* (National Institutes of Health, Bethesda, Md., 1987 and 1991); see US 20100158909, which is herein incorporated reference). The presence of an additional cysteine residue may allow interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγRI receptor (see, e.g., U.S. Pat. Nos. 6,624,821, 5,624,821.) A preferred combination of mutations is S239D, A330L and I332E, which increases the affinity of the Fc domain for FcγRIIIA and consequently increases ADCC.

The in vivo half-life of an antibody can also impact its effector functions. The half-life of an antibody can be increased or decreased to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, *Annu. Rev. Immunol.* 18:739-766; Ghetie and Ward, 2002, *Immunol. Res.* 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, *Ann. Rev. Immunol.* 18:739-766; Ghetie and Ward, 2002, *Immunol. Res.* 25:97-113). The region on human IgG1 involved in FcRn binding has been mapped (Shields et al., 2001, *J. Biol. Chem.* 276:6591-604). Alanine substitutions at positions Pro238, Thr256, Thr307, Gln311, Asp312, Glu380, Glu382, or Asn434 of human IgG1 enhance FcRn binding (Shields et al., 2001, *J Biol. Chem.* 276:6591-604). IgG1 molecules harboring these substitutions have longer serum half-lives. Consequently, these modified IgG1 molecules may be able to carry out their effector functions, and hence exert their therapeutic efficacies, over a longer period of time compared to unmodified IgG1. Other exemplary substitutions for increasing binding to FcRn include a Gln at position 250 and/or a Leu at position 428. EU numbering is used for all positions in the constant region.

Oligosaccharides covalently attached to the conserved Asn297 are involved in the ability of the Fc region of an IgG to bind FcγR (Lund et al., 1996, *J. Immunol.* 157:4963-69; Wright and Morrison, 1997, *Trends Biotechnol.* 15:26-31). Engineering of this glycoform on IgG can significantly improve IgG-mediated ADCC. Addition of bisecting N-acetylglucosamine modifications (Umana et al., 1999, *Nat. Biotechnol.* 17:176-180; Davies et al., 2001, *Biotech. Bioeng.* 74:288-94) to this glycoform or removal of fucose (Shields et al., 2002, *J. Biol. Chem.* 277:26733-40; Shinkawa et al., 2003, *J. Biol. Chem.* 278:6591-604; Niwa et al., 2004, *Cancer Res.* 64:2127-33) from this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al., 2001, *J. Biol. Chem.* 276:6591-604). When compared to parental IgG1, a subset of these variants involving substitutions at Thr256/Ser298, Ser298/Glu333, Ser298/Lys334, or Ser298/Glu333/Lys334 to Ala demonstrate increased in both binding affinity toward FcγR and ADCC activity (Shields et al., 2001, *J. Biol. Chem.* 276:6591-604; Okazaki et al., 2004, *J. Mol. Biol.* 336:1239-49).

Complement fixation activity of antibodies (both C1q binding and CDC activity) can be improved by substitutions at Lys326 and Glu333 (Idusogie et al., 2001, *J. Immunol.* 166:2571-2575). The same substitutions on a human IgG2 backbone can convert an antibody isotype that binds poorly to C1q and is severely deficient in complement activation activity to one that can both bind C1q and mediate CDC (Idusogie et al., 2001, *J. Immunol.* 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al., 1995, *J. Immunol.* 154:2226-36). Also, substituting Ser444 located close to the carboxy-terminal of IgG1 heavy chain with Cys induced tail-to-tail dimerization of IgG1 with a 200-fold increase of CDC activity over monomeric IgG1 (Shopes et al., 1992, *J. Immunol.* 148:2918-22). In addition, a bispecific diabody construct with specificity for C1q also confers CDC activity (Kontermann et al., 1997, *Nat. Biotech.* 15:629-31).

Complement activity can be reduced by mutating at least one of the amino acid residues 318, 320, and 322 of the heavy chain to a residue having a different side chain, such as Ala. Other alkyl-substituted non-ionic residues, such as Gly, Ile, Leu, or Val, or such aromatic non-polar residues as Phe, Tyr, Trp and Pro in place of any one of the three residues also reduce or abolish C1q binding. Ser, Thr, Cys, and Met can be used at residues 320 and 322, but not 318, to reduce or abolish C1q binding activity. Replacement of the 318 (Glu) residue by a polar residue may modify but not abolish C1q binding activity. Replacing residue 297 (Asn) with Ala results in removal of lytic activity but only slightly reduces (about three fold weaker) affinity for C1q. This alteration destroys the glycosylation site and the presence of carbohydrate that is required for complement activation. Any other substitution at this site also destroys the glycosylation site. The following mutations and any combination thereof also reduce C1q binding: D270A, K322A, P329A, and P311S (see WO 06/036291).

Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fcγ receptor binding or increase binding to FcRN.

Nucleic Acids, Vectors, and Host Cells

In some embodiments, the anti-TIGIT antibodies as described herein are prepared using recombinant methods. Accordingly, in some aspects, the invention provides isolated nucleic acids comprising a nucleic acid sequence encoding any of the anti-TIGIT antibodies as described herein (e.g., any one or more of the CDRs described herein); vectors comprising such nucleic acids; and host cells into which the nucleic acids are introduced that are used to replicate the antibody-encoding nucleic acids and/or to express the antibodies. In some embodiments, the host cell is eukaryotic, e.g., a Chinese Hamster Ovary (CHO) cell; or a human cell.

In some embodiments, a polynucleotide (e.g., an isolated polynucleotide) comprises a nucleotide sequence encoding an antibody described herein. In some embodiments, the polynucleotide comprises a nucleotide sequence encoding one or more amino acid sequences (e.g., CDR, heavy chain, light chain, and/or framework regions) disclosed in the Sequence Table. In some embodiments, the polynucleotide comprises a nucleotide sequence encoding an amino acid sequence having at least 85% sequence identity (e.g., at least 85%, at least 90%, at least 91%, at least 92%, at least 93%, at least 94%, at least 95%, at least 96%, at least 97%, at least 98%, or at least 99% sequence identity) to a sequence (e.g., a CDR, heavy chain, light chain, or framework region sequence) disclosed in the Sequence Table below.

In some embodiments, a polynucleotide (e.g., an isolated polynucleotide) comprises a nucleotide sequence encoding a heavy chain variable region as described herein. In some embodiments, a polynucleotide comprises a nucleotide sequence encoding a heavy chain variable region comprising an amino acid sequence that has at least 90% sequence identity to SEQ ID NO:1, SEQ ID NO:19, SEQ ID NO:37, SEQ ID NO:55, SEQ ID NO:73, SEQ ID NO:91, SEQ ID NO:109, SEQ ID NO:127, SEQ ID NO:145, SEQ ID NO:163, SEQ ID NO:181, SEQ ID NO:199, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, or SEQ ID NO:257. In some embodiments, the polynucleotide comprises a nucleotide sequence that has at least 90%, 91%, 92%, 93%, 94%, 95%, 96%, 97%, 98%, 99%, or 100% sequence identity to SEQ ID NO:2, SEQ ID NO:20, SEQ ID NO:38, SEQ ID NO:56, SEQ ID NO:74, SEQ ID NO:92, SEQ ID NO:110, SEQ ID NO:128, SEQ ID NO:146, SEQ ID NO:164, SEQ ID NO:182, SEQ ID NO:200, SEQ ID NO:259, SEQ ID NO:265, SEQ ID NO:267, SEQ ID NO:269, or SEQ ID NO:271.

In some embodiments, a polynucleotide (e.g., an isolated polynucleotide) comprises a nucleotide sequence encoding a light chain variable region as described herein. In some embodiments, a polynucleotide comprises a nucleotide sequence encoding a light chain variable region comprising an amino acid sequence that has at least 90% sequence identity to SEQ ID NO:10, SEQ ID NO:28, SEQ ID NO:46, SEQ ID NO:64, SEQ ID NO:82, SEQ ID NO:100, SEQ ID NO:118, SEQ ID NO:136, SEQ ID NO:154, SEQ ID NO:172, SEQ ID NO:190, or SEQ ID NO:208. In some embodiments, the polynucleotide comprises a nucleotide sequence that has at least 90%, 91%, 92%, 93%, 94%, 95%, 96%, 97%, 98%, 99%, or 100% sequence identity to SEQ ID NO:11, SEQ ID NO:29, SEQ ID NO:47, SEQ ID NO:65, SEQ ID NO:83, SEQ ID NO:101, SEQ ID NO:119, SEQ ID NO:137, SEQ ID NO:155, SEQ ID NO:173, SEQ ID NO:191, SEQ ID NO:209, or SEQ ID NO: 273.

In some embodiments, the polynucleotide comprises a nucleotide sequence encoding comprises a nucleotide sequence encoding a heavy chain variable region and a light chain variable region as described herein. In some embodiments, a polynucleotide comprises a nucleotide sequence encoding a heavy chain variable region comprising an amino acid sequence that has at least 90% sequence identity to SEQ ID NO:1, SEQ ID NO:19, SEQ ID NO:37, SEQ ID NO:55, SEQ ID NO:73, SEQ ID NO:91, SEQ ID NO:109, SEQ ID NO:127, SEQ ID NO:145, SEQ ID NO:163, SEQ ID NO:181, SEQ ID NO:199, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, or SEQ ID NO:257 and encoding a light chain variable region comprising an amino acid sequence that has at least 90% sequence identity to SEQ ID NO:10, SEQ ID NO:28, SEQ ID NO:46, SEQ ID NO:64, SEQ ID NO:82, SEQ ID NO:100, SEQ ID NO:118, SEQ ID NO:136, SEQ ID NO:154, SEQ ID NO:172, SEQ ID NO:190, or SEQ ID NO:208. In some embodiments, the polynucleotide comprises a nucleotide sequence that has at least 90%, 91%, 92%, 93%, 94%, 95%, 96%, 97%, 98%, 99%, or 100% sequence identity to SEQ ID NO:2, SEQ ID NO:20, SEQ ID NO:38, SEQ ID NO:56, SEQ ID NO:74, SEQ ID NO:92, SEQ ID NO:110, SEQ ID NO:128, SEQ ID NO:146, SEQ ID NO:164, SEQ ID NO:182, SEQ ID NO:200, SEQ ID NO:259, SEQ ID NO:265, SEQ ID NO:267, SEQ ID NO:269, or SEQ ID NO:271, and further comprises a nucleotide sequence that has at least 90%, 91%, 92%, 93%, 94%, 95%, 96%, 97%, 98%, 99%, or 100% sequence identity to SEQ ID NO:11, SEQ ID NO:29, SEQ ID NO:47, SEQ ID NO:65, SEQ ID NO:83, SEQ ID NO:101, SEQ ID NO:119, SEQ ID NO:137, SEQ ID NO:155, SEQ ID NO:173, SEQ ID NO:191, SEQ ID NO:209, or SEQ ID NO: 273.

In a further aspect, methods of making an anti-TIGIT antibody as described herein are provided. In some embodiments, the method includes culturing a host cell as described herein (e.g., a host cell expressing a polynucleotide or vector as described herein) under conditions suitable for expression of the antibody. In some embodiments, the antibody is subsequently recovered from the host cell (or host cell culture medium).

Suitable vectors containing polynucleotides encoding antibodies of the present disclosure, or fragments thereof, include cloning vectors and expression vectors. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. Cloning vectors are available from commercial vendors such as BioRad, Stratagene, and Invitrogen.

Expression vectors generally are replicable polynucleotide constructs that contain a nucleic acid of the present disclosure. The expression vector may replicate in the host cells either as episomes or as an integral part of the chromosomal DNA. Suitable expression vectors include but are not limited to plasmids, viral vectors, including adenoviruses, adeno-associated viruses, retroviruses, and any other vector.

Expression of Recombinant Antibodies

Antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, *From Genes to Clones*, (VCH Publishers, N Y, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Once expressed, antibodies can be purified according to standard procedures of the art, including HPLC purification, column chromatography, gel electrophoresis and the like (see generally, Scopes, *Protein Purification* (Springer-Verlag, NY, 1982)).

Glycosylation Variants

Antibodies may be glycosylated at conserved positions in their constant regions (Jefferis and Lund, (1997) Chem. Immunol. 65:111-128; Wright and Morrison, (1997) TibTECH 15:26-32). The oligosaccharide side chains of the immunoglobulins affect the protein's function (Boyd et al., (1996) Mol. Immunol. 32:1311-1318; Wittwe and Howard, (1990) Biochem. 29:4175-4180), and the intramolecular interaction between portions of the glycoprotein which can affect the conformation and presented three-dimensional surface of the glycoprotein (Hefferis and Lund, supra; Wyss and Wagner, (1996) Current Opin. Biotech. 7:409-416). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., (1995) Nature Med. 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., (1996) Mol. Immunol. 32:1311-1318), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al. (1999) Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc.

Addition of glycosylation sites to the antibody can be accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include isolation from a natural source (in the case of naturally-occurring amino acid sequence variants) or preparation by oligonucleotide-mediated (or site-directed) mutagenesis, PCR mutagenesis, and cassette mutagenesis of an earlier prepared variant or a non-variant version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. See, e.g., Hse et al., (1997) J. Biol. Chem. 272:9062-9070. In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261; 5,278,299). Glycosylation, or certain types of glycosylation, can be enzymatically removed from the glycoprotein, for example using endoglycosidase H (Endo H). In addition, the recombinant host cell can be genetically engineered, e.g., make defective in processing certain types of polysaccharides. These and similar techniques are known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides A preferred form of modification of glycosylation of antibodies is reduced core fucosylation. "Core fucosylation" refers to addition of fucose ("fucosylation") to N-acetylglucosamine ("GlcNAc") at the reducing terminal of an N-linked glycan.

A "complex N-glycoside-linked sugar chain" is typically bound to asparagine 297 (according to the number of Kabat). As used herein, the complex N-glycoside-linked sugar chain has a biantennary composite sugar chain, mainly having the following structure:

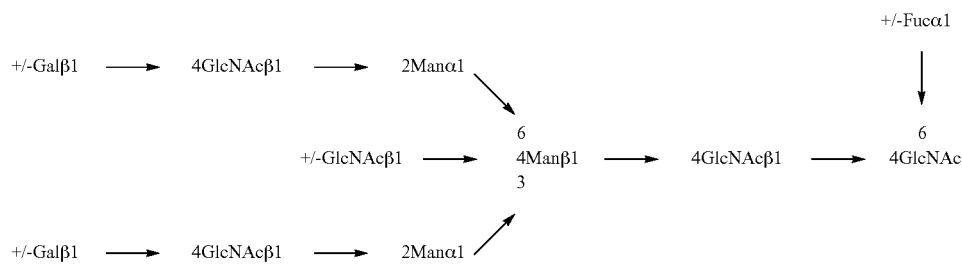

where ± indicates the sugar molecule can be present or absent, and the numbers indicate the position of linkages between the sugar molecules. In the above structure, the sugar chain terminal which binds to asparagine is called a reducing terminal (at right), and the opposite side is called a non-reducing terminal. Fucose is usually bound to N-acetylglucosamine ("GlcNAc") of the reducing terminal, typically by an α1,6 bond (the 6-position of GlcNAc is linked to the 1-position of fucose). "Gal" refers to galactose, and "Man" refers to mannose.

A "complex N-glycoside-linked sugar chain" includes 1) a complex type, in which the non-reducing terminal side of the core structure has zero, one or more branches of galactose-N-acetylglucosamine (also referred to as "gal- GlcNAc") and the non-reducing terminal side of gal-GlcNAc optionally has a sialic acid, bisecting N-acetylglucosamine or the like; and 2) a hybrid type, in which the non-reducing terminal side of the core structure has both branches of a high mannose N-glycoside-linked sugar chain and complex N-glycoside-linked sugar chain.

According to the present methods, typically only a minor amount of fucose is incorporated into the complex N-glycoside-linked sugar chain(s) of the anti-TIGIT antibodies. For example, in various embodiments, less than about 60%, less than about 50%, less than about 40%, less than about 30%, less than about 20%, less than about 15%, less than about 10%, less than about 5%, or less than about 3% of the antibodies in a composition have core fucosylation by fucose. In some embodiments, about 2% of the antibodies in the composition have core fucosylation by fucose. In various embodiments, when less that 60% of the antibodies in a composition have core fucosylation by fucose, the antibodies of the composition may be referred to as "nonfucosylated" or "afucosylated." In some embodiments, at least 90%, at least 91%, at least 92%, at least 93%, at least 94%, at least 95%, at least 96%, at least 97%, at least 98%, or at least 99% of the antibodies in the composition are afucosylated.

In certain embodiments, only a minor amount of a fucose analog (or a metabolite or product of the fucose analog) is incorporated into the complex N-glycoside-linked sugar chain(s). For example, in various embodiments, less than about 60%, less than about 50%, less than about 40%, less than about 30%, less than about 20%, less than about 15%, less than about 10%, less than about 5%, or less than about 3% of anti-TIGIT antibodies have core fucosylation by a fucose analog or a metabolite or product of the fucose analog. In some embodiments, about 2% of the anti-TIGIT antibodies have core fucosylation by a fucose analog or a metabolite or product of the fucose analog.

In some embodiments, less that about 60%, less than about 50%, less than about 40%, less than about 30%, less than about 20%, less than about 15%, less than about 10%, less than about 5%, or less than about 3% of the antibodies in a composition have a fucose residue on a G0, G1, or G2 glycan structure. (See, e.g., Raju et al., 2012, MAbs 4: 385-391, FIG. 3.) In some embodiments, about 2% of the antibodies in the composition have a fucose residue on a G0, G1, or G2 glycan structure. In various embodiments, when less that 60% of the antibodies in a composition have a fucose residue on a G0, G1, or G2 glycan structure, the antibodies of the composition may be referred to as "afucosylated." In some embodiments, at least 90%, at least 91%, at least 92%, at least 93%, at least 94%, at least 95%, at least 96%, at least 97%, at least 98%, or at least 99% of the antibodies in the composition lack fucose on a G0, G1, or G2 glycan structure. It should be noted that G0 glycans include G0-GN glycans. G0-GN glycans are monoantenary glycans with one terminal GlcNAc residue. G1 glycans include G1-GN glycans. G1-GN glycans are monoantenary glycans with one terminal galactose residue. G0-GN and G1-GN glycans can be fucosylated or non-fucosylated.

Methods of making afucosylated antibodies by incubating antibody-producing cells with a fucose analogue are described, e.g., in WO2009/135181. Briefly, cells that have been engineered to express anti-TIGIT antibodies are incubated in the presence of a fucose analogue or an intracellular metabolite or product of the fucose analog. An intracellular metabolite can be, for example, a GDP-modified analog or a fully or partially de-esterified analog. A product can be, for example, a fully or partially de-esterified analog. In some embodiments, a fucose analogue can inhibit an enzyme(s) in the fucose salvage pathway. For example, a fucose analog (or an intracellular metabolite or product of the fucose analog) can inhibit the activity of fucokinase, or GDP-fucose-pyrophosphorylase. In some embodiments, a fucose analog (or an intracellular metabolite or product of the fucose analog) inhibits fucosyltransferase (preferably a 1,6-fucosyltransferase, e.g., the FUT8 protein). In some embodiments, a fucose analog (or an intracellular metabolite or product of the fucose analog) can inhibit the activity of an enzyme in the de novo synthetic pathway for fucose. For example, a fucose analog (or an intracellular metabolite or product of the fucose analog) can inhibit the activity of GDP-mannose 4,6-dehydratase or/or GDP-fucose synthetase. In some embodiments, the fucose analog (or an intracellular metabolite or product of the fucose analog) can inhibit a fucose transporter (e.g., GDP-fucose transporter).

In one embodiment, the fucose analogue is 2-flurofucose. Methods of using fucose analogues in growth medium and other fucose analogues are disclosed, e.g., in WO 2009/135181, which is herein incorporated by reference.

Other methods for engineering cell lines to reduce core fucosylation included gene knock-outs, gene knock-ins and RNA interference (RNAi). In gene knock-outs, the gene encoding FUT8 (alpha 1,6-fucosyltransferase enzyme) is inactivated. FUT8 catalyzes the transfer of a fucosyl residue from GDP-fucose to position 6 of Asn-linked (N-linked) GlcNac of an N-glycan. FUT8 is reported to be the only enzyme responsible for adding fucose to the N-linked biantennary carbohydrate at Asn297. Gene knock-ins add genes encoding enzymes such as GNTIII or a golgi alpha mannosidase II. An increase in the levels of such enzymes in cells diverts monoclonal antibodies from the fucosylation pathway (leading to decreased core fucosylation), and having increased amount of bisecting N-acetylglucosamines. RNAi typically also targets FUT8 gene expression, leading to decreased mRNA transcript levels or knocking out gene expression entirely. Any of these methods can be used to generate a cell line that would be able to produce an afucosylated antibody, e.g., a anti-TIGIT antibody antibody.

Many methods are available to determine the amount of fucosylation on an antibody. Methods include, e.g., LC-MS via PLRP-S chromatography, electrospray ionization quadrupole TOF MS, Capillary Electrophoresis with Laser-Induced Fluorescence (CE-LIF) and, Hydrophilic Interaction Chromatography with Fluorescence Detection (HILIC).

IV. Therapeutic Methods Using Anti-TIGIT Antibodies

In some embodiments, methods for treating or preventing a cancer in a subject are provided. In some embodiments, the method comprises administering to the subject a therapeutic amount of an anti-TIGIT antibody. In some embodiments, the anti-TIGIT antibody is afucosylated. In some embodiments, the method comprises administering to the subject a therapeutic amount of a pharmaceutical composition comprising anti-TIGIT antibodies, wherein at least 90%, at least 91%, at least 92%, at least 93%, at least 94%, at least 95%, at least 96%, at least 97%, at least 98%, or at least 99% of the antibodies in the composition are afucosylated. In some embodiments, the subject is a human.

In some embodiments, the cancer is a cancer or cancer cell that is enriched for expression of CD112 and/or CD155. In some embodiments, CD112- and/or CD155-enriched cancers are identified by immunohistochemistry assessment of tumor samples using antibodies specific for CD112 or CD155. In some embodiments, CD112 or CD155 expression is enriched or increased in tumor cells or in tumor infiltrating leukocytes. In some embodiments, the cancer is identified based on the assessment of CD112 and/or CD155 mRNA levels in tumor samples (e.g., by methods known in the art such as quantitative RT-PCR). In some embodiments, measurements of soluble CD112 or CD155 in blood samples obtained from cancer patients may be used to identify a cancer that is enriched for expression of CD112 and/or CD155. In some embodiments, the method comprises obtaining a sample from a subject (e.g., a tumor sample or a blood sample), measuring the level of CD112 and/or CD155 in the sample from the subject, and comparing the level of CD112 and/or CD155 in the sample from the subject to a control value (e.g., a sample from a healthy control subject or a level of CD112 and/or CD155 expression determined for a population of healthy controls). In some embodiments, the method comprises determining that the level of CD112 and/or CD155 in the sample from the subject is higher than a control value, and subsequently administering to the subject an anti-TIGIT antibody as described herein.

In some embodiments, the cancer is a cancer or cancer cell that is enriched for T cells or natural killer (NK) cells that express TIGIT. In some embodiments, TIGIT-enriched cancers are identified by immunohistochemistry assessment of tumor samples using antibodies specific for TIGIT. In some embodiments, an antibody that is specific for T cells or NK cells (e.g., anti-CD3, anti-CD4, anti-CD8, anti-CD25, or anti-CD56) is used to determine a subset or subsets of tumor infiltrating cells that express TIGIT. In some embodiments, the cancer is identified based on the assessment of TIGIT mRNA levels in tumor samples. In some embodiments, measurements of soluble TIGIT in blood samples obtained from cancer patients may be used (optionally in combination with an antibody that is specific for T cells or NK cells) to identify a cancer that is enriched for T cells or NK cells that express TIGIT. In some embodiments, the method comprises obtaining a sample from a subject (e.g., a tumor sample or a blood sample), measuring the level of TIGIT in the sample from the subject, optionally detecting the presence of T cells or NK cells (e.g., using an antibody that is specific for T cells or NK cells such as anti-CD3, anti-CD4, anti-CD8, anti-CD25, or anti-CD56) and comparing the level of TIGIT in the sample from the subject to a control value (e.g., a sample from a healthy control subject or a level of TIGIT expression determined for a population of healthy controls). In some embodiments, the method comprises determining that the level of TIGIT in the sample from the subject is higher than a control value, and subsequently administering to the subject an anti-TIGIT antibody as described herein.

In some embodiments, the cancer is bladder cancer, breast cancer, uterine cancer, cervical cancer, ovarian cancer, prostate cancer, testicular cancer, esophageal cancer, gastrointestinal cancer, gastric cancer, pancreatic cancer, colorectal cancer, colon cancer, kidney cancer, clear cell renal carcinoma, head and neck cancer, lung cancer, lung adenocarcinoma, stomach cancer, germ cell cancer, bone cancer, liver cancer, thyroid cancer, skin cancer, melanoma, neoplasm of the central nervous system, mesothelioma, lymphoma, leukemia, chronic lymphocytic leukemia, diffuse large B cell lymphoma, follicular lymphoma, Hodgkin lymphoma, myeloma, or sarcoma. In some embodiments, the cancer is selected from gastric cancer, testicular cancer, pancreatic cancer, lung adenocarcinoma, bladder cancer, head and neck cancer, prostate cancer, breast cancer, mesothelioma, and clear cell renal carcinoma. In some embodiments, the cancer is a lymphoma or a leukemia, including but not limited to acute myeloid, chronic myeloid, acute lymphocytic or chronic lymphocytic leukemia, diffuse large B-cell lymphoma, follicular lymphoma, mantle cell lymphoma, small lymphocytic lymphoma, primary mediastinal large B-cell lymphoma, splenic marginal zone B-cell lymphoma, or extranodal marginal zone B-cell lymphoma. In some embodiments, the cancer is selected from chronic lymphocytic leukemia, diffuse large B cell lymphoma, follicular lymphoma, and Hodgkin lymphoma. In some embodiments, the cancer is a metastatic cancer.

In some embodiments, the method further comprises administering to the subject a therapeutic amount of an additional therapeutic agent. In some embodiments, the additional therapeutic agent is an immuno-oncology agent. In some embodiments, the immuno-oncology agent is an agent (e.g., an antibody, small molecule, or peptide) that antagonizes or inhibits a component of an immune checkpoint pathway, such as the PD-1 pathway, the CTLA-4 pathway, the Lag3 pathway, or the TIM-3 pathway. In some embodiments, the immuno-oncology agent is an agonist of a T cell coactivator (i.e., an agonist of a protein that stimulates T cell activation) by targeting the OX-40 pathway, the 4-1BB (CD137) pathway, the CD27 pathway, the ICOS pathway, or the GITR pathway.

In some embodiments, the immuno-oncology agent is a PD-1 pathway inhibitor. In some embodiments, the PD-1 pathway inhibitor is an anti-PD-1 antibody or anti-PD-L1 antibody, such as but not limited to pembrolizumab, nivolumab, durvalumab, pidilizumab, avelumab, or atezolizumab. PD-1 pathway inhibitors are described in the art. See, e.g., Dolan et al., *Cancer Control*, 2014, 21:231-237; Luke et al., Oncotarget, 2014, 6:3479-3492; US 2016/0222113; US 2016/0272708; US 2016/0272712; and US 2016/0319019.

In some embodiments, the immuno-oncology agent is an agonist of a T cell coactivator. In some embodiments, the immuno-oncology agent is an agonist of CD28, CD28H, CD3, 4-1BB (CD137), ICOS, OX40, GITR, CD27, or CD40. In some embodiments, the immuno-oncology agent is an immune stimulatory cytokine. In some embodiments, the immune stimulatory cytokine is granulocyte-macrophage colony stimulating factor (GM-CSF), macrophage colony stimulating factor (M-CSF), granulocyte colony stimulating factor (G-CSF), interleukin 1 (IL-1), interleukin 2 (IL-2), interleukin 3 (IL-3), interleukin 12 (IL-12), interleukin 15 (IL-15), or interferon gamma (IFN-γ). In some embodiments, the immuno-oncology agent is SGN-2FF (Seattle Genetics; see, e.g., WO 2009/135181 A2, WO 2012/019165 A2, and WO 2017/096274 A1).

In some embodiments, the additional therapeutic agent is selected from an anti-CD25 antibody, anti-PD-1 antibody, anti-PD-L1 antibody, anti-Tim3 antibody, anti-Lag3 antibody, anti-CTLA4 antibody, anti-41BB antibody, anti-OX40 antibody, anti-CD3 antibody, anti-CD40 antibody, anti-CD47M antibody, anti-CSF1R antibody, anti-TLR antibody, anti-STING antibody, anti-MGI antibody, anti-TAM receptor kinase antibody, anti-NKG2A antibody, an anti-NKG2D antibody, an anti-GD2 antibody, an anti-HER2 antibody, an anti-EGFR antibody, an anti-PDGFR-α-antibody, an anti-SLAMF7 antibody, an anti-VEGF antibody, an anti-CTLA-4 antibody, an anti-CD20 antibody, an anti-cCLB8 antibody, an anti-KIR antibody, and an anti-CD52 antibody. In some embodiments, the additional therapeutic agent is selected from SEA-CD40 (Seattle Genetics; see, e.g., WO 2006/128103 A2 and WO 2016/069919 A1), avelumab, durvalumab, nivolumab, pembrolizumab, pidilizumab, atezolizumab, Hu14.18K322A (anti-GD2 antibody, St. Jude), Hu3F8 (anti-GD2 antibody, MSKCC), dinituximab, trastuzumab, cetuximab, olaratumab, necitumumab, elotuzumab, ramucirumab, pertuzumab, ipilimumab, bevacizumab, rituximab, obinutuzumab, siltuximab, ofatumumab, and alemtuzumab.

In some embodiments, treatment with an anti-TIGIT antibody as described herein is combined with one or more other anti-cancer treatments, such as surgery or radiation. In some embodiments, treatment with an anti-TIGIT antibody as described herein is combined with one or more other anti-cancer agents, such as chemotherapeutic agents. Non-limiting exemplary chemotherapeutic agents include an alkylating agent (e.g., cyclophosphamide, ifosfamide, chlorambucil, busulfan, melphalan, mechlorethamine, uramustine, thiotepa, nitrosoureas, or temozolomide), an anthracycline (e.g., doxorubicin, adriamycin, daunorubicin, epirubicin, or mitoxantrone), a cytoskeletal disruptor (e.g., paclitaxel or docetaxel), a histone deacetylase inhibitor (e.g., vorinostat or romidepsin), an inhibitor of topoisomerase (e.g., irinotecan, topotecan, amsacrine, etoposide, or teniposide), a kinase inhibitor (e.g., bortezomib, erlotinib, gefitinib, imatinib, vemurafenib, or vismodegib), a nucleoside analog or precursor analog (e.g., azacitidine, azathioprine, capecitabine, cytarabine, fluorouracil, gemcitabine, hydroxyurea, mercaptopurine, methotrexate, or thioguanine), a peptide antibiotic (e.g., actinomycin or bleomycin), a platinum-based agent (e.g., cisplatin, oxaloplatin, or carboplatin), or a plant alkaloid (e.g., vincristine, vinblastine, vinorelbine, vindesine, podophyllotoxin, paclitaxel, or docetaxel), galardin, thalidomide, lenalidomide, and pomalidomide.

In some embodiments, the anti-TIGIT antibody (and optionally an additional therapeutic agent) is administered at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

The route of administration of an anti-TIGIT antibody or pharmaceutical composition comprising an anti-TIGIT antibody (and optionally an immuno-oncology agent or other therapeutic treatment) can be oral, intraperitoneal, transdermal, subcutaneous, intravenous, intramuscular, inhalational, topical, intralesional, rectal, intrabronchial, nasal, transmucosal, intestinal, ocular or otic delivery, or any other methods known in the art. In some embodiments, the anti-TIGIT antibody (and optionally an immuno-oncology agent) is administered orally, intravenously, or intraperitoneally.

Co-administered therapeutic agents (e.g., the anti-TIGIT antibody and an additional therapeutic agent) can be administered together or separately, simultaneously or at different times. When administered, the therapeutic agents independently can be administered once, twice, three, four times daily or more or less often, as needed. In some embodiments, the administered therapeutic agents are administered once daily. In some embodiments, the administered therapeutic agents are administered at the same time or times, for instance as an admixture. In some embodiments, one or more of the therapeutic agents is administered in a sustained-release formulation.

In some embodiments, the anti-TIGIT antibody and an additional therapeutic agent are administered concurrently. In some embodiments, the anti-TIGIT antibody and an additional therapeutic agent are administered sequentially. For example, in some embodiments, an anti-TIGIT antibody is administered first, for example for about 1, 2, 3, 4, 5, 6, 7, 8, 9, 10, 15, 20, 25, 30, 40, 50, 60, 70, 80, 90, 100 days or more prior to administering an additional therapeutic agent. In some embodiments, an additional therapeutic agent is administered first, for example for about 1, 2, 3, 4, 5, 6, 7, 8, 9, 10, 15, 20, 25, 30, 40, 50, 60, 70, 80, 90, 100 days or more prior to administering an anti-TIGIT antibody.

In some embodiments, the anti-TIGIT antibody (and optionally the additional therapeutic agent) is administered to the subject over an extended period of time, e.g., for at least 30, 40, 50, 60, 70, 80, 90, 100, 150, 200, 250, 300, 350 days or longer.

V. Compositions and Kits

In another aspect, compositions and kits comprising an anti-TIGIT antibody for use in treating or preventing a cancer in a subject are provided.
Pharmaceutical Compositions In some embodiments, pharmaceutical compositions comprising an anti-TIGIT antibody for use in administering to a subject having a cancer are provided. In some embodiments, the anti-TIGIT antibody is as described herein, e.g., an anti-TIGIT antibody having a binding affinity, activity, cross-reactivity, epitope recognition, and/or one or more CDR, VH, and/or VL sequences as disclosed herein. In some embodiments, the anti-TIGIT antibody is afucosylated.

In some embodiments, an anti-TIGIT antibody and an additional therapeutic agent are formulated into pharmaceutical compositions, together or separately, as described herein. In some embodiments, the additional therapeutic agent is an immuno-oncology agent, such as a PD-1 pathway inhibitor or a CTLA-4 pathway inhibitor. In some embodiments, the immuno-oncology agent is an agonist of a T cell coactivator. In some embodiments, the PD-1 pathway inhibitor is an anti-PD-1 antibody or anti-PD-L1 antibody, such as but not limited to pembrolizumab, nivolumab, durvalumab, pidilizumab, or atezolizumab.

Guidance for preparing formulations for use in the present invention is found in, for example, *Remington: The Science and Practice of Pharmacy*, 21$^{st}$ Ed., 2006, supra; *Martindale: The Complete Drug Reference*, Sweetman, 2005, London: Pharmaceutical Press; Niazi, *Handbook of Pharmaceutical Manufacturing Formulations*, 2004, CRC Press; and Gibson, *Pharmaceutical Preformulation and Formulation: A Practical Guide from Candidate Drug Selection to Commercial Dosage Form*, 2001, Interpharm Press, which are hereby incorporated herein by reference. The pharmaceutical compositions described herein can be manufactured in a manner that is known to those of skill in the art, i.e., by means of conventional mixing, dissolving, granulating, dragee-making, emulsifying, encapsulating, entrapping or lyophilizing processes. The following methods and excipients are merely exemplary and are in no way limiting.

In some embodiments, an anti-TIGIT antibody (and optionally an additional therapeutic agent) is prepared for delivery in a sustained-release, controlled release, extended-release, timed-release or delayed-release formulation, for example, in semi-permeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

For oral administration, an anti-TIGIT antibody (and optionally an additional therapeutic agent) can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

The anti-TIGIT antibody (and optionally the additional therapeutic agent) can be formulated for parenteral administration by injection, e.g., by bolus injection or continuous infusion. For injection, the compound or compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, compounds can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

The anti-TIGIT antibody (and optionally the additional therapeutic agent) can be administered systemically by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplary transdermal delivery formulations include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

In some embodiments, a pharmaceutical composition comprises an acceptable carrier and/or excipients. A pharmaceutically acceptable carrier includes any solvents, dispersion media, or coatings that are physiologically compatible and that preferably does not interfere with or otherwise inhibit the activity of the therapeutic agent. In some embodiments, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, *Remington: The Science and Practice of Pharmacy*, 21st Edition, Philadelphia, Pa. Lippincott Williams & Wilkins, 2005. Various pharmaceutically acceptable excipients are well-known in the art and can be found in, for example, Handbook of Pharmaceutical Excipients (5$^{th}$ ed., Ed. Rowe et al., Pharmaceutical Press, Washington, D.C.).

Dosages and desired drug concentration of pharmaceutical compositions of the disclosure may vary depending on the particular use envisioned. The determination of the appropriate dosage or route of administration is well within the skill of one in the art. Suitable dosages are also described herein.

Kits

In some embodiments, kits for use in treating a subject having a cancer are provided. In some embodiments, the kit comprises:

an anti-TIGIT antibody; and an additional therapeutic agent.

In some embodiments, anti-TIGIT antibody is as described herein, e.g., an anti-TIGIT antibody having a binding affinity, activity, cross-reactivity, epitope recognition, and/or one or more CDR, VH, and/or VL sequences as disclosed herein. In some embodiments, the anti-TIGIT antibody is afucosylated. In some embodiments, the additional therapeutic agent is an immuno-oncology agent, such as a PD-1 pathway inhibitor or a CTLA-4 pathway inhibitor. In some embodiments, the immuno-oncology agent is an agonist of a T cell coactivator. In some embodiments, the PD-1 pathway inhibitor is an anti-PD-1 antibody or anti-PD-L1 antibody. In some embodiments, the immuno-oncology agent is pembrolizumab, nivolumab, durvalumab, pidilizumab, or atezolizumab.

In some embodiments, the kits can further comprise instructional materials containing directions (i.e., protocols) for the practice of the methods of this invention (e.g., instructions for using the kit for treating a cancer). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VI. Examples

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Anti-TIGIT Antibodies

Fully human anti-TIGIT monoclonal antibodies were generated using yeast-based antibody presentation system (see, e.g., Xu et al, "Addressing polyspecificity of antibodies selected from an in vitro yeast presentation system: a FACS-based, high-throughput selection and analytical tool," *PEDS*, 2013, 26:663-670; WO 2009/036379; WO 2010/105256; and WO 2012/009568). Eight naïve human synthetic yeast libraries each of ~$10^9$ diversity were screened. For the first two rounds of selection, a magnetic bead sorting technique utilizing the Miltenyi MACS system was performed, as previously described (see, e.g., Siegel et al, "High efficiency recovery and epitope-specific sorting of an scFv yeast display library," *J Immunol Methods*, 2004, 286:141-153). Briefly, yeast cells (~$10^{10}$ cells/library) were incubated with 5 mL of 10 nM biotinylated Fc-fusion antigen for 30 minutes at 30° C. in wash buffer (phosphate-buffered saline (PBS)/0.1% bovine serum albumin (BSA)). After washing once with 40 mL ice-cold wash buffer, the cell pellet was resuspended in 20 mL wash buffer, and Streptavidin MicroBeads (500 µL) were added to the yeast and incubated for 15 minutes at 4° C. Next, the yeast were pelleted, resuspended in 20 mL wash buffer, and loaded onto a Miltenyi LS column. After the 20 mL were loaded, the column was washed 3 times with 3 mL wash buffer. The column was then removed from the magnetic field, and the yeast were eluted with 5 mL of growth media and then grown overnight. The following rounds of selection were performed using flow cytometry. Approximately 2×$10^7$ yeast were pelleted, washed three times with wash buffer, and incubated at 30° C. with 10 nM Fc-fusion antigen and decreasing concentrations of biotinylated monomeric antigen (100 to 1 nM) under equilibrium conditions, 10 nM biotinylated Fc-fusion antigens or 100 nM monomeric antigens of different species in order to obtain species cross-reactivity, or with a poly-specificity depletion reagent (PSR) to remove non-specific antibodies from the selection. For the PSR depletion, the libraries were incubated with a 1:10 dilution of biotinylated PSR reagent as previously described (see, e.g., Xu et al, supra). Yeast were then washed twice with wash buffer and stained with LC-FITC (diluted 1:100) and either SA-633 (diluted 1:500) or EA-PE (extravidin-R-PE, diluted 1:50) secondary reagents for 15 minutes at 4° C. After washing twice with wash buffer, the cell pellets were resuspended in 0.3 mL wash buffer and transferred to strainer-capped sort tubes. Sorting was performed using a FACS ARIA sorter (BD Biosciences) and sort gates were determined to select for antibodies with desired characteristics. Selection rounds were repeated until a population with all of the desired characteristics was obtained. After the final round of sorting, yeast were plated and individual colonies were picked for characterization.

Antigens included recombinant dimeric human TIGIT-Fc (Acro Biosystems TIT-H5254), monomeric human TIGIT (Sino Biological 10917-H08H), dimeric mouse TIGIT-Fc (R&D Systems, 7267-TG), and monomeric mouse TIGIT (Sino Biologics 50939-MO8H).

Naïve Campaign:

744 clones were sequenced yielding 345 unique clones (unique CDRH3). 18 VH germlines were represented in the clones.

Light Chain Batch Diversification Campaign:

Heavy chain (VH) plasmids from an enriched binder pool from round six of the naïve discovery selections were extracted from the yeast via smash and grab, propagated in and subsequently purified from *E. Coli*, and then transformed into a light chain library with a diversity of $10^7$.

Selections were performed under essentially the same conditions as that for the naïve discovery. Briefly, one round of magnetic bead enrichment was followed by three rounds of selections by flow cytometry. In the magnetic bead enrichment round, 10 nM biotinylated Fc-fusion antigen was used. The first round on the flow cytometer consisted of a positive selection round using 100 nM biotinylated monovalent antigen. This was followed by a second round, which consisted of a negative selection round for PSR depletion. The final (third) round consisted of a positive selection round, in which the monovalent antigen was titrated at 100 nM, 10 nM, 1 nM. For all libraries, the yeasts from the 1 nM sorts from this third round were plated, and individual colonies were picked and characterized. In total, 728 clones were sequenced, yielding 350 unique HC/LC combinations (93 unique CDRH3s).

A total of 695 unique clones were identified between the naïve and the light chain batch shuffle campaigns.

Example 2: Characterization of Anti-TIGIT Antibodies 65 clones were selected for production and further evaluation, representing 12 VH germlines and 9 VL germlines.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

Binding of Anti-TIGIT Antibodies to Recombinant Human and Mouse Protein

ForteBio affinity measurements were performed on an Octet RED384 generally as previously described (see, e.g., Estep et al., "High throughput solution-based measurement of antibody-antigen affinity and epitope binning," *Mabs*, 2013, 5:270-278). Briefly, ForteBio affinity measurements were performed by loading IgGs on-line onto AHQ sensors. Sensors were equilibrated off-line in assay buffer for 30 minutes and then monitored on-line for 60 seconds for baseline establishment. Sensors with loaded IgGs were exposed to 100 nM antigen (dimeric Fc-fusion antigen or monomeric antigen) for 3 minutes, and afterwards were transferred to assay buffer for 3 minutes for off-rate measurement. All binding and dissociation kinetics were analyzed using the 1:1 binding model.

Of the 65 IgG clones, 43 had an affinity for TIGIT monomer of <100 nM. Of the 65 IgG clones, 34 cross-reacted with mouse TIGIT-Fc. Binding affinity for selected clones is shown in Table 1 below.

Epitope Binning/Ligand Competition Assay

Epitope binning/ligand blocking was performed using a standard sandwich format cross-blocking assay on the ForteBio Octet RED384 system. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand (human CD155-Fc (Sino Biological, 10109-H02H)). Additional binding by the second antibody or ligand after antigen association indicates an unoccupied epitope (non-competitor), while no binding indicates epitope blocking (competitor or ligand blocking).

Four binning antibodies (not mutually exclusive) were used for bin assessment and five overlapping binning profiles were identified. 63 of the 65 anti-TIGIT antibodies competed with the ligand for binding to hTIGIT-Fc. Binning profiles and ligand competition results for selected clones are shown in Table 1 below.

TABLE 1

Epitope binning, ligand competition, and affinity data for selected anti-TIGIT clones

| Clone | Bin Code | CD155 Competition | IgG KD Human TIGIT-Fc (M) | IgG KD Human TIGIT monomer (M) | IgG KD Mouse TIGIT-Fc (M) |
| --- | --- | --- | --- | --- | --- |
| 2 | 1, 2, 3, 4 | Yes | 9.56E−10 | 1.01E−08 | 2.03E−09 |
| 3 | 1, 2, 3, 4 | Yes | 2.77E−09 | 7.36E−08 | 5.64E−09 |
| 5 | 1, 2, 3, 4 | Yes | 9.85E−10 | 1.41E−08 | 3.25E−09 |
| 13 | 1, 2, 3 | Yes | 5.43E−10 | 2.56E−09 | 1.16E−10 |
| 14 | 1, 2, 3 | Yes | 2.01E−09 | 5.87E−08 | 2.43E−09 |
| 16 | 1, 2, 3 | Yes | 6.90E−10 | 2.06E−09 | 1.05E−08 |
| 18 | 1, 2, 3 | Yes | 2.39E−09 | 5.08E−08 | 8.82E−09 |
| 21 | 1, 2, 3 | Yes | 5.85E−10 | 2.18E−09 | N.B. |
| 22 | 1, 2, 3 | Yes | 7.90E−10 | 1.38E−08 | 1.05E−08 |
| 25 | 1, 2, 3 | Yes | 6.20E−10 | 6.18E−10 | 1.10E−09 |
| 27 | 1, 2, 3 | Yes | 5.58E−10 | 2.32E−09 | N.B. |
| 54 | 1, 2, 3 | Yes | 6.89E−10 | 3.49E−09 | N.B. |

Notes:
N.B. = Non-Binder under the conditions of this assay
Bin code and CD155 competition data was generated on ForteBio Octet RED384 system using a standard sandwich format cross-blocking assay as described in Example 2.
KD affinity data was generated on ForteBio Octet RED384 system as described in Example 2.

Binding of Anti-TIGIT Antibodies to Human, Mouse, and Cynomolgus Monkey TIGIT Overexpressed in HEK 293 Cells HEK 293 cells were engineered to stably express high levels of human, mouse or cynomolgus monkey TIGIT by lentiviral transduction. Approximately 100,000 parental HEK 293 (TIGIT-negative) cells or HEK 293 cells overexpressing human, mouse or cynomolgus monkey were stained with 100 nM of each anti-TIGIT antibody for 5 minutes at room temperature. Cells were then washed twice with wash buffer and incubated with anti-human IgG conjugated to PE for 15 minutes on ice. Cells were then washed twice with wash buffer and analyzed by flow cytometry on a FACS Canto II instrument (BD Biosciences). Fold over background (FOB) was calculated as the median fluorescence intensity (MFI) of the anti-TIGIT clone bound to target-positive cells divided by the MFI of the anti-TIGIT clone bound to target-negative cells.

As shown in FIG. 1, all 65 antibodies showed specific binding to the 293-hTIGIT line (FOB>10, as indicated by the horizontal black line in the chart). 53 clones specifically bound the 293-cyTIGIT line while 31 clones specifically bound the 293-mTIGIT line.

Polyspecificity Reagent (PSR) Assay

Assessment of binding to a polyspecificity reagent was conducted to determine specificity for TIGIT as previously described (see, e.g., Xu et al, supra). Briefly, biotinylated PSR reagent diluted 1:10 from stock was incubated with IgG-presenting yeast for 20 minutes on ice. Cells were washed and labeled with EA-PE (extravidin-R-PE) and read on a FACS analyzer. Scoring of polyspecific binding is on a 0 to 1 scale and is correlated to control IgGs with low, medium and high non-specific binding with a score of 0 indicating no binding and a score of 1 indicating very high non-specific binding.

62 of the 65 clones were scored as non-polyspecific binders with a PSR score of <0.10. Three clones scored as low polyspecific binders (PSR score 0.10-0.33).

Hydrophobic Interaction Chromatography Assay

Hydrophobic interaction chromatography (HIC) was performed as described previously (Estep et al., supra). Briefly, 5 µg IgG samples were spiked in with a mobile phase A solution (1.8 M ammonium sulfate and 0.1 M sodium phosphate at pH 6.6) to achieve a final ammonium sulfate concentration of about 1 M before analysis. A Sepax Proteomix HIC butyl-NP5 column was used with a linear gradient of mobile phase A and mobile phase B solution (0.1 M sodium phosphate, pH 6.5) over 20 minutes at a flow rate of 1 mL/minute with UV absorbance monitoring at 280 nM.

Increased retention of antibodies on hydrophobic columns has been correlated with increased hydrophobicity and a propensity for poor expression, aggregation or precipitation during purification. Five of the 65 clones had high HIC retention time of >11.5 minutes, 10 clones had a medium HIC retention time of 10.5-11.5 minutes, and the remainder of the clones had low HIC retention times.

Example 3: Binding of Anti-TIGIT Antibodies to Human, Mouse, and Cynomolgus Monkey TIGIT Endogenously Expressed on Primary T Cells 65 antibodies shown to be specific for human TIGIT recombinant protein and human TIGIT expressed on HEK 293 cells were evaluated for their ability to bind endogenous TIGIT on primary human peripheral blood T cells. Antibodies were also evaluated for cross reactivity to cynomolgus TIGIT on peripheral blood T cells and 35 of the 65 clones were evaluated for cross reactivity to mouse TIGIT on activated splenic T cells.

Human pan T cells were negatively isolated from leukapheresis product to 99% purity. 100,000 cells were stained at 4° C. for 30 minutes with 20 µg/mL of each anti-TIGIT antibody. The anti-TIGIT antibodies were detected with polyclonal goat anti-human IgG conjugated to PE (Jackson ImmunoResearch 109-116-098). Samples were analyzed on a CytoFLEX flow cytometer. Percent TIGIT+ of the FSC/SSC gated lymphocyte population was determined for each antibody using anti-human IgG-PE only staining to determine the threshold for positivity.

Cynomolgus white blood cells were isolated from whole blood by red blood cell lysis (eBioscience 00-4300). 200,000 cells were stained at 4° C. for 30 minutes with 20 µg/mL of each anti-TIGIT antibody. The anti-TIGIT antibodies were detected with polyclonal goat anti-human IgG adsorbed against monkey immunoglobulins conjugated to AlexaFluor647 (SouthernBiotech 2049-31) and T cells were identified by counterstaining with FITC-conjugated anti-CD3 clone SP34 (BD Pharmingen 556611). Samples were analyzed on a CytoFLEX flow cytometer. Percent TIGIT+ of the CD3+ population was determined for each antibody using anti-human IgG-PE only staining to determine the threshold for positivity.

BALB/c mouse T cells were isolated from spleens by negative selection (Stem Cell Technologies 19851A) to >99% purity. The cells were activated for 24 hours with plate bound anti-CD3 clone 145-2C11 (BioLegend 100302) to upregulate TIGIT. 200,000 activated cells were stained at 4° C. for 30 minutes with 20 µg/mL of each anti-TIGIT antibody (35 of 65 clones tested). The anti-TIGIT antibodies were detected with polyclonal goat anti-human IgG conjugated to PE (Jackson ImmunoResearch 109-116-098). Samples were analyzed on a FACSCalibur flow cytometer. Median fluorescence intensity of the FSC/SSC gated lymphocyte population was determined for each antibody.

Figure 2:
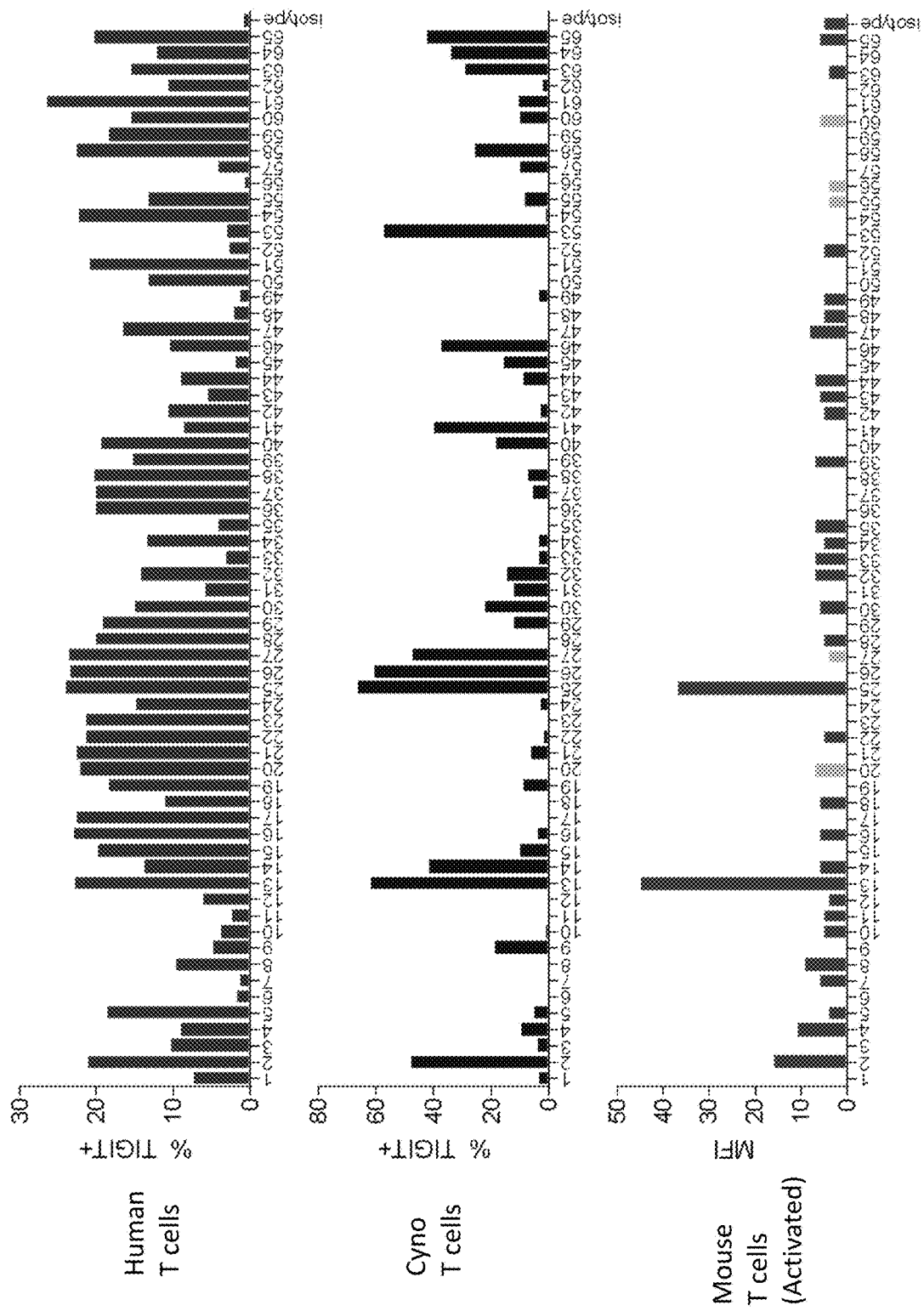
FIG. 2. Binding of 65 anti-TIGIT antibody clones and an irrelevant isotype control antibody to primary human T cells (top panel), cynomolgus monkey T cells (middle panel), and mouse T cells (bottom panel). For the bottom panel, 35 of 65 clones were evaluated. Of the 35 clones evaluated, 5 of the 35 did not bind mTIGIT-Fc protein (clones 20, 27, 55, 56, and 60), as indicated by the light green bars.
Figures 3C, 3D:
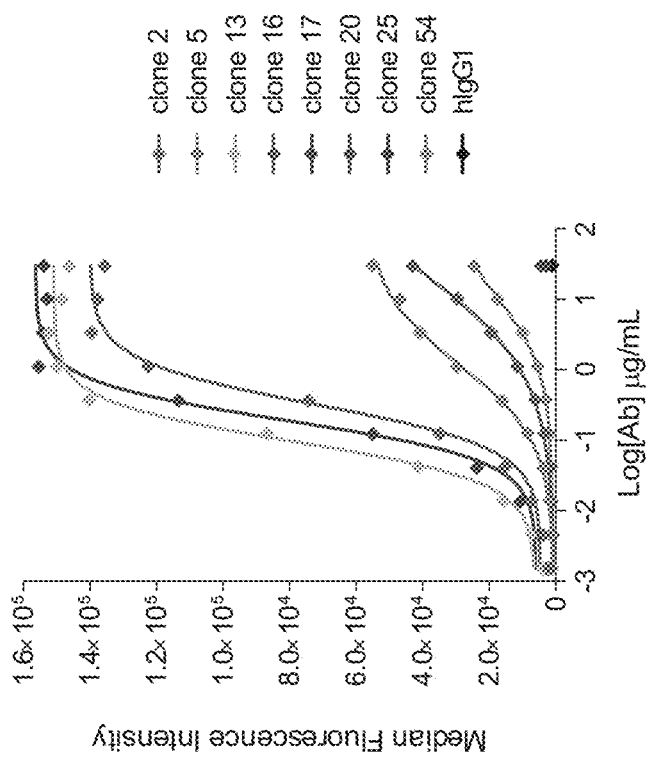

FIG. 2 shows binding of 65 anti-TIGIT antibody clones and an irrelevant isotype control antibody to primary human, cynomolgus monkey and mouse T cells. Clones 13 and 25 both showed strong binding to all three species of T cells. Titratable Binding of Anti-TIGIT Antibodies to Cell Surface Expressed TIGIT HEK 293 cells were engineered to stably express high levels of human, mouse or cynomolgus monkey TIGIT by lentiviral transduction. 200,000 293-TIGIT cells were stained at 4° C. for 30 minutes with a 10-point, 3-fold titration (30 to 0.002 µg/mL) of each anti-TIGIT antibody. The anti-TIGIT antibodies were detected with polyclonal goat anti-human IgG conjugated to PE (Jackson ImmunoResearch 109-116-098). Samples were analyzed on a CytoFLEX flow cytometer. Median fluorescence intensity of the FSC/SSC gated population was determined for each antibody concentration. NonLinear regression of Log(X) transformed data was used to generate EC50 values in GraphPad Prism 6. None of the anti-TIGIT antibodies showed binding to parental HEK 293 cells (TIGIT−) (data not shown). FIG. 3A-C shows the binding titration and FIG. 3D shows the EC50 of binding of eight anti-TIGIT antibody clones (clone 2, clone 5, clone 13, clone 16, clone 17, clone 20, clone 25, and clone 54) to human, cynomolgus monkey, and mouse TIGIT expressed on HEK 293 cells.

Figure 4:
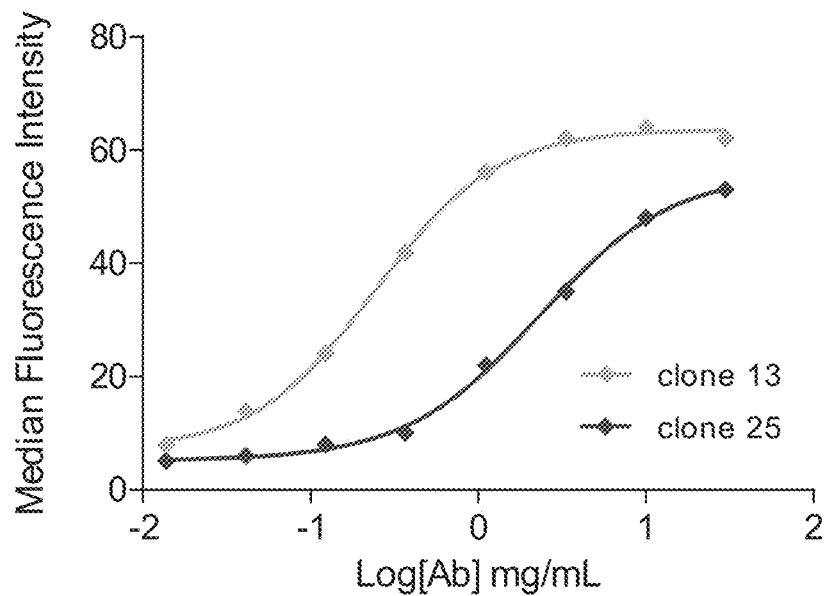
FIG. 4. Binding titration of anti-TIGIT antibody clones 13 and 25 to activated mouse splenic T cells. Results are shown for singlicate wells. Clone 13 had an EC50 of 0.24 µg/mL. Clone 25 had an EC50 of 2.28 µg/mL.

C57BL/6 mouse T cells were isolated from spleens by negative selection (Stem Cell Technologies 19851A) to >99% purity. The cells were activated for 24 hours with plate bound anti-CD3 clone 145-2C11 (BioLegend 100302) to upregulate TIGIT. 200,000 cells were stained at 4° C. for 30 minutes with an 8-point, 3-fold titration (30 to 0.014 µg/mL) of each anti-TIGIT antibody. The anti-TIGIT antibodies were detected with polyclonal goat anti-human IgG conjugated to PE (Jackson ImmunoResearch 109-116-098). Samples were analyzed on a FACSCalibur flow cytometer. Median fluorescence intensity of the FSC/SSC gated lymphocyte population was determined for each antibody. NonLinear regression of Log(X) transformed data was used to generate EC50 values in GraphPad Prism 6. FIG. 4 shows the binding titration and EC50 of binding of anti-TIGIT clones 13 and 25 to activated mouse splenic T cells.

Example 4: Anti-TIGIT Antibodies Block Binding of CD155 and CD112 Ligand to Cell Surface-Expressed TIGIT HEK 293 cells were engineered to stably express high levels of human or mouse TIGIT by lentiviral transduction. hCD155-Fc (Sino Biological 10109-H02H), hCD112-Fc (Sino Biological 10005-H02H) and mCD155-Fc (Sino Biological 50259-MO3H) were conjugated to AlexaFluor647 (ThermoFisher A30009). 200,000 293-hTIGIT or 293-mTIGIT cells were co-incubated with 1 µg/mL CD155-Fc-AlexaFluor647 or 5 µg/mL CD112-Fc-AlexaFluor647 and a 12-point, 2-fold titration (10 to 0.005 µg/mL) of each anti-TIGIT antibody or an isotype control antibody. Samples were analyzed on a CytoFLEX flow cytometer. Median fluorescence intensity of the FSC/SSC gated population was determined for each antibody concentration. Percent blockade was calculated relative to the MFI of the no antibody control. NonLinear regression of Log(X) transformed data was performed in GraphPad Prism 6.

As shown in FIG. 5A-B, six anti-TIGIT antibody clones (clone 2, clone 5, clone 13, clone 17, clone 25, and clone 55) were tested, and five of the six clones (clone 2, clone 5, clone 13, clone 17, and clone 25) significantly blocked CD155 interaction with TIGIT expressed on HEK 293 cells for both human CD155/human TIGIT and for mouse CD155/mouse TIGIT. Clone 55 specifically binds human TIGIT but did not compete with hCD155-Fc for binding to hTIGIT-Fc in the ForteBio Octet ligand competition assay. Similarly, clone 55 did not efficiently block hCD155 interaction with the 293-hTIGIT cell line. Clone 2, clone 5, clone 13, clone 17, and clone 25 were also able to interrupt binding of human CD112 to human TIGIT. As observed for CD155, clone 55 was much less effective at blocking the CD112-TIGIT interaction. See FIG. 6.

Example 5: In Vitro Activity of Anti-TIGIT Antibodies in a TIGIT/CD155 Blockade Bioassay The activity of anti-TIGIT antibodies can be functionally characterized using a TIGIT/CD155 blockade bioassay (e.g., TIGIT/CD155 Blockade Bioassay Kit, Promega Corp., Madison, Wis.), in which expression of a reporter gene is induced or enhanced when an antibody blocks TIGIT/CD155 interaction. The TIGIT/CD155 blockade bioassay comprises two cell types: an effector cell expressing TIGIT, CD226, and a TCR complex on the cell surface and containing a luciferase reporter gene; and an artificial antigen presenting cell that expresses CD155 and a TCR activator on the cell surface. In this bioassay, luciferase expression requires TCR engagement plus a co-stimulatory signal. The CD155-TIGIT interaction has higher affinity than the CD155-CD226 interaction, resulting in net inhibitory signaling and no luciferase expression. Blockade of the CD155-TIGIT interaction allows CD155-CD226 co-stimulation driving luciferase expression.

Jurkat effector cells expressing both TIGIT and CD226 were co-cultured with CHO-K1 artificial antigen presenting cells (aAPCs) expressing a TCR activator and CD155. The Jurkat effector cells contain a luciferase reporter gene driven by the IL-2 promoter. In the absence of blocking anti-TIGIT antibodies, CD155-TIGIT engagement leads to T cell co-inhibition and no IL-2 promoter activity. Upon addition of anti-TIGIT antibodies, CD155-TIGIT interaction is interrupted allowing CD155 to associate with CD226 to send a co-stimulatory signal and drive luciferase expression.

aAPCs were plated in 96-well plates and allowed to adhere overnight. The following day, 20 µg/mL of each anti-TIGIT antibody or an isotype control antibody and Jurkat effector cells were added to the plate. After a 6 hour incubation at 37° C., cells were lysed and luciferase substrate was added. Luciferase activity was quantified on a plate reader. Luciferase activity was calculated as a fold over the signal in the no antibody control.

Figure 7B:
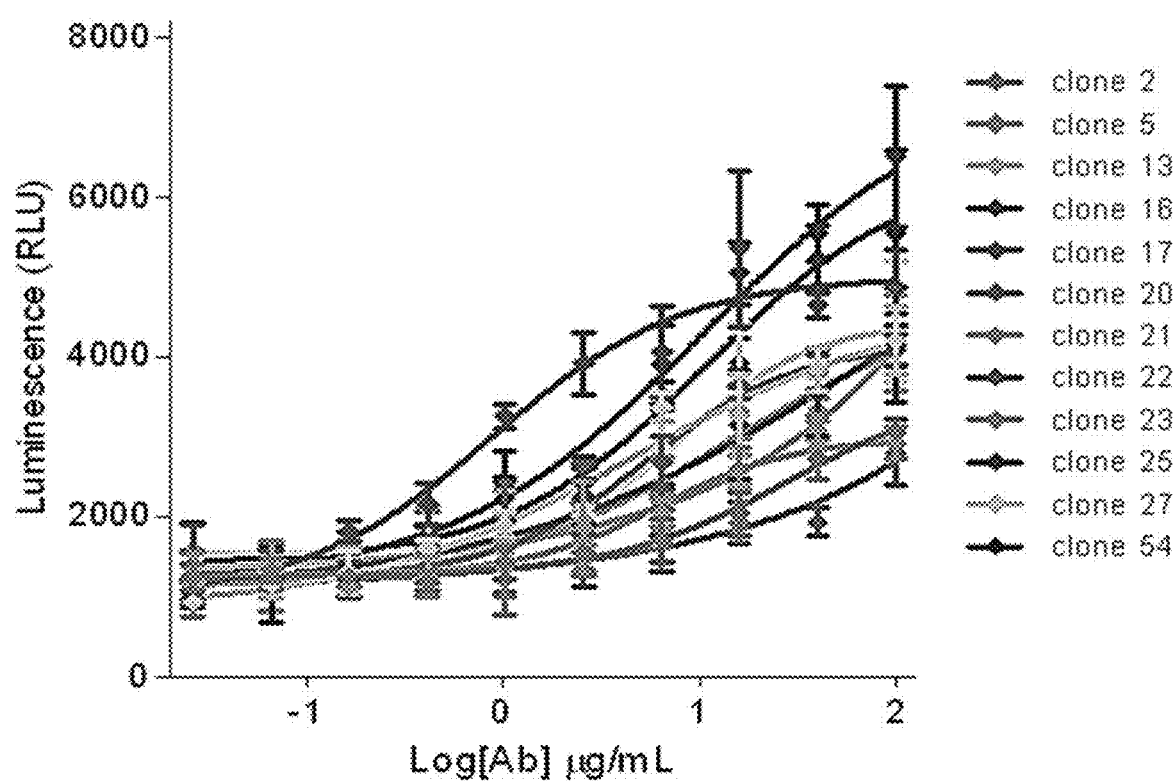
Figure 12:
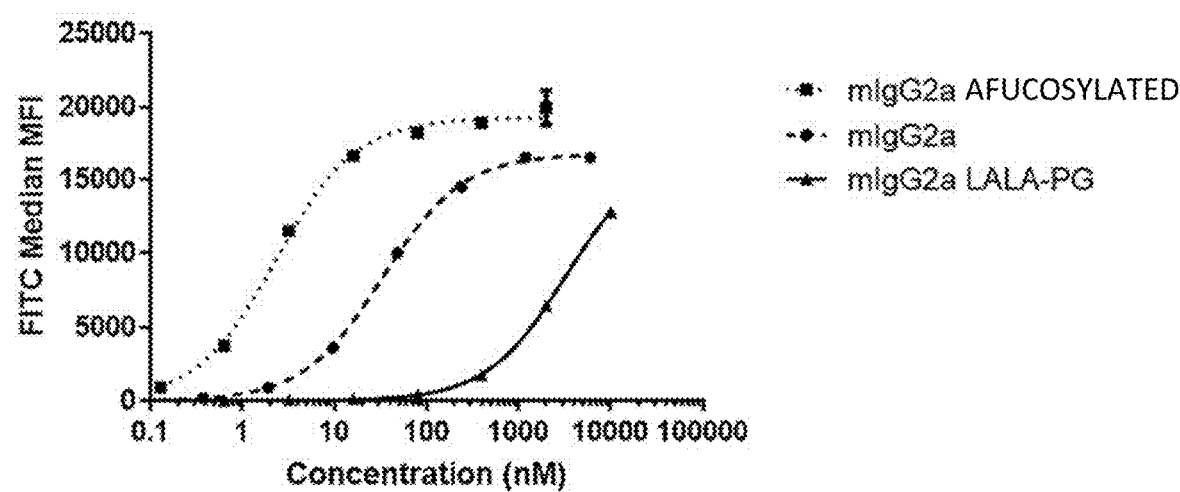
FIG. 12. Binding of anti-TIGIT mIgG2a antibodies to CHO cells expressing mCD16 (the murine form of FcγRIVa). Afucosylated clone 13 mIgG2a (black squares) bound with significantly greater affinity compared to wild-type mIgG2a (black circles) or mIgG2a LALA-PG (black triangles). Binding data is summarized in the table below.
Figure 13:
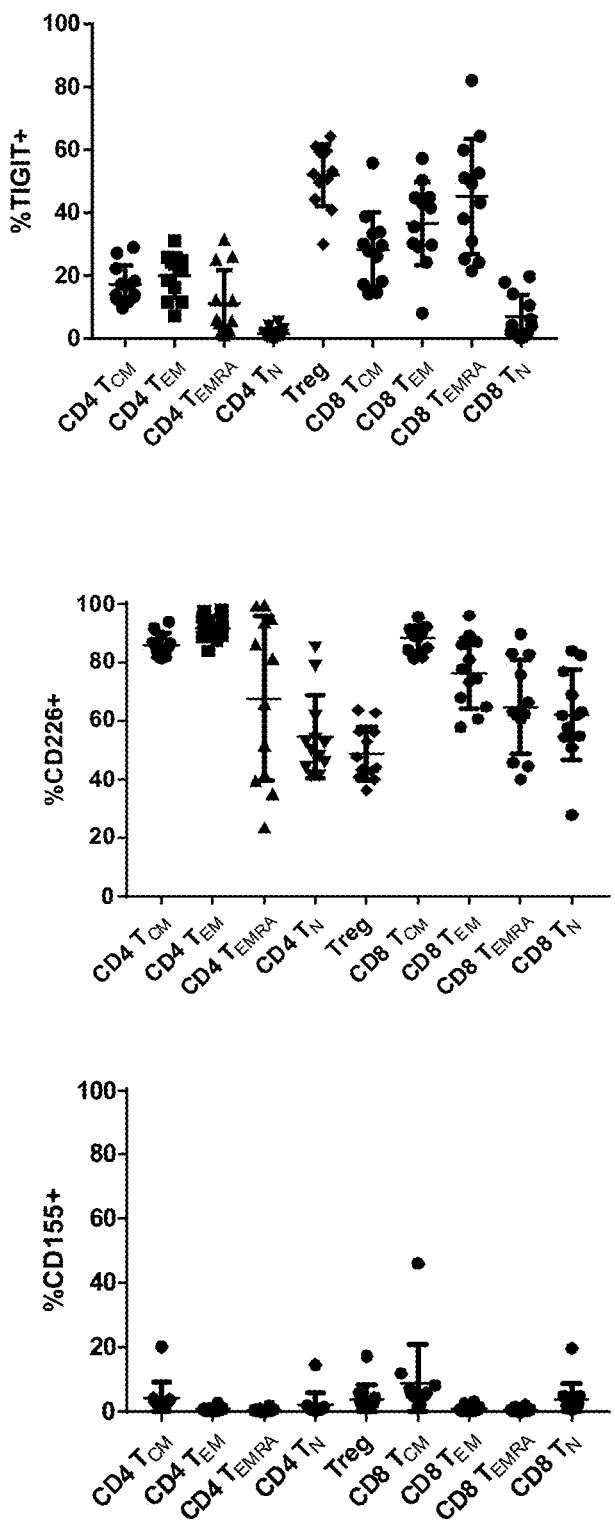
FIG. 13. Expression of TIGIT (top panel), CD226 (middle panel) and CD155 (bottom panel) by T-cell subsets from healthy donors. Tregs expressed the highest levels of TIGIT, while all T cell subsets tested expressed the activating receptor CD226. Expression of CD155 was mostly absent.

As shown in FIG. 7A-7B, 12 anti-TIGIT antibody clones demonstrated functional blockade in this bioassay.

Example 6: In Vitro Activity of Anti-TIGIT Antibodies in a TIGIT/PD-1 Combination Bioassay The synergistic activity of anti-TIGIT antibodies in combination with anti-PD-1 agents (e.g., anti-PD-1 antibodies) can be functionally characterized using a TIGIT/PD-1 combination bioassay, in which expression of a reporter gene is enhanced when antibodies block both the TIGIT/CD155 interaction and the PD-1/PD-L1 interaction. The bioassay comprises two cell types: an effector cell expressing TIGIT, CD226, PD-1, and a TCR complex on the cell surface and containing a luciferase reporter gene; and an artificial antigen presenting cell that expresses CD155, PD-L1, and a TCR activator on the cell surface. In this bioassay, luciferase expression requires TCR engagement plus a co-stimulatory signal. The CD155-TIGIT interaction has higher affinity than the CD155-CD226 interaction, resulting in net inhibitory signaling and no luciferase expression. Additionally, binding of PD-L1 to PD-1 inhibits luciferase expression. Blockade of both the CD155-TIGIT interaction and the PD-1/PD-L1 interaction relieves the inhibition and allows CD155-CD226 co-stimulation driving luciferase expression.

Figure 8:
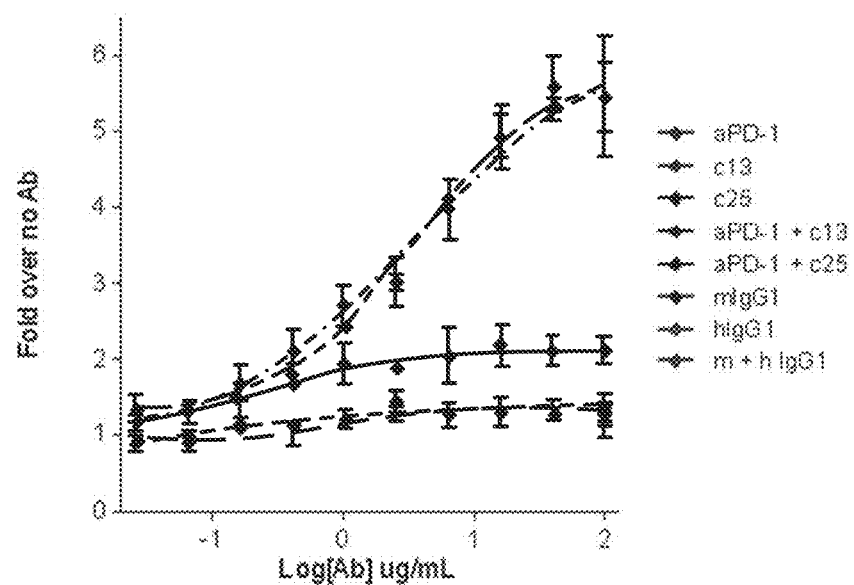
FIG. 8. Select anti-TIGIT antibodies synergized with anti-PD-1, resulting in T cell activation. Mean and SD are of triplicate wells. Both clone 13 and clone 25 showed synergy with anti-PD-1 in combination bioassay.
Figure 9B:
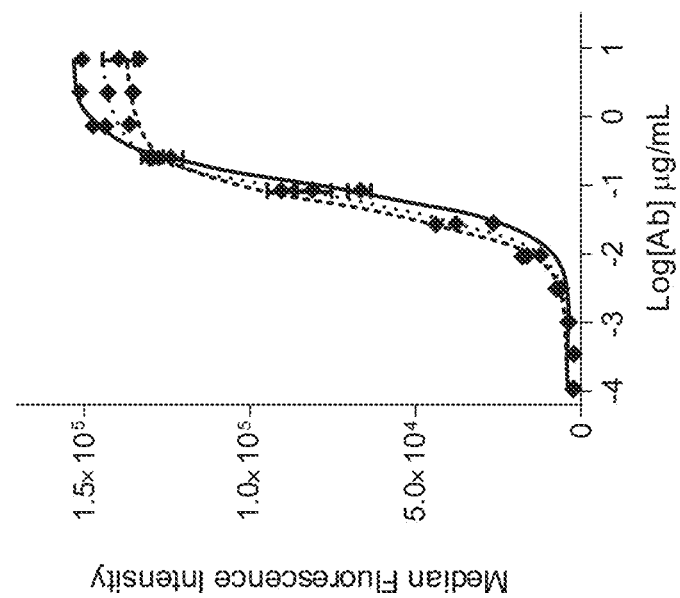
Figure 9A:
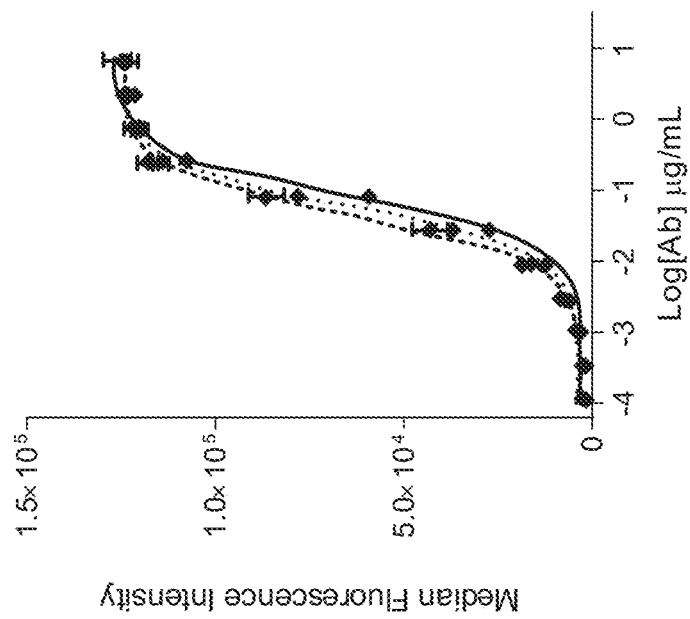
Figure 9E:
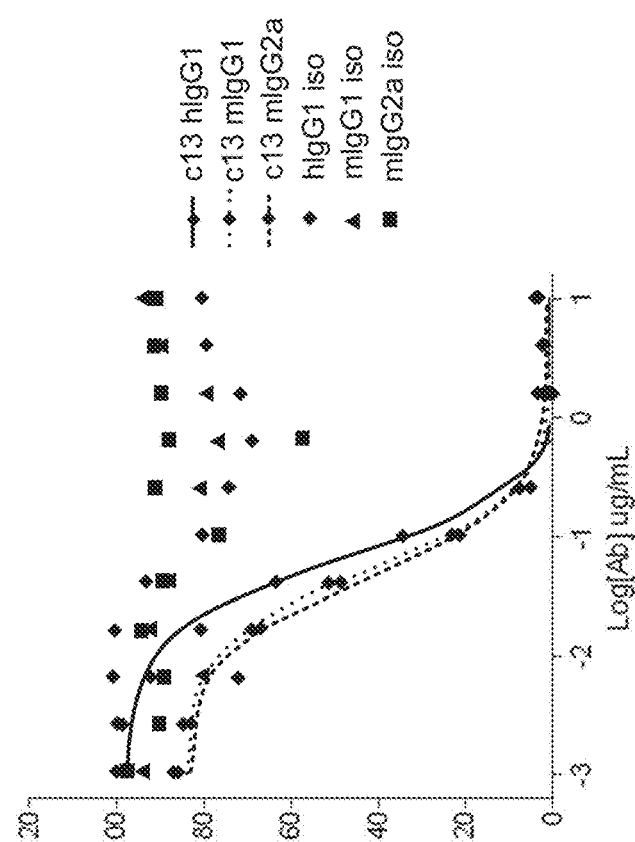
Figure 9F:
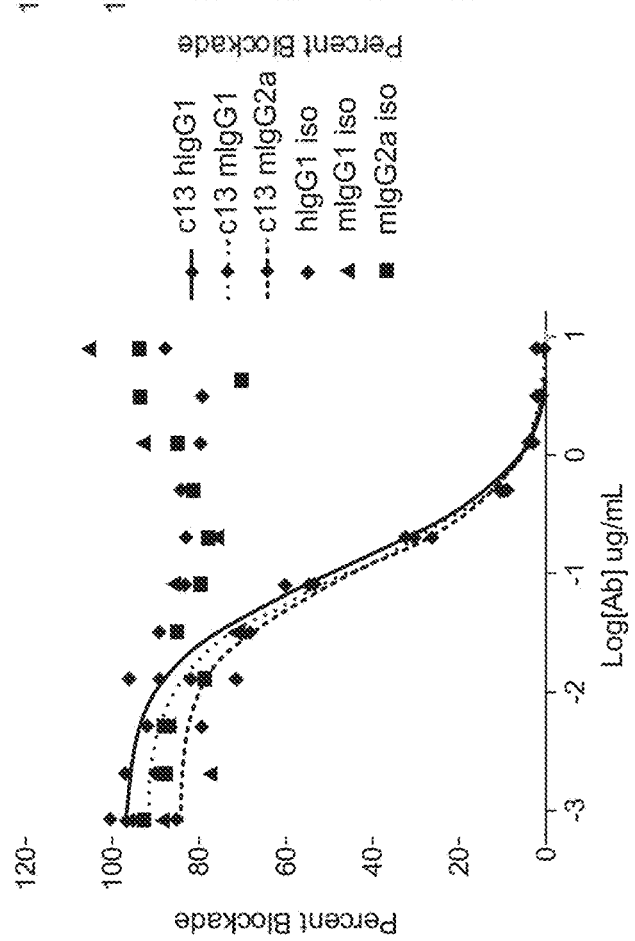
Figure 9G:
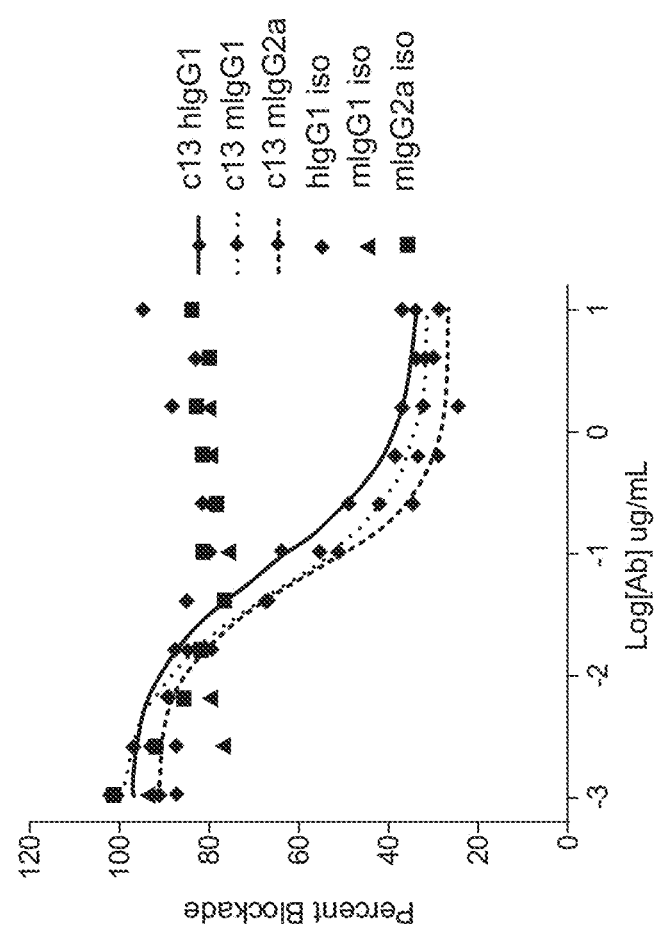

Jurkat effector cells expressing PD-1, TIGIT and CD226 were co-cultured with CHO-K1 artificial antigen presenting cells (aAPCs) expressing a TCR activator, PD-L1 and CD155. The Jurkat effector cells contain a luciferase reporter gene driven by the IL-2 promoter. In the absence of blocking anti-TIGIT antibodies, PD-L1-PD-1 and CD155-TIGIT engagement leads to T cell co-inhibition and no IL-2 promoter activity. Upon addition of anti-PD-1 and anti-TIGIT antibodies, PD-L1-PD-1 interaction is blocked, relieving one co-inhibitory signal, and CD155-TIGIT interaction is interrupted, allowing CD155 to associate with CD226 to send a co-stimulatory signal and drive luciferase production.

aAPCs were plated in 96-well plates and allowed to adhere overnight. The following day, a 10-point 2.5-fold titration (100 to 0.03 µg/mL) of each anti-TIGIT antibody alone, or anti-PD-1 antibody (clone EH12.2H7, BioLegend, San Diego, Calif.), or each anti-TIGIT antibody+anti-PD-1 antibody (1:1 ratio) and Jurkat effector cells were added to the plate. After a 6 hour incubation at 37° C., cells were lysed and luciferase substrate was added. Luciferase activity was quantified on a plate reader. Luciferase activity was calculated as a fold over the signal in the no antibody control. As shown in FIG. 8, neither anti-TIGIT nor anti-PD-1 alone led to dramatic Jurkat activation, however, the combination of either anti-TIGIT clone 13 or clone 25 with anti-PD-1 yielded strong activation.

Example 7: In Vivo Activity of Anti-TIGIT Antibodies in a CT26 Syngeneic Tumor Model in BALB/c Mice Based on affinity for murine TIGIT, anti-TIGIT clone 13 was chosen for evaluation in a murine syngeneic tumor model. Mouse IgG1 and mouse IgG2a chimeras of the parental fully human anti-TIGIT clone 13 were generated for in vivo experiments in order to address the question of whether Fc isotype has an effect on in vivo efficacy of antagonistic TIGIT antibodies. In vitro, the chimeric antibodies showed similar activity to the parental hIgG1 antibody with regards to (1) binding to human, mouse and cynomolgus monkey TIGIT, (2) blockade of CD155 and CD112 ligand binding to cell-surface expressed TIGIT and (3) activity in the CD155-TIGIT blockade bioassay. See FIG. 9A-9H.

8 week old BALB/c mice with an average body weight of 19 g were obtained from Charles River Laboratories. Mice were implanted subcutaneously with 300,000 CT26 colon carcinoma cells on the right lateral flank. Tumors were allowed to progress until the group average tumor volume was 72 mm$^3$ (range of 48-88 mm$^3$) on day 7 after tumor inoculation. Animals were allocated into 10 treatment groups of n=10 by pair match such that the group mean tumor volume was similar across all treatment groups. Tumor length and width were measured and tumor volume was calculated using the formula Volume (mm$^3$)=0.5*Length*Width$^2$ where length is the longer dimension. Anti-TIGIT clone 13 mIgG1, anti-TIGIT clone 13 mIgG2a and anti-PD-1 clone RMP1-14 (BioXCell) were diluted to the appropriate concentration for dosing in sterile PBS. Sterile PBS was used as the vehicle control. TIGIT antibodies were dosed at 5 or 20 mg/kg via intraperitoneal injection twice weekly for 3 weeks (6 doses total). Anti-PD-1 antibody was dosed at 5 mg/kg via intraperitoneal injection twice weekly for 2 weeks (4 doses total). Dosing initiated on the day of allocation (study day 1). Tumor volume and body weight measurements were collected twice weekly until mice reached a tumor volume cutoff of 2000 mm$^3$. None of the animals exhibited body weight loss relative to pre-dose weights indicating exceptional tolerability of all test agents.

Figure 10C:
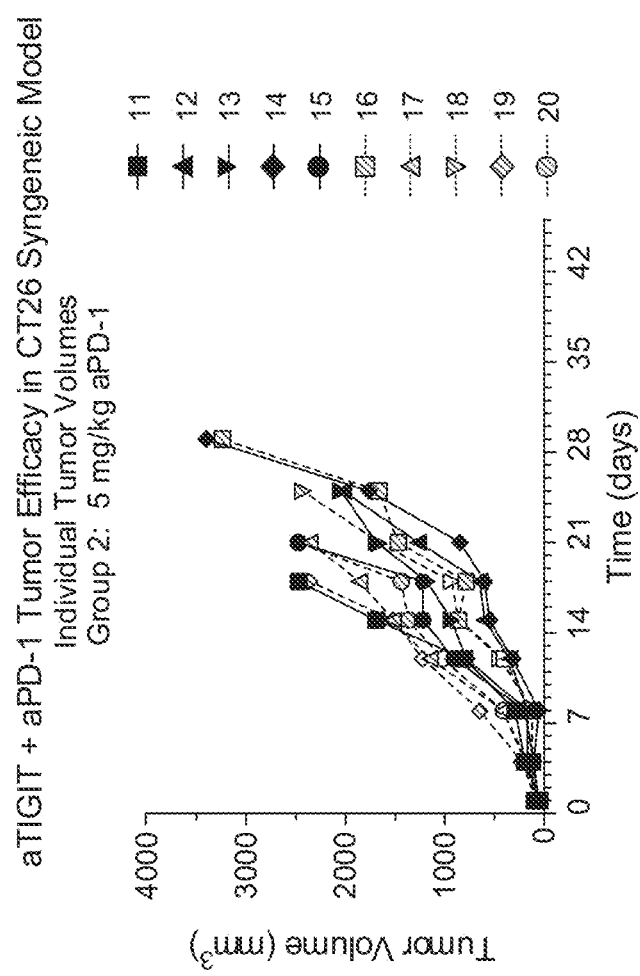
Figure 10E:
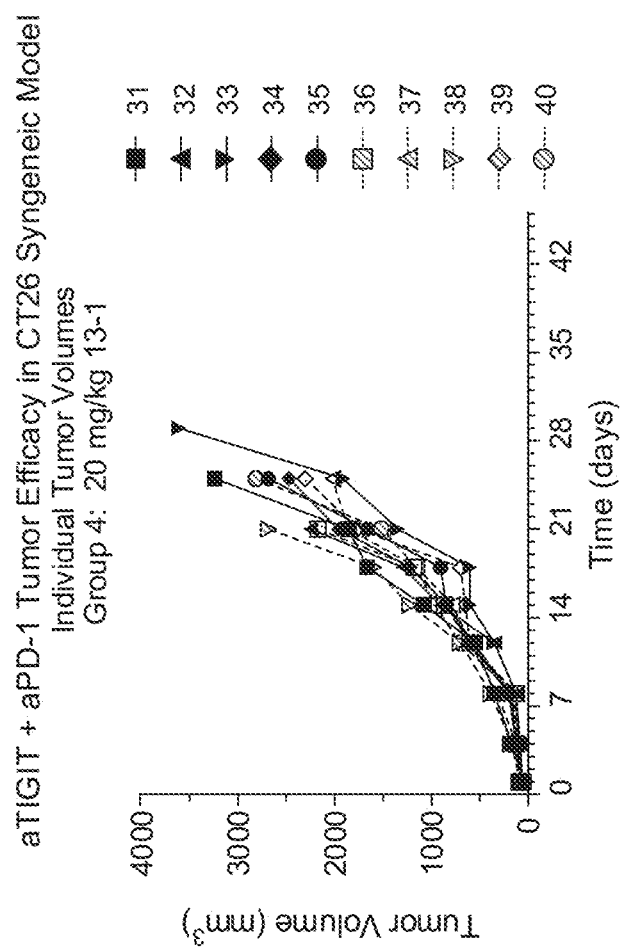
Figure 10F:
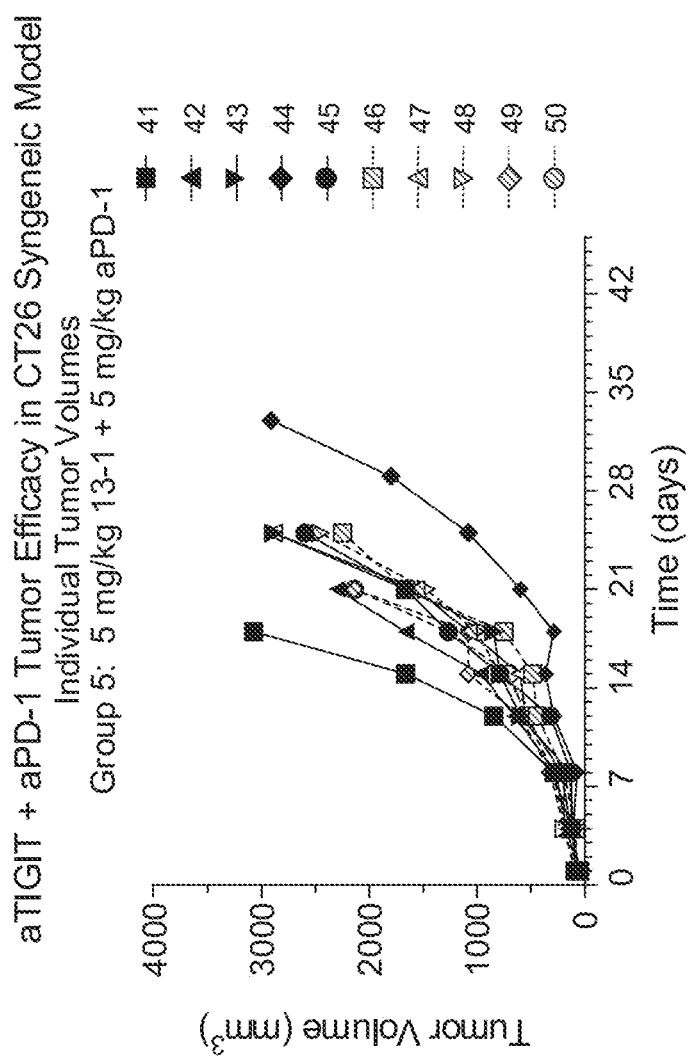
Figure 10G:
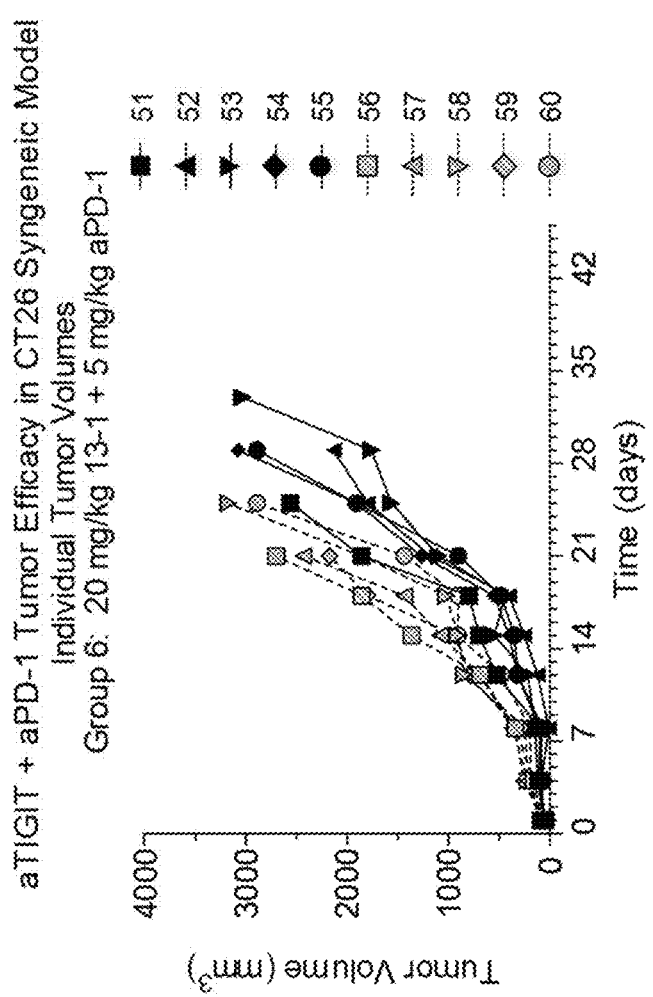
Figure 10H:
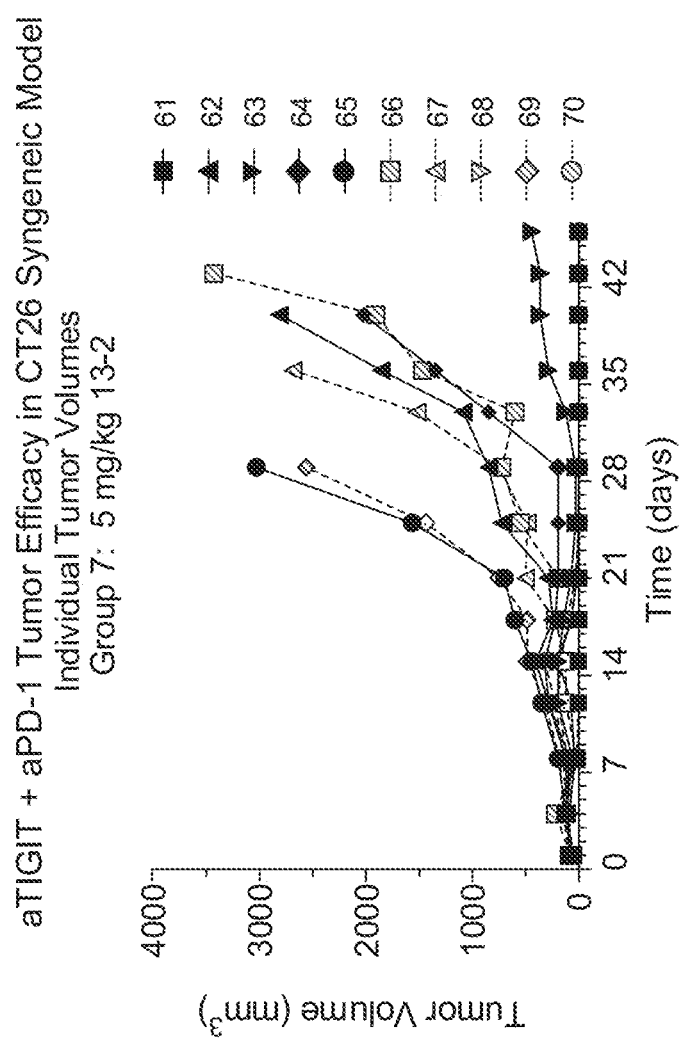
Figure 10I:
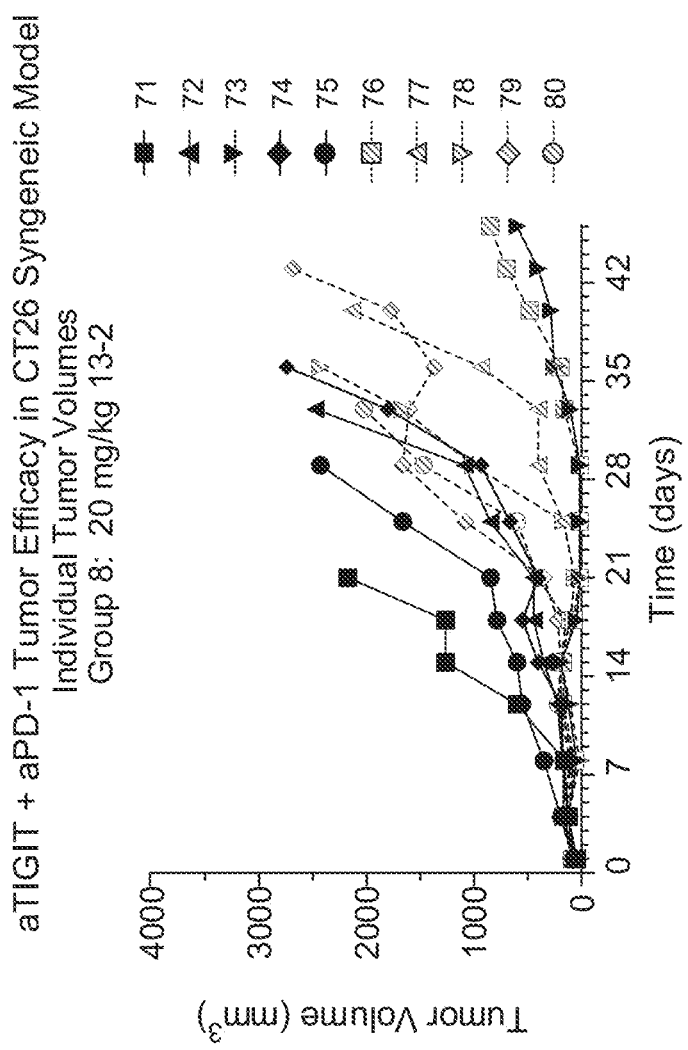
Figure 10K:
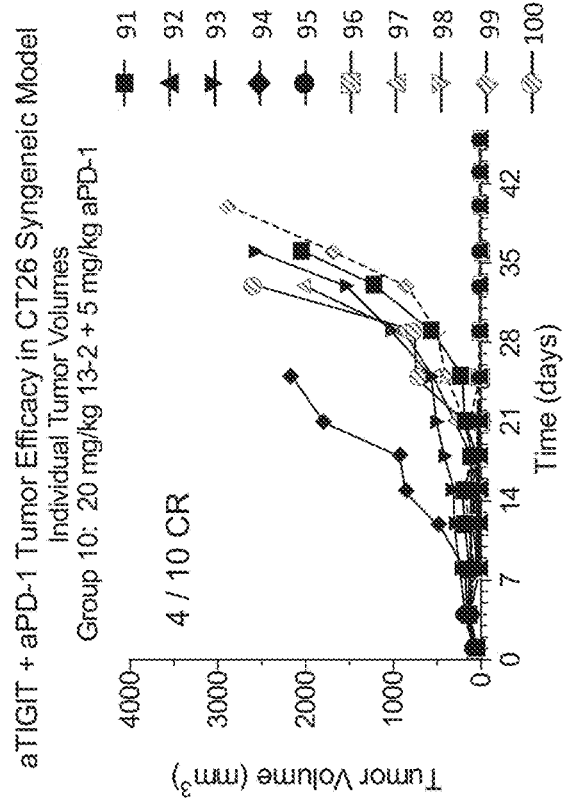
Figure 10J:
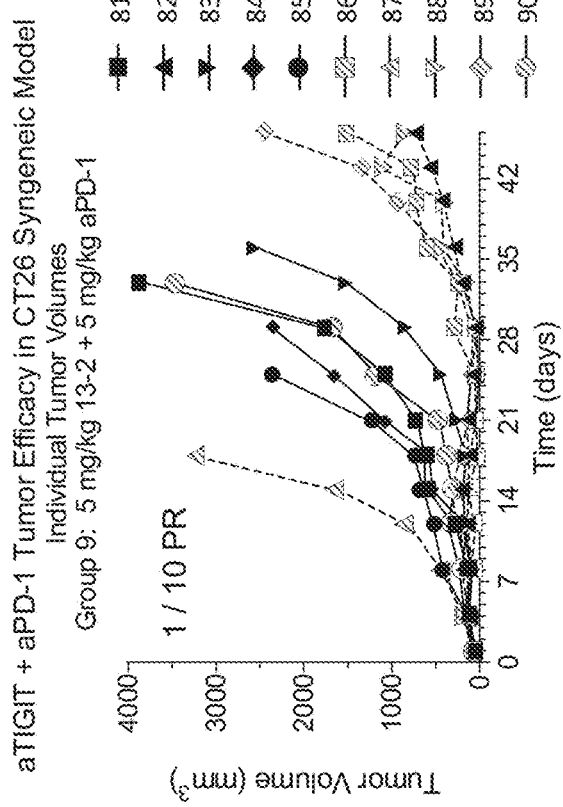
Figure 11:
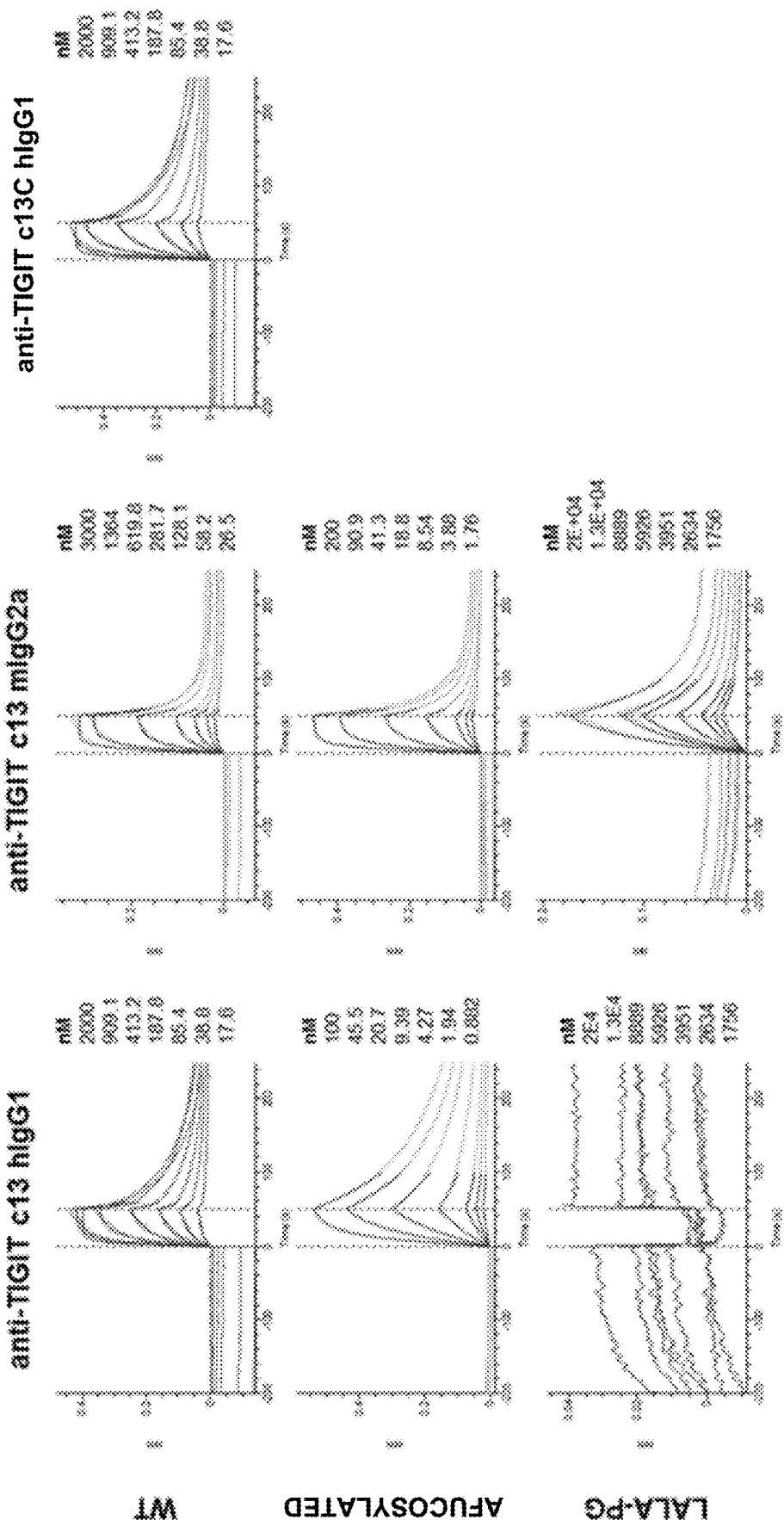
FIG. 11. Sensorgrams of human FcγRIIIa 158V binding titrated anti-TIGIT antibodies by BLI. The results are shown for anti-TIGIT clone 13 hIgG1 wild-type, afucosylated, and LALA-PG (left panels), anti-TIGIT clone 13 mIgG2a wild-type, afucosylated, and LALA-PG (center panels), and anti-TIGIT clone 13C hIgG1 wild-type (right panel).

As shown in FIG. 10A, anti-mPD-1 alone did not have any effect on tumor progression. The mIgG1 anti-TIGIT chimera of clone 13 ("13-1"), which does not efficiently engage activating Fcgamma receptors, did not mediate any anti-tumor activity, either as a single agent or in combination with anti-PD-1. In contrast, the mIgG2a chimera of clone 13 ("13-2"), which is capable of binding activating Fcgamma receptors, slowed tumor progression (86.5% (5 mg/kg) or 74.4% (20 mg/kg) tumor growth inhibition on day 18). Three of ten animals in the 5 mg/kg 13-2 single agent group showed complete tumor regressions that were stable through the end of the study (study day 46). In the 20 mg/kg 13-2 single agent group, two of ten animals showed partial tumor regressions (defined as tumor volume<50% of initial volume for three consecutive measurements). FIG. 10A shows that the addition of anti-PD-1 to the mIgG2a clone 13 chimera (13-2) did not increase efficacy relative to 13-2 alone (day 18 tumor growth inhibition of 53.8% (5 mg/kg anti-TIGIT+5 mg/kg anti-PD-1) vs 86.5% (5 mg/kg anti-TIGIT alone) and 89.6% (20 mg/kg anti-TIGIT+5 mg/kg anti-PD-1) vs 74.4% (20 mg/kg anti-TIGIT alone). Similar numbers of complete and partial responders were observed in the combination groups. See, e.g., FIG. 10B-10K.

Example 8: Antibody Optimization and Characterization of Optimized Antibodies

Antibody clones 2, 13, 16, and 25 from the primary discovery output were selected for further affinity maturation. Optimization of antibodies was performed via introducing diversities into the heavy chain variable region. Two cycles of optimization were applied to the above lineages. The first cycle was comprised of a CDRH1 and CDRH2 diversification approach, while in the second cycle a CDRH3 mutagenesis approach was applied.

CDRH1 and CDRH2 approach: The CDRH3 of a single antibody was recombined into a premade library with CDRH1 and CDRH2 variants of a diversity of 1×10$^8$. Selections were then performed with one round of MACS and four rounds of FACS as described for the naïve discovery.

In the first FACS round, the libraries were sorted for 1 nM monomeric TIGIT binding. The second FACS round was a PSR depletion round to reduce poly-specificity. The final two rounds were positive selection rounds using the parental Fab or IgG to pressure for high affinity. Fab/IgG pressure was performed as follows: antigen was incubated with 10 fold parental Fab or IgG and then incubated with the yeast libraries. Selections enriched for IgGs with better affinities than the parental Fab or IgG. Species cross-reactivity was checked in the last two rounds of FACS.

CDRH3 mutagenesis: Libraries were generated with CDRH3 diversification by randomizing positions in CDRH3. Selections were performed with one round of MACS and three rounds of FACS as described previously. PSR negative selections, species cross-reactivity, affinity pressure, and sorting was performed in order to obtain a population with the desired characteristics.

MSD-SET $K_D$ Measurements

Equilibrium affinity measurements were performed generally as previously described (Estep et al., supra). Briefly, solution equilibrium titrations (SET) were performed in PBS+0.1% IgG-Free BSA (PBSF) with biotinylated human TIGIT-His monomer held constant at 50 pM and incubated with 3- to 5-fold serial dilutions of antibody starting at around 5 nM. Antibodies (20 nM in PBS) were coated onto standard bind MSD-ECL plates overnight at 4° C. or at room temperature for 30 min. Plates were then blocked with 1% BSA for 30 min with shaking at 700 rpm, followed by three washes with wash buffer (PBSF+0.05% Tween 20). SET samples were applied and incubated on the plates for 150 s with shaking at 700 rpm followed by one wash. Antigen captured on a plate was detected with 250 ng/ml sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

Binding of the optimized antibodies to His-tagged human TIGIT, cyno TIGIT-Fc, and mouse TIGIT-Fc was measured using the ForteBio system as described above. The optimized antibodies were also tested for ligand blocking in a CD155 ligand competition assay, and for binding to human TIGIT HEK, cyno TIGIT HEK, mouse TIGIT HEK, and parental HEK cell lines, as described above.

The affinity data and cell binding data for the affinity optimized antibodies is shown in Table 2 below.

TABLE 2

Affinity and Cell Binding Data for Affinity Optimzed Antibodies

| Clone Index | ForteBio IgG $K_D$ Human TIGIT-His (M) Monovalent | ForteBio IgG $K_D$ Cyno TIGIT-Fc (M) Avid | ForteBio IgG $K_D$ Murine TIGIT-Fc (M) Avid | MSD IgG $K_D$ (M) Human TIGIT-His | Cell binding Human TIGIT HEK Cell (FOB Fold Over Background) | Cell binding Cyno TIGIT HEK Cell (FOB Fold Over Background) | Cell binding Mouse TIGIT HEK Cell (FOB Fold Over Background) |
|---|---|---|---|---|---|---|---|
| 2 | 8.18E−09 | 1.34E−09 | 1.76E−09 | NA | 158 | 162 | 73 |
| 2C | 5.18E−10 | 9.84E−10 | 3.92E−10 | 1.60E−11 | 193 | 224 | 100 |
| 13 | 2.63E−09 | 1.04E−09 | 3.41E−10 | NA | 212 | 224 | 119 |
| 13A | 6.27E−10 | 1.12E−09 | 3.70E−10 | 2.50E−11 | 206 | 240 | 115 |
| 13B | 6.10E−10 | 1.05E−09 | 3.30E−10 | 5.30E−12 | 201 | 235 | 102 |
| 13C | 5.63E−10 | 1.07E−09 | 3.29E−10 | 8.60E−12 | 194 | 281 | 116 |
| 13D | 5.71E−10 | 1.16E−09 | 3.64E−10 | 5.00E−12 | 190 | 245 | 116 |
| 16 | 2.52E−09 | 4.67E−09 | 9.07E−09 | NA | 192 | 27 | 19 |
| 16C | 9.11E−10 | 4.25E−09 | 8.01E−10 | 6.30E−12 | 208 | 157 | 99 |
| 16D | 5.96E−10 | 1.15E−09 | 2.63E−09 | 1.30E−11 | 199 | 241 | 63 |
| 16E | 7.78E−10 | 1.36E−09 | 3.70E−09 | 1.10E−11 | 195 | 186 | 56 |
| 25 | 1.27E−09 | 1.50E−09 | 9.67E−10 | NA | 205 | 247 | 117 |
| 25A | 1.10E−09 | 1.64E−09 | 8.23E−10 | 1.80E−11 | 207 | 238 | 119 |
| 25B | 1.16E−09 | 1.40E−09 | 7.19E−10 | 2.20E−11 | 222 | 291 | 129 |
| 25C | 6.97E−10 | 1.24E−09 | 4.94E−10 | 5.60E−12 | 216 | 286 | 124 |
| 25D | 8.46E−10 | 1.18E−09 | 5.80E−10 | 2.70E−11 | 225 | 272 | 137 |
| 25E | 8.51E−10 | 1.18E−09 | 5.66E−10 | 1.30E−11 | 204 | 252 | 116 |

Example 9: Epitope Mapping

The epitopes of two of the monoclonal antibodies disclosed herein, Clone 13 and Clone 25, were characterized by peptide array. To reconstruct epitopes of the target molecule a library of peptide based epitope mimics was synthesized using solid-phase Fmoc synthesis. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer).

Synthesis of structural mimics was performed using proprietary Chemically Linked Peptides on Scaffolds (CLIPS) technology (Pepscan). CLIPS technology allows to structure peptides into single loops, double-loops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the P2 CLIPS (2,6-bis(bromomethyl)pyridine) is dissolved in ammonium bicarbonate (20 mM, pH 7.8)/acetonitrile (1:3 (v/v)). This solution is added onto the peptide arrays. The CLIPS template will bind to side-chains of two cysteines as present in the solid-phase bound peptides of the peptide-arrays (455 wells plate with 3 µl wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were made in a similar way but with three cysteines.

Different sets of peptides were synthesized according to the following designs. Set 1 comprised a set of linear peptides having a length of 15 amino acids derived from the target sequence of human TIGIT with an offset of one residue. Set 2 comprised a set of linear peptides of Set 1, but with residues on positions 10 and 11 replaced by Ala. When a native Ala would occur on either position, it was replaced by Gly. Set 3 comprised a set of linear peptides of Set 1, which contained Cys residues. In this set, native Cys were replaced by Cys-acetamidomethyl ("Cys-acm"). Set 4 comprised a set of linear peptides having a length of 17 amino acids derived from the target sequence of human TIGIT with an offset of one residue. On positions 1 and 17 were Cys residues used to create looped mimics by means of mP2 CLIPS. Native Cys were replaced with Cys-acm. Set 6 comprised a set of linear peptides having a length of 22 amino acids derived from the target sequence of human TIGIT with an offset of one residue. Residues on positions 11 and 12 were replaced with "PG" motif, while Cys residues were placed on positions 1 and 22 to create a constrained mimic with mP2. Native Cys residues were replaced by Cys-acm. Set 7 contained a set of linear peptides having a length of 27 amino acids. On positions 1-11 and 17-27 were 11-mer peptide sequences derived from the target sequence and joined via "GGSGG" (SEQ ID NO: 309) linker. Combinations were made based on the UniProt info on disulfide bridging for human TIGIT. Set 8 comprised a set of combinatorial peptides having a length of 33 amino acids. On positions 2-16 and 18-32 were 15-mer peptides derived from the target sequence of human TIGIT. On positions 1, 17 and 33 were Cys residues used to create discontinuous mimics by means of T3 CLIPS.

The binding of antibody to each of the synthesized peptides was tested in a pepscan-based ELISA. The peptide arrays were incubated with primary antibody solution (overnight at 4° C.). After washing, the peptide arrays were incubated with a 1/1000 dilution of a goat anti-human HRP conjugate (Southern Biotech) for one hour at 25° C. After washing, the peroxidase substrate 2,2'-azino-di-3-ethylbenzthiazoline sulfonate (ABTS) and 20 µl/ml of 3 percent $H_2O_2$ were added. After one hour, the color development was measured. The color development was quantified with a charge coupled device (CCD)—camera and an image processing system. The values obtained from the CCD camera range from 0 to 3000 mAU, similar to a standard 96-well plate ELISA-reader.

To verify the quality of the synthesized peptides, a separate set of positive and negative control peptides was synthesized in parallel. These were screened with commercial antibodies 3C9 and 57.9 (Posthumus et al., *J. Viral.*, 1990, 64:3304-3309).

For Clone 13, when tested under high stringency conditions Clone 13 weakly bound discontinuous epitope mimics. The antibody was also tested under moderate stringency conditions and detectable binding of the antibody was observed. The highest signal intensities were recorded with discontinuous epitope mimics containing the core stretches $_{68}$ICNADLGWHISPSFK$_{82}$ (SEQ ID NO: 258), $_{42}$ILQCHLSSTTAQV$_{54}$ (SEQ ID NO: 298), $_{108}$CIYHTYPDGTYTGRI$_{122}$ (SEQ ID NO: 299). Additional, weaker binding was observed with peptides containing peptide stretch $_{80}$SFKDRVAPGPG$_{90}$ (SEQ ID NO: 300). Binding of the antibody to linear and simple conformational epitope mimics was generally lower and was only observed for motifs $_{68}$ICNADLGWHISPSFK$_{82}$ (SEQ ID NO: 258), $_{108}$CIYHTYPDGTYTGRI$_{122}$ (SEQ ID NO: 299) and $_{80}$SFKDRVAPGPG$_{90}$ (SEQ ID NO: 300).

For Clone 25, when tested under high stringency conditions Clone 25 detectably bound peptides from all sets. Strongest binding was observed with discontinuous epitope mimics. While binding to peptides containing residues within stretch $_{68}$ICNADLGWHISPSFK$_{82}$ (SEQ ID NO: 258) was also observed in other sets, binding to peptide stretch $_{50}$TTAQVTQ$_{56}$ (SEQ ID NO: 301) was only observed in combination with $_{68}$ICNADLGWHISPSFK$_{82}$ (SEQ ID NO: 258). Additional, weaker binding was also observed with peptides containing peptide stretch $_{80}$SFKDRVAPGPGLGL$_{93}$ (SEQ ID NO: 300).

Based on these epitope mapping results for Clone 13 and Clone 25, fine mapping of the epitopes of Clone 13 and Clone 25 was performed using the methods described above using the following sets of peptides. Set 1 comprised a library of single residue epitope mutants based on the sequence CILQ2HLSSTTAQVTQCI2NADLGWHISPSFKC (SEQ ID NO: 302). Residues ADHIQRY (SEQ ID NO: 304) were subjected to replacement. Positions 1, 17, 19, 30 and 33 were not replaced. Native Cys residues were replaced by Cys-acm (denoted "2" throughout). Set 2 comprised a library of walking double Ala mutants derived from the sequence CILQ2HLSSTTAQVTQCI2NADLGWHISPSFKC (SEQ ID NO: 302). Positions 1, 17 and 33 were not replaced. Native Cys residues were replaced by Cys-acm. Set 3 comprised a library of single residue epitope mutants based on the sequence CKDRVAPGPGLGLTLQCI2NADLGWHISPSFKC (SEQ ID NO: 303). Residues ADHIQRY (SEQ ID NO: 304) were used for the replacement. Positions 1, 2, 17, 19, 30 and 33 were not replaced. Set 4 comprised a library of walking double Ala mutants derived from sequence CKDRVAPGPGLGLTLQCI2NADLGWHISPSFKC (SEQ ID NO: 303). Positions 1, 17 and 33 were not replaced.

Clone 13 was tested with four series of discontinuous epitope mutants derived from peptides CILQ2HLSSTTAQVTQCI2NADLGWHISPSFKC (SEQ ID NO: 302) and CKDRVAPGPGLGLTLQCI2NADLGWHISPSFKC (SEQ ID NO: 303) under high and moderate stringency conditions. Data analysis indicated that in all instances, replacements of residues $_{81}$FK$_{82}$ with either single residues or double Ala impaired binding of Clone 13. Single mutations of other residues within discontinuous epitope mimics did not have drastic effects on binding. On the contrary, double Ala epitope mutants displayed a more pronounced effect on binding when compared with the series of single residue mutants for the corresponding discontinuous mimics. It was also found that double Ala replacements of residues $_{51}$TAQVT$_{55}$ (SEQ ID NO: 305) within CILQ2HLSSTTAQVTQCI2NADLGWHISPSFKC (SEQ ID NO: 302) notably impacted binding of Clone 13. Signal intensities recorded for Clone 13 with epitope mimics derived from sequence CKDRVAPGPGLGLTLQCI2NADLGWHISPSFKC (SEQ ID NO: 303) were lower than those recorded with CILQ2HLSSTTAQVTQCI2NADLGWHISPSFKC (SEQ ID NO: 302). It was further found that that in addition to $_{81}FK_{82}$ double Ala replacements of $_{74}GWHI_{77}$ (SEQ ID NO: 306) notably reduce binding of Clone 13. In addition, double Ala mutations within the stretch $_{87}PGPGLGL_{93}$ (SEQ ID NO: 307) somewhat weakened binding.

Clone 25 was tested on four series of discontinuous epitope mutants derived from peptides CILQ2HLSSTTAQVTQCI2NADLGWHISPSFKC (SEQ ID NO: 302) and CKDRVAPGPGLGLTLQCI2NADLGWHISPSFKC (SEQ ID NO: 303) under high and moderate stringency conditions. Analysis of data collected from individual sets of epitope mutants indicated that single or double replacements of residues $_{81}FK_{82}$ drastically affected binding. Single residue replacements of other residues within CILQ2HLSSTTAQVTQCI2NADLGWHISPSFKC (SEQ ID NO: 302) and CKDRVAPGPGLGLTLQCI2NADLGWHISPSFKC (SEQ ID NO: 303) did not cause a notable decrease in signal intensities. A series of double walking Ala mutants displayed more pronounced effects on Clone 25 binding to the mimic. In addition to $_{81}FK_{82}$, double Ala replacements of residues $_{52}AQ_{53}$ and P79 also mildly affected binding of the antibody to the epitope mimic CILQ2HLSSTTAQVTQCI2NADLGWHISPSFKC (SEQ ID NO: 302). Analysis of binding of Clone 25 to double Ala mutant series derived from CKDRVAPGPGLGLTLQCI2NADLGWHISPSFKC (SEQ ID NO: 303) again confirmed the importance of $_{81}FK_{82}$, but also indicated that double Ala replacements of residues $_{73}LGW_{75}$ and $_{82}KDRVA_{86}$ (SEQ ID NO: 308) moderately affected the binding.

In summary, for the monoclonal antibodies Clone 13 and Clone 25 it was found that residues $_{81}FK_{82}$ were crucial for the binding of both antibodies to TIGIT epitope mimics. For Clone 13, the residues $_{51}TAQVT_{55}$ (SEQ ID NO: 305), $_{74}GWHI_{77}$ (SEQ ID NO: 306), and $_{87}PGPGLGL_{93}$ (SEQ ID NO: 307) were also found to contribute to binding. For Clone 25, the residues $_{52}AQ_{53}$, $_{73}LGW_{75}$, P79, and, $_{82}KDRVA_{86}$ (SEQ ID NO: 308) were also found to contribute to binding.

Example 10: Backbone-Altered Anti-TIGIT Antibodies

In order to potentially improve upon the current generation of anti-TIGIT antibodies, an afucosylated anti-TIGIT antibody and Fc mutated version of an anti-TIGIT antibody with reduced effector function (IgG1 LALA-PG) were developed. It is expected that the afucosylated and LALA-PG antibodies will still block the CD155 and CD112 interactions with TIGIT. Without intending to be bound by any particular theory, it was hypothesized that an afucosylated anti-TIGIT antibody may bind directly to tumor infiltrated Tregs and lead to greater Fc mediated ADCC and/or ADCP and ultimately elicit greater anti-tumor immune response, or alternatively, that effector function could lead to depletion of effector T cells, so an effector null antibody may allow for preservation of activated CD8 T cells.

DNA & Vector Generation (Genewiz):

Antibody variable and constant domains sequences are synthesized using non-template PCR. The virtual gene sequence is converted into oligonucleotide sequences using Genewiz's bioinformatics tool. Oligonucleotides are synthesized, pooled and amplified using PCR. Full length amplicon from the PCR reaction is cloned into the vector and the product is then transformed into *E. coli* and unique colonies are isolated. Colonies are grown up overnight in liquid media and plasmid DNA isolated, purified, and sequence verified using Sanger sequencing. Light chains and heavy chains are cloned into pcDNA3.4 vectors.

Antibody Expression (Seattle Genetics):

A 1:1 ratio of antibody heavy chain and light chain vectors are diluted into ThermoFisher OptiPRO SFM medium with ExpiFectamine CHO transfection reagent. The DNA/transfection reagent is then added to an ExpiCHO culture in ThermoFisher ExpiCHO Expression medium and cultured for nine days with ExpiCHO enhancer added on day one and ExpiCHO feeds added on days one and two. To make antibodies with reduced core fucosylation on the N297 glycan (afucosylated antibodies), fucose analog 2-fluorofucose is added to the ExpiCHO culture on the day before and the day of transfection. Culture is harvested by centrifugation and 0.2 μm filtration.

Antibody Purification (Seattle Genetics):

GE HiTrap mAb Select SuRe columns are used for the purification of each IgG. Prior to elution, the resin is washed with 5CV PBS+0.1% Triton, 5CV PBS+0.5M NaCl, and 7.5CV of PBS. The IgG is eluted using 25 mM Acetic Acid pH3 Buffer. The sample is buffer exchanged using a 26/60 HiPrep Desalt columns into PBS. The sample is then filter sterilized before a sample is taken for the characterization. Characterization includes A280 concentration, aSEC HPLC, aHIC HPLC, and reduced glycosylated and deglycosylated PLRP-MS (QToF).

Example 11: Backbone-Altered Antibody Characterization

In vivo, monocytes, macrophages, neutrophils, dendritic cells, and NK cells can mediate ADCP (antibody-dependent cell-mediated phagocytosis) and ADCC (antibody-dependent cell-mediated cytoxicity via FcγRI, FcγRIIa, FcγRI and FcγRIIIa. While all three receptors can participate in ADCP, FcγRIIIa is believed to be the predominant Fcγ receptor involved in ADCC. Afucosylation of $IgG_1$ antibodies results in higher affinity binding to FcγRIIIa and b, and thus can increase ADCC and ADCP activity.

Biolayer interferometry (BLI) was utilized to assess the binding kinetics of human FcγRIIIa 158V to various anti-TIGIT antibodies to understand the effects of afucosylated antibodies and the LALA-PG mutations at 30° C. An N-hydroxysuccinimide (NHS)-ester biotinylated human FcγRIIIa 158V-mono Fc N297A fusion protein (expressed at Seattle Genetics) was loaded onto high precision streptavidin biosensors (Pall ForteBio) at 3 μg/mL for 300 seconds following a 300 second sensor check. After a 200 second baseline, titrated anti-TIGIT antibodies were associated for 50 seconds and dissociated for 200 seconds. Prior to analysis, the references were subtracted in each assay. The data were corrected with a Y-axis alignment at the start of association, an inter-step dissociation correction and Savitzky-Golay filtering. A 1:1 Langmuir isotherm global fit model was used to fit the curves.

Representative data are shown in FIG. 10. The sensorgrams for the TIGIT hIgG1 variants were similar to what has typically been observed for hFcγRIIIa binding by BLI: wild-type IgG1 in the 100-200 nM range and afucosylated IgG1 about 10-20 nM due to a 10-fold increase in $k_{on}$ caused by an increased enthalpy, or increased interactions between hFcγRIIIa and hIgG1. hIgG1 LALA-PG had no quantifiable binding, even at the highest concentration of 5000 nM. The results are summarized in Table 3.

TABLE 3

Global fit analysis of anti-TIGIT antibodies binding human FcγRIIIa 158V by BLI using a 1:1 Langmuir isotherm model.

| Ab | $K_D$ (M) | $k_{on}$ (1/Ms) | $k_{off}$ (1/s) | RMax | Req/Rmax (%) | Full X^2 | Full R^2 |
|---|---|---|---|---|---|---|---|
| anti-TIGIT Clone13C hIgG1 | 2.53E−07 | 1.46E+05 | 3.71E−02 | 0.57 | 89-67 | 0.18 | 0.9931 |
| anti-TIGIT Clone13 hIgG1 | 3.7E−07 | 1.29E+05 | 4.80E−02 | 0.47 | 84-5 | 0.16 | 0.9900 |
| anti-TIGIT Clone13 afucosylated hIgG1 | 1.35E−08 | 7.31E+05 | 9.85E−03 | 0.62 | 88-6 | 0.024 | 0.9993 |
| anti-TIGIT Clone13 hIgG1 LALA-PG | NB* | — | — | — | — | — | — |

*NB (non-binding). No observable binding of hFcγRIIIa 158V to anti-TIGIT Clone13 hIgG1 LALA-PG at concentrations of 20 μM To evaluate the impact of Fc modification of anti-TIGIT antibodies on anti-tumor activity, chimeric antibodies comprised of human CDRs and murine IgG2a backbone in wild-type, or with afucosylated or LALA-PG modifications were made. Afucosylation of murine IgG2a antibodies are similar to production of afucosylated human IgG1 backbone and result in increased binding to murine FcγRIV, the cognate receptor to human FcγRIV. To assess the extent of altered FcγRIV binding, antibody affinity to FcγRIV expressed on CHO cells was determined by FACS using anti-mouse IgG FITC. As shown in FIG. 12, unfucosulated clone 13 mIgG2a bound to a significantly greater extent than both the wild type or LALA-PG modified backbone. Afucosylated clone 13 mIgG2a bound with an affinity of $K_D$ 2.37 nM compared to the wild-type clone 13 mIgG2a, which bound with a $K_D$ of 33.4.

Example 12: TIGIT Expression on T Cell Subsets in Healthy Donor T Cells

TIGIT expression on T cell subsets in healthy donors was evaluated by flow cytometery. Frozen PBMC from 12 healthy donors were purchased from Astarte Biologics (Bothell, Wash.) and Folio Conversant (Huntsville, Ala.). Donor ages ranged from 21 to 74 with a median age of 48. Cells were stained with a viability dye and the following anti-human antibodies following Fc receptor blocking: CD3, CD96, CD226, CCR7, CD25, CD127, CD45RA, CD8, CD4, CD226, CD155 (Biolegend), and TIGIT (eBioscience). Stained cells were then analyzed on an Attune Nxt flow cytometer (Life Technologies). Treg subsets were defined by appropriate expression of CD4, CD25 and CD127 (CD4$^+$CD25$^+$CD127$^{lo}$). CD4$^+$ and CD8$^+$ effector memory ($T_{EM}$; CD45RA$^-$CCR7$^-$), CD45RA$^+$ effector memory ($T_{EMRA}$; CD45RA$^+$CCR7$^-$), central memory ($T_{CM}$; CD45RA$^-$CCR7$^+$), and naïve ($T_N$; CD45RA$^+$CCR7$^+$) cell subsets were defined according to CD45RA and CCR7 expression. As shown in FIG. 3, TIGIT expression is highest on Tregs, while the activating receptor CD226 expression is lower on both memory and naïve CD8 T cell subsets and shows similar levels to naïve CD4 T cell subsets. CD155 expression is mostly absent among T cells but was seen on antigen presenting cells.

Example 13: Anti-TIGIT Antibody Clone 13 Drives Depletion of Tregs

Figure 14:
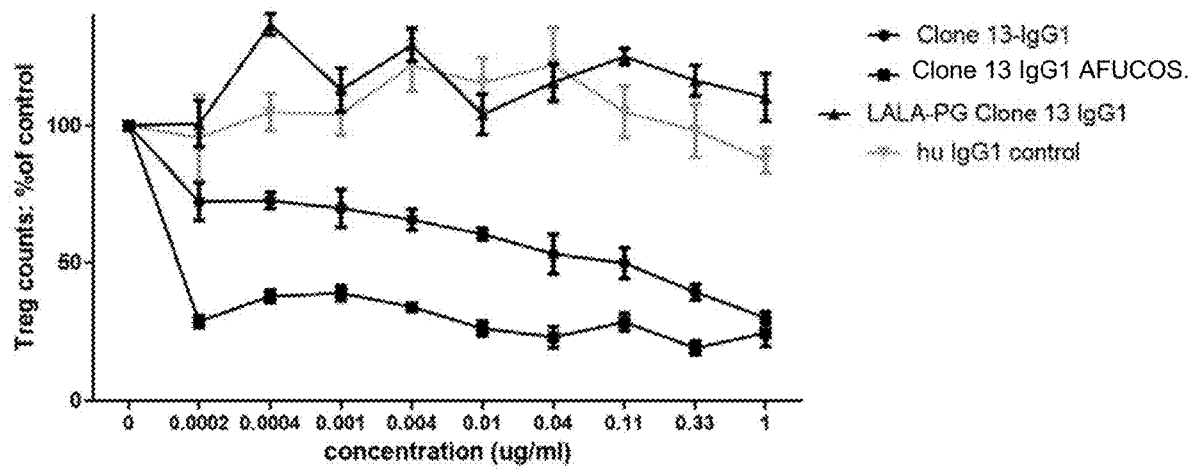
FIG. 14. Depletion of TIGIT-positive Treg cells by clone 13 IgG1 wild-type (black circles), clone 13 IgG1 afucosylated (black squares), clone 13 IgG1 LALA-PG (black triangles), and a human IgG1 isotype control (gray inverted triangles), at various concentrations.

To evaluate the effect of anti-TIGIT antibodies on the absolute numbers of Tregs and other T cell subsets in normal PBMC, healthy donor PBMCs from a donor expressing the V/F alleles of the FcγRIII receptor (Astarte Biologics) were isolated. Cells were cultured in the presence the wild-type, LALA-PG, or afucosylated versions of clone 13 anti-TIGIT antibody or a human IgG1 isotype control (Biolegend) at various concentrations. Cryopreserved PBMC (Astarte Biologics) were incubated in RPMI 1640 with 10% FBS in a 96-well round-bottom plate at 37° C. 2.5×10$^5$ PBMC were plated per well in triplicate wells with a titration of anti-TIGIT or control antibodies. After 24 hours, cells were washed, Fc receptor blocking was performed, and cells were stained with a viability stain and the following anti-human antibodies: CD3, CD4, CD8, CD25, CD127 and CD45RA (Biolegend). Stained cells were analyzed on an Attune NxT flow cytometer and T cell subsets were characterized as described above. As shown in FIG. 14, Tregs were 73% positive for TIGIT at the start of the assay. After 24 hours in culture, the wild-type version of clone 13 IgG1 antibody (black filled circle) elicited a dose dependent-decrease in TIGIT-positive Tregs, with maximal depletion occurring at 1 μg/ml. The afucosylated version of clone 13 (black filled square) conferred greater activity with maximal Treg depletion occurring at 200 pg/ml. The LALA-PG version of clone 13 (black filled triangle) and the human IgG1 isotype control (gray inverted triangle) showed no apparent activity in this assay.

In addition to evaluating the wild-type, afucosylated, and LALA-PG versions of clone 13 anti-TIGIT antibody, a version was made comprising an IgG1 constant region with S293D/A330L/I332E ("DLE") mutations that was previously reported to enhance the affinity for Fcγ receptors. See Lazar, 2006, *PNAS* 103: 4005-4010. The wild-type, afucosylated, LALA-PG, and DLE version of clone 13 were assessed for depletion of Tregs substantially as described above in healthy donor PBMCs from a donor expressing the high-affinity V/V alleles of the FcγRIII receptor.

Figure 35:
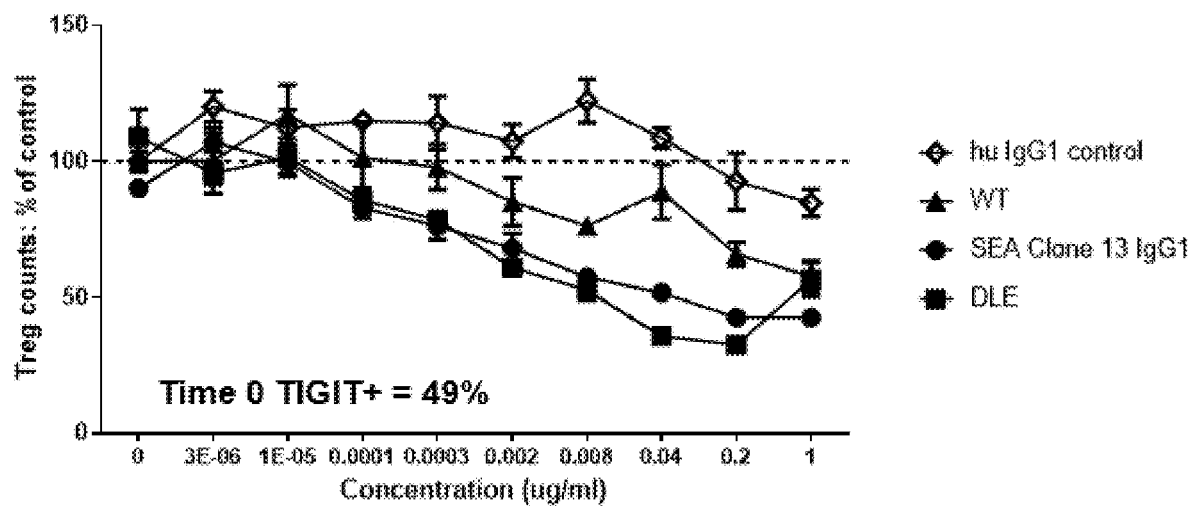
FIG. 35. Treg depletion by anti-TIGIT antibodies clone 13 IgG1 wild-type ("WT"), clone 13 IgG1 afucosylated ("SEA Clone 13 IgG1"), or clone 13 IgG1 DLE ("DLE").

As shown in FIG. 35, the clone 13 IgG1 wild-type antibody (triangles) depleted Tregs with an IC50 of ~0.024 µg/ml, while both the clone 13 IgG1 DLE antibody (squares) and clone 13 IgG1 afucosylated antibody (circles) depleted Tregs with much greater potency, with IC50s of 0.0006 µg/ml and 0.0005 µg/ml, respectively. (In FIG. 35, the IgG1 wild-type data is from a prior experiment using PBMCs from the same donor.)

Figure 36:
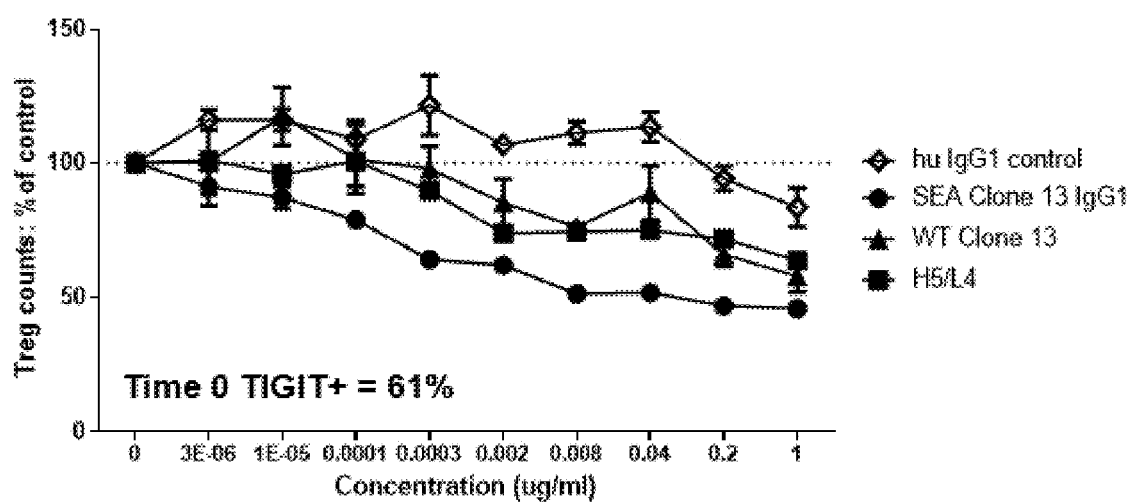
FIG. 36. Treg depletion by anti-TIGIT antibodies clone 13 IgG1 wild-type ("WT Clone 13"), clone 13 IgG1 afucosylated ("SEA Clone 13 IgG1"), or clone H5/L4 IgG1.

Another anti-TIGIT antibody, H5/L4 IgG1 (see WO 2016/028656 A1), was also tested for its ability to deplete Tregs healthy donor PBMCs from a donor expressing the high-affinity V/V alleles of the FcγRIII receptor. As shown in FIG. 36, clone 13 IgG1 afucosylated antibody was most potent at inducing depletion of Tregs, while the two IgG1 wild-type antibodies showed very similar potencies and depletion curves. (In FIG. 36, the clone 13 IgG1 wild-type data is from a prior experiment using PBMCs from the same donor.)

Example 14: Assessment of Treg Depletion in an Allogeneic NK/Treg Co-Culture To look for potential antibody dependent cell-mediated cytotoxicity (ADCC) in a Treg/NK cell co-culture, cryopreserved human CD4$^+$CD25$^+$ T cells (Stem Cell Technologies) were thawed and stimulated with CD3/CD28 MACS iBead particles (Miltenyi Biotec) at a 1:2 bead:cell ratio in in RPMI 10% FBS media supplemented with 20 ng/ml recombinant human IL-2 (R&D systems) for 3 days to increase TIGIT expression. After 3 days, Treg were assessed for cell surface TIGIT expression via flow cytometry and were found to be ~40% positive. The Treg were then washed and labeled with CFSE (Life Technologies) to distinguish them from NK cells following co-culture. That same day, purified human NK cells (Astarte Biologics) were thawed and pre-activated for 2 hours in the presence of 200 ng/ml IL-2. A co-culture of NK cells and Treg at a 2.5:1 NK:Treg ratio was set up in a 96-well plate in the presence of 100 ng/ml IL-2 in RPMI 1640 with 10% FBS. Cells were incubated at 37° C. with wild-type, LALA-PG, or afucosylated versions of clone 13 anti-TIGIT antibody or a human IgG1 isotype control (Biolegend) in triplicate wells, or an afucosylated anti-OKT9 antibody, which served as a positive control. After 24 hours, the cells were washed, stained with a viability dye, and analyzed via FACS on an Attune Nxt flow cytometer. Tregs were identified and enumerated according to viability dye and CFSE staining.

Figure 15:
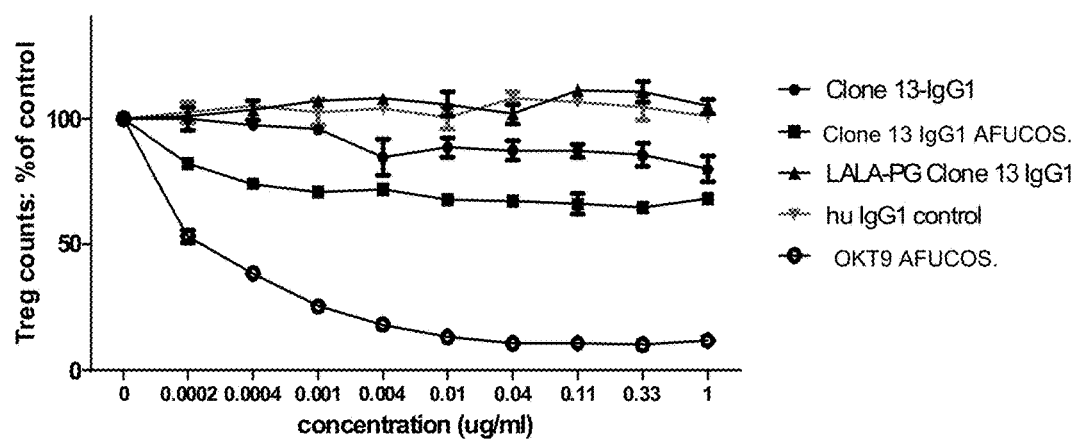
FIG. 15. Depletion of Tregs in allogeneic NK/Treg co-culture experiments by clone 13 IgG1 wild-type (black circles), clone 13 IgG1 afucosylated (black squares), and clone 13 IgG1 LALA-PG (black triangles). Afucosylated OKT9 antibody (open circles) was included as a positive control.

The results are shown in FIG. 15. Treg levels dropped with clone 13 IgG1 wild-type treatment (black filled circles), demonstrating that depletion can in part be due to direct NK-mediated ADCC. The ability of clone 13 IgG1 wild-type to deplete T cells appeared maximal at 1 µg/ml of treatment. The proportion of Treg depletion was more substantial with the clone 13 IgG1 afucosylated version (black filled squares), with maximal activity appearing at 40 ng/ml. The effector-null LALA-PG version of clone 13 IgG1 (black filled triangles) and the human IgG1 isotype control (gray inverted triangles) showed no apparent effect on Treg numbers, while the positive control SEA OKT9 antibody (open circles) showed the largest depletion. The results are consistent with the TIGIT expression data (FIG. 4) that showed Tregs expressed high levels of TIGIT.

Example 15: Anti-TIGIT Antibody Induces Cytokine Production

In addition to binding with higher affinity to FcγRIIIa on NK cells and driving ADCC, afucosylated antibodies also bind to higher affinity to FcγRIIIa and FcγRIIIb on antigen-presenting cells, and neutrophils and can enhance ADCP and antigen-presenting cell activation.

To investigate the impact of anti-TIGIT antibody and Fc variants on antigen presenting cells, PBMCs were isolated as follows. Blood from 3 unique human donors was collected into heparin tubes and, within about four hours of collection, aliquoted into 50 ml conical tubes (Falcon) and spun at 200 g in an Eppendorf 5810R (A-4-62 rotor) for 20 minutes at 25° C. without brakes, in order to separate the platelet-rich fraction. Following centrifugation, three distinct layers were formed: bottom layer, red blood cells (accounting for 50-80% of the total volume); middle layer, very thin band of white blood cells (also called "buffy coat"); top layer, straw-colored platelet rich plasma (PRP). The upper straw colored layer, which is enriched in platelets, was removed with a 1 ml pipette and discarded. Once the platelet rich plasma was removed, the remaining fractions were diluted with equal volumes of sterile PBS (Gibco). 15 ml of Histopaque-1077 (Sigma) warmed to room temperature was underlayered below the diluted fractions. The samples were spun at 1500 rpm for 25 minutes at 25° C. without brakes. Following centrifugation, three layers are formed again: bottom layer, red blood cells (accounting for 50-80% of the total volume); middle layer, thick band of white blood cells; top layer, PBS and remaining platelets. The upper PBS/platelet layer was removed with a 1 ml pipet and discarded. The thick band of white blood cells was gently removed and placed into a clean 50 ml sterile conical tube. Tubes were filled to 50 ml and cells spun at 800 g for 10 minutes. Wash solution was removed and pellets were resuspended in 10 ml of ACK red blood lysis buffer (Gibco) for ten minutes. 35 ml sterile PBS was added and cells were spun at 800 g for 10 minutes. The wash solution was removed and the pellet was resuspended in 50 ml PBS. 500 µl of sample was removed and PBMC were counted with a Vi-cell-XR (Beckman Coulter). Cells were spun again at 800 g for ten minutes.

Cells were resuspended at 1 million cells/ml in complete DMEM containing 10% heat inactivated FBS (Atlantica Biologics) and 1× penicillin/strepA, and 1× glutamine and plated at 100,000 cells/well in a 96 well plate. PBMCs were exposed to increasing concentrations (10, 1.0, 0.1, 0.01, 0.001, 0.0001 or 0 µg/ml) of clone 13 IgG1 wild type, clone 13 IgG1 afucosylated, or the clone 13 IgG1 LALA-PG for 24 hours. Tissue culture supernatents were collected and processed for cytokine production using a Luminex multiplex (Millipore) per the manufacturer's instructions.

Figure 16:
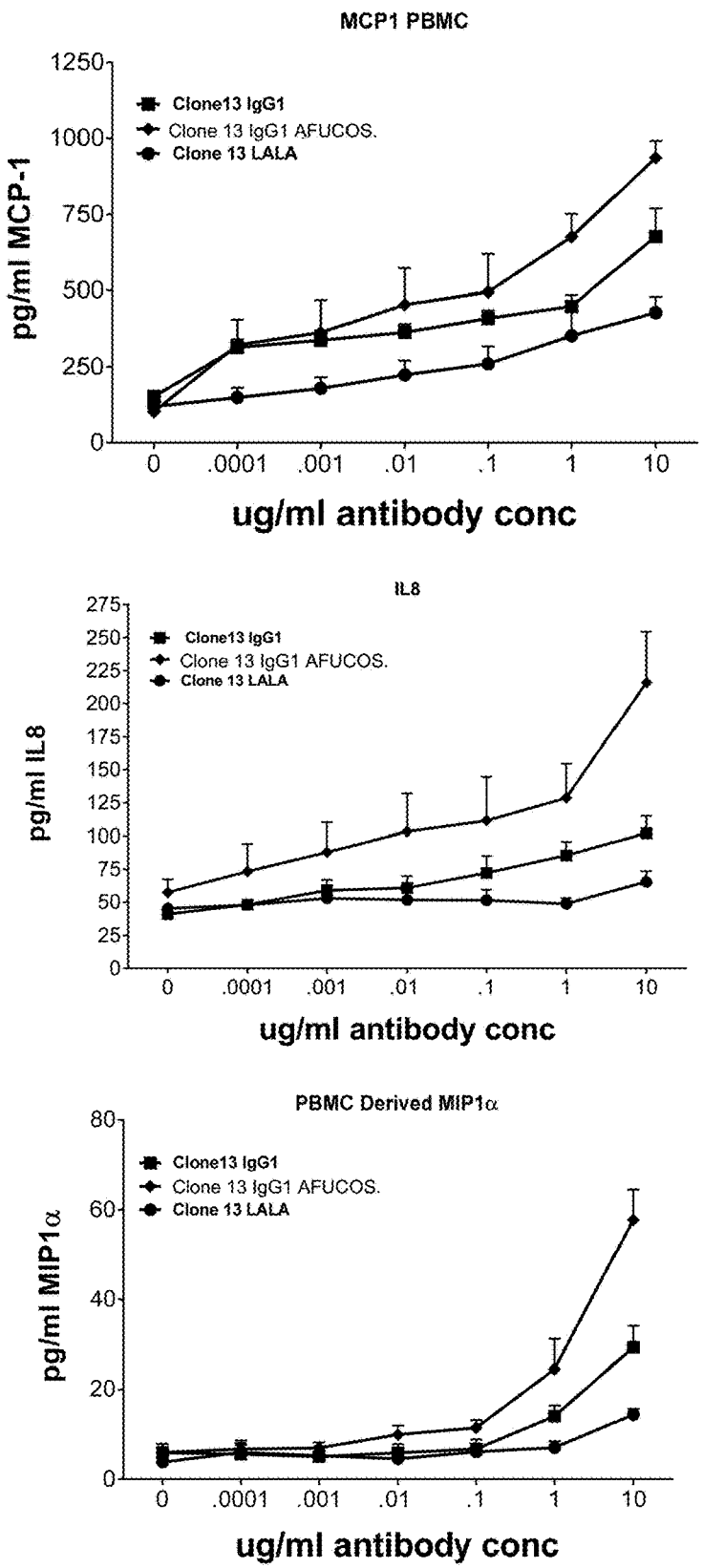
FIG. 16. Production of inflammatory cytokines MCP-1 (top panel), IL-8 (middle panel), and MIP1α (bottom panel) by PBMCs after treatment with clone 13 IgG1 wild-type antibody (black squares), clone 13 IgG1 afucosylated antibody (black diamond), or clone 13 IgG1 LALA-PG antibody (black circles).

The results are shown in FIG. 16. Treatment of PBMCs with clone 13 IgG1 wild type antibody (black filled squares) and clone 13 IgG1 afucosylated antibody (black filled diamonds) resulted in inflammatory cytokine production, including those associated with monocyte/macrophages activation such as MCP1, IL-8, and MIP1α. Exposure of cells to clone 13 IgG1 afucosylated elicited a stronger cytokine response, while the LALA-PG Fc effector null form resulted in very minimal cytokine production.

Example 16: Anti-TIGIT Antibody Induces Activation Markers on APCs

To evaluate the effect of anti-TIGIT antibody on antigen-presenting cells present in the PBMCs, expression of co-stimulatory molecules was assessed on the cell pellets remaining from the cytokine analysis described above. Cell pellets were resuspended in 50 ml of BD FACS buffer and transferred to 96 well round-bottomed microtiter plates. Fc receptors were blocked with human 100 µg/ml Fc fragments (Millipore) for 30 minutes on ice. A master mix composed of anti-CD14 antibody (BD), anti-CD86 antibody (BD), and anti-MHCII antibody (pan anti-DR,DP,DQ antibody, BD) diluted at 1:100 was prepared in BD FACS buffer containing 100 mg/ml human Fc fragments. Five µl of the master mix was added to each well containing 90 µl of resuspended cells, and samples were incubated for one hour on ice. Cells were then spun at 400 g in a pre-cooled Eppendorf 5810R centrifuge for five minutes. Supernatants were removed and cells washed with 200 µl of BD FACS buffer. Cells were washed twice and then resuspended in 200 µl of FACS buffer. Samples were collected on an LSRII flow cytometer (BD Biosciences) with DIVA software (BD biosciences). The mean fluorescence intensity (MFI) of CD86 and MHCII on $CD14^+$ monocyte/macrophages was analyzed using FlowJo software.

Figure 17:
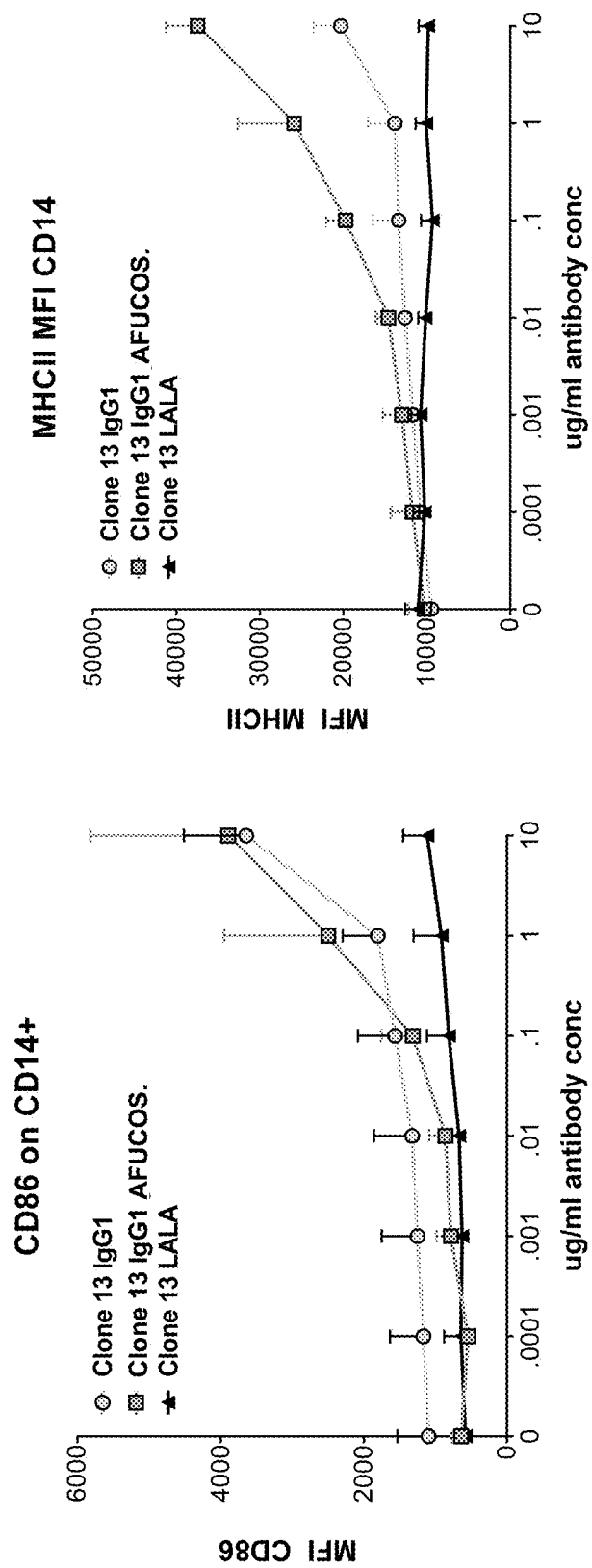
FIG. 17. Dose-dependent upregulation of expression of CD86 (left panel) and MHC class II (right panel) on CD14$^+$ monocytes after treatment with clone 13 IgG1 wild-type antibody (gray circles), clone 13 IgG1 afucosylated antibody (gray squares), and clone 13 IgG1 LALA-PG antibody (black triangles).

The results of that experiment are shown in FIG. 17. Treatment of $CD14^+$ monocyte/macrophages with anti-TIGIT antibody clone 13 IgG1 wild type or clone 13 IgG1 afucosylated resulted in upregulation of activation markers CD86 (left panel) and MHCII (right panel), indicating maturation of antigen presenting cells. Treatment with clone 13 IgG1 LALA-PG did not increase expression of CD86 or MHCII by $CD14^+$ cells.

Example 17: In Vivo Assessment of Anti-TIGIT Antibodies with Differentiated Fc Affinity in Syngeneic Tumor Models The anti-tumor efficacy of afucosylated anti-TIGIT antibody versus effector function null anti-TIGIT antibody comprising the LALA-PG mutation was investigated. This experiment was designed to determine whether the effector function of the anti-TIGIT antibody (enhanced in the afucosylated version and abolished in the LALA-PG version) is involved in the anti-tumor mechanism of action. Murine versions of anti-TIGIT antibody clone 13 with three different Fc domains were generated: 1) wild-type mIgG2a; 2) afucosylated mIgG2a; 3) mIgG2a LALA-PG (reduced effector function). The antibodies were evaluated in CT26 (colon), A20 (B cell lymphoma), and MC38 (colon) syngeneic tumor models, with six mice per antibody group per tumor model. Each antibody was administered intraperitoneal (i.p.) at a dose of 5 mg/kg given every third day for six doses once tumors reached 100 $mm^3$. Subcutaneous tumor length and width was measured using a digital caliper, and tumor volume was calculated using the formula $V=(L \times W^2)/2$.

Figure 18A:
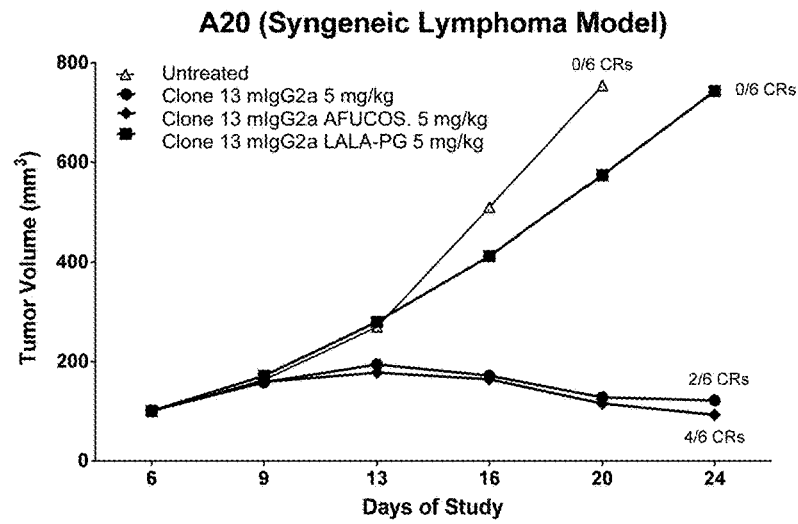
FIG. 18A-18C. In vivo activity of anti-TIGIT antibodies in three different syngeneic tumor models.
Figure 18B:
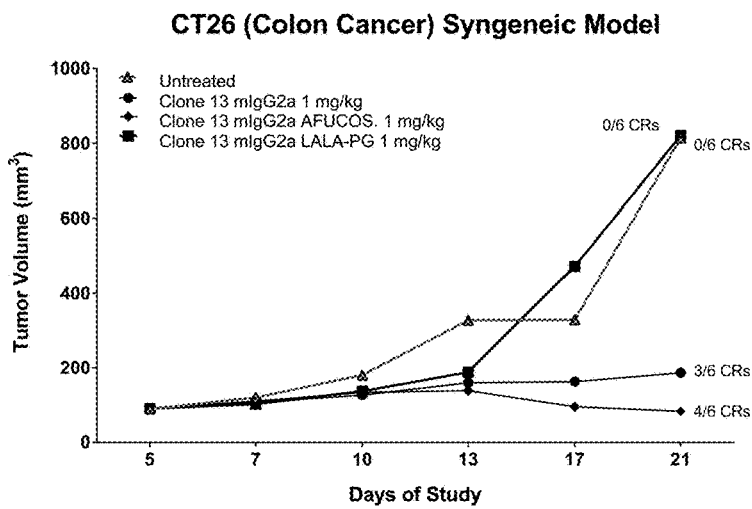
Figure 18C:
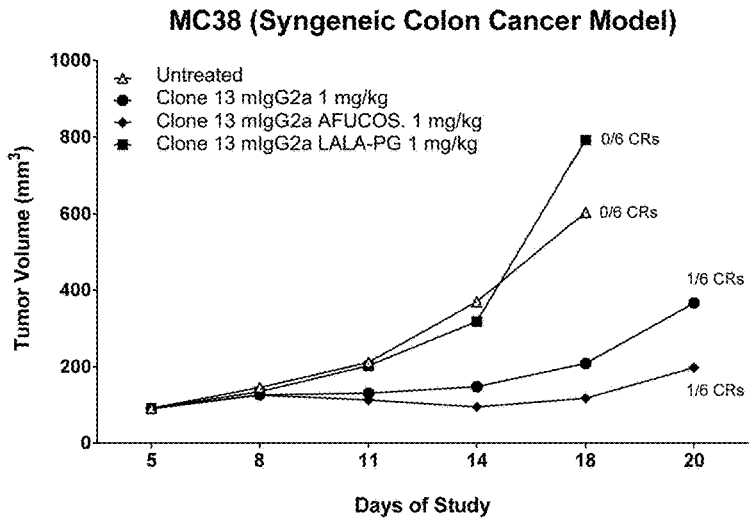

The results of that experiment are shown in FIG. 18. Each line represents median tumor volume ($mm^3$) (N=6 per group). FIG. 18A shows that the treatment of the A20 (syngeneic lymphoma model) model with anti-TIGIT antibodies clone 13 mIgG2a afucosylated, clone 13 mIgG2a wild-type, and clone 13 mIgG2a LALA-PG resulted in 4/6, 2/6, and 0/6 complete responses, respectively. FIG. 18B shows that the treatment of the CT26WT (murine colon carcinoma) model with anti-TIGIT antibodies clone 13 mIgG2a afucosylated, clone 13 mIgG2a wild-type, and clone 13 mIgG2a LALA-PG resulted in 4/6, 3/6, and 0/6 complete responses, respectively. FIG. 18C shows that treatment of the MC38 (murine colon carcinoma) model with anti-TIGIT antibodies clone 13 mIgG2a afucosylated, clone 13 mIgG2a wild-type, and clone 13 mIgG2a LALA-PG resulted in 1/6, 1/6, and 0/6 complete responses, respectively.

The dichotomy in responses induced in the different syngeneic models is interesting in light of their reported differential immune profiles. The CT26 and A20 tumor models are reported to be more highly infiltrated with NK and T cells, while the MC38 model is known to be more infiltrated with myeloid-derived suppressor cells (Mosely, et al., 2017, Canc. Immunol. Res. 5(1): 29-41). The increased activity of the anti-TIGIT antibodies in the A20 and CT26 tumor models supports the T cell modulatory activity of these antibodies and suggests that infiltrated T cells may serve as a positive predictive biomarker for this therapy. Collectively this data demonstrates that the anti-tumor activity in vivo of murine anti-TIGIT antibodies is dependent on Fc effector function, and that the afucosylated IgG2a has enhanced efficacy compared to wild-type.

Example 18: Combinatorial Activity of Anti-TIGIT Antibodies

TIGIT is expressed not only on T cells, but also NK and antigen-presenting cells. Given the pleotropic expression, TIGIT function can potentially drive multifactorial activity and anti-TIGIT antibodies may have impact on a multitude of cellular functions, including for example NK cell ADCC activity, T cell activation, and optimal antigen recall responses. In addition to single agent activity, anti-TIGIT antibodies may amplifying the activity of T cells, NK, or antigen presenting cells in combination with other therapeutics. TIGIT and CD226 are expressed on NK cells and TIGIT expression may not only actively inhibit optimal NK activity and ADCC potential, but may also prevent CD226 mediated activation. Blockade of TIGIT may therefore amplify NK mediated ADCC of human IgG1 targeted agents and ADCC directed therapeutics may show enhanced activity when combined with anti-TIGIT antibodies.

To investigate this possibility, the non-small cell lung carcinoma cell line, A549, was radiolabeled with $Na_2[^{51}Cr]O_4$ (100 µCi added to cells), washed and mixed with titrations of cetuximab alone, or cetuximab combined with 10 µg/mL anti-TIGIT antibody clone 13 hIgG1 wild-type. An isotype control at 10 µg/mL was also included in the experiment. Effector cells were isolated from cryopreserved normal donor PBMC using the Easy Sep Human NK Cell Enrichment Kit (Stem Cell Technologies). The donor cells were of the FcγRIIIa 158 V/V genotype. Effector cells were added at an effector-to-target cell ratio of 10:1 (50,000: 5000). After a 4 hour incubation, the radioactivity released into the culture supernatant was measured and the percent specific cell lysis was calculated as (test sample cpm−spontaneous cpm)/(total cpm−spontaneous cpm)×100. Spontaneous and total cpm values were determined from the supernatants of target cells incubated in medium alone and from target cells lysed with 1% Triton X-100, respectively.

Figure 19:
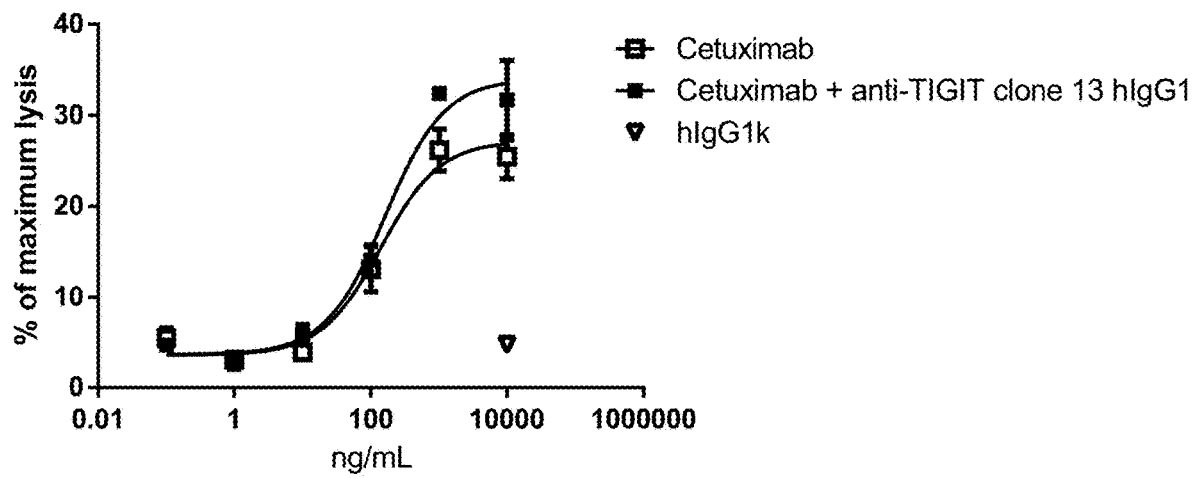
FIG. 19. ADCC activity against A549 cells contacted with cetuximab alone (open squares), the combination of cetuximab with anti-TIGIT antibody clone 13 IgG1 (black squares), and an IgG1 isotype control antibody (open triangles).

As shown in FIG. 19, treatment of A549 target cells with anti-TIGIT antibody clone 13 IgG1 antibody alone did not drive ADCC activity, but when A549 target cells were contacted with a combination of cetuximab and anti-TIGIT antibody clone 13 IgG1, the maximum lytic activity was increased over that observed with cetuximab alone.

In addition to modulating NK activity, TIGIT blockade may increase antigen specific memory responses in T cells. Antibodies targeting the checkpoint proteins present on T cells may therefore show enhanced activity when combined with an anti-TIGIT antibody.

To investigate this possibility, antigen recall assays in response to cytomegalovirus (CMV) were performed. Human PBMCs from a CMV reactive donor were purchased from Astarte Bio. Memory T cells from this donor can be reactivated in vitro with CMV antigen to assess their antigen-specific response. PBMCs were resuspended in X-vivo 10 (Lonza) containing 10% FBS (Atlanta Biologics), and 100,000 cells were plated into round bottom 96 well plates. Cells were exposed to 10 μg/ml of CMV antigens in the presence or absence of anti-TIGIT antibodies and/or anti-PD-1 directed antibodies. To assess the combinatorial activity, PBMCs were treated with a suboptimal dose of anti-PD-1 antibodies (pembrolizumab or nivolumab) at 1 μg/ml and increasing concentrations of anti-TIGIT antibody clone 13 IgG1 wild-type (1 pg/ml to 1 μg/ml) were added. Memory recall response to the CMV antigen was allowed to proceed for 5 days, after which tissue culture supernatants were harvested and cytokine responses determined by Luminex assay assessment (Millipore) per the manufacturer's instructions.

Figure 20:
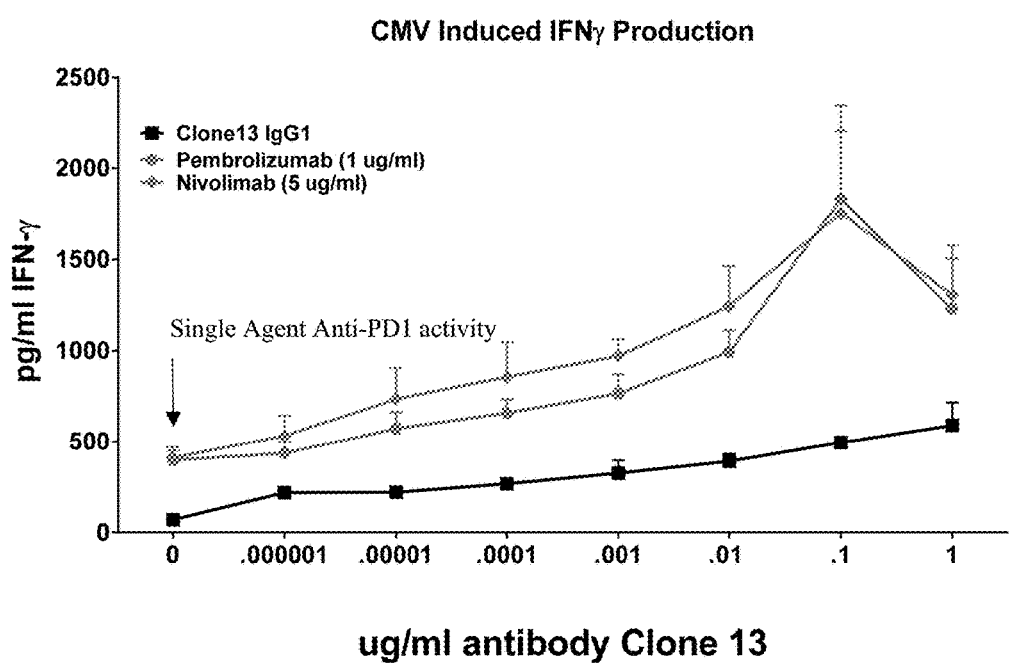
FIG. 20. CMV-induced IFNγ expression in PBMCs exposed to CMV recall antigen and treated with anti-PD-1 antibody (pembrolizumab treatment is shown with gray squares, nivolumab treatment is shown in gray diamonds) and increasing concentrations of anti-TIGIT antibody clone 13 IgG1. Treatment with anti-TIGIT antibody clone 13 IgG1 alone is also shown (black squares).

As shown in FIG. 20, anti-TIGIT antibody clone 13 IgG1 boosted IFNγ secretion by PBMCs treated with anti-PD-1 antibodies and exposed to CMV antigens, in a dose-dependent manner.

To investigate the combinatorial activity in vivo a syngeneic mouse tumor model was used. C57BL/6 mice, 8 per group, were implanted subcutaneously with $1 \times 10^6$ MC38 tumor cells on the flank. When tumors reached ~100 mm$^3$, animals were randomized into groups and treated every three days for 3 doses (Q3dx3) with either 0.3 mg/kg anti-TIGIT antibody clone 13 hIgG1 wild-type, afucosylated clone 13 IgG1, 1 mg/kg anti-PD-1 antibody (anti-mouse PD-1 antibody clone 29F.1A12), a combination of clone 13 hIgG1 wild-type/anti-PD-1 antibody, or a combination of afucosylated clone 13 IgG1/anti-PD-1 antibody. Tumor volume was monitored over time and animals were euthanized when tumor burden reached >1000 mm$^3$.

Figure 37:
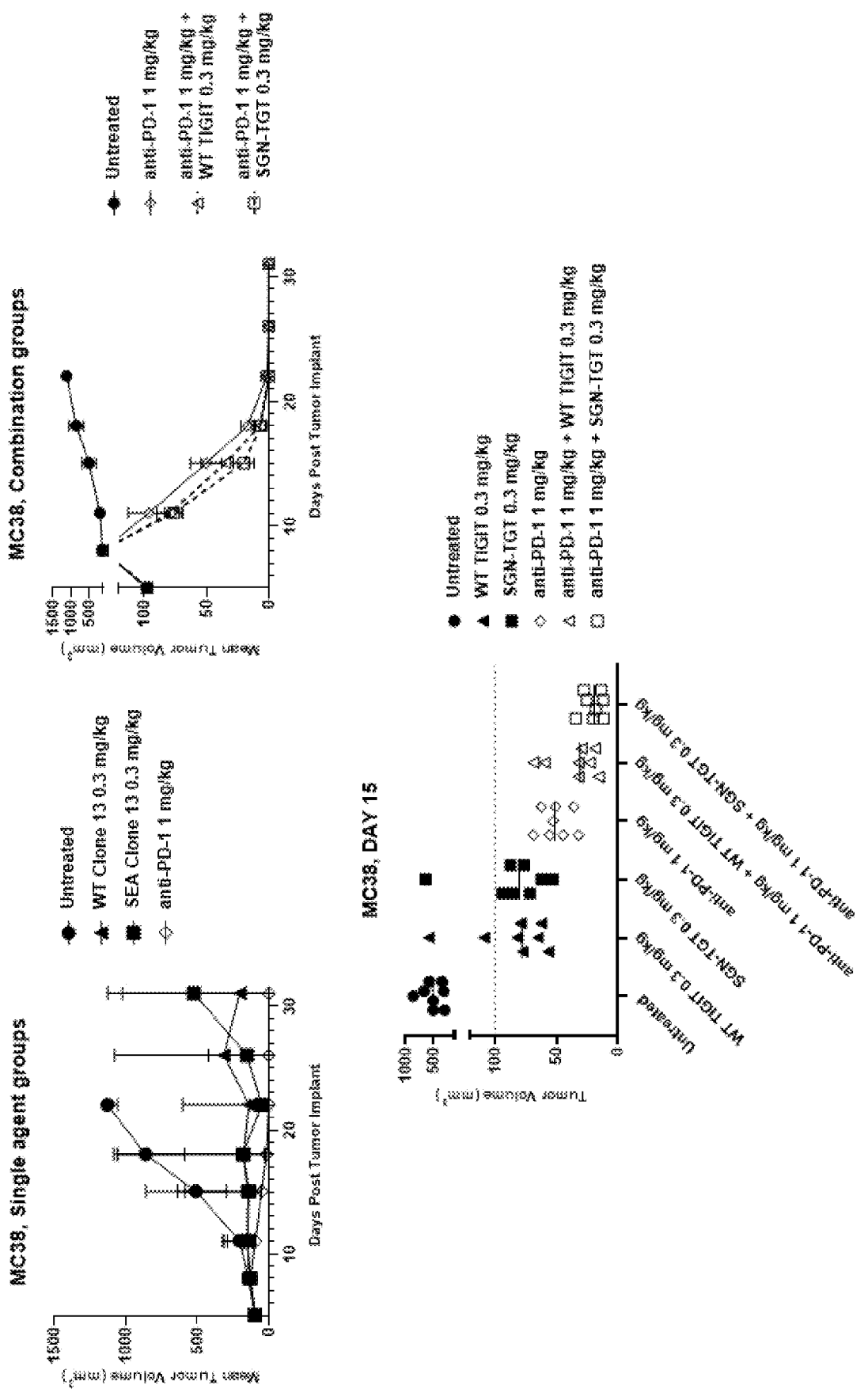
FIG. 37. Efficacy of anti-TIGIT antibodies clone 13 IgG1 wild-type ("WT Clone 13" or "WT TIGIT"), clone 13 IgG1 afucosylated ("SEA Clone 13" or "SGN-TGT"), anti-PD-1 antibody, and combinations of anti-PD-1 antibody and clone 13 IgG1 wild-type or clone 13 IgG1 afucosylated in an MC38 mouse tumor model.

In this experiment, both clone 13 hIgG1 wild-type and afucosylated clone 13 IgG1 demonstrated good tumor growth delay, with 4/8 and 3/8 complete responses for wild-type and afucosylated antibody, respectively. See FIG. 37, upper left. The anti-PD-1 antibody also showed good efficacy in this experiment. The combination therapies showed even faster tumor regression than the single agents alone, as evidenced by the tumor volumes measured on day 15. FIG. 37, upper right and bottom.

Example 19: Activity of Anti-TIGIT Antibodies on Human T Cell Responses In Vitro To investigate memory T cell reactivation antigen recall experiments were performed. Human PBMCs (100,000 cells) from an HLA-A2 donor previously shown to be reactive to CMV peptides were re-suspended in RPMI containing 10% FBS, 1× penicillin and 1× glutamine, and plated into round bottom wells of a 96 well plate. Cells were stimulated with CMV peptides in the presence or absence of increasing concentrations of anti-TIGIT antibodies clone 13 hIgG1 wild type, afucosylated clone 13 IgG1, or clone 13 hIgG1 LALA-PG for five days. Tissue culture supernatants were collected and cytokine production assessed by Luminex multiplex assays as per the manufacturer's instructions.

Figure 21:
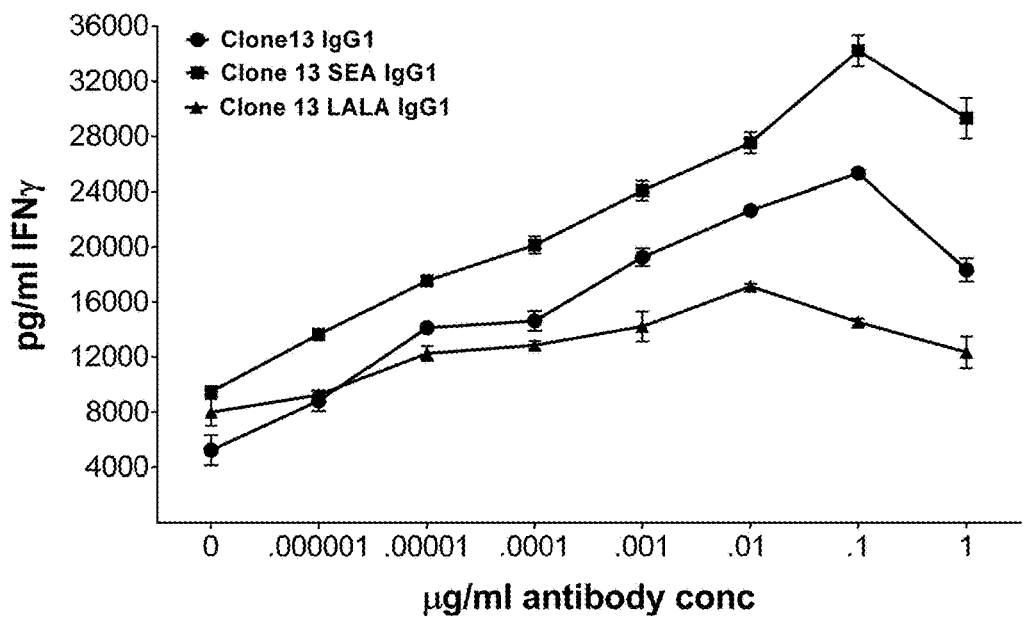
FIG. 21. CMV-induced IFNγ expression in PBMCs exposed to CMB recall antigen and treated with increasing concentrations of anti-TIGIT antibodies clone 13 IgG1 wild-type ("Clone 13 IgG1"), afucosylated clone 13 IgG1 ("Clone 13 SEA IgG1"), and clone 13 IgG1 LALA-PG ("Clone 13 LALA IgG1").

As shown in FIG. 21, anti-TIGIT antibody stimulated cultures showed an increased response to CMV antigen as seen by an increase in IFNγ production. Afucosylated clone 13 IgG1 resulted in an amplified antigen specific T-cell response down to 1 pg/ml and this activity was more robust than the response associated with clone 13 IgG1 wild-type. The effector-null clone 13 IgG1 LALA-PG antibody was inefficient at driving a memory T cell response.

To investigate induction of a naïve effector T cell response a one way mixed lymphocyte reaction (MLR) was performed. Human PBMCs (100,000 cells) from an HLA-A2 donor were re-suspended in RPMI containing 10% FBS, 1× penicillin, and 1× glutamine, and cultured at a 1:1 ratio with irradiated HLA mis-matched allogeneic PBMCs in a round bottom 96 well plate. Cells were stimulated with increasing concentrations of clone 13 hIgG1 wild type, afucosylated clone 13 hIgG1, or clone 13 IgG1 LALA-PG for five days. Tissue culture supernatants were collected and cytokine production assessed by Luminex multiplex assays as per the manufacturer's instructions.

Figure 22:
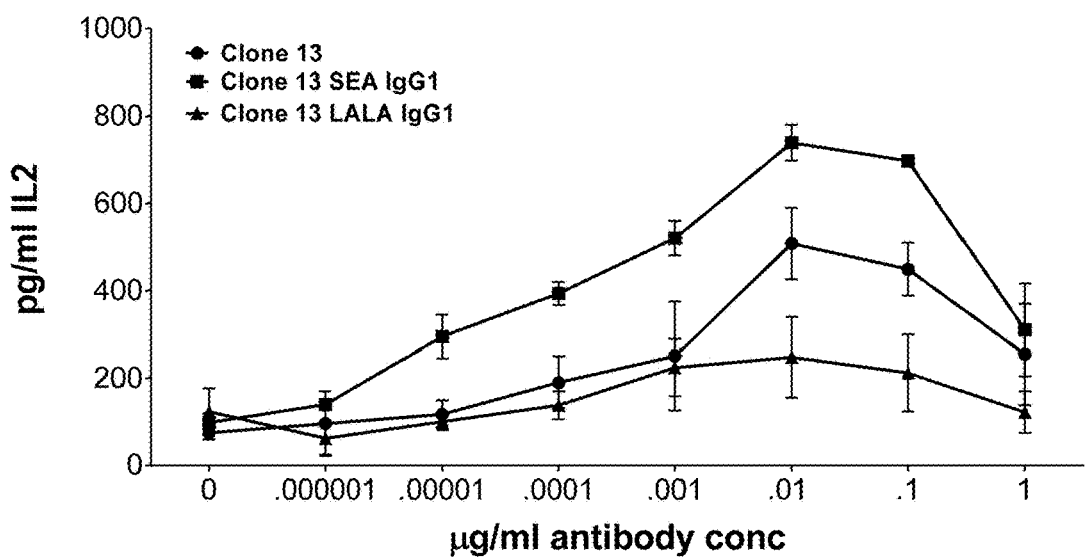
FIG. 22. IL2 expression in HLA mismatched co-cultured PBMCs treated with increasing concentrations of anti-TIGIT antibodies clone 13 IgG1 wild-type ("Clone 13 IgG1"), afucosylated clone 13 IgG1 ("Clone 13 SEA IgG1"), and clone 13 IgG1 LALA-PG ("Clone 13 LALA IgG1").

As shown in FIG. 22, cultures stimulated with anti-TIGIT antibodies showed increased allogenic effector T cell responses as seen by an increase in IL2 production. Afucosylated clone 13 IgG1 resulted in an amplified antigen specific T-cell response down to 100 pg/ml and this activity was more robust than the response associated with clone 13 IgG1 wild type. The effector null clone 13 IgG1 LALA-PG antibody was inefficient at driving a memory T cell response.

Figure 38B:
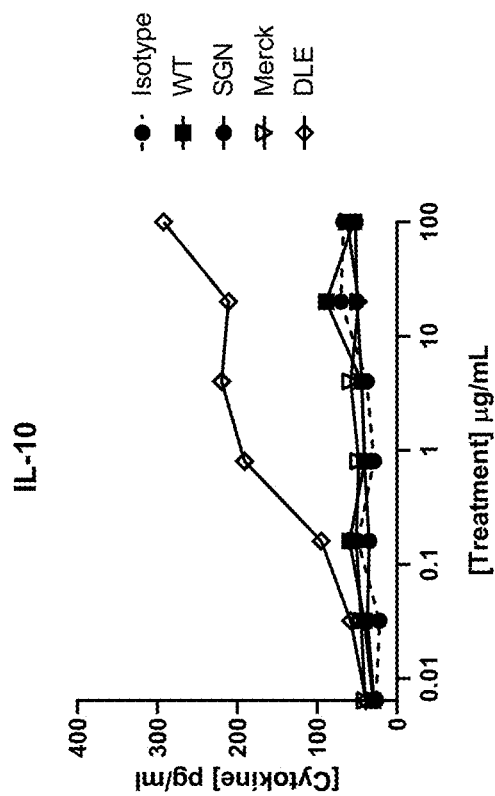
FIG. 38A-38B.
Figure 38A:
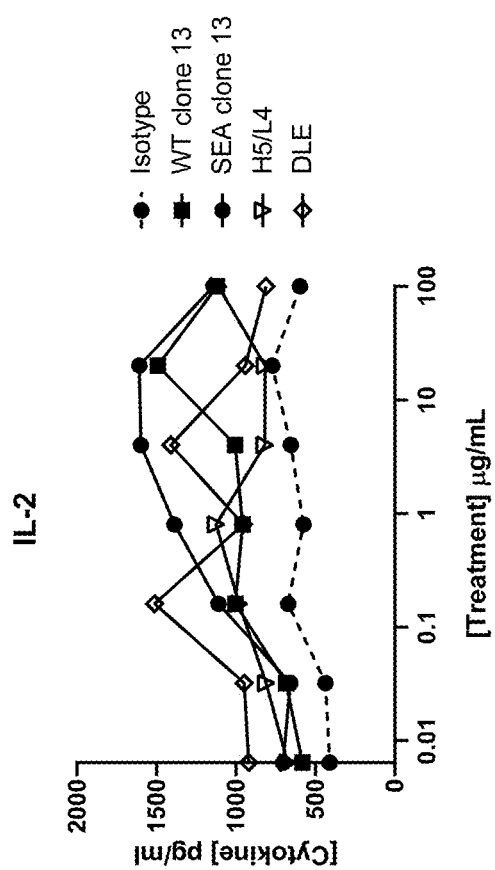

In addition to investigating activation of T cells in antigen-naïve and memory assays, staphylococcal enterotoxin B peptide was used as a superantigen in combination with clone 13 hIgG1 wild type, clone 13 hIgG1 afucosylated, clone 13 IgG1 DLE, and another anti-TIGIT antibody, H5/L4 IgG1. Afucosylated clone 13 hIgG1 was able to induce activation of T cells, as measured by induction of IL-2, more robustly than clone 13 hIgG1 wild type or H5/L4. FIG. 38A. Clone 13 IgG1 DLE was also able to induce IL-2 production roughly equivalently to both clone 13 hIgG1 wild type and clone 13 hIgG1 afucosylated. Clone 13 IgG1 DLE was found to concomitantly induce production of IL-10, in contrast to the other antibodies. FIG. 38B. This result is consistent with reports that engagement of FcγRIIb receptor results in induction of IL-10. IgG1 DLE is expected to engage FcγRIIb.

Example 20: Activity of Anti-TIGIT Antibodies in a Murine Tumor Model

Treatment of tumor-bearing (CT26 colon carcinoma) mice with various forms of an anti-TIGIT antibody, either wild type IgG2a, effector null IgG2a LALA-PG or afucosylated IgG2a resulted in both systemic and tissue specific cytokine induction. To examine potential systemic and tissue-specific effects of treatment with anti-TIGIT antibodies, six Balb/c mice were implanted with CT26 colon cancer cells on the flank and treated with 1 mg/kg anti-TIGIT antibodies clone 13 IgG2a wild type, afucosylated clone 13 IgG2a, clone 13 IgG2a LALA-PG, once every three days for six doses, or no treatment, after tumors reached 100 mm$^3$. 24 hours after the $3^{rd}$ dose of anti-TIGIT antibody, half of the mice were sacrificed and plasma, spleen, and tumor tissue were collected. Half of each spleen and tumor were lysed in RIPA buffer with mechanical disruption. Plasma and tissue lysates were then analyzed for cytokines using the Milipore 25 pre mix Luminex multiplex kit, which allowed for analysis of 25 different inflammatory cytokines. Tissue cytokine levels were normalized to one another via BCA (bicinchoninic acid assay)-determined protein content.

Figure 23:
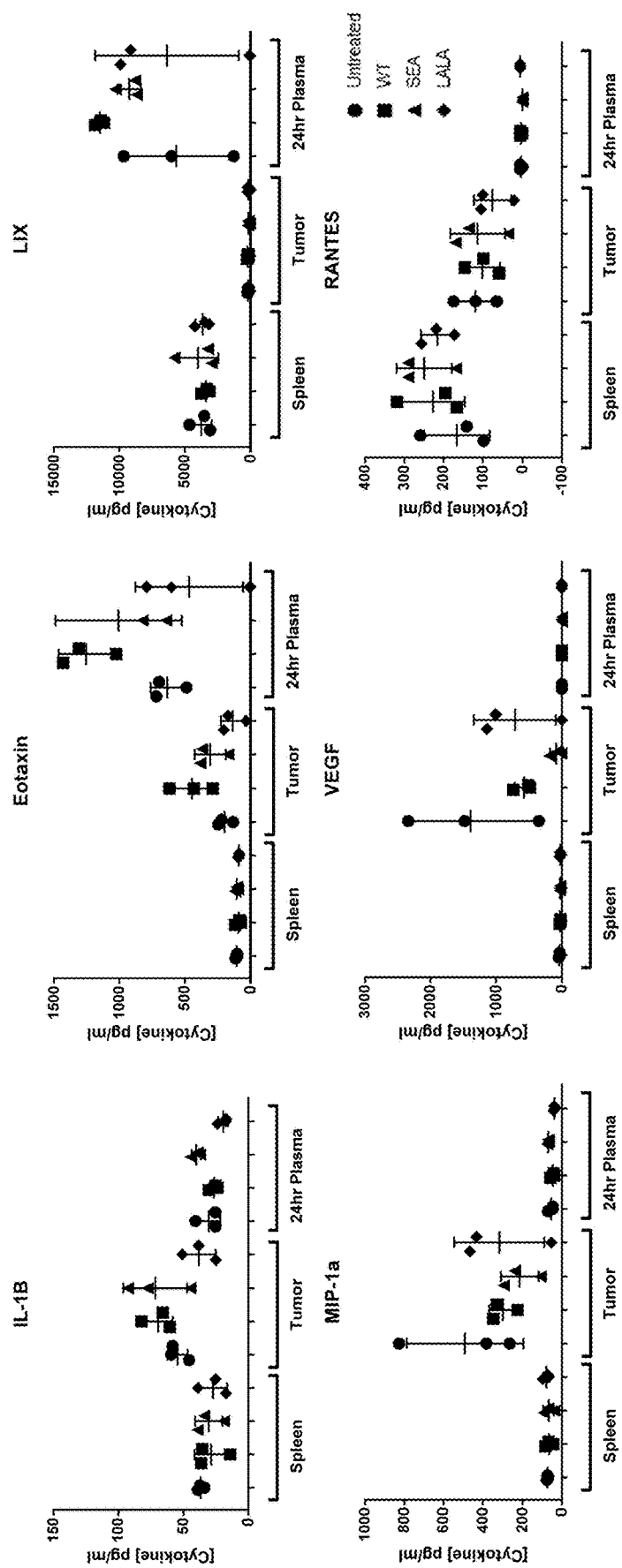
FIG. 23. Cytokine induction in plasma and tissues from CT26 colon cancer xenograft mice in response to anti-TIGIT antibodies. Mice implanted with CT26 colon cancer cells were treated with 1 mg/kg clone 13 IgG2a wild type ("WT"), afucosylated clone 13 IgG1 ("SEA"), or clone 13 IgG2a LALA-PG ("LALA"), and cytokine levels were measured in plasma, spleen, and tumor lysates.

As shown in FIG. 23, cytokine analysis did not show drastically increased cytokines in the plasma, which would be indicative of a systemic response, or in the tissues in response to any antibody treatments. Limited cytokines were observed in untreated mice in the plasma and tumor with only modest changes observed following anti-TIGIT treatment indicating that TIGIT treatment did not initiate a global inflammatory response even with the afucosylated antibody.

In addition to analysis of anti-TIGIT induced cytokine levels, tumor and periphery samples harvested 24 hours after the third dose of anti-TIGIT antibody were analyzed for global changes in the proportion of various T cell subsets by flow cytometry. Tumor and spleen single cell suspensions and PBMCs from the same Balb/c mice as described above for FIG. 23 were stained for various cell surface markers to delineate CD8+, CD4+ subsets of naïve/memory T cells ($CD62L^+CD44^-$ naïve, $CD62L^-CD44^-$ effector, $CD44^+CD62L^+$ central memory, and $CD44^+CD62L^-$ effector memory), and Treg ($CD25^+CD127^-$). Samples were run on an Attune Acoustic Focusing Cytometer and analyzed using FlowJo. Gates were set on $CD45^+$ live cells.

Figure 24:
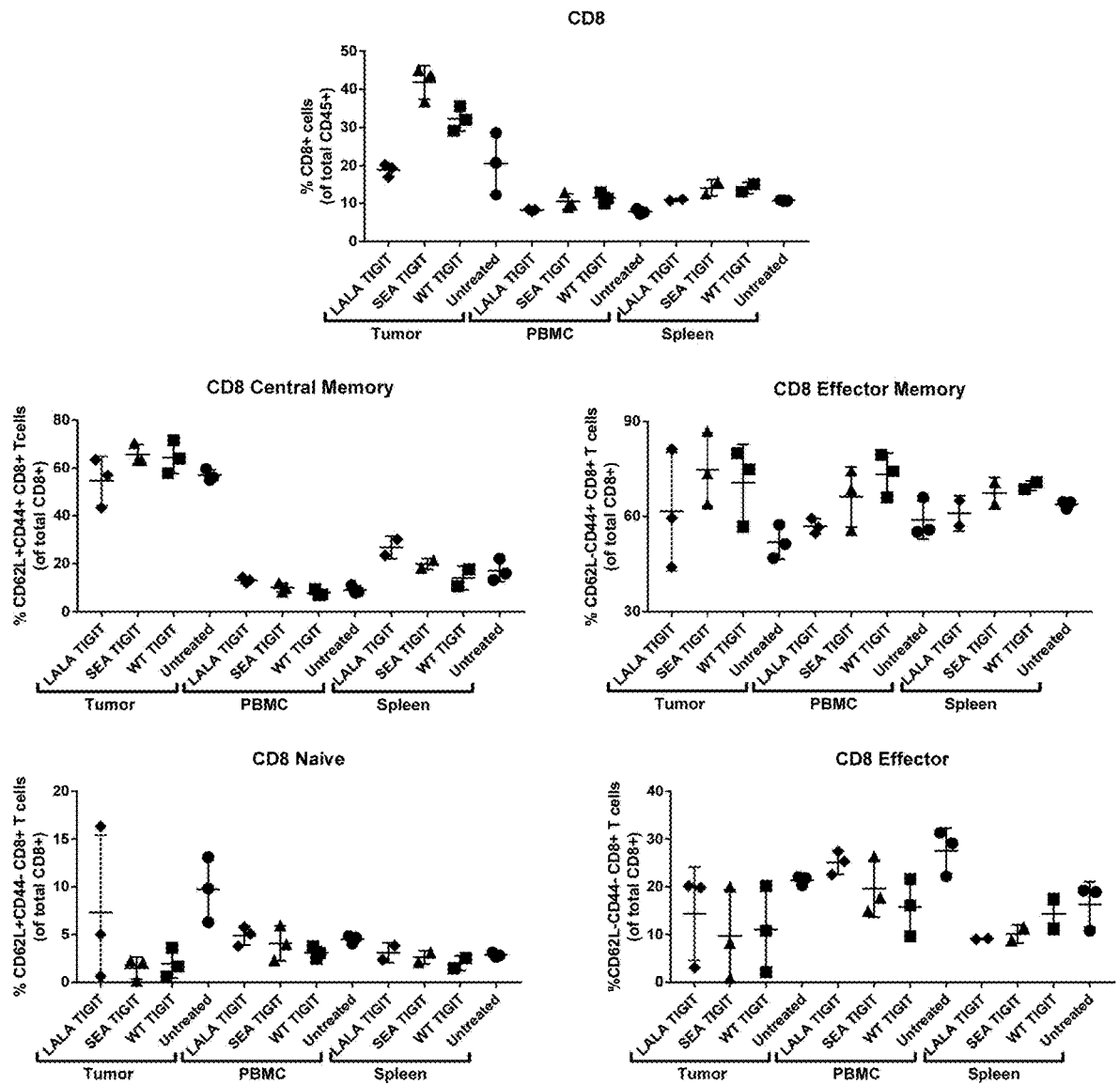
FIG. 24. Changes in intratumoral and peripheral CD8+ T cell subsets in CT26 colon cancer xenograft mice following treatment with anti-TIGIT antibody clone 13 IgG2a wild type ("WT TIGIT"), afucosylated clone 13 IgG2a ("SEA TIGIT"), or clone 13 IgG2a LALA-PG ("LALA TIGIT").

As shown in FIG. 24, increases in CD8+ T cells in the tumor were observed in response to anti-TIGIT antibodies clone 13 mIgG2a wild-type and afucosylated clone 13 mIgG2a antibodies, but not the effector null clone 13 mIgG2a LALA-PG, when compared to untreated animals (FIG. 24 top panel). More modest increases in the percentage of CD8+ cells after anti-TIGIT antibody treatment were observed in the PBMCs and spleen. Intra-tumoral changes in naïve, effector, and memory T cells were also noted. Specifically, levels of intra-tumoral naïve CD8+ T cells were decreased after treatment with clone 13 mIgG2a wild-type and afucosylated clone 13 mIgG2a, but less so with clone 13 mIgG2a LALA-PG (FIG. 24, lower left panel). An increase in the proportion of $CD8^+CD44^+CD62L^-$ effector memory cells (FIG. 24, upper right panel) and $CD8^+CD44^+CD62L^+$ central memory cells (FIG. 24, upper left hand panel) was observed in the tumor in response to the clone 13 mIgG2a wild-type and afucosylated antibodies, but not in response to the clone 13 mIgG2a LALA-PG antibody. These changes were not noted in the spleen or PBMCs, though some mild changes in these tissues did occur.

Figure 25:
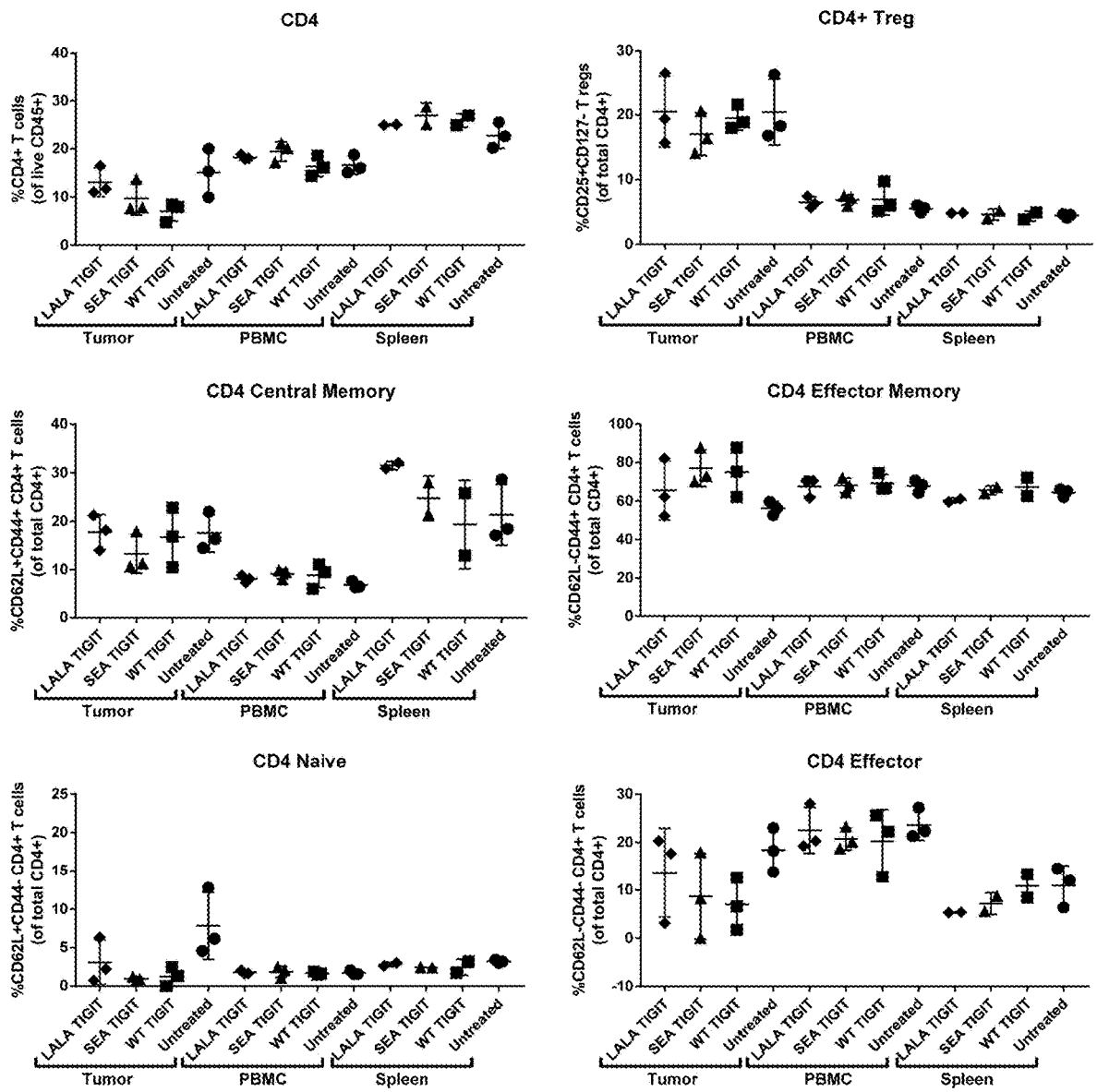
FIG. 25. Changes in intratumoral and peripheral CD4+ T cell subsets in CT26 colon cancer xenograft mice treated with anti-TIGIT antibody clone 13 IgG2a wild type ("WT TIGIT"), afucosylated clone 13 IgG2a ("SEA TIGIT"), or clone 13 IgG2a LALA-PG ("LALA TIGIT").

CD4+ T cell subsets were also analyzed by flow cytometry for changes induced by anti-TIGIT antibody treatment using a similar strategy as described above for CD8+ cells. As shown in FIG. 25 (top left hand panel), treatment with clone 13 mIgG2a wild-type and afucosylated antibodies induced mild decreases in intra-tumoral CD4+ cells compared to treatment with clone 13 mIgG2a LALA-PG antibody or untreated animals. This effect was not seen in the PBMCs or spleen. An intra-tumoral decrease in response to clone 13 mIgG2a wild-type and afucosylated antibodies, but not clone 13 LALA-PG antibody, was also observed to a small extent in the CD4+ Treg population, suggesting that anti-TIGIT antibody treatment is diminishing the immunosuppressive Treg population in the tumor, but not in the normal tissues. Similar to the results with CD8+ T cells, intra-tumoral CD4+ naïve T cells were decreased after treatment with clone 13 mIgG2a wild-type and afucosylated antibodies compared to untreated (FIG. 25 lower left panel) and this finding was concurrent with an increase in the proportion of effector memory CD4+ T cells in the tumor (FIG. 25, middle right panel). Effector memory CD4+ and CD8+ T cells are involved in eliciting anti-tumor responses and elevation with TIGIT directed antibodies may contribute to the anti-tumor response. Many of these prominent intra-tumor T cell population changes were not accompanied by large shifts in these populations in the periphery.

Figure 26A:
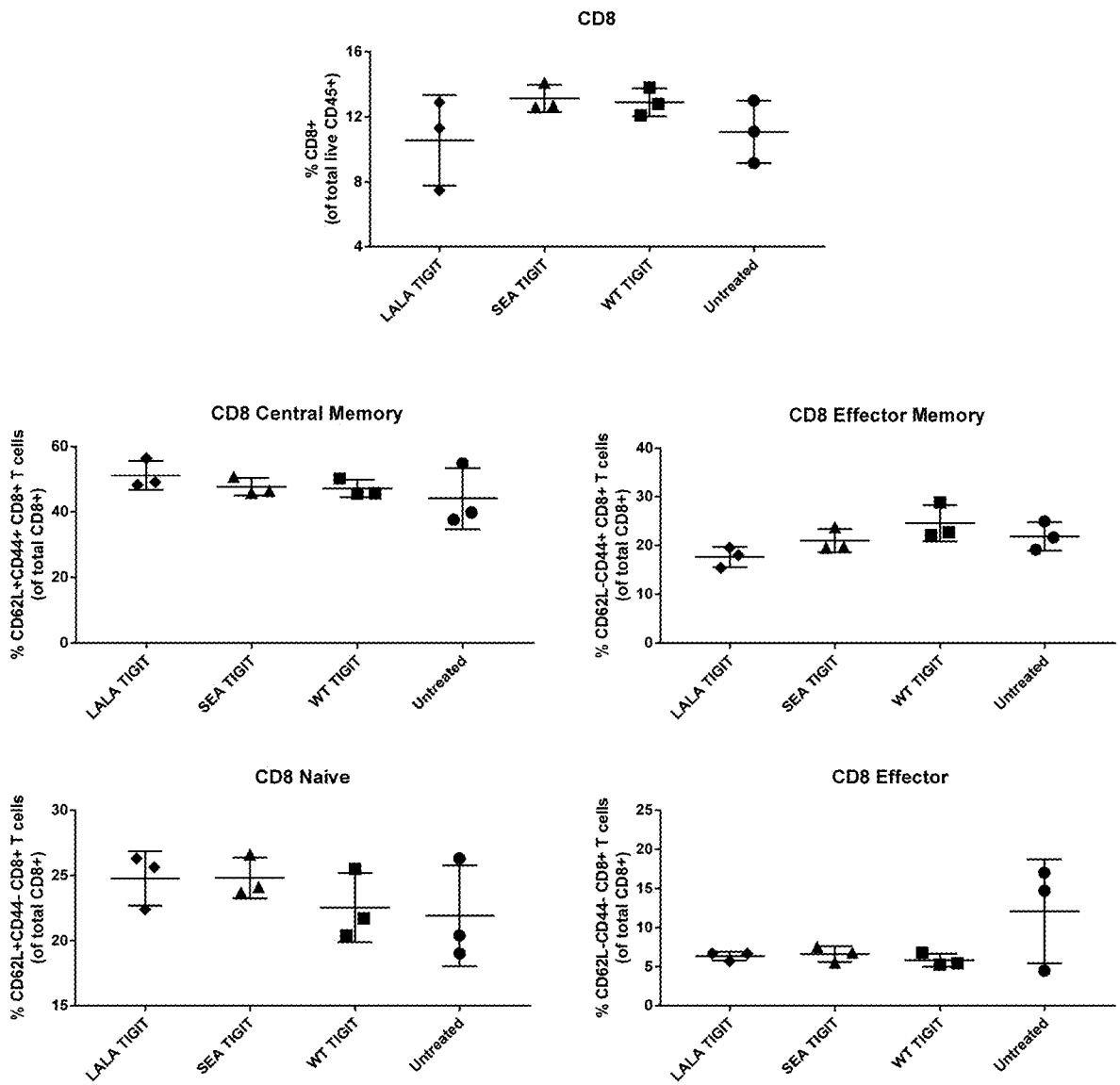
FIG. 26A-B. Changes in splenic CD8+(A) and CD4+(B) T cell subsets in CT26 colon cancer xenograft mice following six doses of anti-TIGIT antibody clone 13 IgG2a wild type ("WT TIGIT"), afucosylated clone 13 IgG2a ("SEA TIGIT"), or clone 13 IgG2a LALA-PG ("LALA TIGIT"). Results from live CD45+ cells gated on CD8+ or CD4+ are shown.
Figure 26B:
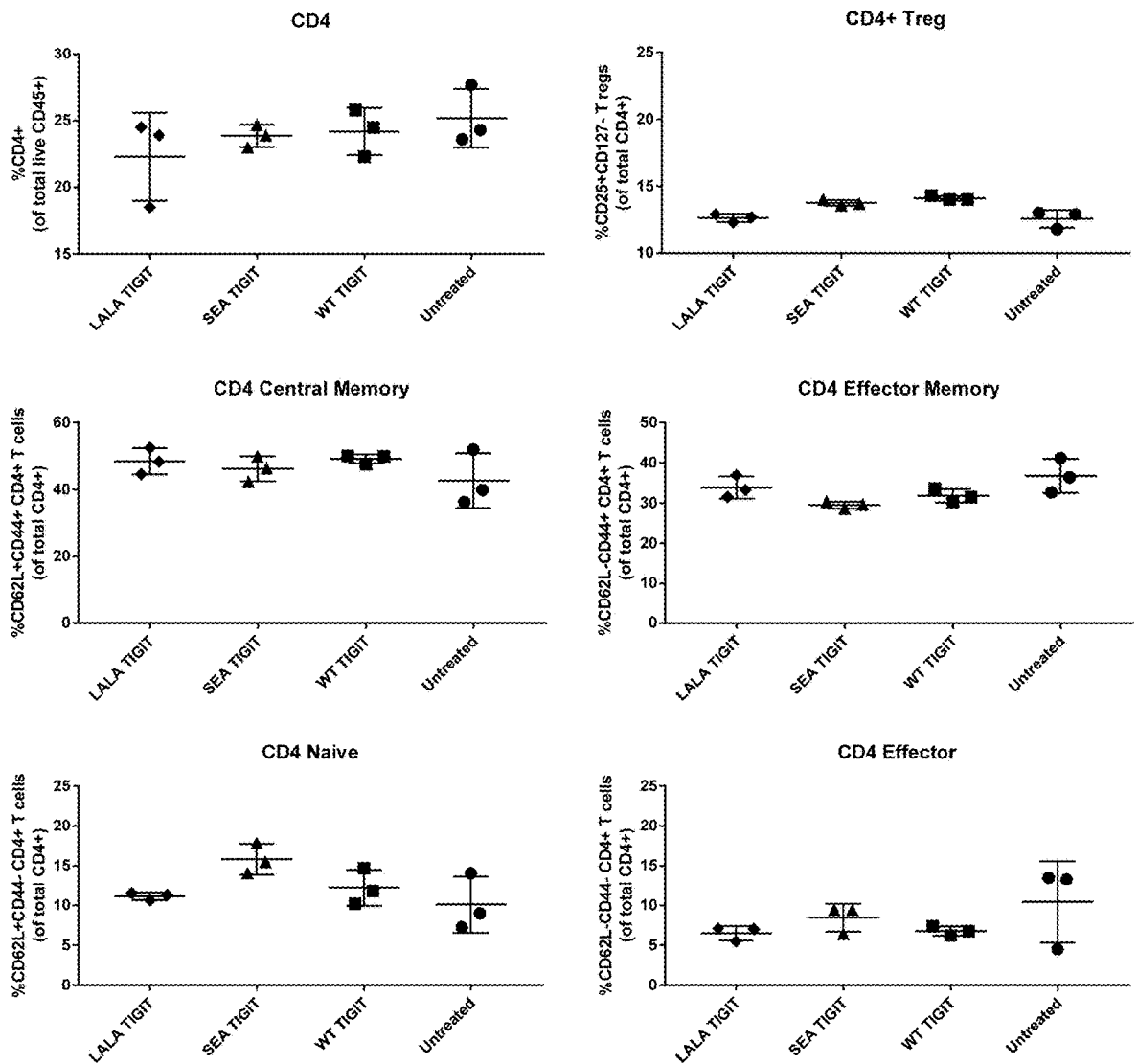

After six doses of anti-TIGIT antibodies, at approximately 20 days after the beginning of treatment, tumors were diminished and almost undetectable. Spleens and plasma were harvested from these mice and cells prepared for flow cytometry as described above. As shown in FIG. 26A-B, analysis of various T cell subsets from spleens of these mice demonstrated no drastic changes in the CD8+ or CD4+ subsets between the groups.

Figure 27:
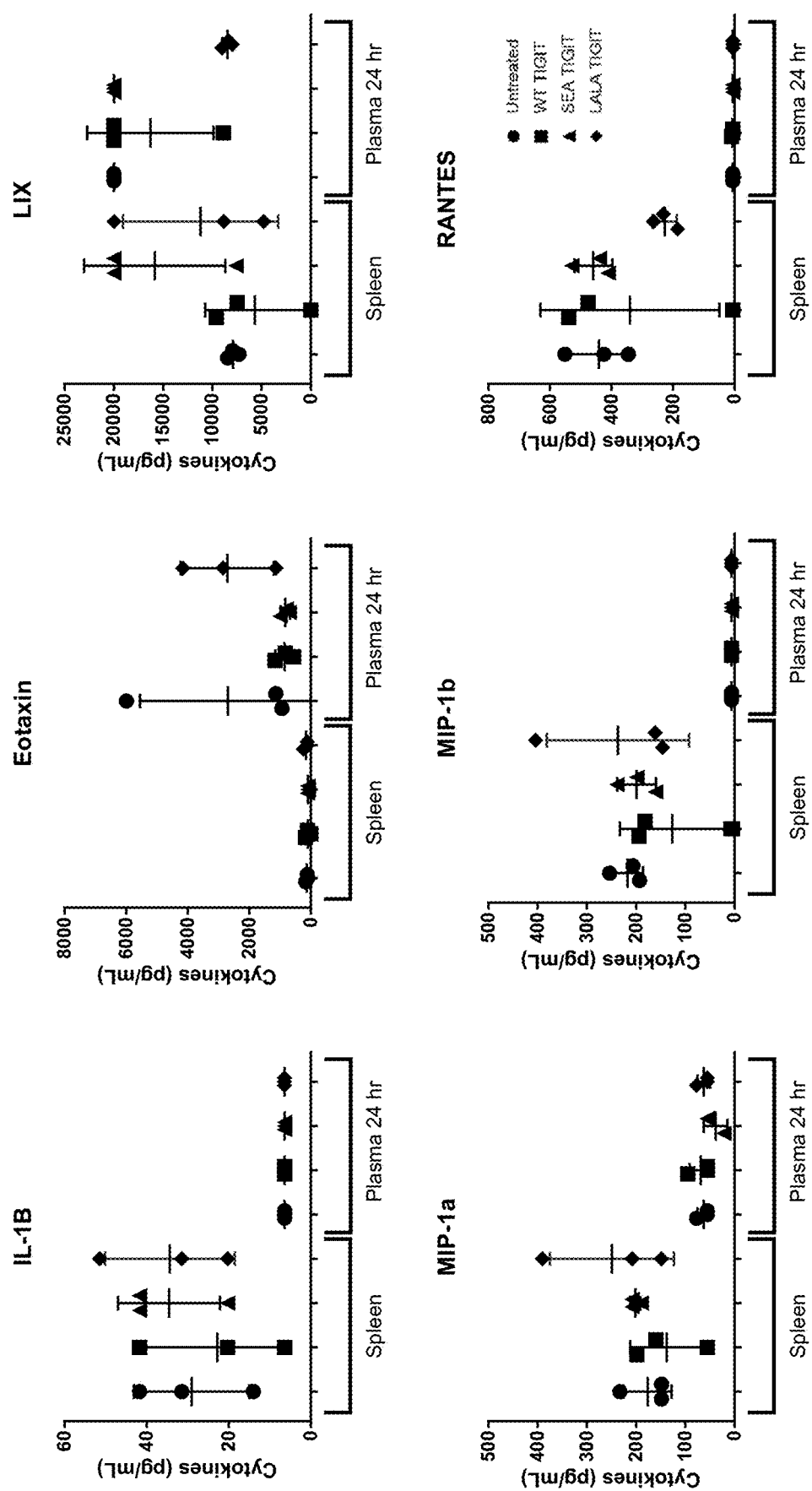
FIG. 27. Cytokine induction in plasma and spleen of CT26 colon cancer xenograft mice treated with anti-TIGIT antibody clone 13 IgG2a wild type ("WT TIGIT"), afucosylated clone 13 IgG2a ("SEA TIGIT"), or clone 13 IgG2a LALA-PG ("LALA TIGIT").

Induction of cytokines in the spleen and plasma of mice treated with anti-TIGIT antibodies was assessed using multiplex analysis and the results are shown in FIG. 27. No elevated cytokine production was observed in the spleens of treated animals when compared to untreated animals and generally low levels of cytokines were detected in the plasma, with the exception of the chemokine LIX (murine IL8 homologue) and eotaxin, which were elevated in untreated and certain anti-TIGIT antibody treated animals.

The generation of antigen-specific memory against the tumor in these animals was evaluated using splenocytes harvested at approximately 20 days after initiation of treatment with anti-TIGIT antibodies. Splenocytes from mice treated with anti-TIGIT antibodies described above were resuspended in culture media and plated in duplicate in wells of a 96-well plate. Cells were either left unstimulated or restimulated with 1 μg/ml AH1 peptide, which is the dominant target for the CD8+ T cell responses against the CT26 colorectal tumor. Forty eight hours later, culture supernatants were collected and analyzed for cytokine production via multiplex analysis.

Figure 28:
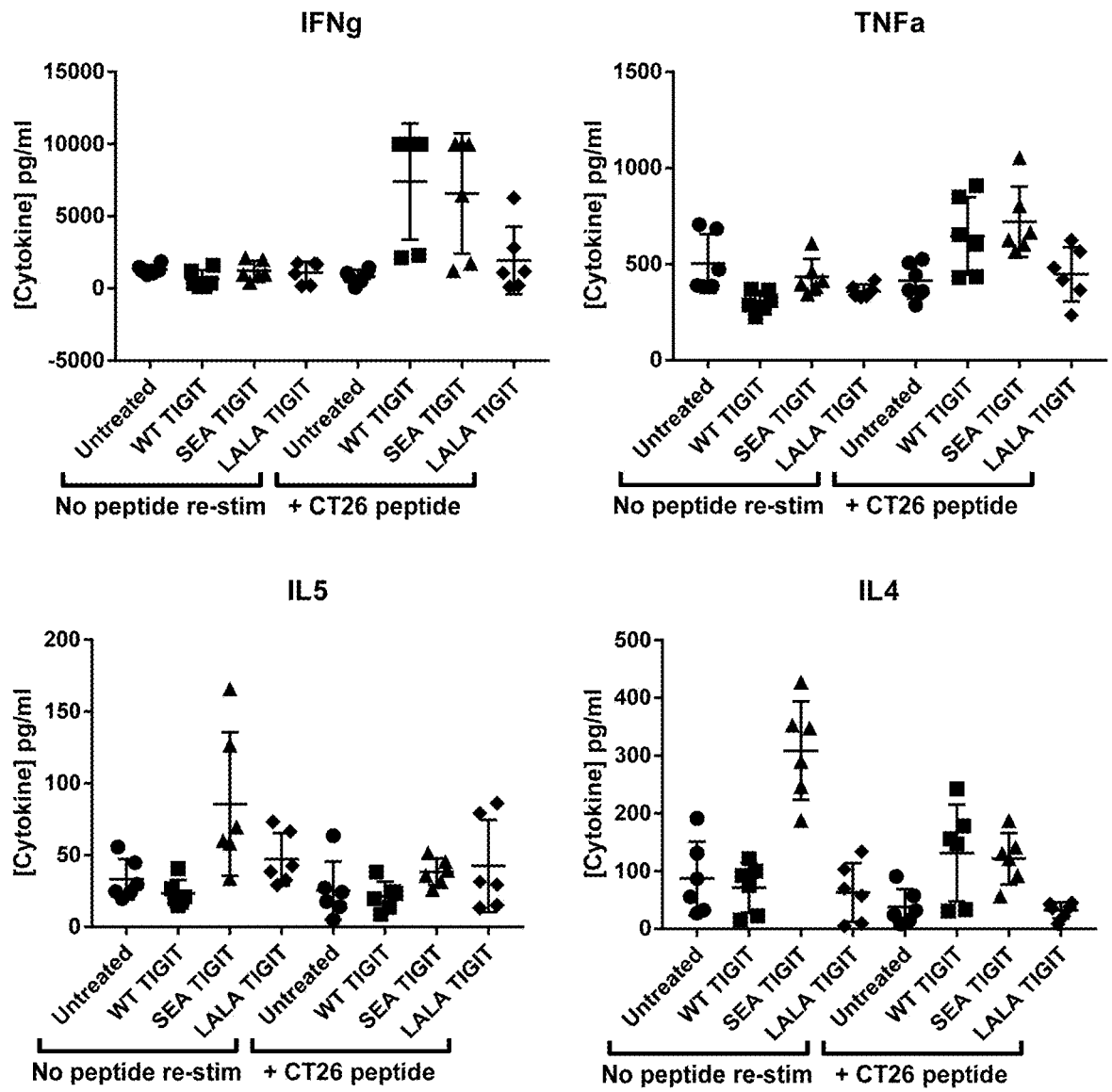
FIG. 28. Induction of antigen-specific T cell responses in mice treated with anti-TIGIT antibody clone 13 IgG2a wild type ("WT TIGIT"), afucosylated clone 13 IgG2a ("SEA TIGIT"), or clone 13 IgG2a LALA-PG ("LALA TIGIT").

As shown in FIG. 28, very little cytokine was produced in the absence of peptide. An interesting exception was the observation of elevated levels of IL5 and IL4 produced by unstimulated splenocytes from the afucosylated clone 13 mIgG2a treated animals (FIG. 28, lower panels). However, stimulation of splenocytes with a CT-26 specific peptide resulted in robust IFNγ and TNFα production in clone 13 mIgG2a wild-type and afucosylated antibody treated animals, but not in clone 13 mIgG2a LALA-PG antibody treated animals (FIG. 28, top panels), indicating that clone 13 mIgG2a wild-type and afucosylated antibody treatments are able to stimulate a long-lasting, antigen-specific memory CD8+ T cell response. Generation of memory T cell responses are involved in driving long term anti-tumor responses. Increases in IL4 production after peptide restimulation of the clone 13 mIgG2a wild-type and afucosylated antibody treated spenocytes was also observed (FIG. 28, bottom right panel). The production of IL4 and IL5 in unstimulated splenocytes in the afucosylated clone 13 mIgG2a group without restimulation may suggest induction of a TH2 response by this antibody.

Example 21: Activity of Anti-TIGIT Antibodies in Additional Murine Tumor Models

Two murine syngeneic tumor models, EMT6 and E0771 breast carcinomas, were treated with 5 mg/kg anti-TIGIT clone 13 antibody comprising wild type mIgG2a or 0.1 mg/kg, 1 mg/kg, or 5 mg/kg anti-TIGIT clone 13 antibody comprising afucosylated mIgG2a. The dosing schedule was q4dx4 (one dose every four days; four total doses). Tumor length and width were measured and tumor volume was calculated using the formula Volume ($mm^3$) $=0.5*Length*Width^2$ where length is the longer dimension.

Figure 29A:
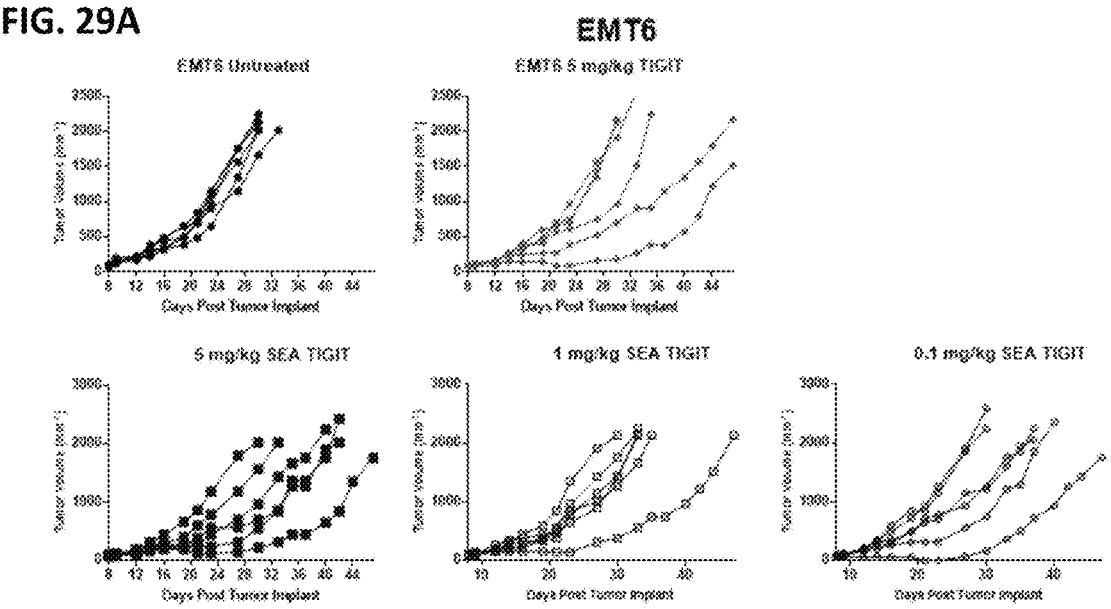
FIG. 29A-C. In vivo activity of anti-TIGIT antibodies in three different syngeneic tumor models.
Figure 29B:
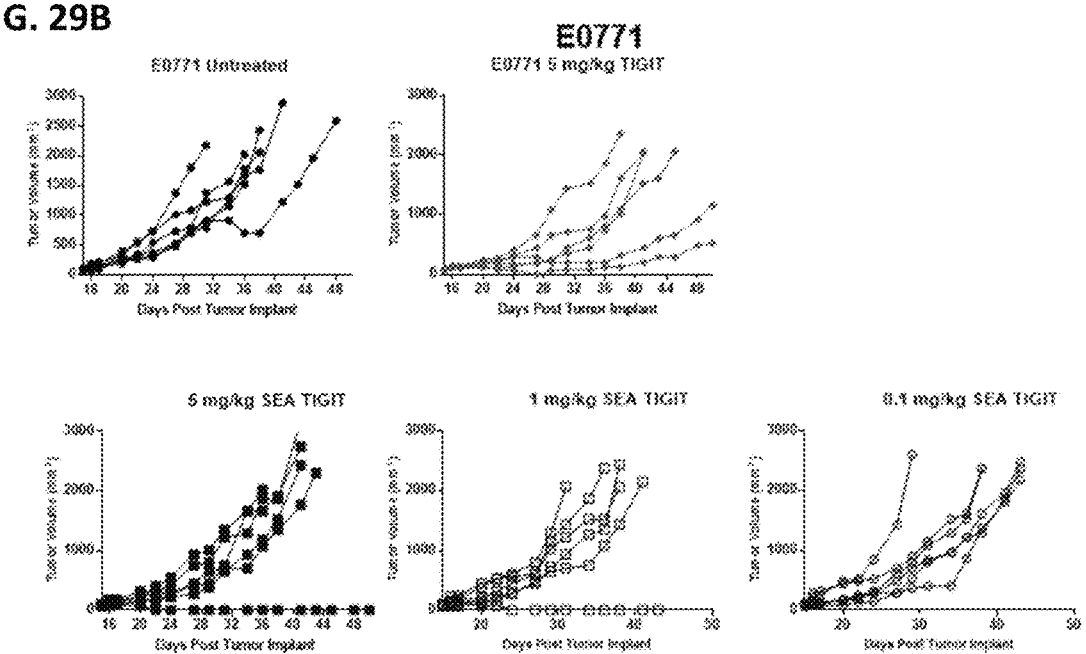

As shown in FIG. 29A-29B, anti-tumor response in the breast cancer models demonstrated tumor growth delay but minimal curative responses. In the EMT6 model, both clone 13 mIgG2a wild-type and afucosylated antibodies at 5 mg/kg demonstrated good tumor growth delay with an increase in average survival from 30.5 days to 37 and 39 days, respectively (FIG. 29A). Additional dose groups for the clone 13 mIgG2a afucosylated antibody demonstrated some loss of activity at the lower doses, with only 35.2 and 36.8 days average overall survival observed with 1 and 0.1 mg/kg doses, but tumor growth was still delayed compared to untreated controls (FIG. 29A).

In the E0771 model, a more modest tumor growth delay was observed for both clone 13 mIgG2a wild-type and afucosylated antibodies at 5 mg/kg, with an increase in average survival from 38.6 days to 44 and 42 days, respectively (FIG. 29B). Furthermore, one out of six mice appeared to be cured with the clone 13 mIgG2a afucosylated antibody at the 1 mg/kg and 5 mg/kg doses. The lower dose groups for the clone 13 mIgG2a afucosylated antibody, 1 mg/kg and 0.1 mg/kg, resulted in 39 days average overall survival (FIG. 29B).

Figure 29C:
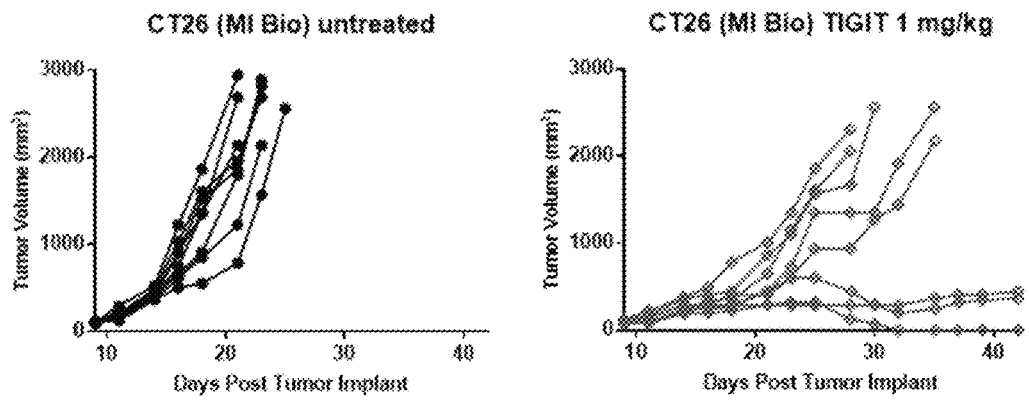

In addition, 1 mg/kg clone 13 mIgG2a wild-type antibody was evaluated in a second CT26 colon cancer model, which was obtained from an external lab (MI Bioresearch). As shown in FIG. 29C, in this CT26 colon cancer model, clone 13 mIgG2a wild-type antibody demonstrated an increase in average overall survival from 30 days to 40 days with treatment but only induced one complete regression (16%). As shown in FIG. 18B, the CT26 colon cancer model that had been maintained at Seattle Genetics showed 50% (3/6) complete regressions with 1 mg/kg clone 13 IgG2a wild-type antibody.

Example 22: RNA-Seq Analysis and Correlation of In Vivo Response with Molecule Signatures To evaluate the differences in the responses of the two CT26 colon cancer models, as well as other syngeneic cancer models, RNA-seq analysis was used to identify underlying changes in the transcriptomes between the models. RNA-seq raw reads (fastq format) for representative untreated tumors for each model was available as follows.

A20 (maintained at Seattle Genetics), 2 replicates
CT26 (maintained at Seattle Genetics), 2 replicates
CT26 (obtained from MIBio), 1 replicate
E0771 (obtained from MIBio), 1 replicate
EMT-6 (obtained from MIBio), 1 replicate
MC38 (maintained at Seattle Genetics), 1 replicate RNA-seq reads for the samples were processed on a standard pipeline consisting of adapter trimming (cutadapt), alignment to the mouse genome/transcriptome (STAR), and transcript quantification (RSEM). Gene expression values normalized to FPKM (fragments per kilobase per million reads) were used for subsequent analyses. Based on inspection of in vivo response curves, models were classified as follows in terms of their overall response to WT TIGIT treatment: complete responders=A20 (Seattle Genetics; FIG. 18A), CT26 (Seattle Genetics; FIG. 18B) and partial responders=CT26 (MIBio; FIG. 29C), EMT-6 (MIBio; FIG. 29A), E0771 (MIBio; FIG. 29B), MC38 (Seattle Genetics; FIG. 18C). Differences between the two CT26 colon cancer models at the transcriptional level were observed, suggesting it may be important to characterize models used for efficacy studies.

Molecular signatures related to the tumor microenvironment (TME) that may correlate with response were also determined by compiling gene signatures pertaining to the immune system and immune response from two published sources: Mosely et al., "Rational selection of syngeneic preclinical tumor models for immunotherapeutic drug discovery," Cancer Immunol Res 2017; 5:29-41; and TCIA, The Cancer Immunome Atlas (tcia.at/home), with signatures taken from Charoentong et al., "Pan-cancer Immunogenomic Analyses Reveal Genotype-Immunophenotype Relationships and Predictors of Response to Checkpoint Blockade," Cell Rep 2017 Jan. 3; 18(1):248-262. Gene signatures from these sources consist of lists of genes whose expression is high in a particular biological context—in CD8+ T cells, for instance. The TCIA gene signatures are human-derived, so the genes in each of those signatures were mapped to the mouse orthologs, using the R library biomaRt. Approximately 50 gene signatures were considered in total, and each of the eight RNA-seq untreated tumor samples were scored against each of the 50 signatures by summing the sample FPKM values of the genes in the signature.

Figure 30:
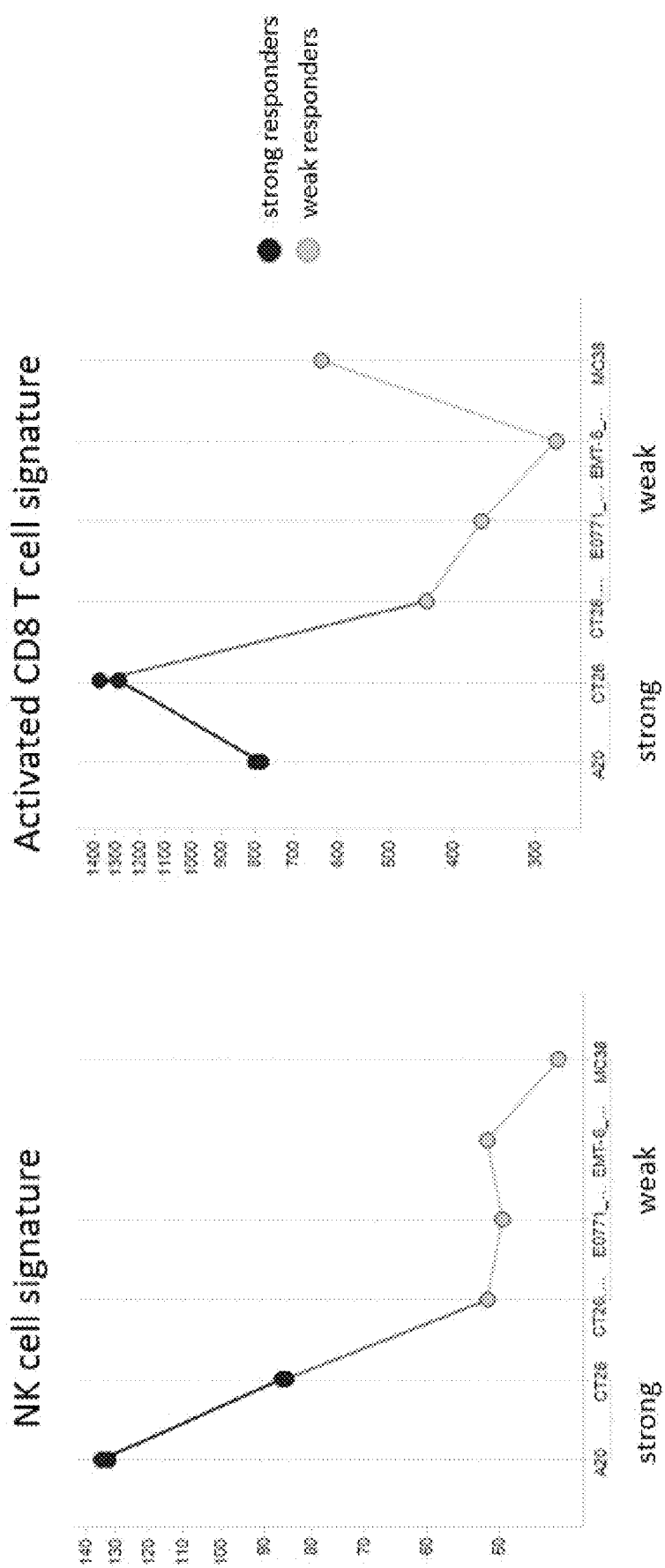
FIG. 30. Correlation of NK cell (left) and activated CD8 T cell (right) molecular signatures with syngeneic tumor model response to anti-TIGIT antibody treatment.

To evaluate quantitatively which gene signature scores separated the strong responders from the weak responders, the vector of signature scores across all samples was correlated with a response vector (Pearson correlation, 0 for weak responders, 1 for strong responders). Signatures with particularly high correlation with response included NK cells and activated CD8 T cells (FIG. 30). In both cases, the stronger responders scored higher the immune subsets compared to the weaker responders. Table 4 shows a summary of the correlation between certain immune cell subsets and response of tumor cells to anti-TIGIT antibody treatment.

TABLE 4

| Gene Signature | Correlation | P value |
| --- | --- | --- |
| Gamma delta T cell | 0.9262 | 0.0009 |
| NK cell | 0.9200 | 0.0012 |
| Activated CD8 T cell | 0.8535 | 0.0070 |
| Activated DC | −0.8437 | 0.0085 |
| Immature B cell | 0.7875 | 0.0203 |
| CD96 | 0.7569 | 0.0297 |
| CD8 T cell | 0.7569 | 0.0297 |
| CD56$^{bright}$ natural killer cell | 0.7319 | 0.0390 |
| T helper 17 cell | 0.7139 | 0.0467 |
| Activated CD4 T cell | 0.7092 | 0.0488 |

Without intending to be bound by any particular theory, as TIGIT blockade may stimulate both NK-cell and CD8 T-cell-mediated tumor killing, a larger available pool of these immune cell populations in the TME may explain the stronger response in the models scoring higher for those subsets.

Figure 31:
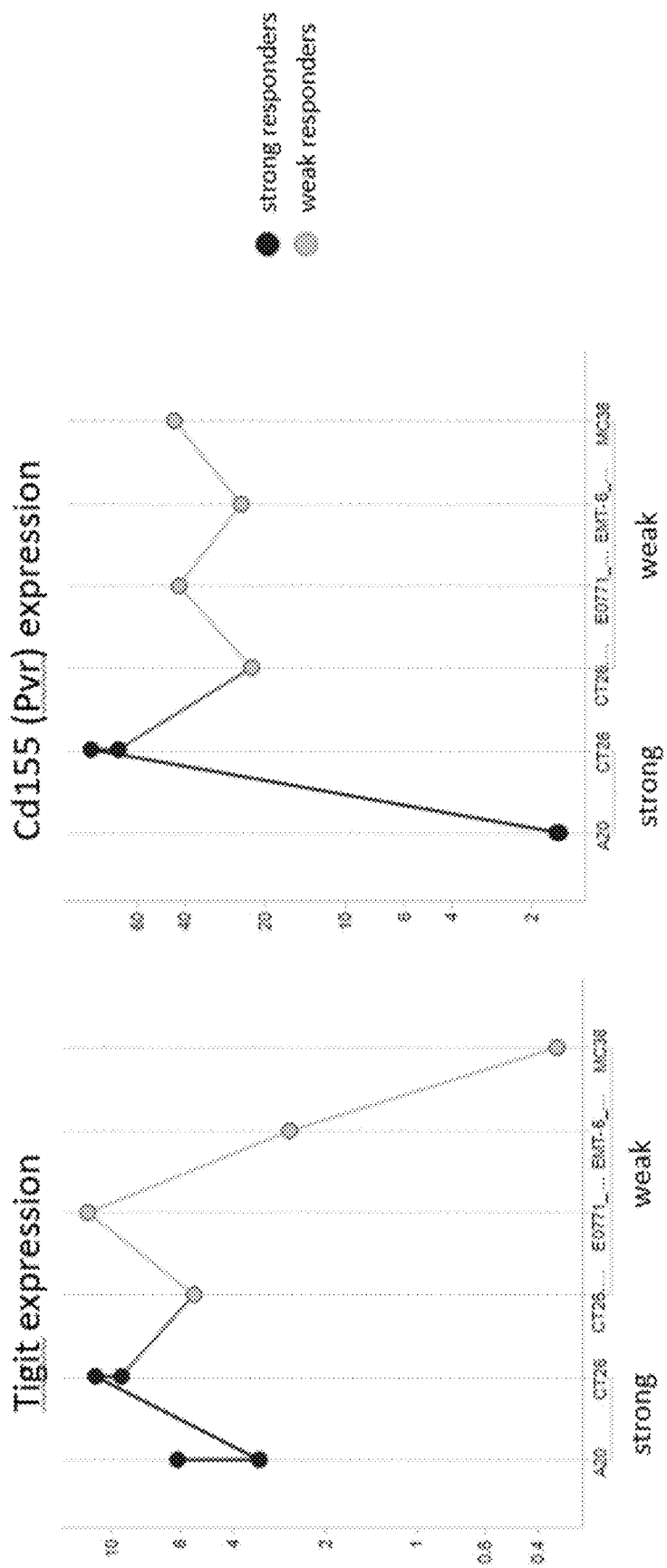
FIG. 31. Correlation of TIGIT (left) and CD155 (right) expression with syngeneic tumor model response to anti-TIGIT antibody treatment.

Interestingly, TIGIT expression was not a strong differentiator of response in this evaluation, nor was CD155 expression (FIG. 31). For example, the Seattle Genetics CT26 colon cancer model showed the highest expression of CD155 of all models, while the A20 lymphoma model had the lowest, although both are strong responders.

Example 23: Anti-TIGIT Antibody Enhances Th1 Response

To assess whether the clone 13 anti-TIGIT antibody aids in driving a naïve antigen-specific T cell response, balb/c mice (5 per group) were vaccinated once with 100 μg of the model antigen ovalbumin (OVA) in the presence of complete Freund's adjuvant (CFA) subcutaneously. At the same time, mice were administered 1 mg/kg clone 13 IgG2a wild-type, clone 13 mIgG2a afucosylated, or clone 13 mIgG2a LALA-PG antibody, and then three more doses three days apart (q3dx4). Fourteen days after vaccination, mice were analyzed for induction of antigen-specific immunity using an anti-OVA IgG1 and IgG2a ELISA. Splenocytes were re-stimulated and assessed for cytokine induction.

The anti-OVA ELISAs demonstrated that co-administration of either clone 13 IgG2a wild-type or clone 13 mIgG2a LALA-PG antibody while mice were undergoing vaccineinduced antigen-specific priming boosted the levels of IgG1 antibodies generated by ~1.5 fold. Clone 13 mIgG2a afucosylated antibody did not boost antigen-specific IgG1 antibody levels in this experiment (FIG. 32, right panel). These data suggest that TIGIT blockade is able to increase priming of a CD4/Th2 response, but enhanced effector function abrogates this effect. TIGIT blockade also boosted levels of IgG2a antigen-specific antibodies (FIG. 32, right panel), but in this case, the clone 13 mIgG2a afucosylated antibody showed the greatest effect. In sum, an inverse correlation was observed between IgG1 levels and enhanced effector function, while IgG2a levels were directly correlated with enhanced effector function, with the clone 13 mIgG2a afucosylated antibody increasing anti-OVA IgG2a levels by over 9 fold. Clone 13 IgG2a wild-type and clone 13 mIgG2a LALA-PG antibody boosted IgG2a levels also, but only by ~4 fold (FIG. 32, right panel). While TIGIT blockade alone wasn't sufficient to skew this heavily Th2-favored system, which is driven by the mouse strain and adjuvant used, toward Th1 in this experiment, TIGIT blockade was shown to enhance a Th1 response, and the response was correlated with effector function.

Figure 33:
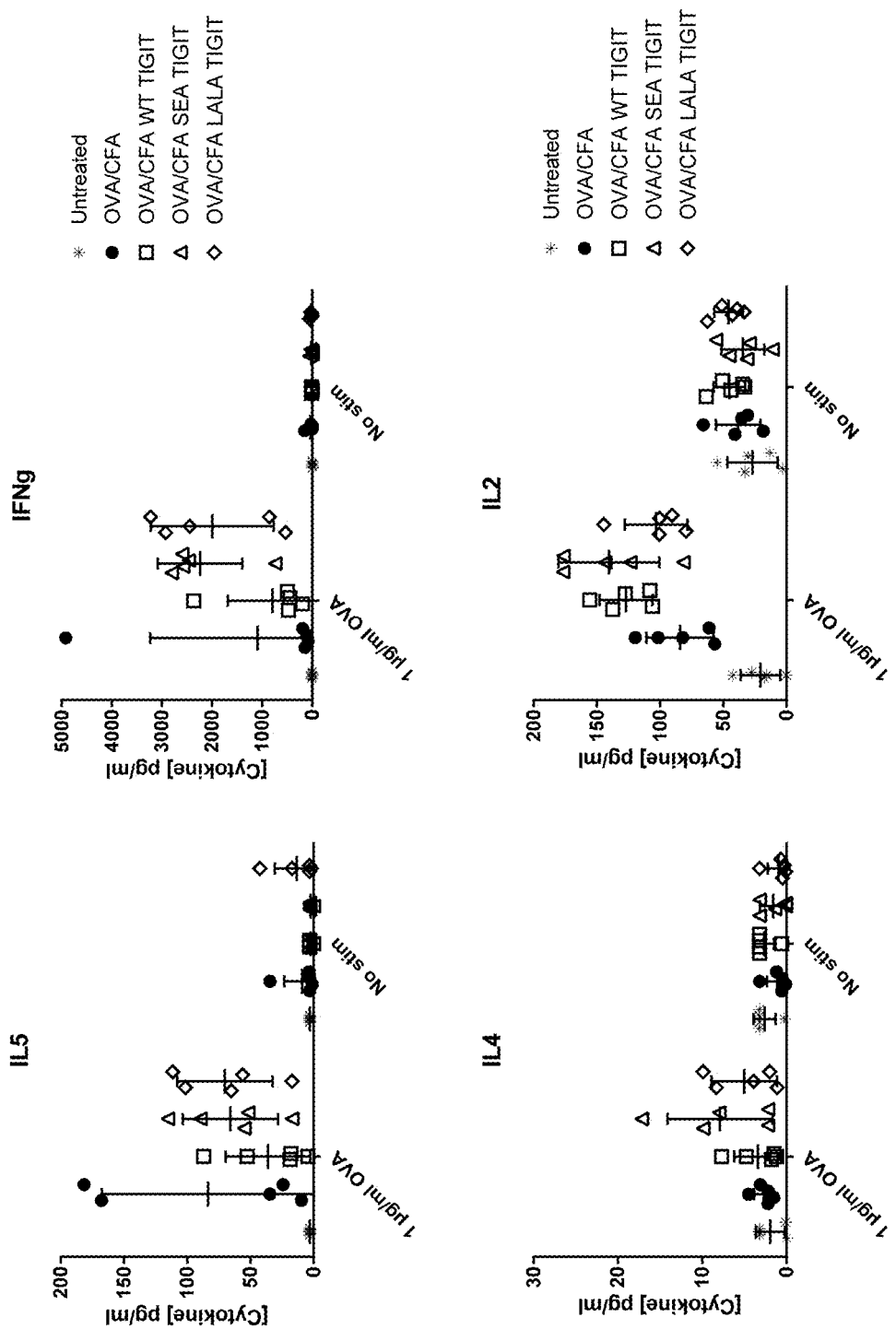
FIG. 33. Cytokine expression following re-stimulation of splenocytes ex vivo from mice treated with OVA vaccination followed by 1 mg/kg clone 13 IgG2a wild-type ("WT TIGIT"), clone 13 mIgG2a afucosylated ("SEA TIGIT"), or clone 13 mIgG2a LALA-PG ("LALA TIGIT") antibody.

In addition to analyzing antigen-specific antibody production, the induction of antigen-specific T cells was also evaluated. Equivalent numbers of splenocytes from each mouse were re-stimulated ex vivo with 1 μg whole protein (OVA) for 72 h followed by T effector cytokine analysis. Production of the activated T cell cytokine IL-2 in response to antigen re-stimulation ("1 μg/ml OVA") was increased in the antigen/adjuvant treated group over untreated animals as expected, and this was further increased in splenocytes from animals treated with effector function enabled (clone 13 IgG2a wild-type) or enhanced (clone 13 mIgG2a afucosylated) anti-TIGIT antibody during priming (FIG. 33, lower right panel). These results are consistent with the ability of TIGIT blockade to enhance generation of a naïve antigen-specific T cell response. Analysis of the Th2 effector cytokines IL-5 and IL-4 demonstrated some additional cytokine induction after antigen re-stimulation over antigen/adjuvant alone from animals treated with anti-TIGIT antibodies, though a less clear correlation between effector function and response was observed (FIG. 33, left panels). For the Th1/CD8 T cell cytokine IFNγ, TIGIT blockade during the antigen priming event more profoundly enhanced the generation of antigen-specific T cells (FIG. 33, upper right panel). The most significant boost was observed in splenocytes from animals treated with the effector enhanced clone 13 mIgG2a afucosylated antibody.

Figure 34:
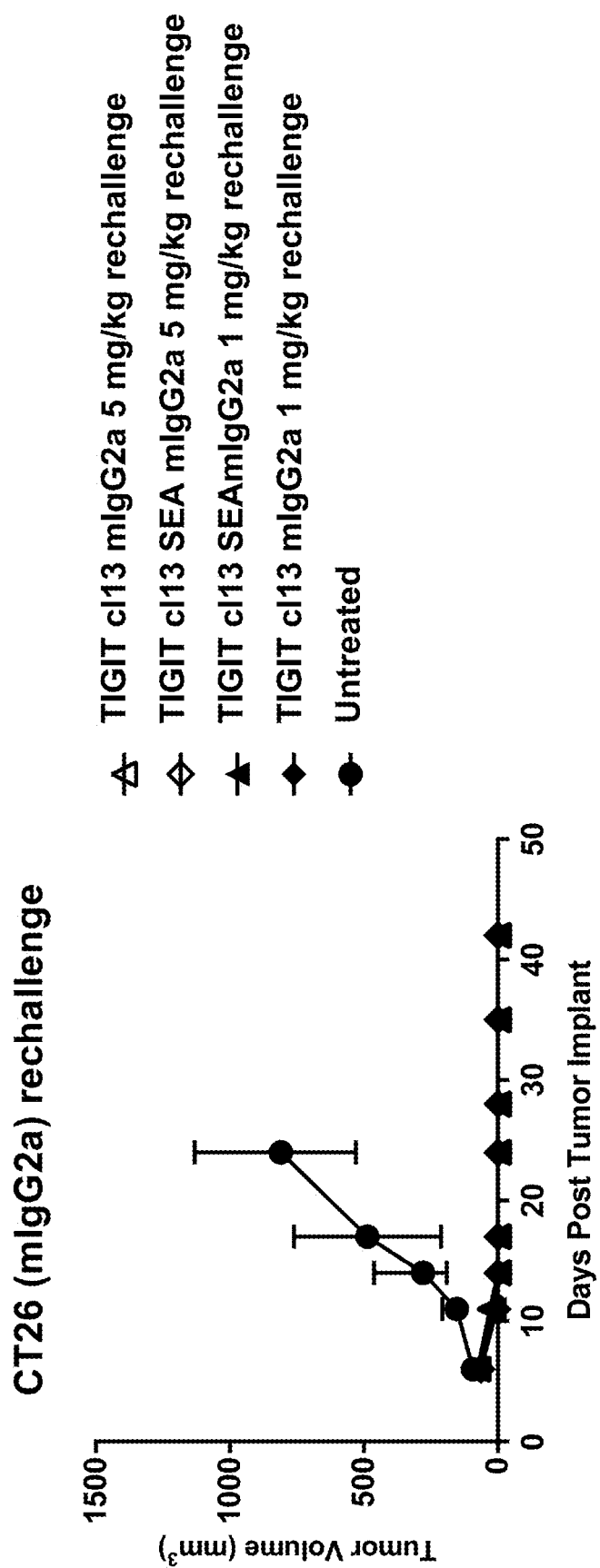
FIG. 34. Re-challenge of mice that showed a complete response in the CT26 syngeneic tumor model following treatment with clone 13 mIgG2a afucosylated antibody.

Example 24: Anti-TIGIT Antibody Induces Long-Lasting Anti-Tumor Memory CD8 T Cells Mice that showed a complete response in the CT26 colon cancer syngeneic tumor model following treatment with clone 13 mIgG2a afucosylated or unmodified antibody and four untreated mice were re-challenged with CT26 colon cancer cells. As shown in FIG. 34, the mice that had shown a complete response following 1 mg/kg or 5 mg/kg treatment with clone 13 mIgG2a afucosylated or unmodified antibody appeared to have long-lasting anti-tumor memory CD8 T cells that were capable of rejecting re-challenged tumor cells.

Although the foregoing invention has been described in some detail by way of illustration and example for purposes of clarity of understanding, one of skill in the art will appreciate that many modifications and variations of this invention can be made without departing from its spirit and scope. The specific embodiments described herein are offered by way of example only and are not meant to be limiting in any way. It is intended that the specification and examples be considered as exemplary only, with the true scope and spirit of the invention being indicated by the following claims.

Example 25: Anti-TIGIT Antibody Binding to Fcγ Receptors

In vivo, monocytes, macrophages, neutrophils, dendritic cells, and natural killer cells can mediate ADCP, ADCC, and CDC via FcγRI, FcγRII, and FcγRIIIa. To assess cellular FcγR binding, CHO cells were transfected with human FcγRI, FcγIIa, FcγIIB, or high affinity FcγRIIIa V/V receptor. Cells were exposed to increasing concentrations of wild-type, afucosylated, LALA-PG, or DLE versions of clone 13 IgG1 anti-TIGIT antibody, or another anti-TIGIT antibody, H5L4. Binding was monitored using a fluorescent-tagged anti-human Fc secondary antibody and flow cytometry.

Figure 39A:
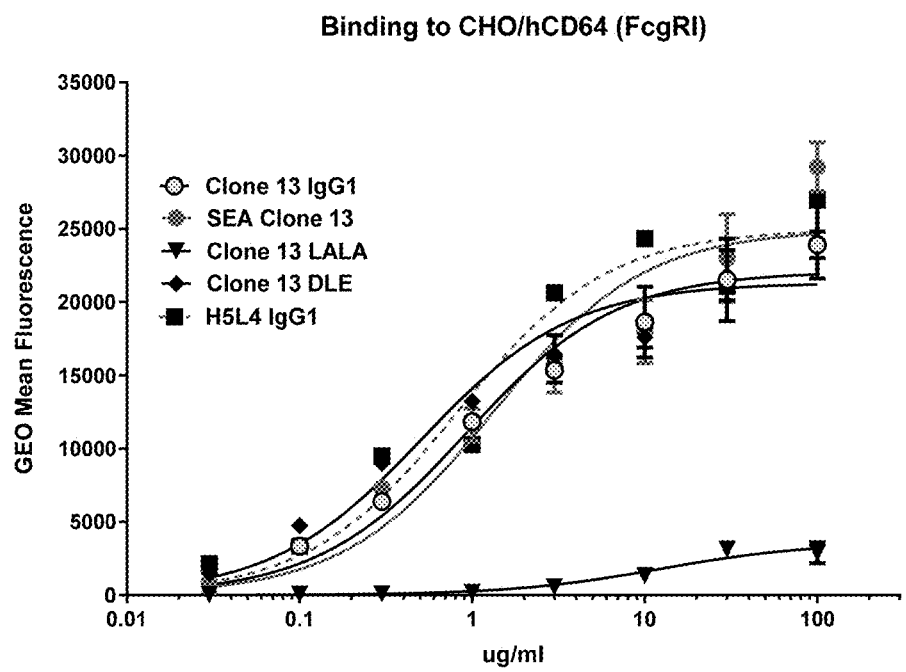
FIG. 39A-39D. Binding of anti-TIGIT antibodies clone 13 IgG1 wild-type ("Clone 13 IgG1"), clone 13 IgG1 afucosylated ("SEA Clone 13"), clone 13 LALA-PG ("Clone 13 LALA"), clone 13 IgG1 DLE ("Clone 13 DLE"), or clone H5/L4 IgG1 to FcγRI (FIG. 39A), FcγRIIIa V/V (FIG. 39B), FcγRIIb (FIG. 39C), or FcγRIIa (FIG. 39D) expressed on the surface of CHO cells.
Figure 39B:
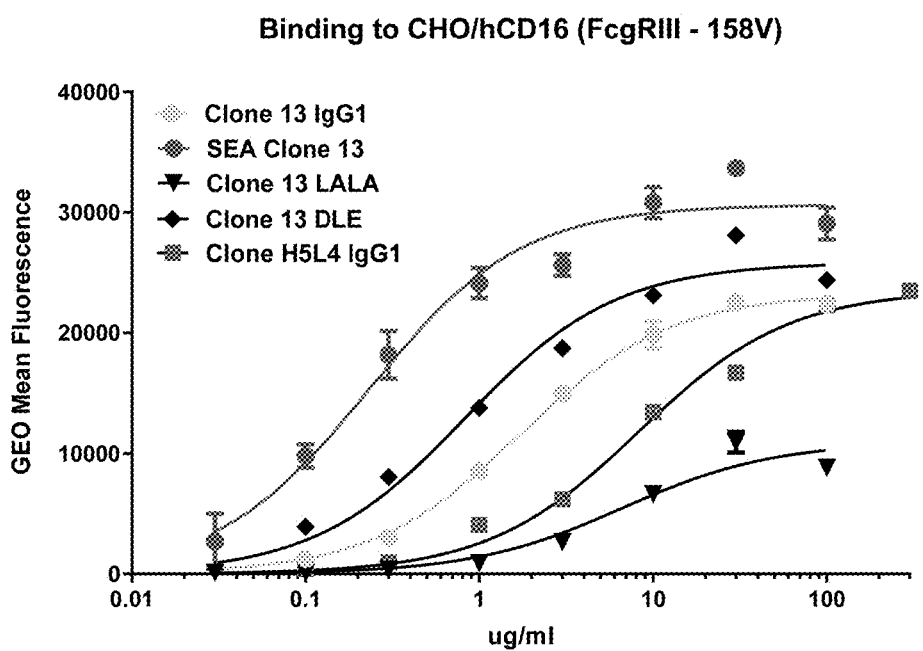
Figure 39C:
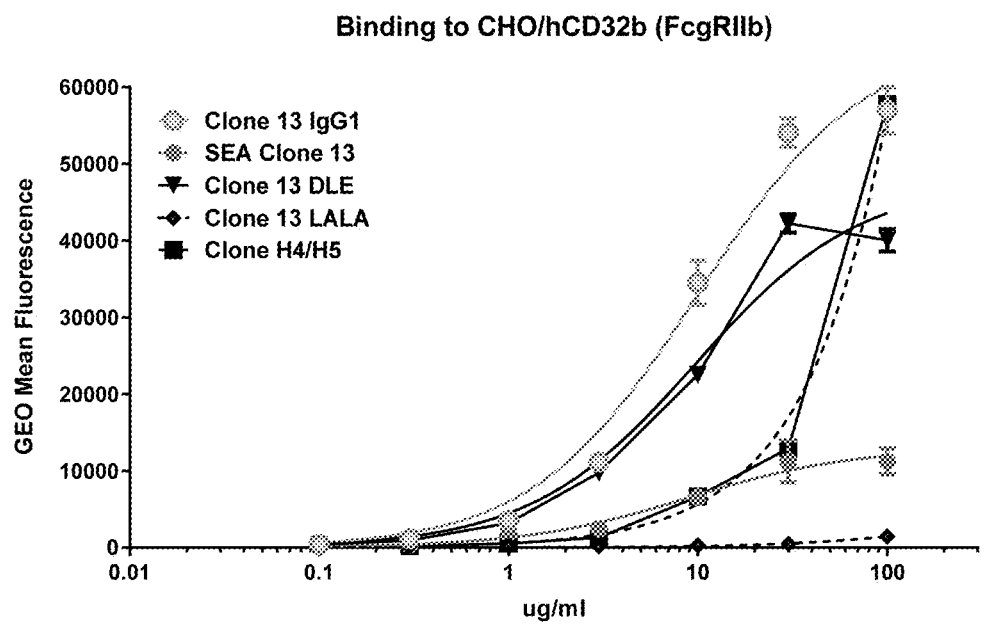
Figure 39D:
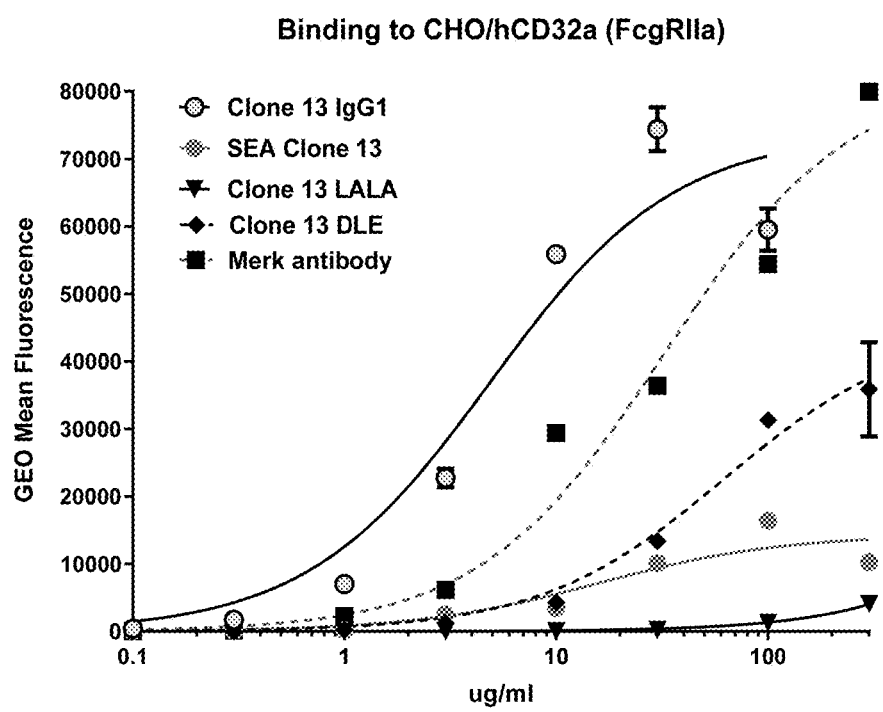

As shown in FIG. 39A, all of the antibodies except the IgG1 LALA-PG inactive backbone bound substantially equivalently to FcγRI on the surface of CHO cells. The IgG1 afucosylated and IgG1 DLE backbones exhibited increased binding to FcγRIIIa on the surface of CHO cells. FIG. 39B. Binding to both FcγRIIa and FcγRIIb on the surface of CHO cells was highest with the wild-type IgG1 backbone and IgG1 DLE effector enhanced backbone. FIG. 39C and FIG. 39D. The afucosylated IgG1 backbone had lower binding affinity to both FcγRIIa and FcγRIIb when compared to the IgG1 wild-type backbone, although its binding affinity was greater than the IgG1 LALA-PG backbone. FIG. 39C and FIG. 39D. Reduced binding to the inhibitory FcγRIIb receptor may influence immune response mediated by the afucosylated IgG1 backbone.

Example 26: Anti-TIGIT Antibody Mediated Phagocytosis

The term "antibody-dependent cellular phagocytosis" or "ADCP" refers to the process by which antibody-bound cells are internalized, either in whole or in part, by phagocytic immune cells (e.g., by macrophages, neutrophils and/or dendritic cells) that bind to an Fc region of an antibody.

Wild-type, afucosylated, and DLE versions of clone 13 IgG1 anti-TIGIT antibody were assayed for antibody-mediated phagocytosis using human monocyte/macrophages and TIGIT-positive Jurkat T cells. Human TIGIT-positive Jurkat T cells labeled with fluorescent red PKH dye were opsonized for 30 minutes with increasing concentrations of anti-TIGIT antibodies. The cells were washed and incubated at a 10:1 ratio with monocyte macrophages for 18 hours. Samples were washed 3 times and subjected to flow cytometry to assess phagocytosis.

Figure 40:
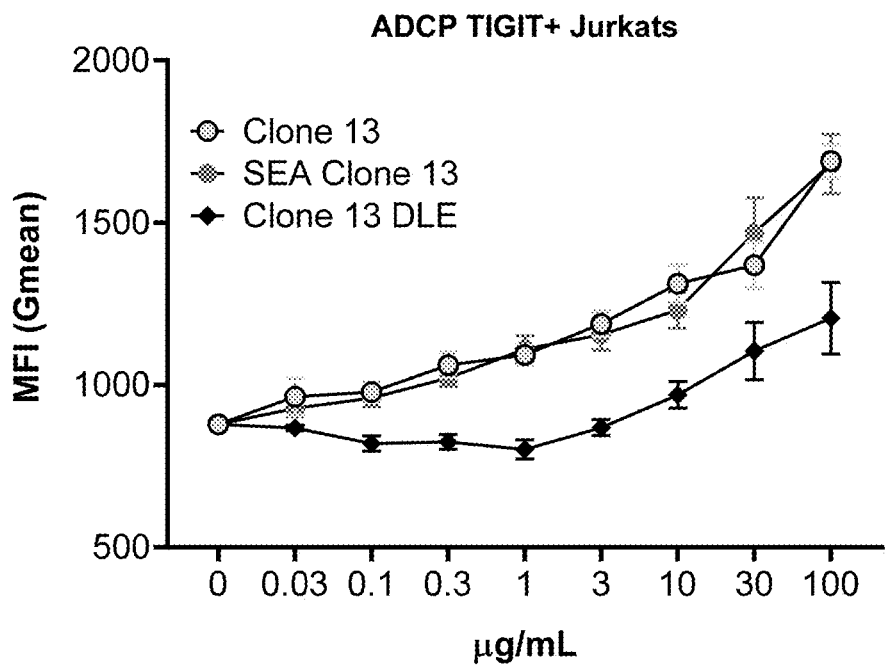
FIG. 40. Phagocytosis of TIGIT-positive Jurkat cells mediated by anti-TIGIT antibodies clone 13 IgG1 wild-type ("Clone 13"), clone 13 IgG1 afucosylated ("SEA Clone 13"), and clone 13 IgG1 DLE ("Clone 13 DLE").

As shown in FIG. 40, the wild type and afucosylated IgG1 clone 13 anti-TIGIT antibodies mediated similar levels of phagocytosis, while the clone 13 IgG1 DLE antibody was less effective at mediating phagocytic activity.

In addition to ADCC and ADCP, Fc regions of cell-bound antibodies can also activate the complement classical pathway, and elicit CDC. C1q of the complement system binds to the Fc regions of antibodies when they are complexed with antigen. Binding of C1q to cell-bound antibodies can initiate a cascade of events involving the proteolytic activation of C4 and C2 to generate the C3 convertase. Cleavage of C3 to C3b by C3 convertase enables the activation of terminal complement components, including C5b, C6, C7, C8 and C9. Collectively, these proteins form membrane-attack complex pores on the antibody-coated cells. These pores disrupt the cell membrane integrity, killing the target cell via complement-dependent cytotoxicity or "CDC".

Wild-type, afucosylated, LALA-PG, and DLE versions of clone 13 IgG1 anti-TIGIT antibody, as well as H5/L4 were assayed for CDC activity using TIGIT+Jurkat T cells as target cells. The Jurkat cells were incubated with increasing doses of the antibodies in the presence of human serum (not heat inactivated) for 2 hours at 37° C. in media containing SYTOX® green, which is excluded from live cells but taken up upon activation of CDC and lysis. After incubation, samples were analyzed on a plate reader, background signal was subtracted, and the % of maximum lysis was calculated by determining the maximum signal from cells killed with a 1% Triton X solution.

Figure 41:
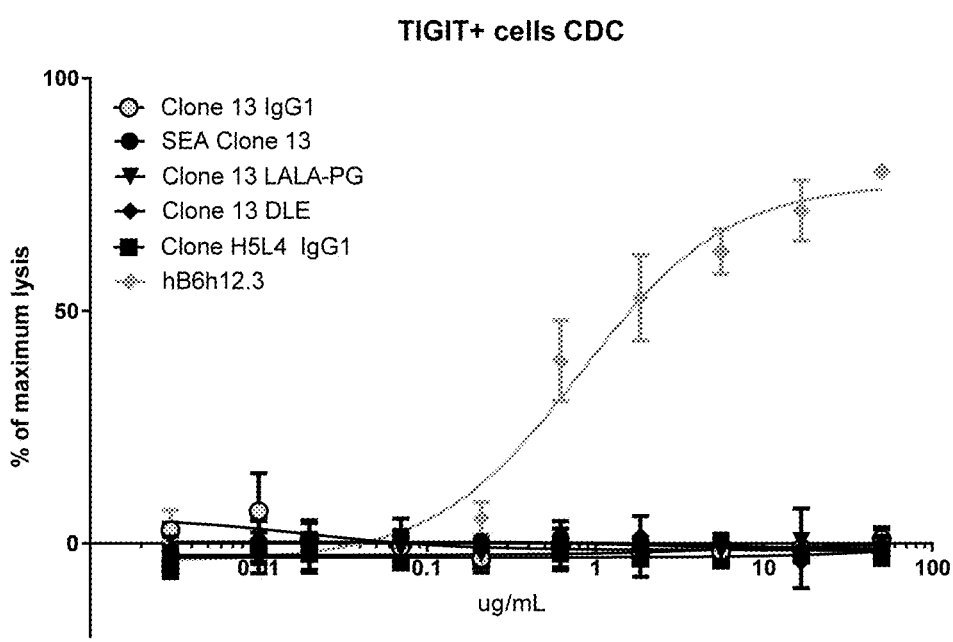
FIG. 41. CDC of TIGIT-positive Jurkat cells mediated by anti-TIGIT antibodies clone 13 IgG1 wild-type ("Clone 13 IgG1"), clone 13 IgG1 afucosylated ("SEA Clone 13"), clone 13 LALA-PG ("Clone 13 LALA-PG"), clone 13 IgG1

As shown in FIG. 41, none of the anti-TIGIT antibodies tested mediated CDC activity. In contrast, the and-CD47 antibody hB6H12.3 mediated robust CDC activity in this system. Induction of CDC by antibodies is conformationally dependent, and often depends on the epitope they bind. These results suggest the TIGIT epitope bound by the antibodies do not allow for appropriate C1q binding.

All publications, patents, patent applications or other documents cited herein are hereby incorporated by reference in their entirety for all purposes to the same extent as if each individual publication, patent, patent application, or other document was individually indicated to be incorporated by reference for all purposes.

TABLE OF SEQUENCES

| Name | SEQ ID NO | Sequence |
|---|---|---|
| Clone 2 VH Protein | 1 | EVQLVESGGGLVQPGGSLRLSCAASGFTFSDHYMDWVRQAPGKGLEWVG RTRNKANSYTTEYAASVKGRFTISRDDSKNSLYLQMNSLKTEDTAVYYCA RGQYYYGSSSRGYYYMDVWGQGTTVTVSS |
| Clone 2 VH DNA | 2 | GAGGTGCAGCTGGTGGAGTCTGGGGGAGGCTTGGTCCAGCCTGGAGGG TCCCTGAGACTCTCCTGTGCAGCCTCTGGATTCACCTTCAGTGACCACTA CATGGACTGGGTCCGCCAGGCTCCAGGGAAGGGGCTGGAGTGGGTTGG CCGTACTAGAAACAAAGCTAACAGTTACACCACAGAATACGCCGCGTC TGTGAAAGGCAGATTCACCATCTCAAGAGATGATTCAAAGAACTCACTG TATCTGCAAATGAACAGCCTGAAAACCGAGGACACGGCGGTGTACTAC TGCGCCAGAGGCCAGTACTACTACGGCAGCAGCAGCAGAGGTTACTAC TACATGGACGTATGGGGCCAGGGAACAACCGTCACCGTCTCCTCA |
| Clone 2 VH FR1 | 3 | EVQLVESGGGLVQPGGSLRLSCAASG |
| Clone 2 VH CDR1 | 4 | FTFSDHYMD |
| Clone 2 VH FR2 | 5 | WVRQAPGKGLEWVG |
| Clone 2 VH CDR2 | 6 | RTRNKANSYTTEYAASVKG |
| Clone 2 VH FR3 | 7 | RFTISRDDSKNSLYLQMNSLKTEDTAVYYC |
| Clone 2 VH CDR3 | 8 | ARGQYYYGSSSRGYYYMDV |
| Clone 2 VH FR4 | 9 | WGQGTTVTVSS |
| Clones 2 and 2C VL Protein | 10 | EIVLTQSPGTLSLSPGERATLSCRASQSVSSSYLAWYQQKPGQAPRLLIYGA SSRATGIPDRFSGSGSGTDFTLTISRLEPEDFAVYYCQQAVPSPLTFGGGTKV EIK |
| Clone 2 VL DNA | 11 | GAAATTGTGTTGACGCAGTCTCCAGGCACCCTGTCTTTGTCTCCAGGGG AAAGAGCCACCCTCTCCTGCAGGGCCAGTCAGAGTGTTAGCAGCAGCT ACTTAGCCTGGTACCAGCAGAAACCTGGCCAGGCTCCCAGGCTCCTCAT CTATGGTGCATCCAGCAGGGCCACTGGCATCCCAGACAGGTTCAGTGGC AGTGGGTCTGGGACAGACTTCACTCTCACCATCAGCAGACTGGAGCCTG AAGATTTTGCAGTGTATTACTGTCAGCAGGCCGTCCCCAGTCCTCTCACT TTTGGCGGAGGGACCAAGGTTGAGATCAAA |
| Clone 2 VL FR1 | 12 | EIVLTQSPGTLSLSPGERATLSC |
| Clones 2 and 2C VL CDR1 | 13 | RASQSVSSSYLA |
| Clone 2 VL FR2 | 14 | WYQQKPGQAPRLLIY |
| Clones 2 and 2C VL CDR2 | 15 | GASSRAT |
| Clone 2 VL FR3 | 16 | GIPDRFSGSGSGTDFTLTISRLEPEDFAVYYC |
| Clones 2 and 2CVL CDR3 | 17 | QQAVPSPLT |
| Clone 2 VL FR4 | 18 | FGGGTKVEIK |

TABLE OF SEQUENCES-continued

| Name | SEQ ID NO | Sequence |
|---|---|---|
| Clone 3 VH Protein | 19 | EVQLVESGGGLVQPGGSLRLSCAASGFTFSDHYMDWVRQAPGKGLEWVG<br>RTRNKANSYTTEYAASVKGRFTISRDDSKNSLYLQMNSLKTEDTAVYYCA<br>RGQYYYGSSSRGYYYMDVWGQGTTVTVSS |
| Clone 3 VH DNA | 20 | GAGGTGCAGCTGGTGGAGTCTGGGGGAGGCTTGGTCCAGCCTGGAGGG<br>TCCCTGAGACTCTCCTGTGCAGCCTCTGGATTCACCTTCAGTGACCACTA<br>CATGGACTGGGTCCGCCAGGCTCCAGGGAAGGGGCTGGAGTGGGTTGG<br>CCGTACTAGAAACAAAGCTAACAGTTACACCACAGAATACGCCGCGTC<br>TGTGAAAGGCAGATTCACCATCTCAAGAGATGATTCAAAGAACTCACTG<br>TATCTGCAAATGAACAGCCTGAAAACCGAGGACACGGCGGTGTACTAC<br>TGCGCCAGAGGCCAGTACTACTACGGCAGCAGCAGCAGAGGTTACTAC<br>TACATGGACGTATGGGGCCAGGGAACAACCGTCACCGTCTCCTCA |
| Clone 3 VH FR1 | 21 | EVQLVESGGGLVQPGGSLRLSCAASG |
| Clone 3 VH CDR1 | 22 | FTFSDHYMD |
| Clone 3 VH FR2 | 23 | WVRQAPGKGLEWVG |
| Clone 3 VH CDR2 | 24 | RTRNKANSYTTEYAASVKG |
| Clone 3 VH FR3 | 25 | RFTISRDDSKNSLYLQMNSLKTEDTAVYYC |
| Clone 3 VH CDR3 | 26 | ARGQYYYGSSSRGYYYMDV |
| Clone 3 VH FR4 | 27 | WGQGTTVTVSS |
| Clone 3 VL Protein | 28 | EIVLTQSPGTLSLSPGERATLSCRASQSVRSSYLAWYQQKPGQAPRLLIYGA<br>SSRATGIPDRFSGSGSGTDFTLTISRLEPEDFAVYYCQQVGPPLTFGGGTKVE<br>IK |
| Clone 3 VL DNA | 29 | GAAATTGTGTTGACGCAGTCTCCAGGCACCCTGTCTTTGTCTCCAGGGG<br>AAAGAGCCACCCTCTCCTGCAGGGCCAGTCAGAGTGTTAGGAGCAGCT<br>ACTTAGCCTGGTACCAGCAGAAACCTGGCCAGGCTCCCAGGCTCCTCAT<br>CTATGGTGCATCCAGCAGGGCCACTGGCATCCCAGACAGGTTCAGTGGC<br>AGTGGGTCTGGGACAGACTTCACTCTCACCATCAGCAGACTGGAGCCTG<br>AAGATTTTGCAGTGTATTACTGTCAGCAGGTCGGACCCCCCCCTCACTTTT<br>GGCGGAGGGACCAAGGTTGAGATCAAA |
| Clone 3 VL FR1 | 30 | EIVLTQSPGTLSLSPGERATLSC |
| Clone 3 VL CDR1 | 31 | RASQSVRSSYLA |
| Clone 3 VL FR2 | 32 | WYQQKPGQAPRLLIY |
| Clone 3 VL CDR2 | 33 | GASSRAT |
| Clone 3 VL FR3 | 34 | GIPDRFSGSGSGTDFTLTISRLEPEDFAVYYC |
| Clone 3 VL CDR3 | 35 | QQVGPPLT |
| Clone 3 VL FR4 | 36 | FGGGTKVEIK |
| Clone 5 VH Protein | 37 | EVQLLESGGGLVQPGGSLRLSCAASGFTFSTYAMSWVRQAPGKGLEWVSA<br>ISGSGGSTYYADSVKGRFTISRDNSKNTLYLQMNSLRAEDTAVYYCAKGPR<br>YQDRAGMDVWGQGTTVTVSS |
| Clone 5 VH DNA | 38 | GAGGTGCAGCTGTTGGAGTCTGGGGGAGGCTTGGTACAGCCTGGGGGG<br>TCCCTGAGACTCTCCTGTGCAGCCTCTGGATTCACCTTTAGCACCTATGC<br>CATGAGCTGGGTCCGCCAGGCTCCAGGGAAGGGGCTGGAGTGGGTCTC<br>AGCTATTAGTGGTAGTGGTGGTAGCACATACTACGCAGACTCCGTGAAG<br>GGCCGGTTCACCATCTCCAGAGACAATTCCAAGAACACGCTGTATCTGC<br>AAATGAACAGCCTGAGAGCCGAGGACACGGCGGTGTACTACTGCGCCA<br>GAGGCCCCAGATACCAAGACAGGGCAGGAATGGACGTATGGGGCCAGG<br>GAACAACTGTCACCGTCTCCTCA |
| Clone 5 VH FR1 | 39 | EVQLLESGGGLVQPGGSLRLSCAASG |
| Clone 5 VH CDR1 | 40 | FTFSTYAMS |
| Clone 5 VH FR2 | 41 | WVRQAPGKGLEWVS |
| Clone 5 VH CDR2 | 42 | AISGSGGSTYYADSVKG |
| Clone 5 VH FR3 | 43 | RFTISRDNSKNTLYLQMNSLRAEDTAVYYC |

TABLE OF SEQUENCES-continued

| Name | SEQ ID NO | Sequence |
|---|---|---|
| Clone 5 VH CDR3 | 44 | AKGPRYQDRAGMDV |
| Clone 5 VH FR4 | 45 | WGQGTTVTVSS |
| Clone 5 VL Protein | 46 | DIQMTQSPSSLSASVGDRVTITCRASQSISSYLNWYQQKPGKAPKLLIYAAS SLQSGVPSRFSGSGSGTDFTLTISSLQPEDFATYYCQQSLATPYTFGGGTKV EIK |
| Clone 5 VL DNA | 47 | GACATCCAGATGACCCAGTCTCCATCCTCCCTGTCTGCATCTGTAGGAG ACAGAGTCACCATCACTTGCCGGGCAAGTCAGAGCATTAGCAGCTATTT AAATTGGTATCAGCAGAAACCAGGGAAAGCCCCTAAGCTCCTGATCTAT GCTGCATCCAGTTTGCAAAGTGGGGTCCCATCAAGGTTCAGTGGCAGTG GATCTGGGACAGATTTCACTCTCACCATCAGCAGTCTGCAACCTGAAGA TTTTGCAACTTACTACTGTCAGCAAAGCCTCGCCACTCCTTACACTTTTG GCGGAGGGACCAAGGTTGAGATCAAA |
| Clone 5 VL FR1 | 48 | DIQMTQSPSSLSASVGDRVTITC |
| Clone 5 VL CDR1 | 49 | RASQSISSYLN |
| Clone 5 VL FR2 | 50 | WYQQKPGKAPKLLIY |
| Clone 5 VL CDR2 | 51 | AASSLQS |
| Clone 5 VL FR3 | 52 | GVPSRFSGSGSGTDFTLTISSLQPEDFATYYC |
| Clone 5 VL CDR3 | 53 | QQSLATPYT |
| Clone 5 VL FR4 | 54 | FGGGTKVEIK |
| Clone 13 VH Protein | 55 | QVQLVQSGAEVKKPGSSVKVSCKASGGTFSSYAISWVRQAPGQGLEWMG SIIPIFGTANYAQKFQGRVTITADESTSTAYMELSSLRSEDTAVYYCARGPSE VGAILGYVWFDPWGQGTLVTVSS |
| Clone 13 VH DNA | 56 | CAGGTGCAGCTGGTGCAGTCTGGGGCTGAGGTGAAGAAGCCTGGGTCC TCGGTGAAGGTCTCCTGCAAGGCTTCTGGAGGCACCTTCAGCAGCTATG CTATCAGCTGGGTGCGACAGGCCCCTGGACAAGGGCTTGAGTGGATGG GAAGCATCATCCCTATCTTTGGTACAGCAAACTACGCACAGAAGTTCCA GGGCAGAGTCACGATTACCGCGGACGAATCCACGAGCACAGCCTACAT GGAGCTGAGCAGCCTGAGATCTGAGGACACGGCGGTGTACTACTGCGC CAGAGGCCCTTCTGAAGTAGGAGCAATACTCGGATATGTATGGTTCGAC CCATGGGGACAGGGTACATTGGTCACCGTCTCCTCA |
| Clone 13 VH FR1 | 57 | QVQLVQSGAEVKKPGSSVKVSCKASG |
| Clone 13 VH CDR1 | 58 | GTFSSYAIS |
| Clone 13 VH FR2 | 59 | WVRQAPGQGLEWMG |
| Clone 13 VH CDR2 | 60 | SIIPIFGTANYAQKFQG |
| Clone 13 VH FR3 | 61 | RVTITADESTSTAYMELSSLRSEDTAVYYC |
| Clones 13 and 13A VH CDR3 | 62 | ARGPSEVGAILGYVWFDP |
| Clone 13 VH FR4 | 63 | WGQGTLVTVSS |
| Clones 13, 13A, 13B, 13C, and 13D VL Protein | 64 | DIVMTQSPLSLPVTPGEPASISCRSSQSLLHSNGYNYLDWYLQKPGQSPQLL IYLGSNRASGVPDRFSGSGSGTDFTLKISRVEAEDVGVYYCMQARRIPITFG GGTKVEIK |
| Clone 13 VL DNA | 65 | GATATTGTGATGACTCAGTCTCCACTCTCCCTGCCCGTCACCCCTGGAG AGCCGGCCTCCATCTCCTGCAGGTCTAGTCAGAGCCTCCTGCATAGTAA TGGATACAACTATTTGGATTGGTACCTGCAGAAGCCAGGGCAGTCTCCA CAGCTCCTGATCTATTTGGGTTCTAATCGGGCCTCCGGGGTCCCTGACA GGTTCAGTGGCAGTGGATCAGGCACAGATTTTACACTGAAAATCAGCA GAGTGGAGGCTGAGGATGTTGGGGTTTATTACTGCATGCAGGCAAGAC GAATCCCTATCACTTTTGGCGGAGGGACCAAGGTTGAGATCAAA |

TABLE OF SEQUENCES-continued

| Name | SEQ ID NO | Sequence |
|---|---|---|
| Clone 13 VL FR1 | 66 | DIVMTQSPLSLPVTPGEPASISC |
| Clones 13, 13A, 13B, 13C, and 13D VL CDR1 | 67 | RSSQSLLHSNGYNYLD |
| Clone 13 VL FR2 | 68 | WYLQKPGQSPQLLIY |
| Clones 13, 13A, 13B, 13C, and 13D VL CDR2 | 69 | LGSNRAS |
| Clone 13 VL FR3 | 70 | GVPDRFSGSGSGTDFTLKISRVEAEDVGVYYC |
| Clones 13, 13A, 13B, 13C, and 13D VL CDR3 | 71 | MQARRIPIT |
| Clone 13 VL FR4 | 72 | FGGGTKVEIK |
| Clone 14 VH Protein | 73 | QVQLVQSGAEVKKPGSSVKVSCKASGGTFSSYAISWVRQAPGQGLEWMG SIIPIFGTANYAQKFQGRVTITADESTSTAYMELSSLRSEDTAVYYCARGPSE VGAILGYVWFDPWGQGTLVTVSS |
| Clone 14 VH DNA | 74 | CAGGTGCAGCTGGTGCAGTCTGGGGCTGAGGTGAAGAAGCCTGGGTCC TCGGTGAAGGTCTCCTGCAAGGCTTCTGGAGGCACCTTCAGCAGCTATG CTATCAGCTGGGTGCGACAGGCCCCTGGACAAGGGCTTGAGTGGATGG GAAGCATCATCCCTATCTTTGGTACAGCAAACTACGCACAGAAGTTCCA GGGCAGAGTCACGATTACCGCGGACGAATCCACGAGCACAGCCTACAT GGAGCTGAGCAGCCTGAGATCTGAGGACACGGCCGTGTACTACTGCGC CAGAGGCCCTTCTGAAGTAGGAGCAATACTCGGATATGTATGGTTCGAC CCATGGGACAGGGTACATTGGTCACCGTCTCCTCA |
| Clone 14 VH FR1 | 75 | QVQLVQSGAEVKKPGSSVKVSCKASG |
| Clone 14 VH CDR1 | 76 | GTFSSYAIS |
| Clone 14 VH FR2 | 77 | WVRQAPGQGLEWMG |
| Clone 14 VH CDR2 | 78 | SIIPIFGTANYAQKFQG |
| Clone 14 VH FR3 | 79 | RVTITADESTSTAYMELSSLRSEDTAVYYC |
| Clone 14 VH CDR3 | 80 | ARGPSEVGAILGYVWFDP |
| Clone 14 VH FR4 | 81 | WGQGTLVTVSS |
| Clone 14 VL Protein | 82 | DIVMTQSPLSLPVTPGEPASISCRSSQSLLHSNGYNYLDWYLQKPGQSPQLL IYLGSNRASGVPDRFSGSGSGTDFTLKISRVEAEDVGVYYCMQAKRLPLTF GGGTKVEIK |
| Clone 14 VL DNA | 83 | GATATTGTGATGACTCAGTCTCCACTCTCCCTGCCCGTCACCCCTGGAG AGCCGGCCTCCATCTCCTGCAGGTCTAGTCAGAGCCTCCTGCATAGTAA TGGATACAACTATTTGGATTGGTACCTGCAGAAGCCAGGGCAGTCTCCA CAGCTCCTGATCTATTTGGGTTCTAATCGGGCCTCCGGGGTCCCTGACA GGTTCAGTGGCAGTGGATCAGGCACAGATTTTACACTGAAAATCAGCA GAGTGGAGGCTGAGGATGTTGGGGTTTATTACTGCATGCAGGCAAAAC GACTCCCTCTCACTTTTGGCGGAGGGACCAAGGTTGAGATCAAA |
| Clone 14 VL FR1 | 84 | DIVMTQSPLSLPVTPGEPASISC |
| Clone 14 VL CDR1 | 85 | RSSQSLLHSNGYNYLD |
| Clone 14 VL FR2 | 86 | WYLQKPGQSPQLLIY |
| Clone 14 VL CDR2 | 87 | LGSNRAS |
| Clone 14 VL FR3 | 88 | GVPDRFSGSGSGTDFTLKISRVEAEDVGVYYC |
| Clone 14 VL CDR3 | 89 | MQAKRLPLT |
| Clone 14 VL FR4 | 90 | FGGGTKVEIK |

TABLE OF SEQUENCES-continued

| Name | SEQ ID NO | Sequence |
|---|---|---|
| Clone 16 VH Protein | 91 | QVQLVQSGAEVKKPGSSVKVSCKASGGTFSSYAISWVRQAPGQGLEWMG GIIPIFGTASYAQKFQGRVTITADESTSTAYMELSSLRSEDTAVYYCARQST WHKLYGTDVWGQGTTVTVSS |
| Clone 16 VH DNA | 92 | CAGGTGCAGCTGGTGCAGTCTGGGGCTGAGGTGAAGAAGCCTGGGTCC TCGGTGAAGGTCTCCTGCAAGGCTTCTGGAGGCACCTTCAGCAGCTATG CTATCAGCTGGGTGCGACAGGCCCCTGGACAAGGGCTTGAGTGGATGG GAGGGATCATCCCTATCTTTGGTACAGCAAGCTACGCACAGAAGTTCCA GGGCAGAGTCACGATTACCGCGGACGAATCCACGAGCACAGCCTACAT GGAGCTGAGCAGCCTGAGATCTGAGGACACGGCGGTGTACTACTGCGC AAGACAGAGCACCTGGCACAAATTGTACGGAACGGACGTATGGGGCCA GGGAACAACTGTCACCGTCTCCTCA |
| Clone 16 VH FR1 | 93 | QVQLVQSGAEVKKPGSSVKVSCKASG |
| Clone 16 VH CDR1 | 94 | GTFSSYAIS |
| Clone 16 VH FR2 | 95 | WVRQAPGQGLEWMG |
| Clone 16 VH CDR2 | 96 | GIIPIFGTASYAQKFQG |
| Clone 16 VH FR3 | 97 | RVTITADESTSTAYMELSSLRSEDTAVYYC |
| Clone 16 VH CDR3 | 98 | ARQSTWHKLYGTDV |
| Clone 16 VH FR4 | 99 | WGQGTTVTVSS |
| Clones 16, 16C, 16D, and 16E VL Protein | 100 | DIQMTQSPSSVSASVGDRVTITCRASQGISSWLAWYQQKPGKAPKLLIYAA SSLQSGVPSRFSGSGSGTDFTLTISSLQPEDFATYYCQQGDSLPPTFGGGTKV EIK |
| Clone 16 VL DNA | 101 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTAT GCTGCATCCAGTTTGCAAAGTGGGGTCCCATCAAGGTTCAGCGGCAGTG GATCTGGGACAGATTTCACTCTCACCATCAGCAGCCTGCAGCCTGAAGA TTTTGCAACTTATTACTGTCAGCAGGGAGACAGTCTCCCTCCTACTTTTG GCGGAGGGACCAAGGTTGAGATCAAA |
| Clone 16 VL FR1 | 102 | DIQMTQSPSSVSASVGDRVTITC |
| Clones 16, 16C, 16D, and 16E VL CDR1 | 103 | RASQGISSWLA |
| Clone 16 VL FR2 | 104 | WYQQKPGKAPKLLIY |
| Clones 16, 16C, 16D, and 16E VL CDR2 | 105 | AASSLQS |
| Clone 16 VL FR3 | 106 | GVPSRFSGSGSGTDFTLTISSLQPEDFATYYC |
| Clones 16, 16C, 16D, and 16E VL CDR3 | 107 | QQGDSLPPT |
| Clone 16 VL FR4 | 108 | FGGGTKVEIK |
| Clone 18 VH Protein | 109 | QVQLVQSGAEVKKPGASVKVSCKASGYTFTSYYMSWVRQAPGQGLEWM GIINPSGGSTSYAQKFQGRVTMTRDTSTSTVYMELSSLRSEDTAVYYCARV RYGYADGMDVWGQGTTVTVSS |
| Clone 18 VH DNA | 110 | CAGGTGCAGCTGGTGCAGTCTGGGGCTGAGGTGAAGAAGCCTGGGGCC TCAGTGAAGGTTTCCTGCAAGGCATCTGGATACACCTTCACCAGCTACT ATATGTCATGGGTGCGACAGGCCCCTGGACAAGGGCTTGAGTGGATGG GAATAATCAACCCTAGTGGTGGTAGCACAAGCTACGCACAGAAGTTCC AGGGCAGAGTCACCATGACCAGGGACACGTCCACGAGCACAGTCTACA TGGAGCTGAGCAGCCTGAGATCTGAGGACACGGCGGTGTACTACTGCG CCAGAGTGAGGTACGGATACGCAGACGGAATGGACGTATGGGGCCAGG GAACAACTGTCACCGTCTCCTCA |
| Clone 18 VH FR1 | 111 | QVQLVQSGAEVKKPGASVKVSCKASG |
| Clone 18 VH CDR1 | 112 | YTFTSYYMS |

TABLE OF SEQUENCES-continued

| Name | SEQ ID NO | Sequence |
|---|---|---|
| Clone 18 VH FR2 | 113 | WVRQAPGQGLEWMG |
| Clone 18 VH CDR2 | 114 | IINPSGGSTSYAQKFQG |
| Clone 18 VH FR3 | 115 | RVTMTRDTSTSTVYMELSSLRSEDTAVYYC |
| Clone 18 VH CDR3 | 116 | ARVRYGYADGMDV |
| Clone 18 VH FR4 | 117 | WGQGTTVTVSS |
| Clone 18 VL Protein | 118 | DIQMTQSPSSLSASVGDRVTITCRASQSISSYLNWYQQKPGKAPKLLIYGAS SLQSGVPSRFSGSGSGTDFTLTISSLQPEDFATYYCQQVYHLPFTFGGGTKV EIK |
| Clone 18 VL DNA | 119 | GACATCCAGATGACCCAGTCTCCATCCTCCCTGTCTGCATCTGTAGGAG ACAGAGTCACCATCACTTGCCGGGCAAGTCAGAGCATTAGCAGCTATTT AAATTGGTATCAGCAGAAACCAGGGAAAGCCCCTAAGCTCCTGATCTAT GGTGCATCCAGTTTGCAAAGTGGGGTCCCATCAAGGTTCAGTGGCAGTG GATCTGGGACAGATTTCACTCTCACCATCAGCAGTCTGCAACCTGAAGA TTTTGCAACTTACTACTGTCAGCAAGTATACCACCTCCCTTTCACTTTTG GCGGAGGGACCAAGGTTGAGATCAAA |
| Clone 18 VL FR1 | 120 | DIQMTQSPSSLSASVGDRVTITC |
| Clone 18 VL CDR1 | 121 | RASQSISSYLN |
| Clone 18 VL FR2 | 122 | WYQQKPGKAPKLLIY |
| Clone 18 VL CDR2 | 123 | GASSLQS |
| Clone 18 VL FR3 | 124 | GVPSRFSGSGSGTDFTLTISSLQPEDFATYYC |
| Clone 18 VL CDR3 | 125 | QQVYHLPFT |
| Clone 18 VL FR4 | 126 | FGGGTKVEIK |
| Clone 21 VH Protein | 127 | QLQLQESGPGLVKPSETLSLTCTVSGGSISSSSYYWGWIRQPPGKGLEWIGSI YYSGSTYYNPSLKSRVTISVDTSKNQFSLKLSSVTAADTAVYYCARDPLYQ DAPFDYWGQGTLVTVSS |
| Clone 21 VH DNA | 128 | CAGCTGCAGCTGCAGGAGTCGGGCCCAGGACTGGTGAAGCCTTCGGAG ACCCTGTCCCTCACCTGCACTGTCTCTGGTGGCTCCATCAGCAGTAGTA GTTACTACTGGGGCTGGATCCGCCAGCCCCCAGGGAAGGGGCTGGAGT GGATTGGGAGTATCTATTATAGTGGGAGCACCTACTACAACCCGTCCCT CAAGAGTCGAGTCACCATATCCGTAGACACGTCCAAGAACCAGTTCTCC CTGAAGCTGAGTTCTGTGACCGCCGCAGACACGGCCGGTGTACTACTGCG CCAGAGATCCTTTGTACCAAGACGCTCCCTTCGACTATTGGGGACAGGG TACATTGGTCACCGTCTCCTCA |
| Clone 21 VH FR1 | 129 | QLQLQESGPGLVKPSETLSLTCTVSG |
| Clone 21 VH CDR1 | 130 | GSISSSSYYWG |
| Clone 21 VH FR2 | 131 | WIRQPPGKGLEWIG |
| Clone 21 VH CDR2 | 132 | SIYYSGSTYYNPSLKS |
| Clone 21 VH FR3 | 133 | RVTISVDTSKNQFSLKLSSVTAADTAVYYC |
| Clone 21 VH CDR3 | 134 | ARDPLYQDAPFDY |
| Clone 21 VH FR4 | 135 | WGQGTLVTVSS |
| Clone 21 VL Protein | 136 | EIVLTQSPATLSLSPGERATLSCRASQSVSSYLAWYQQKPGQAPRLLIYDAS NRATGIPARFSGSGSGTDFTLTISSLEPEDFAVYYCQQRANFPTFGGGTKVEI K |
| Clone 21 VL DNA | 137 | GAAATTGTGTTGACACAGTCTCCAGCCACCCTGTCTTTGTCTCCAGGGG AAAGAGCCACCCTCTCCTGCAGGGCCAGTCAGAGTGTTAGCAGCTACTT AGCCTGGTACCAACAGAAACCTGGCCAGGCTCCCAGGCTCCTCATCTAT GATGCATCCAACAGGGCCACTGGCATCCCAGCCAGGTTCAGTGGCAGT GGGTCTGGGACAGACTTCACTCTCACCATCAGCAGCCTAGAGCCTGAAG ATTTTGCAGTTTATTACTGTCAGCAGAGAGCCAACTTCCCTACTTTTGGC GGAGGGACCAAGGTTGAGATCAAA |

TABLE OF SEQUENCES-continued

| Name | SEQ ID NO | Sequence |
|---|---|---|
| Clone 21 VL FR1 | 138 | EIVLTQSPATLSLSPGERATLSC |
| Clone 21 VL CDR1 | 139 | RASQSVSSYLA |
| Clone 21 VL FR2 | 140 | WYQQKPGQAPRLLIY |
| Clone 21 VL CDR2 | 141 | DASNRAT |
| Clone 21 VL FR3 | 142 | GIPARFSGSGSGTDFTLTISSLEPEDFAVYYC |
| Clone 21 VL CDR3 | 143 | QQRANFPT |
| Clone 21 VL FR4 | 144 | FGGGTKVEIK |
| Clone 22 VH Protein | 145 | QVQLQESGPGLVKPSETLSLTCAVSGYSISSGYYWAWIRQPPGKGLEWIGSI YHSGSTYYNPSLKSRVTISVDTSKNQFSLKLSSVTAADTAVYYCARQGYYY GSSGSVDFDLWGRGTLVTVSS |
| Clone 22 VH DNA | 146 | CAGGTGCAGCTGCAGGAGTCGGGCCCAGGACTGGTGAAGCCTTCGGAG ACCCTGTCCCTCACCTGCGCTGTCTCTGGTTACTCCATCAGCAGTGGTTA CTACTGGGCTTGGATCCGGCAGCCCCCAGGGAAGGGGCTGGAGTGGAT TGGGAGTATCTATCATAGTGGGAGCACCTACTACAACCCGTCCCTCAAG AGTCGAGTCACCATATCAGTAGACACGTCCAAGAACCAGTTCTCCCTGA AGCTGAGTTCTGTGACCGCCGCAGACACGGCGGTGTACTACTGCGCCAG GCAGGGATACTACTACGGCAGCAGCGGCAGTGTAGACTTCGACCTATG GGGGAGAGGTACCTTGGTCACCGTCTCCTCA |
| Clone 22 VH FR1 | 147 | QVQLQESGPGLVKPSETLSLTCAVSG |
| Clone 22 VH CDR1 | 148 | YSISSGYYWA |
| Clone 22 VH FR2 | 149 | WIRQPPGKGLEWIG |
| Clone 22 VH CDR2 | 150 | SIYHSGSTYYNPSLKS |
| Clone 22 VH FR3 | 151 | RVTISVDTSKNQFSLKLSSVTAADTAVYYC |
| Clone 22 VH CDR3 | 152 | ARQGYYYGSSGSVDFDL |
| Clone 22 VH FR4 | 153 | WGRGTLVTVSS |
| Clone 22 VL Protein | 154 | DIQMTQSPSSVSASVGDRVTITCRASQGISSWLAWYQQKPGKAPKLLIYAA SNLQSGVPSRFSGSGSGTDFTLTISSLQPEDFATYYCQQANSLPPWTFGGGT KVEIK |
| Clone 22 VL DNA | 155 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTAT GCTGCATCCAATTTGCAAAGTGGGGTCCCATCAAGGTTCAGCGGCAGTG GATCTGGGACAGATTTCACTCTCACCATCAGCAGCCTGCAGCCTGAAGA TTTTGCAACTTATTACTGTCAACAGGCAAATAGTCTCCCTCCTTGGACTT TTGGCGGAGGGACCAAGGTTGAGATCAAA |
| Clone 22 VL FR1 | 156 | DIQMTQSPSSVSASVGDRVTITC |
| Clone 22 VL CDR1 | 157 | RASQGISSWLA |
| Clone 22 VL FR2 | 158 | WYQQKPGKAPKLLIY |
| Clone 22 VL CDR2 | 159 | AASNLQS |
| Clone 22 VL FR3 | 160 | GVPSRFSGSGSGTDFTLTISSLQPEDFATYYC |
| Clone 22 VL CDR3 | 161 | QQANSLPPWT |
| Clone 22 VL FR4 | 162 | FGGGTKVEIK |
| Clone 25 VH Protein | 163 | QVQLVQSGAEVKKPGASVKVSCKASGYTFTSYAISWVRQAPGQGLEWMG WISAYNGNTNYAQKLQGRVTMTTDTSTSTAYMELRSLRSDDTAVYYCAR DLSSFWSGDVLGAFDIWGQGTMVTVSS |
| Clone 25 VH DNA | 164 | CAGGTTCAGCTGGTGCAGTCTGGAGCTGAGGTGAAGAAGCCTGGGGCC TCAGTGAAGGTCTCCTGCAAGGCTTCTGGTTACACCTTTACCAGCTATG CCATCAGCTGGGTGCGACAGGCCCCTGGACAAGGGCTTGAGTGGATGG GATGGATCAGCGCTTACAATGGTAACACAAACTATGCACAGAAGCTCC AGGGCAGAGTCACCATGACCACAGACACATCCACGAGCACAGCCTACA |

TABLE OF SEQUENCES-continued

| Name | SEQ ID NO | Sequence |
|---|---|---|
| | | TGGAGCTGAGGAGCCTGAGATCTGACGACACGGCGGTGTACTACTGCG CAAGGGATTTGTCTAGCTTCTGGAGCGGAGACGTGTTAGGAGCCTTCGA CATATGGGGTCAGGGTACAATGGTCACCGTCTCCTCA |
| Clone 25 VH FR1 | 165 | QVQLVQSGAEVKKPGASVKVSCKASG |
| Clones 25 and 25A VH CDR1 | 166 | YTFTSYAIS |
| Clone 25 VH FR2 | 167 | WVRQAPGQGLEWMG |
| Clones 25 and 25E VH CDR2 | 168 | WISAYNGNTNYAQKLQG |
| Clone 25 VH FR3 | 169 | RVTMTTDTSTSTAYMELRSLRSDDTAVYYC |
| Clones 25, 25A, and 25B VH CDR3 | 170 | ARDLSSFWSGDVLGAFDI |
| Clone 25 VH FR4 | 171 | WGQGTMVTVSS |
| Clones 25, 25A, 25B, 25C, 25D, and 25E VL Protein | 172 | DIQMTQSPSSLSASVGDRVTITCRASQSISSYLNWYQQKPGKAPKLLIYAAS SLQSGVPSRFSGSGSGTDFTLTISSLQPEDFATYYCQQSVPPRTFGGGTKVEI K |
| Clone 25 VL DNA | 173 | GACATCCAGATGACCCAGTCTCCATCCTCCCTGTCTGCATCTGTAGGAG ACAGAGTCACCATCACTTGCCGGGCAAGTCAGAGCATTAGCAGCTATTT AAATTGGTATCAGCAGAAACCAGGGAAAGCCCCTAAGCTCCTGATCTAT GCTGCATCCAGTTTGCAAAGTGGGGTCCCATCAAGGTTCAGTGGCAGTG GATCTGGGACAGATTTCACTCTCACCATCAGCAGTCTGCAACCTGAAGA TTTTGCAACTTACTACTGTCAGCAAAGCGTCCCCCCCAGGACTTTTGGC GGAGGGACCAAGGTTGAGATCAAA |
| Clone 25 VL FR1 | 174 | DIQMTQSPSSLSASVGDRVTITC |
| Clones 25, 25A, 25B, 25C, 25D, and 25E VL CDR1 | 175 | RASQSISSYLN |
| Clone 25 VL FR2 | 176 | WYQQKPGKAPKLLIY |
| Clones 25, 25A, 25B, 25C, 25D, and 25E VL CDR2 | 177 | AASSLQS |
| Clone 25 VL FR3 | 178 | GVPSRFSGSGSGTDFTLTISSLQPEDFATYYC |
| Clones 25, 25A, 25B, 25C, 25D, and 25E VL CDR3 | 179 | QQSVPPRT |
| Clone 25 VL FR4 | 180 | FGGGTKVEIK |
| Clone 27 VH Protein | 181 | QVQLVQSGAEVKKPGASVKVSCKASGYTFTSYAISWVRQAPGQGLEWMG WISAYNGNTNYAQKLQGRVTMTTDTSTSTAYMELRSLRSDDTAVYYCAR DLSSFWSGDVLGAFDIWGQGTMVTVSS |
| Clone 27 VH DNA | 182 | CAGGTTCAGCTGGTGCAGTCTGGAGCTGAGGTGAAGAAGCCTGGGGCC TCAGTGAAGGTCTCCTGCAAGGCTTCTGGTTACACCTTTACCAGCTATG CCATCAGCTGGGTGCGACAGGCCCCTGGACAAGGGCTTGAGTGGATGG GATGGATCAGCGCTTACAATGGTAACACAAACTATGCACAGAAGCTCC AGGGCAGAGTCACCATGACCACAGACACATCCACGAGCACAGCCTACA TGGAGCTGAGGAGCCTGAGATCTGACGACACGGCGGTGTACTACTGCG CAAGGGATTTGTCTAGCTTCTGGAGCGGAGACGTGTTAGGAGCCTTCGA CATATGGGGTCAGGGTACAATGGTCACCGTCTCCTCA |
| Clone 27 VH FR1 | 183 | QVQLVQSGAEVKKPGASVKVSCKASG |
| Clone 27 VH CDR1 | 184 | YTFTSYAIS |
| Clone 27 VH FR2 | 185 | WVRQAPGQGLEWMG |
| Clone 27 VH CDR2 | 186 | WISAYNGNTNYAQKLQG |
| Clone 27 VH FR3 | 187 | RVTMTTDTSTSTAYMELRSLRSDDTAVYYC |

TABLE OF SEQUENCES-continued

| Name | SEQ ID NO | Sequence |
|---|---|---|
| Clone 27 VH CDR3 | 188 | ARDLSSFWSGDVLGAFDI |
| Clone 27 VH FR4 | 189 | WGQGTMVTVSS |
| Clone 27 VL Protein | 190 | EIVMTQSPATLSVSPGERATLSCRASQSVSSNLAWYQQKPGQAPRLLIYGASTRATGIPARFSGSGSGTEFTLTISSLQSEDFAVYYCQQHANHITFGGGTKVEIK |
| Clone 27 VL DNA | 191 | GAAATAGTGATGACGCAGTCTCCAGCCACCCTGTCTGTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCAGCACGCCAATCACATCACTTTTGGCGGAGGGACCAAGGTTGAGATCAAA |
| Clone 27 VL FR1 | 192 | EIVMTQSPATLSVSPGERATLSC |
| Clone 27 VL CDR1 | 193 | RASQSVSSNLA |
| Clone 27 VL FR2 | 194 | WYQQKPGQAPRLLIY |
| Clone 27 VL CDR2 | 195 | GASTRAT |
| Clone 27 VL FR3 | 196 | GIPARFSGSGSGTEFTLTISSLQSEDFAVYYC |
| Clone 27 VL CDR3 | 197 | QQHANHIT |
| Clone 27 VL FR4 | 198 | FGGGTKVEIK |
| Clone 54 VH Protein | 199 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARASDSYGVGLYYGMDVWGQGTTVTVSS |
| Clone 54 VH DNA | 200 | CAGGTGCAGCTGGTGCAGTCTGGGGCTGAGGTGAAGAAGCCTGGGGCCTCAGTGAAGGTTTCCTGCAAGGCATCTGGATACACCTTCACCAGCTACTATATGCACTGGGTGCGACAGGCCCCTGGACAAGGGCTTGAGTGGATGGGAATAATCAACCCTAGTGGTGGTAGCACAAGCTACGCACAGAAGTTCCAGGGCAGAGTCACCATGACCAGGGACACGTCCACGAGCACAGTCTACATGGAGCTGAGCAGCCTGAGATCTGAGGACACGGCGGTGTACTACTGCGCTAGGGCATCTGACTCCTACGGAGTGGGCCTCTACTACGGAATGGACGTATGGGGCCAGGGAACAACTGTCACCGTCTCCTCA |
| Clone 54 VH FR1 | 201 | QVQLVQSGAEVKKPGASVKVSCKASG |
| Clone 54 VH CDR1 | 202 | YTFTSYYMH |
| Clone 54 VH FR2 | 203 | WVRQAPGQGLEWMG |
| Clone 54 VH CDR2 | 204 | IINPSGGSTSYAQKFQG |
| Clone 54 VH FR3 | 205 | RVTMTRDTSTSTVYMELSSLRSEDTAVYYC |
| Clone 54 VH CDR3 | 206 | ARASDSYGVGLYYGMDV |
| Clone 54 VH FR4 | 207 | WGQGTTVTVSS |
| Clone 54 VL Protein | 208 | EIVLTQSPGTLSLSPGERATLSCRASQSVRSSYLAWYQQKPGQAPRLLIYGASSRATGIPDRFSGSGSGTDFTLTISRLEPEDFAVYYCQQYYVSPLTFGGGTKVEIK |
| Clone 54 VL DNA | 209 | GAAATTGTGTTGACGCAGTCTCCAGGCACCCTGTCTTTGTCTCCAGGGGAAAGAGCCACCCTCTCCTGCAGGGCCAGTCAGAGTGTTAGGAGCAGCTACTTAGCCTGGTACCAGCAGAAACCTGGCCAGGCTCCCAGGCTCCTCATCTATGGTGCATCCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCAGTACTACGTCAGTCCTCTCACTTTTGGCGGAGGGACCAAGGTTGAGATCAAA |
| Clone 54 VL FR1 | 210 | EIVLTQSPGTLSLSPGERATLSC |
| Clone 54 VL CDR1 | 211 | RASQSVRSSYLA |
| Clone 54 VL FR2 | 212 | WYQQKPGQAPRLLIY |
| Clone 54 VL CDR2 | 213 | GASSRAT |

TABLE OF SEQUENCES-continued

| Name | SEQ ID NO | Sequence |
|---|---|---|
| Clone 54 VL FR3 | 214 | GIPDRFSGSGSGTDFTLTISRLEPEDFAVYYC |
| Clone 54 VL CDR3 | 215 | QQYYVSPLT |
| Clone 54 VL FR4 | 216 | FGGGTKVEIK |
| Human TIGIT cDNA sequence (GenBank Accession No. NM_173799.3) | 217 | CGTCCTATCTGCAGTCGGCTACTTTCAGTGGCAGAAGAGGCCACATCTG<br>CTTCCTGTAGGCCCTCTGGGCAGAAGCATGCGCTGGTGTCTCCTCCTGA<br>TCTGGGCCCAGGGGCTGAGGCAGGCTCCCCTCGCCTCAGGAATGATGAC<br>AGGCACAATAGAAACAACGGGGAACATTTCTGCAGAGAAAGGTGGCTC<br>TATCATCTTACAATGTCACCTCTCCTCCACCACGGCACAAGTGACCCAG<br>GTCAACTGGGAGCAGGACCAGCTTCTGGCCATTTGTAATGCTGACT<br>TGGGGTGGCACATCTCCCCATCCTTCAAGGATCGAGTGGCCCCAGGTCC<br>CGGCCTGGGCCTCACCCTCCAGTCGCTGACCGTGAACGATACAGGGGA<br>GTACTTCTGCATCTATCACACCTACCCTGATGGGACGTACACTGGGAGA<br>ATCTTCCTGGAGGTCCTAGAAAGCTCAGTGGCTGAGCACGGTGCCAGGT<br>TCCAGATTCCATTGCTTGGAGCCATGGCCGCGACGCTGGTGGTCATCTG<br>CACAGCAGTCATCGTGGTGGTCGCGTTGACTAGAAAGAAGAAAGCCCT<br>CAGAATCCATTCTGTGGAAGGTGACCTCAGGAGAAAATCAGCTGGACA<br>GGAGGAATGGAGCCCAGTGCTCCCTCACCCCCAGGAAGCTGTGTCCA<br>GGCAGAAGCTGCACCTGCTGGGCTCTGTGGAGAGCAGCGGGGAGAGGA<br>CTGTGCCGAGCTGCATGACTACTTCAATGTCCTGAGTTACAGAAGCCTG<br>GGTAACTGCAGCTTCTTCACAGAGACTGGTTAGCAACCAGAGGCATCTT<br>CTGGAAGATACACTTTTGTCTTTGCTATTATAGATGAATATATAAGCAG<br>CTGTACTCTCCATCAGTGCTGCGTGTGTGTGTGTGTATGTGTGTGT<br>GTGTTCAGTTGAGTGAATAAATGTCATCCTCTTCTCCATCTTCATTTCCT<br>TGGCCTTTTCGTTCTATTCCATTTTGCATTATGGCAGGCCTAGGGTGAGT<br>AACGTGGATCTTGATCATAAATGCAAAATTAAAAAATATCTTGACCTGG<br>TTTTAAATCTGGCAGTTTGAGCAGATCCTATGTCTCTGAGAGACACATT<br>CCTCATAATGGCCAGCATTTTGGGCTACAAGGTTTTGTGGTTGATGATG<br>AGGATGGCATGACTGCAGAGCCATCCTCATCTCATTTTTTCACGTCATTT<br>TCAGTAACTTTCACTCATTCAAAGGCAGGTTATAAGTAAGTCCTGGTAG<br>CAGCCTCTATGGGGAGATTTGAGAGTGACTAAATCTTGGTATCTGCCCT<br>CAAGAACTTACAGTTAAATGGGGAGACAATGTTGTCATGAAAAGGTAT<br>TATAGTAAGGAGAGAAGGAGACATACACAGGCCTTCAGGAAGAGACGA<br>CAGTTTGGGGTGAGGTAGTTGGCATAGGCTTATCTGTGATGAAGTGGCC<br>TGGGAGCACCAAGGGGATGTTGAGGCTAGTCTGGGAGGAGCAGGAGTT<br>TTGTCTAGGGAACTTGTAGGAAATTCTTGGAGCTGAAAGTCCCACAAAG<br>AAGGCCCTGGCACCAAGGGAGTCAGCAAACTTCAGATTTTATTCTCTGG<br>GCAGGCATTTCAAGTTTCCTTTTGCTGTGACATACTCATCCATTAGACAG<br>CCTGATACAGGCCTGTAGCCTCTTCCGGCCGTGTGTGCTGGGGAAGCCC<br>CAGGAAACGCACATGCCCACACAGGGAGCCAAGTCGTAGCATTTGGGC<br>CTTGATCTACCTTTTCTGCATCAATACACTCTTGAGCCTTTGAAAAAAGA<br>ACGTTTCCCACTAAAAAGAAAATGTGGATTTTTAAAATAGGGACTCTTC<br>CTAGGGGAAAAAGGGGGGCTGGGAGTGATAGAGGGTTTAAAAAATAA<br>ACACCTTCAAACTAACTTCTTCGAACCCTTTTATTCACTCCCTGACGACT<br>TTGTGCTGGGGTTGGGGTAACTGAACCGCTTATTTCTGTTTAATTGCATT<br>CAGGCTGGATCTTAGAAGACTTTTATCCTTCCACCATCTCTCTCAGAGG<br>AATGAGCGGGAGGTTGGATTTACTGGTGACTGATTTTCTTTCATGGGC<br>CAAGGAACTGAAAGAGAATGTGAAGCAAGGTTGTGTCTTGCGCATGGT<br>TAAAAATAAAGCATTGTCCTGCTTCCTAAGACTTAGACTGGGGTTGACA<br>ATTGTTTTAGCAACAAGACAATTCAACTATTTCTCCTAGGATTTTTATTA<br>TTATTATTTTTTCACTTTTCTACCAAATGGGTTACATAGGAAGAATGAAC<br>TGAAATCTGTCCAGAGCTCCAAGTCCTTTGGAAGAAAGATTAGATGAAC<br>GTAAAAATGTTGTTGTTGCTGTGGCAGTTTACAGCATTTTTCTTGCAAA<br>ATTAGTGCAAATCTGTTGGAAATAGAACACAATTCACAAATTGGAAGTG<br>AACTAAAATGTAATGACGAAAAGGGAGTAGTGTTTTGATTTGGAGGAG<br>GTGTATATTCGGCAGAGGTTGGACTGAGAGTTGGGTGTTATTTAACATA<br>ATTATGGTAATTGGGAAACATTTATAAACACTATTGGGATGGTGATAAA<br>ATACAAAAGGGCCTATAGATGTTAGAAATGGGTCAGGTTACTGAAATG<br>GGATTCAATTTGAAAAAAATTTTTTAAATAGAACTCACTGAACTAGAT<br>TCTCCTCTGAGAACCAGAGAAGACCATTTCATAGTTGGATTCCTGGAGA<br>CATGCGCTATCCACCACGTAGCCACTTTCCACATGTGGCCATCAACCAC<br>TTAAGATGGGGTTAGTTTAAATCAAGATGTGCTGTTATAATTGGTATAA<br>GCATAAAATCACACTAGATTCTGGAGATTTAA<br>TATGAATAATAAGAATACTATTTCAGTAGTTTTGGTATATTGTGTGTCAA<br>AAATGATAATATTTTGGATGTATTGGGTGAAATAAAATATTAACATTAA<br>AAAAAAAA |
| Human TIGIT protein (GenBank Accession No. NP_776160.2) | 218 | MRWCLLLIWAQGLRQAPLASGMMTGTIETTGNISAEKGGSIILQCHLSSTT<br>AQVTQVNWEQQDQLLAICNADLGWHISPSFKDRVAPGPGLGLTLQSLTVN<br>DTGEYFCIYHTYPDGTYTGRIFLEVLESSVAEHGARFQIPLLGAMAATLVVI<br>CTAVIVVVALTRKKKALRIHSVEGDLRRKSAGQEEWSPSAPSPPGSCVQAE<br>AAPAGLCGEQRGEDCAELHDYFNVLSYRSLGNCSFFTETG |

TABLE OF SEQUENCES-continued

| Name | SEQ ID NO | Sequence |
|---|---|---|
| Cynomolgus monkey TIGIT protein | 219 | MAFLVAPPMQFVYLLKTLCVFNMVFAKPGFSETVFSHRLSFTVLSAVGYFR WQKRPHLLPVSPLGRSMRWCLFLIWAQGLRQAPLASGMMTGTIETTGNIS AKKGGSVILQCHLSSTMAQVTQVNWEQHDHSLLAIRNAELGWHIYPAFKD RVAPGPGLGLTLQSLTMNDTGEYFCTYHTYPDGTYRGRIFLEVLESSVAEH SARFQIPLLGAMAMMLVVICIAVIVVVLARKKKSLRIHSVESGLQRKSTG QEEQIPSAPSPPGSCVQAEAAPAGLCGEQQGDDCAELHDYFNVLSYRSLGS CSFFTETG |
| Mouse TIGIT protein | 220 | MHGWLLLLVWVQGLIQAAFLATGATAGTIDTKRNISAEEGGSVILQCHFSSD TAEVTQVDWKQQDQLLAIYSVDLGWHVASVFSDRVVPGPSLGLTFQSLTM NDTGEYFCTYHTYPGGIYKGRIFLKVQESSVAQFQTAPLGGTMAAVLGLIC LMVTGVTVLARKKSIRMHSIESGLGRTEAEPQEWNLRSLSSPGSPVQTQTA PAGPCGEQAEDDYADPQEYFNVLSYRSLESFIAVSKTG |
| Clone 2C VH CDR1 | 221 | FTFTDYYMD |
| Clone 2C VH CDR2 | 222 | RTRNKVNSYYIEYAASVKG |
| Clone 2C VH CDR3 | 223 | ARGQYYYGSDRRGYYYMDV |
| Clones 13A, 13C, and 13D VH CDR1 | 224 | GTFLSSAIS |
| Clone 13A VH CDR2 | 225 | SLIPYFGTANYAQKFQG |
| Clone 13B VH CDR1 | 226 | GTFSAWAIS |
| Clones 13B and 13D VH CDR2 | 227 | SIIPYFGKANYAQKFQG |
| Clone 13B VH CDR3 | 228 | ARGPSEVSGILGYVWFDP |
| Clone 13C VH CDR2 | 229 | SIIPLFGKANYAQKFQG |
| Clones 13C and 13D VH CDR3 | 230 | ARGPSEVKGILGYVWFDP |
| Clone 16C VH CDR1 | 231 | GTFREYAIS |
| Clone 16C VH CDR2 | 232 | GIHPIFGTARYAQKFQG |
| Clones 16D and 16E VH CDR1 | 233 | GTFSDYPIS |
| Clones 16B, 16D, and 16E VH CDR2 | 234 | GIIPIVGGANYAQKFQG |
| Clone 16C VH CDR3 | 235 | TRQSTWHKLYGTDV |
| Clone 16D VH CDR3 | 236 | TRQSTWHKLFGTDV |
| Clone 16E VH CDR3 | 237 | ARQSTWHKVYGTDV |
| Clone 25A VH CDR2 | 238 | WISAYNGNTKYAQKLQG |
| Clones 25B, 25C, and 25D VH CDR1 | 239 | YTFTSYPIG |
| Clones 25B, 25C, and 25D VH CDR2 | 240 | WISSYNGNTNYAQKLQG |
| Clone 25C VH CDR3 | 241 | ARGASSFWSGDVLGAFDI |
| Clone 25D VH CDR3 | 242 | ARDLKSFWSGDVLGAFDI |

TABLE OF SEQUENCES-continued

| Name | SEQ ID NO | Sequence |
|---|---|---|
| Clone 25E VH CDR1 | 243 | YTFTSYAIA |
| Clone 25E VH CDR3 | 244 | ARSGSSFWSGDVLGAFDI |
| Clone 2C VH | 245 | EVQLVESGGGLVQPGGSLRLSCAASGFTFTDYYMDWVRQAPGKGLEWVG RTRNKVNSYYTEYAASVKGRFTISRDDSKNSLYLQMNSLKTEDTAVYYCA RGQYYYGSDRRGYYYMDVWGQGTTVTSS |
| Clone 13A VH | 246 | QVQLVQSGAEVKKPGSSVKVSCKASGGTFLSSAISWVRQAPGQGLEWMGS LIPYFGTANYAQKFQGRVTITADESTSTAYMELSSLRSEDTAVYYCARGPSE VGAILGYVWFDPWGQGTLVTVSS |
| Clone 13B VH | 247 | QVQLVQSGAEVKKPGSSVKVSCKASGGTFSAWAISWVRQAPGQGLEWMG SIIPYFGKANYAQKFQGRVTITADESTSTAYMELSSLRSEDTAVYYCARGPS EVSGILGYVWFDPWGQGTLVTVSS |
| Clone 13C VH | 248 | QVQLVQSGAEVKKPGSSVKVSCKASGGTFLSSAISWVRQAPGQGLEWMGS IIPLFGKANYAQKFQGRVTITADESTSTAYMELSSLRSEDTAVYYCARGPSE VKGILGYVWFDPWGQGTLVTVSS |
| Clone 13D VH | 249 | QVQLVQSGAEVKKPGSSVKVSCKASGGTFLSSAISWVRQAPGQGLEWMGS IIPYFGKANYAQKFQGRVTITADESTSTAYMELSSLRSEDTAVYYCARGPSE VKGILGYVWFDPWGQGTLVTVSS |
| Clone 16C VH | 250 | QVQLVQSGAEVKKPGSSVKVSCKASGGTFREYAISWVRQAPGQGLEWMG GIHPIFGTARYAQKFQGRVTITADESTSTAYMELSSLRSEDTAVYYCTRQST WHKLYGTDVWGQGTTVTVSS |
| Clone 16D VH | 251 | QVQLVQSGAEVKKPGSSVKVSCKASGGTFSDYPISWVRQAPGQGLEWMG GIIPIVGGANYAQKFQGRVTITADESTSTAYMELSSLRSEDTAVYYCTRQST WHKLFGTDVWGQGTTVTVSS |
| Clone 16E VH | 252 | QVQLVQSGAEVKKPGSSVKVSCKASGGTFSDYPISWVRQAPGQGLEWMG GIIPIVGGANYAQKFQGRVTITADESTSTAYMELSSLRSEDTAVYYCARQST WHKVYGTDVWGQGTTVTVSS |
| Clone 25A VH | 253 | QVQLVQSGAEVKKPGASVKVSCKASGYTFTSYAISWVRQAPGQGLEWMG WISAYNGNTKYAQKLQGRVTMTTDTSTSTAYMELRSLRSDDTAVYYCAR DLSSFWSGDVLGAFDIWGQGTMVTVSS |
| Clone 25B VH | 254 | QVQLVQSGAEVKKPGASVKVSCKASGYTFTSYPIGWVRQAPGQGLEWMG WISSYNGNTNYAQKLQGRVTMTTDTSTSTAYMELRSLRSDDTAVYYCAR DLSSFWSGDVLGAFDIWGQGTMVTVSS |
| Clone 25C VH | 255 | QVQLVQSGAEVKKPGASVKVSCKASGYTFTSYPIGWVRQAPGQGLEWMG WISSYNGNTNYAQKLQGRVTMTTDTSTSTAYMELRSLRSDDTAVYYCAR GASSFWSGDVLGAFDIWGQGTMVTVSS |
| Clone 25D VH | 256 | QVQLVQSGAEVKKPGASVKVSCKASGYTFTSYPIGWVRQAPGQGLEWMG WISSYNGNTNYAQKLQGRVTMTTDTSTSTAYMELRSLRSDDTAVYYCAR DLKSFWSGDVLGAFDIWGQGTMVTVSS |
| Clone 25E VH | 257 | QVQLVQSGAEVKKPGASVKVSCKASGYTFTSYAIAWVRQAPGQGLEWMG WISAYNGNTNYAQKLQGRVTMTTDTSTSTAYMELRSLRSDDTAVYYCAR SGSSFWSGDVLGAFDIWGQGTMVTVSS |
| hTIGIT68-82 epitope | 258 | ICNADLGWHISPSFK |
| Clone 13 heavy chain hIgG1 (and hIgG1 afucosylated) nucleotide sequence; bold indicates nucleotide sequence of variable region (VH) | 259 | CAGGTGCAGCTGGTGCAGTCTGGGGCTGAGGTGAAGAAGCCTGGG TCCTCTGTGAAGGTCTCCTGCAAGGCTTCTGGAGGCACCTTCAGCA GCTATGCTATCAGCTGGGTGCGACAGGCCCCTGGACAAGGGCTTGA GTGGATGGGAAGCATCATCCCTATCTTTGGTACAGCAAACTACGCA CAGAAGTTCCAGGGCAGAGTCACCATTACTGCTGATGAATCCACCA GCACAGCCTACATGGAGCTGAGCAGCCTGAGATCTGAGGACACTGC TGTGTACTACTGTGCCAGAGGCCCTTCTGAAGTAGGAGCAATACTG GGATATGTATGGTTTGACCCATGGGGACAGGGTACATTGGTCACCG TCTCCTCAGCTAGCACCAAGGGCCCATCTGTCTTCCCCCTGGCACCCTC CTCCAAGAGCACCTCTGGGGGCACAGCGGCCCTGGGCTGCCTGGTCAAG GACTACTTCCCTGAACCTGTGACAGTGTCCTGGAACTCAGGAGCCCTGA CCAGCGGCGTGCACACCTTCCCGGCTGTCCTACAGTCCTCAGGACTCTA CTCCCTCAGCAGCGTGGTGACCGTGCCCTCAGCAGCTTGGGCACCCAG ACCTACATCTGCAACGTGAATCACAAGCCCAGCAACACCAAGGTGGAC |

TABLE OF SEQUENCES-continued

| Name | SEQ ID NO | Sequence |
|---|---|---|
| | | AAGAAAGTTGAGCCCAAATCTTGTGACAAAACTCACACATGCCCACCGT GCCCAGCACCTGAACTCCTGGGGGGACCGTCAGTCTTCCTCTTCCCCCC AAAACCCAAGGACACCCTCATGATCTCCCGGACCCCTGAGGTCACATGC GTGGTGGTGGACGTGAGCCACGAAGACCCTGAGGTCAAGTTCAACTGG TACGTGGACGGCGTGGAGGTGCATAATGCCAAGACAAAGCCGCGGGAG GAGCAGTACAACAGCACGTACCGTGTGGTCAGCGTCCTCACCGTCCTGC ACCAGGACTGGCTGAATGGCAAGGAGTACAAGTGCAAGGTCTCCAACA AAGCCCTCCCAGCCCCCATCGAGAAAACCATCTCCAAAGCCAAAGGGC AGCCCCGAGAACCACAGGTTTACACCCTGCCCCCATCCCGGGATGAGCT GACCAAGAACCAGGTCAGCCTGACCTGCCTGGTCAAAGGCTTCTATCCC AGCGACATCGCCGTGGAGTGGGAGAGCAATGGGCAGCCGGAGAACAAC TACAAGACCACGCCTCCCGTGCTGGACTCCGACGGCTCCTTCTTCCTCTA CAGCAAGCTCACCGTGGACAAGAGCAGGTGGCAGCAGGGGAACGTCTT CTCATGCTCCGTGATGCATGAGGCTCTGCACAACCACTACACACAGAAG AGCCTCTCCCTGTCTCCGGGCAAA |
| Clone 13 heavy chain hIgG1 (and hIgG1 afucosylated) amino acid sequence; bold indicates VH | 260 | QVQLVQSGAEVKKPGSSVKVSCKASGGTFSSYAISWVRQAPGQGLEW MGSIIPIFGTANYAQKFQGRVTITADESTSTAYMELSSLRSEDTAVYYCA RGPSEVGAILGYVWFDPWGQGTLVTVSSASTKGPSVFPLAPSSKSTSGGT AALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSL SPGK |
| Clone 13 heavy chain hIgG1 LALA-PG nucleotide sequence; bold indicates nucleotide sequence of VH | 261 | CAGGTGCAGCTGGTGCAGTCTGGGGCTGAGGTGAAGAAGCCTGGG TCCTCTGTGAAGGTCTCCTGCAAGGCTTCTGGAGGCACCTTCAGCA GCTATGCTATCAGCTGGGTGCGACAGGCCCCTGGACAAGGGCTTGA GTGGATGGGAAGCATCATCCCTATCTTTGGTACAGCAAACTACGCA CAGAAGTTCCAGGGCAGAGTCACCATTACTGCTGATGAATCCACCA GCACAGCCTACATGGAGCTGAGCAGCCTGAGATCTGAGGACACTGC TGTGTACTACTGTGCCAGAGGCCCTTCTGAAGTAGGAGCAATACTG GGATATGTATGGTTTGACCCATGGGGACAGGGTACATTGGTCACCG TCTCCTCAGCTAGCACCAAGGGCCCATCTGTCTTCCCCCTGGCACCCTC CTCCAAGAGCACCTCTGGGGGCACAGCTGCCCTGGGCTGCCTGGTCAAG GACTACTTCCCTGAACCTGTGACAGTGTCCTGGAACTCAGGAGCCCTGA CCAGCGGCGTGCACACCTTCCCGGCTGTCCTACAGTCCTCAGGACTCTA CTCCCTCAGCAGCGTGGTGACCGTGCCCTCCAGCAGCTTGGGCACCCAG ACCTACATCTGCAACGTGAATCACAAGCCCAGCAACACCAAGGTGGAC AAGAAAGTTGAGCCCAAATCTTGTGACAAAACTCACACATGCCCACCGT GCCCAGCACCTGAAGCTGCTGGGGGACCGTCAGTCTTCCTCTTCCCCCC AAAACCCAAGGACACCCTCATGATCTCCCGGACCCCTGAGGTCACATGC GTGGTGGTGGACGTGAGCCACGAAGACCCTGAGGTCAAGTTCAACTGG TACGTGGACGGCGTGGAGGTGCATAATGCCAAGACAAAGCCGCGGGAG GAGCAGTACAACAGCACGTACCGTGTGGTCAGCGTCCTCACCGTCCTGC ACCAGGACTGGCTGAATGGCAAGGAGTACAAGTGCAAGGTCTCCAACA AAGCCCTCGGGGCCCCATCGAGAAAACCATCTCCAAAGCCAAAGGGC AGCCCCGAGAACCACAGGTTTACACCCTGCCCCCATCCCGGGATGAGCT GACCAAGAACCAGGTCAGCCTGACCTGCCTGGTCAAAGGCTTCTATCCC AGCGACATCGCCGTGGAGTGGGAGAGCAATGGGCAGCCGGAGAACAAC TACAAGACCACGCCTCCCGTGCTGGACTCCGACGGCTCCTTCTTCCTCTA CAGCAAGCTCACCGTGGACAAGAGCAGGTGGCAGCAGGGGAACGTCTT CTCATGCTCCGTGATGCATGAGGCTCTGCACAACCACTACACACAGAAG AGCCTCTCCCTGTCTCCGGGCAAA |
| Clone 13 heavy chain hIgG1 LALA-PG amino acid sequence; bold indicates VH | 262 | QVQLVQSGAEVKKPGSSVKVSCKASGGTFSSYAISWVRQAPGQGLEW MGSIIPIFGTANYAQKFQGRVTITADESTSTAYMELSSLRSEDTAVYYCA RGPSEVGAILGYVWFDPWGQGTLVTVSSASTKGPSVFPLAPSSKSTSGGT AALGCLVKDYFPEPVTVSWNSGALTSGVHTFPAVLQSSGLYSLSSVVTVPS SSLGTQTYICNVNHKPSNTKVDKKVEPKSCDKTHTCPPCPAPEAAGGPSVF LFPPKPKDTLMISRTPEVTCVVVDVSHEDPEVKFNWYVDGVEVHNAKTKP REEQYNSTYRVVSVLTVLHQDWLNGKEYKCKVSNKALGAPIEKTISKAKG QPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLS LSPGK |
| Clone 13 heavy chain hIgG4 S228P nucleotide sequence; bold indicates nucleotide sequence of VH | 263 | CAGGTGCAGCTGGTGCAGTCTGGGGCTGAGGTGAAGAAGCCTGGG TCCTCTGTGAAGGTCTCCTGCAAGGCTTCTGGAGGCACCTTCAGCA GCTATGCTATCAGCTGGGTGCGACAGGCCCCTGGACAAGGGCTTGA GTGGATGGGAAGCATCATCCCTATCTTTGGTACAGCAAACTACGCA CAGAAGTTCCAGGGCAGAGTCACCATTACTGCTGATGAATCCACCA GCACAGCCTACATGGAGCTGAGCAGCCTGAGATCTGAGGACACTGC TGTGTACTACTGTGCCAGAGGCCCTTCTGAAGTAGGAGCAATACTG GGATATGTATGGTTTGACCCATGGGGACAGGGTACATTGGTCACCG |

TABLE OF SEQUENCES-continued

| Name | SEQ ID NO | Sequence |
|---|---|---|
| | | TCTCCTCAGCTAGCACCAAGGGCCCATCTGTCTTCCCCCTGGCCCCTTG<br>CTCCAGAAGCACATCTGAGAGCACAGCGGCCCTGGGATGCCTGGTCAA<br>GGACTATTTCCCTGAGCCGGTGACCGTAAGCTGGAACTCTGGAGCCCTG<br>ACCAGCGGCGTGCACACCTTCCCAGCTGTCCTGCAGTCTTCAGGGCTCT<br>ACTCCCTCAGCAGTGTGGTGACTGTACCCTCCAGCAGCTTGGGCACCAA<br>GACCTACACCTGCAACGTAGATCACAAGCCCAGCAACACCAAGGTGGA<br>CAAGAGAGTTGAGTCCAAATATGGTCCCCCATGCCCACCCTGCCCAGCA<br>CCAGAGTTCCTGGGGGACCATCTGTCTTCCTCTTCCCCCCAAAACCCA<br>AGGATACCCTCATGATCTCCCGGACCCCTGAGGTCACATGTGTGGTGGT<br>GGACGTGAGCCAGGAGGACCCCGAGGTCCAGTTCAACTGGTATGTGGA<br>TGGCGTGGAAGTGCATAATGCTAAGACAAAGCCACGGGAGGAGCAGTT<br>CAACAGCACCTACCGTGTGGTCAGCGTCCTCACAGTGCTGCACCAGGAC<br>TGGCTGAATGGCAAGGAGTACAAATGCAAGGTCTCCAACAAAGGCCTC<br>CCATCCTCCATCGAGAAAACCATCTCCAAAGCCAAAGGGCAACCCCGG<br>GAACCACAGGTATACACCCTGCCTCCATCCCAAGAAGAGATGACCAAG<br>AACCAGGTCAGCCTGACCTGCCTGGTCAAAGGCTTCTACCCCTCTGACA<br>TTGCCGTGGAGTGGGAGAGCAATGGGCAGCCAGAGAACAACTACAAGA<br>CCACACCTCCCGTGCTGGACTCCGATGGCTCCTTCTTCCTGTACTCCCGG<br>CTCACAGTGGACAAGAGCAGGTGGCAGGAGGGAAATGTCTTCTCCTGC<br>TCCGTGATGCATGAGGCTCTGCACAACCACTACACACAGAAGAGCCTCT<br>CCCTGTCTCTGGGCAAA |
| Clone 13 heavy chain hIgG4 S228P amino acid sequence; bold indicates VH | 264 | QVQLVQSGAEVKKPGSSVKVSCKASGGTFSSYAISWVRQAPGQGLEW<br>MGSIIPIFGTANYAQKFQGRVTITADESTSTAYMELSSLRSEDTAVYYCA<br>RGPSEVGAILGYVWFDPWGQGTLVTVSSASTKGPSVFPLAPCSRSTSEST<br>AALGCLVKDYFPEPVTVSWNSGALTSGVHTFPAVLQSSGLYSLSSVVTVPS<br>SSLGTKTYTCNVDHKPSNTKVDKRVESKYGPPCPPCPAPEFLGGPSVFLFPP<br>KPKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPREP<br>QVYTLPPSQEEMTKNQVSLTCLVKGFYPSDIAVEWESNGQPENNYKTTPPV<br>LDSDGSFFLYSRLTVDKSRWQEGNVFSCSVMHEALHNHYTQKSLSLSLGK |
| Clone 13A heavy chain hIgG1 (and hIgG1 afucosylated) nucleotide sequence; bold indicates nucleotide sequence of VH | 265 | CAGGTGCAGCTGGTGCAGTCTGGGGCTGAGGTGAAGAAGCCTGGG<br>TCCTCTGTGAAGGTCTCCTGCAAGGCTTCTGGAGGCACCTTCCTTA<br>GCTCTGCTATCAGCTGGGTGCGACAGGCCCCTGGACAAGGGCTTGA<br>GTGGATGGGATCTCTCATCCCTTATTTTGGTACAGCAAACTACGCA<br>CAGAAGTTCCAGGGCAGAGTCACCATTACTGCTGATGAATCCACCA<br>GCACAGCCTACATGGAGCTGAGCAGCCTGAGATCTGAGGACACTGC<br>TGTGTACTACTGTGCCAGAGGCCCTTCTGAAGTAGGAGCAATACTG<br>GGATATGTATGGTTTGACCCATGGGGACAGGGTACATTGGTCACCG<br>TCTCCTCAGCTAGCACCAAGGGCCCATCTGTCTTCCCCCTGGCACCCTC<br>CTCCAAGAGCACCTCTGGGGGCACAGCGGCCCTGGGCTGCCTGGTCAAG<br>GACTACTTCCCTGAACCTGTGACAGTGTCCTGGAACTCAGGAGCCCTGA<br>CCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAG<br>ACCTACATCTGCAACGTGAATCACAAGCCCAGCAACACCAAGGTGGAC<br>AAGAAAGTTGAGCCCAAATCTTGTGACAAAACTCACACATGCCCACCGT<br>GCCCAGCACCTGAACTCCTGGGGGGACCGTCAGTCTTCCTCTTCCCCCC<br>AAAACCCAAGGACACCCTCATGATCTCCCGGACCCCTGAGGTCACATGC<br>GTGGTGGTGGACGTGAGCCACGAAGACCCTGAGGTCAAGTTCAACTGG<br>TACGTGGACGGCGTGGAGGTGCATAATGCCAAGACAAAGCCGCGGGAG<br>GAGCAGTACAACAGCACGTACCGTGTGGTCAGCGTCCTCACCGTCCTGC<br>ACCAGGACTGGCTGAATGGCAAGGAGTACAAGTGCAAGGTCTCCAACA<br>AAGCCCTCCCAGCCCCCATCGAGAAAACCATCTCCAAAGCCAAAGGGC<br>AGCCCCGAGAACCACAGGTTTACACCCTGCCCCCATCCCGGGATGAGCT<br>GACCAAGAACCAGGTCAGCCTGACCTGCCTGGTCAAAGGCTTCTATCCC<br>AGCGACATCGCCGTGGAGTGGGAGAGCAATGGGCAGCCGGAGAACAAC<br>TACAAGACCACGCCTCCCGTGCTGGACTCCGACGGCTCCTTCTTCCTCTA<br>CAGCAAGCTCACCGTGGACAAGAGCAGGTGGCAGCAGGGGAACGTCTT<br>CTCATGCTCCGTGATGCATGAGGCTCTGCACAACCACTACACACAGAAG<br>AGCCTCTCCCTGTCTCCGGGCAAA |
| Clone 13A heavy chain hIgG1 (and hIgG1 afucosylated) amino acid sequence; bold indicates VH | 266 | QVQLVQSGAEVKKPGSSVKVSCKASGGTFLSSAISWVRQAPGQGLEW<br>MGSLIPYFGTANYAQKFQGRVTITADESTSTAYMELSSLRSEDTAVYYC<br>ARGPSEVGAILGYVWFDPWGQGTLVTVSSASTKGPSVFPLAPSSKSTSGG<br>TAALGCLVKDYFPEPVTVSWNSGALTSGVHTFPAVLQSSGLYSLSSVVTVP<br>SSSLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| Clone 13B heavy chain hIgG1 (and hIgG1 afucosylated) | 267 | CAGGTGCAGCTGGTGCAGTCTGGGGCTGAGGTGAAGAAGCCTGGG<br>TCCTCTGTGAAGGTCTCCTGCAAGGCTTCTGGAGGCACCTTCTCTG<br>CCTGGGCTATCAGCTGGGTGCGACAGGCCCCTGGACAAGGGCTTG |

TABLE OF SEQUENCES-continued

| Name | SEQ ID NO | Sequence |
|---|---|---|
| nucleotide sequence; bold indicates nucleotide sequence of VH | | **AGTGGATGGGATCCATCATCCCTTATTTTGGTAAGGCAAACTACGC
ACAGAAGTTCCAGGGCAGAGTCACCATTACTGCTGATGAATCCACC
AGCACAGCCTACATGGAGCTGAGCAGCCTGAGATCTGAGGACACTG
CTGTGTACTACTGTGCCAGAGGCCCTTCTGAAGTAAGTGGTATACT
GGGATATGTATGGTTTGACCCATGGGGACAGGGTACATTGGTCACC
GTCTCCTCA**GCTAGCACCAAGGGCCCATCTGTCTTCCCCCTGGCACCCT
CCTCCAAGAGCACCTCTGGGGGCACAGCTGCCCTGGGCTGCCTGGTCAA
GGACTACTTCCCTGAACCTGTGACAGTGTCCTGGAACTCAGGAGCCCTG
ACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCA
GACCTACATCTGCAACGTGAATCACAAGCCCAGCAACACCAAGGTGGA
CAAGAAAGTTGAGCCCAAATCTTGTGACAAAACTCACACATGCCCACC
GTGCCCAGCACCTGAACTCCTGGGGGGACCGTCAGTCTTCCTCTTCCCC
CCAAAACCCAAGGACACCCTCATGATCTCCCGGACCCCTGAGGTCACAT
GCGTGGTGGTGGACGTGAGCCACGAAGACCCTGAGGTCAAGTTCAACT
GGTACGTGGACGGCGTGGAGGTGCATAATGCCAAGACAAAGCCGCGGG
AGGAGCAGTACAACAGCACGTACCGTGTGGTCAGCGTCCTCACCGTCCT
GCACCAGGACTGGCTGAATGGCAAGGAGTACAAGTGCAAGGTCTCCAA
CAAAGCCCTCCCAGCCCCCATCGAGAAAACCATCTCCAAAGCCAAAGG
GCAGCCCCGAGAACCACAGGTTTACACCCTGCCCCCATCCCGGGATGAG
CTGACCAAGAACCAGGTCAGCCTGACCTGCCTGGTCAAAGGCTTCTATC
CCAGCGACATCGCCGTGGAGTGGGAGAGCAATGGGCAGCCGGAGAACA
ACTACAAGACCACGCCTCCCGTGCTGGACTCCGACGGCTCCTTCTTCCT
CTACAGCAAGCTCACCGTGGACAAGAGCAGGTGGCAGCAGGGGAACGT
CTTCTCATGCTCCGTGATGCATGAGGCTCTGCACAACCACTACACACAG
AAGAGCCTCTCCCTGTCTCCGGGCAAA |
| Clone 13B heavy chain hIgG1 (and hIgG1 afucosylated) amino acid sequence; bold indicates VH | 268 | **QVQLVQSGAEVKKPGSSVKVSCKASGGTFSAWAISWVRQAPGQGLEW
MGSIIPYFGKANYAQKFQGRVTITADESTSTAYMELSSLRSEDTAVYYC
ARGPSEVSGILGYVWFDPWGQGTLVTVSS**ASTKGPSVFPLAPSSKSTSGG
TAALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPGK |
| Clone 13C heavy chain hIgG1 (and hIgG1 afucosylated) nucleotide sequence; bold indicates nucleotide sequence of VH | 269 | **CAGGTGCAGCTGGTGCAGTCTGGGGCTGAGGTGAAGAAGCCTGGG
TCCTCTGTGAAGGTCTCCTGCAAGGCTTCTGGAGGCACCTTCTTA
GCTCTGCTATCAGCTGGGTGCGACAGGCCCCTGGACAAGGGCTTGA
GTGGATGGGAAGTATCATCCCTCTGTTTGGTAAGGCAAACTACGCA
CAGAAGTTCCAGGGCAGAGTCACCATTACTGCTGATGAATCCACCA
GCACAGCCTACATGGAGCTGAGCAGCCTGAGATCTGAGGACACTGC
TGTGTACTACTGTGCCAGAGGCCCTTCTGAAGTAAAGGGTATACTG
GGATATGTATGGTTTGACCCATGGGGACAGGGTACATTGGTCACCG
TCTCCTCA**GCTAGCACCAAGGGCCCATCTGTCTTCCCCCTGGCACCCTC
CTCCAAGAGCACCTCTGGGGGCACAGCTGCCCTGGGCTGCCTGGTCAAG
GACTACTTCCCTGAACCTGTGACAGTGTCCTGGAACTCAGGAGCCCTGA
CCAGCGGCGTGCACACCTTCCCGGCTGTCCTACAGTCCTCAGGACTCTA
CTCCCTCAGCAGCGTGGTGACCGTGCCCTCCAGCAGCTTGGGCACCCAG
ACCTACATCTGCAACGTGAATCACAAGCCCAGCAACACCAAGGTGGAC
AAGAAAGTTGAGCCCAAATCTTGTGACAAAACTCACACATGCCCACCGT
GCCCAGCACCTGAACTCCTGGGGGGACCGTCAGTCTTCCTCTTCCCCCC
AAAACCCAAGGACACCCTCATGATCTCCCGGACCCCTGAGGTCACATGC
GTGGTGGTGGACGTGAGCCACGAAGACCCTGAGGTCAAGTTCAACTGG
TACGTGGACGGCGTGGAGGTGCATAATGCCAAGACAAAGCCGCGGGAG
GAGCAGTACAACAGCACGTACCGTGTGGTCAGCGTCCTCACCGTCCTGC
ACCAGGACTGGCTGAATGGCAAGGAGTACAAGTGCAAGGTCTCCAACA
AAGCCCTCCCAGCCCCCATCGAGAAAACCATCTCCAAAGCCAAAGGGC
AGCCCCGAGAACCACAGGTTTACACCCTGCCCCCATCCCGGGATGAGCT
GACCAAGAACCAGGTCAGCCTGACCTGCCTGGTCAAAGGCTTCTATCCC
AGCGACATCGCCGTGGAGTGGGAGAGCAATGGGCAGCCGGAGAACAAC
TACAAGACCACGCCTCCCGTGCTGGACTCCGACGGCTCCTTCTTCCTCTA
CAGCAAGCTCACCGTGGACAAGAGCAGGTGGCAGCAGGGGAACGTCTT
CTCATGCTCCGTGATGCATGAGGCTCTGCACAACCACTACACACAGAAG
AGCCTCTCCCTGTCTCCGGGCAAA |
| Clone 13C heavy chain hIgG1 (and hIgG1 afucosylated) amino acid sequence; bold indicates VH | 270 | **QVQLVQSGAEVKKPGSSVKVSCKASGGTFLSSAISWVRQAPGQGLEW
MGSIIPLFGKANYAQKFQGRVTITADESTSTAYMELSSLRSEDTAVYYC
ARGPSEVKGILGYVWFDPWGQGTLVTVSS**ASTKGPSVFPLAPSSKSTSGG
TAALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYK |

TABLE OF SEQUENCES-continued

| Name | SEQ ID NO | Sequence |
|---|---|---|
| | | TTPPVLDSDGSFFLYSKLTVDKSRWQQGNVFSCSVMHEALHNHYTQKSLS<br>LSPGK |
| Clone 13D heavy chain hIgG1 (and hIgG1 afucosylated) nucleotide sequence; bold indicates nucleotide sequence of VH | 271 | CAGGTGCAGCTGGTGCAGTCTGGGGCTGAGGTGAAGAAGCCTGGG<br>TCCTCTGTGAAGGTCTCCTGCAAGGCTTCTGGAGGCACCTTCCTTA<br>GCTCTGCTATCAGCTGGGTGCGACAGGCCCCTGGACAAGGGCTTGA<br>GTGGATGGGATCCATCATCCCTTATTTTGGTAAGGCAAACTACGCA<br>CAGAAGTTCCAGGGCAGAGTCACCATTACTGCTGATGAATCCACCA<br>GCACAGCCTACATGGAGCTGAGCAGCCTGAGATCTGAGGACACTGC<br>TGTGTACTACTGTGCCAGAGGCCCTTCTGAAGTAAAGGGTATACTG<br>GGATATGTATGGTTTGACCCATGGGGACAGGGTACATTGGTCACCG<br>TCTCCTCAGCTAGCACCAAGGGCCCATCTGTCTTCCCCCTGGCACCCTC<br>CTCCAAGAGCACCTCTGGGGGCACAGCTGCCCTGGGCTGCCTGGTCAAG<br>GACTACTTCCCTGAACCTGTGACAGTGTCCTGGAACTCAGGAGCCCTGA<br>CCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAG<br>ACCTACATCTGCAACGTGAATCACAAGCCCAGCAACACCAAGGTGGAC<br>AAGAAAGTTGAGCCCAAATCTTGTGACAAAACTCACACATGCCCACCGT<br>GCCCAGCACCTGAACTCCTGGGGGGACCGTCAGTCTTCCTCTTCCCCCC<br>AAAACCCAAGGACACCCTCATGATCTCCCGGACCCCTGAGGTCACATGC<br>GTGGTGGTGGACGTGAGCCACGAAGACCCTGAGGTCAAGTTCAACTGG<br>TACGTGGACGGCGTGGAGGTGCATAATGCCAAGACAAAGCCGCGGGAG<br>GAGCAGTACAACAGCACGTACCGTGTGGTCAGCGTCCTCACCGTCCTGC<br>ACCAGGACTGGCTGAATGGCAAGGAGTACAAGTGCAAGGTCTCCAACA<br>AAGCCCTCCCAGCCCCCATCGAGAAAACCATCTCCAAAGCCAAAGGGC<br>AGCCCCGAGAACCACAGGTTTACACCCTGCCCCCATCCCGGGATGAGCT<br>GACCAAGAACCAGGTCAGCCTGACCTGCCTGGTCAAAGGCTTCTATCCC<br>AGCGACATCGCCGTGGAGTGGGAGAGCAATGGGCAGCCGGAGAACAAC<br>TACAAGACCACGCCTCCCGTGCTGGACTCCGACGGCTCCTTCTTCCTCTA<br>CAGCAAGCTCACCGTGGACAAGAGCAGGTGGCAGCAGGGGAACGTCTT<br>CTCATGCTCCGTGATGCATGAGGCTCTGCACAACCACTACACACAGAAG<br>AGCCTCTCCCTGTCTCCGGGCAAA |
| Clone 13D heavy chain hIgG1 (and hIgG1 afucosylated) amino acid sequence; bold indicates VH | 272 | QVQLVQSGAEVKKPGSSVKVSCKASGGTFLSSAISWVRQAPGQGLEW<br>MGSIIPYFGKANYAQKFQGRVTITADESTSTAYMELSSLRSEDTAVYYC<br>ARGPSEVKGILGYVWFDPWGQGTLVTVSSASTKGPSVFPLAPSSKSTSGG<br>TAALGCLVKDYFPEPVTVSWNSGALTSGVHTFPAVLQSSGLYSLSSVVTVP<br>SSSLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| Clone 13, 13A, 13B, 13C, and 13D light chain hkappa (and afucosylated) nucleotide sequence; bold indicates nucleotide sequence of VL | 273 | GATATTGTGATGACTCAGTCTCCACTCTCCCTGCCCGTCACCCCTG<br>GAGAGCCGGCCTCCATCTCCTGCAGGTCTAGTCAGAGCCTCCTGCA<br>TAGTAATGGATACAACTATTTGGATTGGTACCTGCAGAAGCCAGGG<br>CAGTCTCCACAGCTCCTGATCTATTTGGGTTCTAATCGGGCCTCCG<br>GGGTCCCTGACAGGTTCAGTGGCAGTGGATCAGGCACAGATTTTAC<br>ACTGAAAATCAGCAGAGTGGAGGCTGAGGATGTTGGGGTTTATTAC<br>TGCATGCAGGCAAGACGAATCCCTATCACTTTTGGCGGAGGGACCA<br>AGGTTGAGATCAAACGTACGGTGGCTGCACCATCTGTCTTCATCTTCCC<br>GCCATCTGATGAGCAGTTGAAATCTGGAACTGCCTCTGTTGTGTGCCTG<br>CTGAATAACTTCTATCCCAGAGAGGCCAAAGTACAGTGGAAGGTGGAT<br>AACGCCCTCCAATCGGGTAACTCCCAGGAGAGTGTCACAGAGCAGGAC<br>AGCAAGGACAGCACCTACAGCCTCAGCAGCACCCTGACGCTGAGCAAA<br>GCAGACTACGAGAAACACAAAGTCTACGCCTGCGAAGTCACCCATCAG<br>GGCCTGAGCTCGCCCGTCACAAAGAGCTTCAACAGGGGAGAGTGT |
| Clone 13, 13A, 13B, 13C, and 13D light chain hkappa (and afucosylated) amino acid sequence; bold indicates VL | 274 | DIVMTQSPLSLPVTPGEPASISCRSSQSLLHSNGYNYLDWYLQKPGQSP<br>QLLIYLGSNRASGVPDRFSGSGSGTDFTLKISRVEAEDVGVYYCMQAR<br>RIPITFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHKVYAC<br>EVTHQGLSSPVTKSFNRGEC |
| Clone 13 heavy chain mIgG2a (and afucosylated) nucleotide sequence; bold indicates nucleotide sequence of VH | 275 | CAGGTGCAGCTGGTGCAGTCTGGGGCTGAGGTGAAGAAGCCTGGG<br>TCCTCTGTGAAGGTCTCCTGCAAGGCTTCTGGAGGCACCTTCAGCA<br>GCTATGCTATCAGCTGGGTGCGACAGGCCCCTGGACAAGGGCTTGA<br>GTGGATGGGAAGCATCATCCCTATCTTTGGTACAGCAAACTACGCA<br>CAGAAGTTCCAGGGCAGAGTCACCATTACTGCTGATGAATCCACCA<br>GCACAGCCTACATGGAGCTGAGCAGCCTGAGATCTGAGGACACTGC<br>TGTGTACTACTGTGCCAGAGGCCCTTCTGAAGTAGGAGCAATACTG<br>GGATATGTATGGTTTGACCCATGGGGACAGGGTACATTGGTCACCG<br>TCTCCTCAGCTAAAACAACAGCCCCATCGGTCTATCCGCTAGCCCTGT<br>GTGTGGAGATACAACTGGCTCCTCGGTGACTCTAGGATGCCTGGTCAAG |

TABLE OF SEQUENCES-continued

| Name | SEQ ID NO | Sequence |
|---|---|---|
| | | GGTTATTTCCCTGAGCCAGTGACCTTGACCTGGAACTCTGGATCCCTGTC CAGTGGTGTGCACACCTTCCCAGCTGTCCTGCAGTCTGACCTCTACACC CTCAGCAGCTCAGTGACTGTAACCTCTAGCACCTGGCCCAGCCAGTCCA TCACCTGCAATGTGGCCCACCCGGCAAGCAGCACCAAGGTGGACAAGA AAATTGAGCCCAGAGGGCCCACAATCAAGCCCTGTCCTCCATGCAAATG CCCAGCACCTAACGCTGCTGGTGGACCATCCGTCTTCATCTTCCCTCCAA AGATCAAGGATGTACTCATGATCTCCCTGAGCCCCATAGTCACATGTGT GGTGGTGGATGTGAGCGAGGATGACCCAGATGTCCAGATCAGCTGGTTT GTGAACAACGTGGAAGTACACACAGCTCAGACACAAACCCATAGAGAG GATTACAACAGTACTCTCCGGGTGGTCAGTGCCCTCCCCATCCAGCACC AGGACTGGATGAGTGGCAAGGAGTTCAAATGCAAGGTCAACAACAAAG ACCTCGGGGCGCCCATCGAGAGAACCATCTCAAAACCCAAAGGCTCAG TAAGAGCTCCACAGGTATATGTCTTGCCTCCACCAGAAGAAGAGATGAC TAAGAAACAGGTCACTCTGACCTGCATGGTCACAGACTTCATGCCTGAA GACATTTACGTGGAGTGGACCAACAACGGGAAAACAGAGCTAAACTAC AAGAACACTGAACCAGTCCTGGACTCTGATGGTTCTTACTTCATGTACA GCAAGCTGAGAGTGGAAAAGAAGAACTGGGTGGAAAGAAATAGCTACT CCTGTTCAGTGGTCCACGAGGGTCTGCACAATCACCACACGACTAAGAG CTTCTCCCGGACTCCGGGCAAA |
| Clone 13 heavy chain mIgG2a (and afucosylated) amino acid sequence; bold indicates VH | 276 | QVQLVQSGAEVKKPGSSVKVSCKASGGTFSSYAISWVRQAPGQGLEW MGSIIPIFGTANYAQKFQGRVTITADESTSTAYMELSSLRSEDTAVYYCA RGPSEVGAILGYVWFDPWGQGTLVTVSSAKTTAPSVYPLAPVCGDTTGS SVTLGCLVKGYFPEPVTLTWNSGSLSSGVHTFPAVLQSDLYTLSSSVTVTSS TWPSQSITCNVAHPASSTKVDKKIEPRGPTIKPCPPCKCPAPNLLGGPSVFIF PPKIKDVLMISLSPIVTCVVVDVSEDDPDVQISWFVNNVEVHTAQTQTHRE DYNSTLRVVSALPIQHQDWMSGKEFKCKVNNKDLGAPIERTISKPKGSVRA PQVYVLPPPEEEMTKKQVTLTCMVTDFMPEDIYVEWTNNGKTELNYKNIL PVLDSDGSYFMYSKLRVEKKNWVERNSYSCSVVHEGLHNHHTTKSFSRTP GK |
| Clone 13 heavy chain mIgG2a LALA-PG nucleotide sequence; bold indicates nucleotide sequence of VH | 277 | CAGGTGCAGCTGGTGCAGTCTGGGGCTGAGGTGAAGAAGCCTGGG TCCTCTGTGAAGGTCTCCTGCAAGGCTTCTGGAGGCACCTTCAGCA GCTATGCTATCAGCTGGGTGCGACAGGCCCCTGGACAAGGGCTTGA GTGGATGGGAAGCATCATCCCTATCTTTGGTACAGCAAACTACGCA CAGAAGTTCCAGGGCAGAGTCACCATTACTGCTGATGAATCCACCA GCACAGCCTACATGGAGCTGAGCAGCCTGAGATCTGAGGACACTGC TGTGTACTACTGTGCCAGAGGCCCTTCTGAAGTAGGAGCAATACTG GGATATGTATGGTTTGACCCATGGGGACAGGGTACATTGGTCACCG TCTCCTCAGCTAAAACAACAGCCCCATCGGTCTATCCGCTAGCCCCTGT GTGTGGAGATACAACTGGCTCCTCGGTGACTCTAGGATGCCTGGTCAAG GGTTATTTCCCTGAGCCAGTGACCTTGACCTGGAACTCTGGATCCCTGTC CAGTGGTGTGCACACCTTCCCAGCTGTCCTGCAGTCTGACCTCTACACC CTCAGCAGCTCAGTGACTGTAACCTCTAGCACCTGGCCCAGCCAGTCCA TCACCTGCAATGTGGCCCACCCGGCAAGCAGCACCAAGGTGGACAAGA AAATTGAGCCCAGAGGGCCCACAATCAAGCCCTGTCCTCCATGCAAATG CCCAGCACCTAACGCTGCTGGTGGACCATCCGTCTTCATCTTCCCTCCAA AGATCAAGGATGTACTCATGATCTCCCTGAGCCCCATAGTCACATGTGT GGTGGTGGATGTGAGCGAGGATGACCCAGATGTCCAGATCAGCTGGTTT GTGAACAACGTGGAAGTACACACAGCTCAGACACAAACCCATAGAGAG GATTACAACAGTACTCTCCGGGTGGTCAGTGCCCTCCCCATCCAGCACC AGGACTGGATGAGTGGCAAGGAGTTCAAATGCAAGGTCAACAACAAAG ACCTCGGGGCGCCCATCGAGAGAACCATCTCAAAACCCAAAGGCTCAG TAAGAGCTCCACAGGTATATGTCTTGCCTCCACCAGAAGAAGAGATGAC TAAGAAACAGGTCACTCTGACCTGCATGGTCACAGACTTCATGCCTGAA GACATTTACGTGGAGTGGACCAACAACGGGAAAACAGAGCTAAACTAC AAGAACACTGAACCAGTCCTGGACTCTGATGGTTCTTACTTCATGTACA GCAAGCTGAGAGTGGAAAAGAAGAACTGGGTGGAAAGAAATAGCTACT CCTGTTCAGTGGTCCACGAGGGTCTGCACAATCACCACACGACTAAGAG CTTCTCCCGGACTCCGGGCAAA |
| Clone 13 heavy chain mIgG2a LALA-PG amino acid sequence; bold indicates VH | 278 | QVQLVQSGAEVKKPGSSVKVSCKASGGTFSSYAISWVRQAPGQGLEW MGSIIPIFGTANYAQKFQGRVTITADESTSTAYMELSSLRSEDTAVYYCA RGPSEVGAILGYVWFDPWGQGTLVTVSSAKTTAPSVYPLAPVCGDTTGS SVTLGCLVKGYFPEPVTLTWNSGSLSSGVHTFPAVLQSDLYTLSSSVTVTSS TWPSQSITCNVAHPASSTKVDKKIEPRGPTIKPCPPCKCPAPNAAGGPSVFIF PPKIKDVLMISLSPIVTCVVVDVSEDDPDVQISWFVNNVEVHTAQTQTHRE DYNSTLRVVSALPIQHQDWMSGKEFKCKVNNKDLGAPIERTISKPKGSVRA PQVYVLPPPEEEMTKKQVTLTCMVTDFMPEDIYVEWTNNGKTELNYKNIL PVLDSDGSYFMYSKLRVEKKNWVERNSYSCSVVHEGLHNHHTTKSFSRTP GK |
| Clone 13 heavy chain mIgG1 nucleotide sequence; bold indicates | 279 | CAGGTGCAGCTGGTGCAGTCTGGGGCTGAGGTGAAGAAGCCTGGG TCCTCTGTGAAGGTCTCCTGCAAGGCTTCTGGAGGCACCTTCAGCA GCTATGCTATCAGCTGGGTGCGACAGGCCCCTGGACAAGGGCTTGA GTGGATGGGAAGCATCATCCCTATCTTTGGTACAGCAAACTACGCA |

TABLE OF SEQUENCES-continued

| Name | SEQ ID NO | Sequence |
|---|---|---|
| nucleotide sequence of VH | | CAGAAGTTCCAGGGCAGAGTCACCATTACTGCTGATGAATCCACCA GCACAGCCTACATGGAGCTGAGCAGCCTGAGATCTGAGGACACTGC TGTGTACTACTGTGCCAGAGGCCCTTCTGAAGTAGGAGCAATACTG GGATATGTATGGTTTGACCCATGGGACAGGGTACATTGGTCACCG TCTCCTCAGCCAAAACGACACCCCCATCTGTCTATCCGCTAGCCCCTGG ATCTGCTGCCCAAACTAACTCCATGGTGACCCTGGGATGCCTGGTCAAG GGCTATTTCCCTGAGCCAGTGACAGTGACCTGGAACTCTGGATCCCTGT CCAGCGGTGTGCACACCTTCCCAGCTGTCCTGGAGTCTGACCTCTACAC TCTGAGCAGCTCAGTGACTGTCCCCTCCAGCCCTCGGCCCAGCGAGACC GTCACCTGCAACGTTGCCCACCCGGCCAGCAGCACCAAGGTGGACAAG AAAATTGTGCCCAGGGATTGTGGTTGTAAGCCTTGCATCTGTACAGTCC CAGAAGTATCATCTGTCTTCATCTTCCCCCCAAAGCCCAAGGATGTGCT CACCATTACTCTGACTCCTAAGGTCACGTGTGTTGTGGTAGACATCAGC AAGGATGATCCCGAGGTCCAGTTCAGCTGGTTTGTAGATGATGTGGAGG TGCACACAGCTCAGACGCAACCCCGGGAGGAGCAGTTCAACAGCACTT TCCGCTCAGTCAGTGAACTTCCCATCATGCACCAGGACTGGCTCAATGG CAAGGAGTTCAAATGCAGGGTCAACAGTGCAGCTTTCCCTGCCCCCATC GAGAAACCATCTCCAAAACCAAAGGCAGACCGAAGGCTCCACAGGTG TACACCATTCCACCTCCCAAGGAGCAGATGGCCAAGGATAAAGTCAGT CTGACCTGCATGATAACAGACTTCTTCCCTGAAGACATTACTGTGGAGT GGCAGTGGAATGGGCAGCCAGCGGAGAACTACAAGAACACTCAGCCCA TCATGAACACGAATGGCTCTTACTTCGTCTACAGCAAGCTCAATGTGCA GAAGAGCAACTGGGAGGCAGGAAATACTTTCACCTGCTCTGTGTTACAT GAGGGCCTGCACAACCACCATACTGAGAAGAGCCTCTCCCACTCTCCTG GCAAA |
| Clone 13 heavy chain mIgG1 amino acid sequence; bold indicates VH | 280 | QVQLVQSGAEVKKPGSSVKVSCKASGGTFSSYAISWVRQAPGQGLEW MGSIIPIFGTANYAQKFQGRVTITADESTSTAYMELSSLRSEDTAVYYCA RGPSEVGAILGYVWFDPWGQGTLVTVSSAKTTPPSVYPLAPGSAAQTNS MVTLGCLVKGYFPEPVTVTWNSGSLSSGVHTFPAVLESDLYTLSSSVTVPS SPRPSETVTCNVAHPASSTKVDKKIVPRDCGCKPCICTVPEVSSVFIFPPPKPK DVLTITLTPKVTCVVVDISKDDPEVQFSWFVDDVEVHTAQTQPREEQFNST FRSVSELPIMHQDWLNGKEFKCRVNSAAPPAPIEKTISKTKGRPKAPQVYTI PPPKEQMAKDKVSLTCMITDFFPEDITVEWQWNGQPAENYKNTQPIMNTN GSYFVYSKLNVQKSNWEAGNTFTCSVLHEGLHNHHTEKSLSHSPGK |
| Clone 13 light chain mKappa nucleotide sequence; bold indicates nucleotide sequence of VH | 281 | GATATTGTGATGACTCAGTCTCCACTCTCCCTGCCCGTCACCCCTG GAGAGCCGGCCTCCATCTCCTGCAGGTCTAGTCAGAGCCTCCTGCA TAGTAATGGATACAACTATTTGGATTGGTACCTGCAGAAGCCAGGG CAGTCTCCACAGCTCCTGATCTATTTGGGTTCTAATCGGGCCTCCG GGGTCCCTGACAGGTTCAGTGGCAGTGGATCAGGCACAGATTTTAC ACTGAAAATCAGCAGAGTGGAGGCTGAGGATGTTGGGGTTTATTAC TGCATGCAGGCAAGACGAATCCCTATCACTTTTGGCGGAGGGACCA AGGTTGAGATCAAACGTGCAGATGCGGCGCCAACTGTATCCATCTTCC CACCATCCAGTGAGCAGTTAACATCTGGAGGTGCCTCAGTCGTGTGCTT CTTGAACAACTTCTACCCCAAAGACATCAATGTCAAGTGGAAGATTGAT GGCAGTGAACGACAAAATGGCGTCCTGAACAGTTGGACTGATCAGGAC AGCAAAGACAGCACCTACAGCATGAGCAGCACCCTCACGTTGACCAAG GACGAGTATGAACGACATAAACAGCTATACCTGTGAGGCCACTCACAAG ACATCAACTTCACCCATTGTCAAGAGCTTCAACAGGAATGAGTGT |
| Clone 13 light chain mKappa amino acid sequence; bold indicates VL | 282 | DIVMTQSPLSLPVTPGEPASISCRSSQSLLHSNGYNYLDWYLQKPGQSP QLLIYLGSNRASGVPDRFSGSGSGTDFTLKISRVEAEDVGVYYCMQAR RIPITFGGGTKVEIKRADAAPTVSIFPPSSEQLTSGGASVVCFLNNFYPKDI NVKWKIDGSERQNGVLNSWTDQDSKDSTYSMSSTLTLTKDEYERHNSYTC EATHKTSTSPIVKSFNRNEC |

What is claimed is:

1. An isolated antibody that binds to human TIGIT (T-cell immunoreceptor with Ig and ITIM domains), wherein the antibody comprises a heavy chain CDR1, CDR2, and CDR3 and a light chain CDR1, CDR2, and CDR3 comprising the sequences of:
   (a) SEQ ID NOs: 58, 60, 62, 67, 69, and 71, respectively; or
   (b) SEQ ID NOs: 224, 225, 62, 67, 69, and 71, respectively; or
   (c) SEQ ID NOs: 226, 227, 228, 67, 69, and 71, respectively; or
   (d) SEQ ID NOs: 224, 229, 230, 67, 69, and 71, respectively; or
   (e) SEQ ID NOs: 224, 227, 230, 67, 69, and 71, respectively.

2. The isolated antibody of claim 1, comprising a heavy chain variable region comprising the amino acid sequence of SEQ ID NO:55, SEQ ID NO:246, SEQ ID NO:247, SEQ ID NO:248, or SEQ ID NO:249 and a light chain variable region comprising the amino acid sequence of SEQ ID NO:64.

3. The isolated antibody of claim 1, comprising a heavy chain comprising an amino acid sequence selected from SEQ ID NOs: 260, 262, 264, 266, 268, 270, and 272; and a light chain comprising the amino acid sequence of SEQ ID NO: 274.

4. The isolated antibody of claim 1, wherein the antibody is afucosylated.

5. A pharmaceutical formulation comprising the isolated antibody of claim 1 and a pharmaceutically acceptable carrier.

6. A bispecific antibody comprising the antibody of claim 1.

7. An antibody-drug conjugate comprising the antibody of claim 1 conjugated to a cytotoxic agent.

8. An isolated polynucleotide that encodes an antibody that binds to human TIGIT (T-cell immunoreceptor with Ig and ITIM domains), wherein the antibody comprises a heavy chain CDR1, CDR2, and CDR3 and a light chain CDR1, CDR2, and CDR3 comprising the sequences of:
   (a) SEQ ID NOs: 58, 60, 62, 67, 69, and 71, respectively; or
   (b) SEQ ID NOs: 224, 225, 62, 67, 69, and 71, respectively; or
   (c) SEQ ID NOs: 226, 227, 228, 67, 69, and 71, respectively; or
   (d) SEQ ID NOs: 224, 229, 230, 67, 69, and 71, respectively; or
   (e) SEQ ID NOs: 224, 227, 230, 67, 69, and 71, respectively.

9. The isolated polynucleotide of claim 8, wherein the polynucleotide comprises a nucleotide sequence selected from SEQ ID NOs: 259, 261, 163, 265, 267, 269, and 271; and/or the nucleotide sequence of SEQ ID NO: 273.

10. A vector comprising the isolated polynucleotide of claim 8.

11. A host cell comprising the isolated polynucleotide of claim 8.

12. A host cell that expresses the antibody of claim 1.

13. A method of producing an antibody, comprising culturing the host cell of claim 12 under conditions suitable for producing the antibody.

14. A composition comprising isolated antibodies that bind to human TIGIT, wherein at least 90% of the antibodies in the composition are afucosylated, and wherein each of the antibodies in the composition comprises a heavy chain CDR1, CDR2, and CDR3 and a light chain CDR1, CDR2, and CDR3 comprising the sequences of:
   (a) SEQ ID NOs: 58, 60, 62, 67, 69, and 71, respectively; or
   (b) SEQ ID NOs: 224, 225, 62, 67, 69, and 71, respectively; or
   (c) SEQ ID NOs: 226, 227, 228, 67, 69, and 71, respectively; or
   (d) SEQ ID NOs: 224, 229, 230, 67, 69, and 71, respectively; or
   (e) SEQ ID NOs: 224, 227, 230, 67, 69, and 71, respectively.

15. The composition of claim 14, wherein each of the antibodies comprises a heavy chain variable region comprising the amino acid sequence of SEQ ID NO:55, SEQ ID NO:246, SEQ ID NO:247, SEQ ID NO:248, or SEQ ID NO:249 and a light chain variable region comprising the amino acid sequence of SEQ ID NO:64.

16. The composition of claim 14, wherein each of the antibodies comprises a heavy chain comprising an amino acid sequence selected from SEQ ID NOs: 260, 262, 264, 266, 268, 270, and 272; and a light chain comprising the amino acid sequence of SEQ ID NO: 274.

17. The composition of claim 14, wherein each antibody is a bispecific antibody.

18. The composition of claim 14, wherein each antibody is conjugated to a cytotoxic agent.

19. A pharmaceutical formulation comprising the composition of claim 14 and a pharmaceutically acceptable carrier.

20. A host cell that expresses an antibody that binds to human TIGIT (T-cell immunoreceptor with Ig and ITIM domains), wherein the host cell is engineered to produce afucosylated antibodies, and wherein the antibody comprises a heavy chain CDR1, CDR2, and CDR3 and a light chain CDR1, CDR2, and CDR3 comprising the sequences of:
   (a) SEQ ID NOs: 58, 60, 62, 67, 69, and 71, respectively; or
   (b) SEQ ID NOs: 224, 225, 62, 67, 69, and 71, respectively; or
   (c) SEQ ID NOs: 226, 227, 228, 67, 69, and 71, respectively; or
   (d) SEQ ID NOs: 224, 229, 230, 67, 69, and 71, respectively; or
   (e) SEQ ID NOs: 224, 227, 230, 67, 69, and 71, respectively.

21. A method of producing afucosylated antibodies that bind TIGIT, comprising culturing the host cell of claim 20 under conditions suitable for producing the afucosylated antibodies.

22. A method of producing afucosylated antibodies that bind TIGIT (T-cell immunoreceptor with Ig and ITIM domains), comprising culturing a host cell that expresses an antibody that binds human TIGIT in the presence of a fucose analogue under conditions suitable for producing afucosylated antibodies, wherein the antibody comprises a heavy chain CDR1, CDR2, and CDR3 and a light chain CDR1, CDR2, and CDR3 comprising the sequences of:
  (a) SEQ ID NOs: 58, 60, 62, 67, 69, and 71, respectively; or
  (b) SEQ ID NOs: 224, 225, 62, 67, 69, and 71, respectively; or
  (c) SEQ ID NOs: 226, 227, 228, 67, 69, and 71, respectively; or
  (d) SEQ ID NOs: 224, 229, 230, 67, 69, and 71, respectively; or
  (e) SEQ ID NOs: 224, 227, 230, 67, 69, and 71, respectively.

23. The isolated antibody of claim 1, wherein the antibody is an IgG1 antibody, wherein the antibody is afucosylated, and wherein the antibody binds with increased affinity to FcγRIIIa and binds with decreased affinity to FcγRIIa and FcγRIIb, compared to the same antibody that is not afucosylated.

24. The composition of claim 14, wherein each of the antibodies in the composition is an IgG1 antibody, and wherein the antibodies bind with increased affinity to FcγRIIIa and bind with decreased affinity to FcγRIIa and FcγRIIb, compared to a composition of the same antibodies that are not afucosylated.

25. The isolated antibody of claim 1, wherein the antibody is afucosylated, and wherein the antibody has a binding affinity ($K_D$) for human TIGIT of less than 5 nM.

26. A composition of isolated antibodies that bind to human TIGIT, wherein the antibodies are produced by a method comprising (a) culturing a host cell in the presence of a fucose analogue under conditions suitable for producing afucosylated antibodies, or (b) culturing a host cell engineered to produce afucosylated antibodies; wherein the host cell comprises a polynucleotide comprising a nucleotide sequence encoding the antibody of claim 1.

27. The composition of claim 26, wherein at least 90% of the antibodies in the composition are afucosylated.

28. An isolated antibody that binds to human TIGIT (T-cell immunoreceptor with Ig and ITIM domains), wherein the antibody comprises a heavy chain CDR1, CDR2, and CDR3 and a light chain CDR1, CDR2, and CDR3 comprising the sequences of SEQ ID NOs: 58, 60, 62, 67, 69, and 71, respectively.

29. The isolated antibody of claim 28, wherein the antibody comprises a heavy chain variable region comprising the amino acid sequence of SEQ ID NO:55 and a light chain variable region comprising the amino acid sequence of SEQ ID NO:64.

30. The isolated antibody of claim 28, comprising a heavy chain comprising an amino acid sequence of SEQ ID NO: 260 and a light chain comprising the amino acid sequence of SEQ ID NO: 274.

31. An isolated antibody that binds to human TIGIT (T-cell immunoreceptor with Ig and ITIM domains), wherein the antibody comprises a heavy chain CDR1, CDR2, and CDR3 and a light chain CDR1, CDR2, and CDR3 comprising the sequences of SEQ ID NOs: 58, 60, 62, 67, 69, and 71, respectively, wherein the antibody is afucosylated.

32. The isolated antibody of claim 31, wherein the antibody comprises a heavy chain variable region comprising the amino acid sequence of SEQ ID NO:55 and a light chain variable region comprising the amino acid sequence of SEQ ID NO:64.

33. The isolated antibody of claim 32, wherein the antibody comprises a heavy chain comprising an amino acid sequence of SEQ ID NO: 260 and a light chain comprising the amino acid sequence of SEQ ID NO: 274.

34. A pharmaceutical formulation comprising the isolated antibody of claim 28 and a pharmaceutically acceptable carrier.

35. A pharmaceutical formulation comprising the isolated antibody of claim 29 and a pharmaceutically acceptable carrier.

36. A pharmaceutical formulation comprising the isolated antibody of claim 30 and a pharmaceutically acceptable carrier.

37. A pharmaceutical formulation comprising the isolated antibody of claim 31 and a pharmaceutically acceptable carrier.

38. A pharmaceutical formulation comprising the isolated antibody of claim 32 and a pharmaceutically acceptable carrier.

39. A pharmaceutical formulation comprising the isolated antibody of claim 33 and a pharmaceutically acceptable carrier.

40. The isolated polynucleotide of claim 8, wherein the antibody comprises a heavy chain CDR1, CDR2, and CDR3 and a light chain CDR1, CDR2, and CDR3 comprising the sequences of SEQ ID NOs: 58, 60, 62, 67, 69, and 71, respectively.

41. The isolated polynucleotide of claim 40, wherein the antibody comprises a heavy chain variable region comprising the amino acid sequence of SEQ ID NO:55 and a light chain variable region comprising the amino acid sequence of SEQ ID NO:64.

42. The isolated polynucleotide of claim 40, wherein the antibody comprises a heavy chain comprising an amino acid sequence of SEQ ID NO: 260 and a light chain comprising the amino acid sequence of SEQ ID NO: 274.

43. The isolated polynucleotide of claim 40, wherein the polynucleotide comprises the nucleotide sequence of SEQ ID NO: 259 and/or the nucleotide sequence of SEQ ID NO: 273.

44. A vector comprising the isolated polynucleotide of claim 40.

45. A vector comprising the isolated polynucleotide of claim 41.

46. A vector comprising the isolated polynucleotide of claim 42.

47. A vector comprising the isolated polynucleotide of claim 43.

48. A host cell comprising the isolated polynucleotide of claim 40.

49. A host cell comprising the isolated polynucleotide of claim 41.

50. A host cell comprising the isolated polynucleotide of claim 42.

51. A host cell comprising the isolated polynucleotide of claim 43.

52. A host cell that expresses the antibody of claim 28.

53. A host cell that expresses the antibody of claim 29.

54. A host cell that expresses the antibody of claim 30.

55. A host cell that expresses the antibody of claim 31.

56. A host cell that expresses the antibody of claim 32.

57. A host cell that expresses the antibody of claim 33.

58. A method of producing an antibody, comprising culturing the host cell of claim 52 under conditions suitable for producing the antibody.

59. A method of producing an antibody, comprising culturing the host cell of claim 53 under conditions suitable for producing the antibody.

60. A method of producing an antibody, comprising culturing the host cell of claim 54 under conditions suitable for producing the antibody.

61. A method of producing an antibody, comprising culturing the host cell of claim 55 under conditions suitable for producing the antibody.

62. A method of producing an antibody, comprising culturing the host cell of claim 56 under conditions suitable for producing the antibody.

63. A method of producing an antibody, comprising culturing the host cell of claim 57 under conditions suitable for producing the antibody.

64. The method of claim 13, further comprising isolating the antibody.

65. The method of claim 58, further comprising isolating the antibody.

66. The method of claim 59, further comprising isolating the antibody.

67. The method of claim 60, further comprising isolating the antibody.

68. The method of claim 61, further comprising isolating the antibody.

69. The method of claim 62, further comprising isolating the antibody.

70. The method of claim 63, further comprising isolating the antibody.

71. A composition comprising isolated antibodies that bind to human TIGIT, wherein at least 90% of the antibodies in the composition are afucosylated, wherein each of the antibodies in the composition comprises a heavy chain CDR1, CDR2, and CDR3 and a light chain CDR1, CDR2, and CDR3 comprising the sequences of SEQ ID NOs: 58, 60, 62, 67, 69, and 71, respectively.

72. The composition of claim 71, wherein each of the antibodies in the composition comprises a heavy chain variable region comprising the amino acid sequence of SEQ ID NO:55 and a light chain variable region comprising the amino acid sequence of SEQ ID NO:64.

73. The composition of claim 71, wherein each of the antibodies in the composition comprises a heavy chain comprising an amino acid sequence of SEQ ID NO: 260 and a light chain comprising the amino acid sequence of SEQ ID NO: 274.

74. A pharmaceutical formulation comprising the composition of claim 71 and a pharmaceutically acceptable carrier.

75. A pharmaceutical formulation comprising the composition of claim 72 and a pharmaceutically acceptable carrier.

76. A pharmaceutical formulation comprising the composition of claim 73 and a pharmaceutically acceptable carrier.

77. The host cell of claim 20, wherein the antibody comprises a heavy chain CDR1, CDR2, and CDR3 and a light chain CDR1, CDR2, and CDR3 comprising the sequences of SEQ ID NOs: 58, 60, 62, 67, 69, and 71, respectively.

78. The host cell of claim 77, wherein the antibody comprises a heavy chain variable region comprising the amino acid sequence of SEQ ID NO:55 and a light chain variable region comprising the amino acid sequence of SEQ ID NO:64.

79. The host cell of claim 77, wherein the antibody comprises a heavy chain comprising an amino acid sequence of SEQ ID NO: 260 and a light chain comprising the amino acid sequence of SEQ ID NO: 274.

80. A method of producing afucosylated antibodies that bind TIGIT, comprising culturing the host cell of claim 77 under conditions suitable for producing the afucosylated antibodies.

81. A method of producing afucosylated antibodies that bind TIGIT, comprising culturing the host cell of claim 78 under conditions suitable for producing the afucosylated antibodies.

82. A method of producing afucosylated antibodies that bind TIGIT, comprising culturing the host cell of claim 79 under conditions suitable for producing the afucosylated antibodies.

83. The method of claim 80, further comprising isolating the afucosylated antibodies.

84. The method of claim 81, further comprising isolating the afucosylated antibodies.

85. The method of claim 82, further comprising isolating the afucosylated antibodies.

86. The method of claim 22, wherein the antibody comprises a heavy chain CDR1, CDR2, and CDR3 and a light chain CDR1, CDR2, and CDR3 comprising the sequences of SEQ ID NOs: 58, 60, 62, 67, 69, and 71, respectively.

87. The method of claim 86, wherein the antibody comprises a heavy chain variable region comprising the amino acid sequence of SEQ ID NO:55 and a light chain variable region comprising the amino acid sequence of SEQ ID NO:64.

88. The method of claim 86, wherein the antibody comprises a heavy chain comprising an amino acid sequence of SEQ ID NO: 260 and a light chain comprising the amino acid sequence of SEQ ID NO: 274.

89. The method of claim 86, further comprising isolating the afucosylated antibodies.

90. The method of claim 87, further comprising isolating the afucosylated antibodies.

91. The method of claim 88, further comprising isolating the afucosylated antibodies.

92. The isolated antibody of claim 28, wherein the antibody is an IgG1 antibody, wherein the antibody is afucosylated, and wherein the antibody binds with increased affinity to FcγRIIIa and binds with decreased affinity to FcγRIIa and FcγRIIb, compared to the same antibody that is not afucosylated.

93. The isolated antibody of claim 29, wherein the antibody is an IgG1 antibody, wherein the antibody is afucosylated, and wherein the antibody binds with increased affinity to FcγRIIIa and binds with decreased affinity to FcγRIIa and FcγRIIb, compared to the same antibody that is not afucosylated.

94. The isolated antibody of claim 30, wherein the antibody is afucosylated, and wherein the antibody binds with increased affinity to FcγRIIIa and binds with decreased affinity to FcγRIIa and FcγRIIb, compared to the same antibody that is not afucosylated.

95. The composition of claim 71, wherein each of the antibodies in the composition is an IgG1 antibody, and wherein the antibodies bind with increased affinity to FcγRIIIa and bind with decreased affinity to FcγRIIa and FcγRIIb, compared to a composition of the same antibodies that are not afucosylated.

96. The composition of claim 72, wherein each of the antibodies in the composition is an IgG1 antibody, and wherein the antibodies bind with increased affinity to FcγRIIIa and bind with decreased affinity to FcγRIIa and FcγRIIb, compared to a composition of the same antibodies that are not afucosylated.

97. The composition of claim 73, wherein the antibodies bind with increased affinity to FcγRIIIa and bind with decreased affinity to FcγRIIa and FcγRIIb, compared to a composition of the same antibodies that are not afucosylated.

98. The isolated antibody of claim 28, wherein the antibody is afucosylated, and wherein the antibody has a binding affinity ($K_D$) for human TIGIT of less than 5 nM.

99. The isolated antibody of claim 29, wherein the antibody is afucosylated, and wherein the antibody has a binding affinity ($K_D$) for human TIGIT of less than 5 nM.

100. The isolated antibody of claim 30, wherein the antibody is afucosylated, and wherein the antibody has a binding affinity ($K_D$) for human TIGIT of less than 5 nM.

101. A composition of isolated antibodies that bind to human TIGIT, wherein the antibodies are produced by a method comprising (a) culturing a host cell in the presence of a fucose analogue under conditions suitable for producing afucosylated antibodies, or (b) culturing a host cell engineered to produce afucosylated antibodies; wherein the host cell comprises a polynucleotide comprising a nucleotide sequence encoding the antibody of claim 28.

102. A composition of isolated antibodies that bind to human TIGIT, wherein the antibodies are produced by a method comprising (a) culturing a host cell in the presence of a fucose analogue under conditions suitable for producing afucosylated antibodies, or (b) culturing a host cell engineered to produce afucosylated antibodies; wherein the host cell comprises a polynucleotide comprising a nucleotide sequence encoding the antibody of claim 29.

103. A composition of isolated antibodies that bind to human TIGIT, wherein the antibodies are produced by a method comprising (a) culturing a host cell in the presence of a fucose analogue under conditions suitable for producing afucosylated antibodies, or (b) culturing a host cell engineered to produce afucosylated antibodies; wherein the host cell comprises a polynucleotide comprising a nucleotide sequence encoding the antibody of claim 30.

104. The composition of claim 101, wherein at least 90% of the antibodies in the composition are afucosylated.

105. The composition of claim 101, wherein at least 95% of the antibodies in the composition are afucosylated.

106. The composition of claim 101, wherein at least 97% of the antibodies in the composition are afucosylated.

107. The composition of claim 102, wherein at least 90% of the antibodies in the composition are afucosylated.

108. The composition of claim 102, wherein at least 95% of the antibodies in the composition are afucosylated.

109. The composition of claim 102, wherein at least 97% of the antibodies in the composition are afucosylated.

110. The composition of claim 103, wherein at least 90% of the antibodies in the composition are afucosylated.

111. The composition of claim 103, wherein at least 95% of the antibodies in the composition are afucosylated.

112. The composition of claim 103, wherein at least 97% of the antibodies in the composition are afucosylated.

113. The composition of claim 14, wherein at least 95% of the antibodies in the composition are afucosylated.

114. The composition of claim 14, wherein at least 97% of the antibodies in the composition are afucosylated.

115. The composition of claim 27, wherein at least 95% of the antibodies in the composition are afucosylated.

116. The composition of claim 27, wherein at least 97% of the antibodies in the composition are afucosylated.

117. The composition of claim 71, wherein at least 95% of the antibodies in the composition are afucosylated.

118. The composition of claim 71, wherein at least 97% of the antibodies in the composition are afucosylated.

119. The composition of claim 72, wherein at least 95% of the antibodies in the composition are afucosylated.

120. The composition of claim 72, wherein at least 97% of the antibodies in the composition are afucosylated.

121. The composition of claim 73, wherein at least 95% of the antibodies in the composition are afucosylated.

122. The composition of claim 73, wherein at least 97% of the antibodies in the composition are afucosylated.

* * * * *

UNITED STATES PATENT AND TRADEMARK OFFICE
CERTIFICATE OF CORRECTION

PATENT NO. : 11,401,339 B2
APPLICATION NO. : 16/547824
DATED : August 2, 2022
INVENTOR(S) : Julia C. Piasecki et al.

It is certified that error appears in the above-identified patent and that said Letters Patent is hereby corrected as shown below:

In the Claims

In Claim 30, Column 315, Line 61, "comprising an amino" should read as --comprising the amino--.

In Claim 33, Column 316, Line 10, "comprising an amino" should read as --comprising the amino--.

In Claim 42, Column 316, Line 42, "comprising an amino" should read as --comprising the amino--.

In Claim 73, Column 317, Line 52, "comprising an amino" should read as --comprising the amino--.

In Claim 79, Column 318, Line 5, "comprising an amino" should read as --comprising the amino--.

In Claim 88, Column 318, Line 36, "comprising an amino" should read as --comprising the amino--.

Signed and Sealed this
Eleventh Day of October, 2022

Katherine Kelly Vidal
*Director of the United States Patent and Trademark Office*